US012673041B2

(12) United States Patent
Shibata et al.

(10) Patent No.: US 12,673,041 B2
(45) Date of Patent: Jul. 7, 2026

(54) 4-AMINOBUT-2-ENAMIDE DERIVATIVES AND SALT THEREOF

(71) Applicants: TAIHO PHARMACEUTICAL CO., LTD., Tokyo (JP); ASTEX THERAPEUTICS, LTD., Cambridge (GB)

(72) Inventors: Kazuaki Shibata, Ibaraki (JP); Yuichi Kawai, Ibaraki (JP); Hiroki Asakura, Ibaraki (JP); Tetsuya Sugimoto, Ibaraki (JP); Naoki Egashira, Ibaraki (JP); Tomohiro Yamamoto, Ibaraki (JP); Tatsuya Suzuki, Ibaraki (JP); Yuki Kataoka, Ibaraki (JP); Takeshi Sagara, Ibaraki (JP); Toshihiro Sakamoto, Ibaraki (JP); Hitomi Kondo, Ibaraki (JP); Christopher Charles Frederick Hamlett, Cambridge (GB); Patrick Schöpf, London (GB); David Geoffrey Twigg, Cambridge (GB)

(73) Assignees: Taiho Pharmaceutical Co., Ltd., Tokyo (JP); Astex Therapeutics, Ltd., Cambridge (GB)

( * ) Notice: Subject to any disclaimer, the term of this patent is extended or adjusted under 35 U.S.C. 154(b) by 926 days.

(21) Appl. No.: 17/773,215

(22) PCT Filed: Oct. 29, 2020

(86) PCT No.: PCT/JP2020/041642
§ 371 (c)(1),
(2) Date: Apr. 29, 2022

(87) PCT Pub. No.: WO2021/085653
PCT Pub. Date: May 6, 2021

(65) Prior Publication Data

US 2023/0023023 A1 Jan. 26, 2023

(30) Foreign Application Priority Data

Oct. 31, 2019 (JP) ................................ 2019-199140
Dec. 6, 2019 (WO) .................. PCT/JP2019/049075

(51) Int. Cl.
*A61K 31/4184* (2006.01)
*A61K 31/4188* (2006.01)

(52) U.S. Cl.
CPC ...... *A61K 31/4184* (2013.01); *A61K 31/4188* (2013.01)

(58) Field of Classification Search
CPC ........................ A61K 31/4184; A61K 31/4188
See application file for complete search history.

(56) References Cited

U.S. PATENT DOCUMENTS

| | | | |
|---|---|---|---|
| 4,034,075 | A | 7/1977 | Bays et al. |
| 9,840,516 | B2 | 12/2017 | Li et al. |
| 10,125,134 | B2 | 11/2018 | Blake et al. |
| 10,144,724 | B2 | 12/2018 | Li et al. |
| 10,556,906 | B2 | 2/2020 | Kuramoto et al. |
| 10,662,204 | B2 | 5/2020 | Planken et al. |
| 10,988,485 | B2 | 4/2021 | Minatti et al. |
| 11,045,484 | B2 | 6/2021 | Wurz et al. |
| 11,090,304 | B2 | 8/2021 | Allen et al. |
| 11,096,939 | B2 | 8/2021 | Booker et al. |
| 11,299,491 | B2 | 4/2022 | Parsons et al. |
| 11,453,683 | B1 | 9/2022 | Wang et al. |
| 11,459,327 | B1 | 10/2022 | Lv et al. |
| 11,530,218 | B2 | 12/2022 | Zhao et al. |
| 11,697,657 | B2 | 7/2023 | Bharathan et al. |
| 11,932,633 | B2 | 3/2024 | Marx et al. |
| 12,208,099 | B2 | 1/2025 | Aranda et al. |
| 2006/0135532 | A1 | 6/2006 | Bryant et al. |
| 2010/0331305 | A1 | 12/2010 | Bergeron et al. |
| 2014/0275070 | A1 | 9/2014 | Grembecka et al. |
| 2014/0288045 | A1 | 9/2014 | Ren et al. |
| 2014/0371203 | A1 | 12/2014 | Madge et al. |
| 2015/0176010 | A1 | 6/2015 | Wersinger |
| 2015/0239900 | A1 | 8/2015 | Li et al. |
| 2015/0246934 | A1 | 9/2015 | Bensen et al. |
| 2016/0046647 | A1 | 2/2016 | Grembecka et al. |
| 2016/0108019 | A1 | 4/2016 | Li et al. |
| 2016/0137665 | A1 | 5/2016 | Grembecka et al. |
| 2016/0152634 | A1 | 6/2016 | Madge et al. |
| 2016/0159738 | A1 | 6/2016 | Ren et al. |
| 2016/0297774 | A1 | 10/2016 | Li et al. |
| 2016/0318866 | A1 | 11/2016 | Becker-Pelster et al. |
| 2017/0131278 | A1 | 5/2017 | Patricelli et al. |

(Continued)

FOREIGN PATENT DOCUMENTS

| | | | |
|---|---|---|---|
| CN | 104011054 | A | 8/2014 |
| CN | 107556289 | A | 1/2018 |

(Continued)

OTHER PUBLICATIONS

Gentile, Cell Chemical Biology, Dec. 21, 2017, 24 (12) 1455-1466 (Year: 2017).*
Liu, Nature Cancer Gene Therapy, 2021 (Year: 2021).*
Quanaj, Frontiers in Oncology, 2023 (Year: 2023).*
International Search Report and Written Opinion in corresponding international application No. PCT/JP2019/049075 dated Jan. 17, 2020 (9 pages).

(Continued)

*Primary Examiner* — Andrew D Kosar
*Assistant Examiner* — Phillip Matthew Rzeczycki
(74) *Attorney, Agent, or Firm* — Venable LLP

(57) ABSTRACT

The present invention provides an antitumor agent comprising a compound or a pharmaceutically acceptable salt thereof that covalently binds to GTP-bound KRASG12C as an active ingredient.

19 Claims, 1 Drawing Sheet

Specification includes a Sequence Listing.

(56) References Cited

U.S. PATENT DOCUMENTS

| | | | |
|---|---|---|---|
| 2017/0197945 | A1 | 7/2017 | Li et al. |
| 2017/0253611 | A1 | 9/2017 | Grembecka et al. |
| 2018/0072723 | A1 | 3/2018 | Blake et al. |
| 2018/0118757 | A1 | 5/2018 | Li et al. |
| 2018/0127396 | A1 | 5/2018 | Li et al. |
| 2018/0141927 | A1 | 5/2018 | Li et al. |
| 2018/0162812 | A1 | 6/2018 | Ren et al. |
| 2018/0177767 | A1 | 6/2018 | Lanman et al. |
| 2018/0334454 | A1 | 11/2018 | Anman et al. |
| 2019/0062313 | A1 | 2/2019 | Li et al. |
| 2019/0062330 | A1 | 2/2019 | Blake et al. |
| 2019/0127336 | A1 | 5/2019 | Li et al. |
| 2019/0144444 | A1 | 5/2019 | Blake et al. |
| 2019/0233440 | A1 | 8/2019 | Planken et al. |
| 2019/0248767 | A1 | 8/2019 | Planken et al. |
| 2019/0270743 | A1 | 9/2019 | Marx et al. |
| 2019/0276432 | A1 | 9/2019 | Beaumont et al. |
| 2019/0284144 | A1 | 9/2019 | Li et al. |
| 2019/0292182 | A1 | 9/2019 | Kuramoto et al. |
| 2019/0343838 | A1 | 11/2019 | Allen et al. |
| 2019/0374542 | A1 | 12/2019 | Allen et al. |
| 2019/0375749 | A1 | 12/2019 | Chen et al. |
| 2020/0055845 | A1 | 2/2020 | Anman et al. |
| 2020/0069657 | A1 | 3/2020 | Anman et al. |
| 2020/0115363 | A1 | 4/2020 | Li et al. |
| 2020/0115375 | A1 | 4/2020 | Barda et al. |
| 2020/0140437 | A1 | 5/2020 | Kuramoto et al. |
| 2020/0165231 | A1 | 5/2020 | Shin et al. |
| 2020/0181118 | A1 | 6/2020 | Malhotra et al. |
| 2020/0237771 | A1 | 7/2020 | Hallur et al. |
| 2020/0262837 | A1 | 8/2020 | Marx et al. |
| 2020/0289503 | A1 | 9/2020 | Huang |
| 2020/0331911 | A1 | 10/2020 | Marx et al. |
| 2021/0009577 | A1 | 1/2021 | Lanman et al. |
| 2021/0024501 | A1 | 1/2021 | Li et al. |
| 2021/0040089 | A1 | 2/2021 | Gao et al. |
| 2021/0047297 | A1 | 2/2021 | Schulze et al. |
| 2021/0122764 | A1 | 4/2021 | Bharathan et al. |
| 2021/0395234 | A1 | 12/2021 | Sakamoto et al. |
| 2022/0064141 | A1 | 3/2022 | Fang et al. |
| 2022/0298174 | A1 | 9/2022 | Guo et al. |
| 2022/0315597 | A1 | 10/2022 | Su et al. |
| 2022/0315598 | A1 | 10/2022 | Xu et al. |
| 2022/0370416 | A1 | 11/2022 | Chu et al. |
| 2022/0389029 | A1 | 12/2022 | Guo et al. |
| 2022/0402916 | A1 | 12/2022 | Hoover et al. |
| 2023/0049402 | A1 | 2/2023 | Sakamoto et al. |
| 2023/0174518 | A1 | 6/2023 | Kawai |
| 2023/0181536 | A1 | 6/2023 | Abe et al. |
| 2023/0348495 | A1 | 11/2023 | Kawai et al. |
| 2023/0416266 | A1 | 12/2023 | Han et al. |
| 2024/0043448 | A1 | 2/2024 | Bharathan et al. |
| 2024/0083913 | A1 | 3/2024 | Bharathan et al. |
| 2024/0124478 | A1 | 4/2024 | Han et al. |
| 2024/0174691 | A1 | 5/2024 | Jiang et al. |
| 2024/0239788 | A1 | 7/2024 | Sloman et al. |
| 2024/0246968 | A1* | 7/2024 | Shibata .................. A61K 45/06 |
| 2024/0262842 | A1 | 8/2024 | Shibata et al. |
| 2024/0317759 | A1 | 9/2024 | Kobayakawa et al. |
| 2024/0376123 | A1 | 11/2024 | Zhou et al. |
| 2024/0417408 | A1 | 12/2024 | Shibata et al. |
| 2025/0136615 | A1 | 5/2025 | Kawamura et al. |

FOREIGN PATENT DOCUMENTS

| | | | |
|---|---|---|---|
| CN | 109843856 | A | 6/2019 |
| CN | 112390788 | A1 | 2/2021 |
| CN | 112430234 | A | 3/2021 |
| CN | 114615981 | A | 6/2022 |
| EP | 3871673 | A1 | 9/2021 |
| EP | 4053120 | A1 | 9/2022 |
| EP | 4397664 | A1 | 10/2024 |
| JP | 2016-519072 | A | 6/2016 |
| JP | 2016-532656 | A | 10/2016 |
| JP | 2017-528498 | A | 9/2017 |
| WO | 03/037898 | A1 | 5/2003 |
| WO | 2005/019177 | A1 | 3/2005 |
| WO | 2009/114575 | A1 | 9/2009 |
| WO | 2010/064705 | A1 | 6/2010 |
| WO | 2013/072694 | A1 | 5/2013 |
| WO | 2014/043272 | A1 | 3/2014 |
| WO | 2014/143659 | A1 | 9/2014 |
| WO | 2014/152588 | A1 | 9/2014 |
| WO | 2014/164543 | A1 | 10/2014 |
| WO | 2015/054572 | A1 | 4/2015 |
| WO | 2015/091415 | A1 | 6/2015 |
| WO | 2015/131005 | A1 | 9/2015 |
| WO | 2016/029454 | A1 | 3/2016 |
| WO | 2016/044772 | A1 | 3/2016 |
| WO | 2016/049524 | A1 | 3/2016 |
| WO | 2016/049565 | A1 | 3/2016 |
| WO | 2016/049568 | A1 | 3/2016 |
| WO | 2016/164675 | A1 | 10/2016 |
| WO | 2016/168540 | A1 | 10/2016 |
| WO | 2017/015562 | A1 | 1/2017 |
| WO | 2017/058728 | A1 | 4/2017 |
| WO | 2017/058768 | A1 | 4/2017 |
| WO | 2017/058792 | A1 | 4/2017 |
| WO | 2017/058805 | A1 | 4/2017 |
| WO | 2017/058807 | A1 | 4/2017 |
| WO | 2017/058902 | A1 | 4/2017 |
| WO | 2017/058915 | A1 | 4/2017 |
| WO | 2017/070256 | A2 | 4/2017 |
| WO | 2017/087528 | A1 | 5/2017 |
| WO | 2017/100546 | A1 | 6/2017 |
| WO | 2017/172979 | A1 | 10/2017 |
| WO | 2017/201161 | A1 | 11/2017 |
| WO | 2018/022897 | A1 | 2/2018 |
| WO | 2018/064510 | A1 | 4/2018 |
| WO | 2018/068017 | A1 | 4/2018 |
| WO | 2018/119183 | A2 | 6/2018 |
| WO | 2018/140512 | A1 | 8/2018 |
| WO | 2018/140513 | A1 | 8/2018 |
| WO | 2018/140514 | A1 | 8/2018 |
| WO | 2018/140598 | A1 | 8/2018 |
| WO | 2018/140599 | A1 | 8/2018 |
| WO | 2018/140600 | A1 | 8/2018 |
| WO | 2018/143315 | A1 | 8/2018 |
| WO | 2018/206539 | A1 | 11/2018 |
| WO | 2018/217651 | A1 | 11/2018 |
| WO | 2018/218069 | A1 | 11/2018 |
| WO | 2018/218070 | A2 | 11/2018 |
| WO | 2018/218071 | A1 | 11/2018 |
| WO | 2019/051291 | A1 | 3/2019 |
| WO | 2019/058132 | A1 | 3/2019 |
| WO | 2019/058393 | A1 | 3/2019 |
| WO | 2019/077631 | A1 | 4/2019 |
| WO | 2019/099524 | A1 | 5/2019 |
| WO | 2019/099703 | A1 | 5/2019 |
| WO | 2019/110751 | A1 | 6/2019 |
| WO | 2019/155399 | A1 | 8/2019 |
| WO | 2019/167000 | A1 | 9/2019 |
| WO | 2019/185525 | A1 | 10/2019 |
| WO | 2019/215203 | A1 | 11/2019 |
| WO | 2019213526 | A1 | 11/2019 |
| WO | 2019217307 | A1 | 11/2019 |
| WO | 2019217691 | A1 | 11/2019 |
| WO | 2019232419 | A1 | 12/2019 |
| WO | 2020/035031 | A1 | 2/2020 |
| WO | 2020/041331 | A1 | 2/2020 |
| WO | 2020/050890 | A2 | 3/2020 |
| WO | 2020047192 | A1 | 3/2020 |
| WO | 2020055755 | A1 | 3/2020 |
| WO | 2020055756 | A1 | 3/2020 |
| WO | 2020055758 | A1 | 3/2020 |
| WO | 2020055760 | A1 | 3/2020 |
| WO | 2020055761 | A1 | 3/2020 |
| WO | 2020/085493 | A1 | 4/2020 |
| WO | 2020/097537 | A2 | 5/2020 |
| WO | 2020/101736 | A1 | 5/2020 |
| WO | 2020102730 | A1 | 5/2020 |
| WO | 2020/113071 | A1 | 6/2020 |
| WO | 2020118066 | A1 | 6/2020 |
| WO | 2020/146613 | A1 | 7/2020 |

(56) References Cited

FOREIGN PATENT DOCUMENTS

| | | | |
|---|---|---|---|
| WO | 2020/156285 | A1 | 8/2020 |
| WO | 2020/177629 | A1 | 9/2020 |
| WO | 2020/178282 | A1 | 9/2020 |
| WO | 2020/221239 | A1 | 11/2020 |
| WO | 2020/233592 | A1 | 11/2020 |
| WO | 2020/234103 | A1 | 11/2020 |
| WO | 2020/236940 | A1 | 11/2020 |
| WO | 2020/238791 | A1 | 12/2020 |
| WO | 2020/239077 | A1 | 12/2020 |
| WO | 2020/239123 | A1 | 12/2020 |
| WO | 2020/244637 | A1 | 12/2020 |
| WO | 2020/259432 | A1 | 12/2020 |
| WO | 2020/259513 | A1 | 12/2020 |
| WO | 2020/259573 | A1 | 12/2020 |
| WO | 2021/000885 | A1 | 1/2021 |
| WO | 2021/023154 | A1 | 2/2021 |
| WO | 2021/027911 | A1 | 2/2021 |
| WO | 2021/027943 | A1 | 2/2021 |
| WO | 2021/031952 | A1 | 2/2021 |
| WO | 2021/037018 | A1 | 3/2021 |
| WO | 2021/041671 | A1 | 3/2021 |
| WO | 2021/043322 | A1 | 3/2021 |
| WO | 2021/052499 | A1 | 3/2021 |
| WO | 2021/055728 | A1 | 3/2021 |
| WO | 2021/057832 | A1 | 4/2021 |
| WO | 2021/058018 | A1 | 4/2021 |
| WO | 2021/063346 | A1 | 4/2021 |
| WO | 2021/078312 | A1 | 4/2021 |
| WO | 2021/081212 | A1 | 4/2021 |
| WO | 2021/083167 | A1 | 5/2021 |
| WO | 2021/086833 | A1 | 5/2021 |
| WO | 2021/088458 | A1 | 5/2021 |
| WO | 2021/093758 | A1 | 5/2021 |
| WO | 2021/098859 | A1 | 5/2021 |
| WO | 2021/104431 | A1 | 6/2021 |
| WO | 2021/106230 | A1 | 6/2021 |
| WO | 2021/106231 | A1 | 6/2021 |
| WO | 2021/107160 | A1 | 6/2021 |
| WO | 2021/109737 | A1 | 6/2021 |
| WO | 2021/113595 | A1 | 6/2021 |
| WO | 2021/118877 | A1 | 6/2021 |
| WO | 2021/121330 | A1 | 6/2021 |
| WO | 2021/121367 | A1 | 6/2021 |
| WO | 2021/121371 | A1 | 6/2021 |
| WO | 2021/124222 | A1 | 6/2021 |
| WO | 2021/127404 | A1 | 6/2021 |
| WO | 2021/129824 | A1 | 7/2021 |
| WO | 2021/147965 | A1 | 7/2021 |
| WO | 2021/147967 | A1 | 7/2021 |
| WO | 2021142252 | A1 | 7/2021 |
| WO | 2021150613 | A1 | 7/2021 |
| WO | 2021/215544 | A1 | 10/2021 |
| WO | 2021/215545 | A1 | 10/2021 |
| WO | 2021211864 | A1 | 10/2021 |
| WO | 2021/219072 | A1 | 11/2021 |
| WO | 2022002102 | A1 | 1/2022 |
| WO | 2022015375 | A1 | 1/2022 |
| WO | 2022031678 | A1 | 2/2022 |
| WO | 2022/066646 | A1 | 3/2022 |
| WO | 2022042630 | A1 | 3/2022 |
| WO | 2022047260 | A1 | 3/2022 |
| WO | 2022061251 | A1 | 3/2022 |
| WO | 2022068921 | A1 | 4/2022 |
| WO | 2022083569 | A1 | 4/2022 |
| WO | 2022087371 | A1 | 4/2022 |
| WO | 2022087375 | A1 | 4/2022 |
| WO | 2022/105857 | A1 | 5/2022 |
| WO | 2022/109485 | A1 | 5/2022 |
| WO | 2022/109487 | A1 | 5/2022 |
| WO | 2022/132200 | A1 | 6/2022 |
| WO | 2022/133038 | A1 | 6/2022 |
| WO | 2022/148422 | A1 | 7/2022 |
| WO | 2022/173870 | A1 | 8/2022 |
| WO | 2022/177917 | A2 | 8/2022 |
| WO | 2022187688 | A1 | 9/2022 |
| WO | 2022/221739 | A1 | 10/2022 |
| WO | 2022/228568 | A1 | 11/2022 |
| WO | 2022/232318 | A1 | 11/2022 |
| WO | 2022/232320 | A1 | 11/2022 |
| WO | 2022/247760 | A1 | 12/2022 |
| WO | 2022/250170 | A1 | 12/2022 |
| WO | 2022/251576 | A1 | 12/2022 |
| WO | 2022/256459 | A1 | 12/2022 |
| WO | 2022/266206 | A1 | 12/2022 |
| WO | 2022248885 | A2 | 12/2022 |
| WO | 2022258974 | A1 | 12/2022 |
| WO | 2022261210 | A1 | 12/2022 |
| WO | 2022262686 | A1 | 12/2022 |
| WO | 2022266069 | A1 | 12/2022 |
| WO | 2022271658 | A1 | 12/2022 |
| WO | 2023018699 | A1 | 2/2023 |
| WO | 2023018809 | A1 | 2/2023 |
| WO | 2023018812 | A1 | 2/2023 |
| WO | 2023020518 | A1 | 2/2023 |
| WO | 2023020519 | A1 | 2/2023 |
| WO | 2023020521 | A1 | 2/2023 |
| WO | 2023020523 | A1 | 2/2023 |
| WO | 2023/046135 | A1 | 3/2023 |
| WO | 2023034290 | A1 | 3/2023 |
| WO | 2023049697 | A1 | 3/2023 |
| WO | 2023/059596 | A1 | 4/2023 |
| WO | 2023/059597 | A1 | 4/2023 |
| WO | 2023/059598 | A1 | 4/2023 |
| WO | 2023056421 | A1 | 4/2023 |
| WO | 2023056951 | A1 | 4/2023 |
| WO | 2023060253 | A1 | 4/2023 |
| WO | 2023061294 | A1 | 4/2023 |
| WO | 2023061463 | A1 | 4/2023 |
| WO | 2023064857 | A1 | 4/2023 |
| WO | 2023072188 | A1 | 5/2023 |
| WO | 2023/097227 | A1 | 6/2023 |
| WO | 2023/103523 | A1 | 6/2023 |
| WO | 2023098425 | A1 | 6/2023 |
| WO | 2023098426 | A1 | 6/2023 |
| WO | 2023098832 | A1 | 6/2023 |
| WO | 2023099592 | A1 | 6/2023 |
| WO | 2023099608 | A1 | 6/2023 |
| WO | 2023099612 | A1 | 6/2023 |
| WO | 2023099620 | A1 | 6/2023 |
| WO | 2023099623 | A1 | 6/2023 |
| WO | 2023099624 | A1 | 6/2023 |
| WO | 2023101928 | A1 | 6/2023 |
| WO | 2023103906 | A1 | 6/2023 |
| WO | 2023104018 | A1 | 6/2023 |
| WO | 2023105491 | A1 | 6/2023 |
| WO | 2023114733 | A1 | 6/2023 |
| WO | 2023117681 | A1 | 6/2023 |
| WO | 2023122154 | A1 | 6/2023 |
| WO | 2023125627 | A1 | 7/2023 |
| WO | 2023125989 | A1 | 7/2023 |
| WO | 2023133183 | A | 7/2023 |
| WO | 2023/150284 | A2 | 8/2023 |
| WO | 2023/159087 | A1 | 8/2023 |
| WO | 2023/173017 | A1 | 9/2023 |
| WO | 2023/179703 | A1 | 9/2023 |
| WO | 2023/193085 | A1 | 10/2023 |
| WO | 2023/197984 | A1 | 10/2023 |
| WO | 2023/244615 | A1 | 12/2023 |
| WO | 2024/009191 | A1 | 1/2024 |
| WO | 2024/012519 | A1 | 1/2024 |
| WO | 2024/015262 | A1 | 1/2024 |
| WO | 2024/032704 | A1 | 2/2024 |
| WO | 2024/041573 | A1 | 2/2024 |
| WO | 2024/044667 | A2 | 2/2024 |
| WO | 2024031088 | A1 | 2/2024 |
| WO | 2024/063578 | A1 | 3/2024 |
| WO | 2024/083168 | A1 | 4/2024 |
| WO | 2024/088069 | A1 | 5/2024 |
| WO | 2024/103010 | A1 | 5/2024 |
| WO | 2024/120433 | A1 | 6/2024 |
| WO | 2024/209339 | A1 | 10/2024 |
| WO | 2024/213979 | A1 | 10/2024 |
| WO | 2024/233776 | A1 | 11/2024 |
| WO | 2024/238343 | A1 | 11/2024 |

(56) References Cited

FOREIGN PATENT DOCUMENTS

| | | | |
|---|---|---|---|
| WO | 2025/019819 | A1 | 1/2025 |
| WO | 2025/019823 | A1 | 1/2025 |
| WO | 2025/085748 | A1 | 4/2025 |
| WO | 2025/230961 | A1 | 11/2025 |
| WO | 2025/235740 | A1 | 11/2025 |

OTHER PUBLICATIONS

International Search Report and Written Opinion in corresponding international application No. PCT/JP2020/041642 dated Feb. 16, 2021 (14 pages).

Examination Report in co-pending Japense Patent Application No. 2022-553421 dated Nov. 25, 2024 (8 pages with English translation).

Examination Report in co-pending European Patent Application No. 20819899.4 dated Nov. 4, 2024 (8 pages).

D.S. Hong, et al., "KRASG12C Inhibition with Sotorasib in Advanced Solid Tumors", The New England Journal of Medicine, vol. 383 No. 13 pp. 1207-1217 (2020).

D. Gentile, et al., "Ras Binder Induces a Modified Switch-II Pocket in GTP and GDP States", Cell Chemical Biology, 24, pp. 1455-1466 (2017).

D. Kessler, et al, "Drugging an undruggable pocket on KRAS", Proceedings of the National Academy of Sciences (PNAS), vol. 116, No. 32, pp. 15823-15829 (2019).

Y. Mao, et al., "Design, synthesis and biological evaluation of novel pyrimidine, 3-cyanopyridine and m-amino-N-phenylbenzamide based monocyclic EGFR tyrosine kinase inhibitors", Bioorganic & Medicinal Chemistry, 21, pp. 3090-3104 (2013).

PubChem CID 10121096, PubChem release Jun. 18, 2019, modify date Nov. 21, 2020, retrieved on Feb. 10, 2021 (9 pages).

G. Palfy, et al., "1H, 15N backbone assignment and comparative analysis of the wild type and G12C, G12D, G12V mutants of K-Ras bound to GDP at physiological pH", Biomolecular NMR Assignment, vol. 14, No. 1, pp. 1-7 (2019).

M.R. Janes, et al., "Targeting KRAS Mutant Cancers with a Covalent G12C-Specific Inhibitor", Cell, 172, pp. 578-589 (2018).

M.P. Patricelli, et al., "Selective Inhibition of Oncogenic KRAS Output with Small Molecules Targeting the Inactive State", Cancer Discovery, 6(3), pp. 316-329 (2016).

H. Chuang, et al., "Pharmacological strategies to target oncogenic KRAS signaling in pancreatic cancer", Pharmacological Research, 117, pp. 370-376 (2017).

Lopez-Tapia, F., et al., "Linker Variation and Structure-Activity Relationship Analyses of Carboxylic Acid-based Small Molecule STAT3 Inhibitors", ACS Med. Chem. Lett. 2018, 9, 250-255.

R.B. Kargbo, "Small Molecule Inhibitors of KRAS G12C Mutant", Acs Med. Chem. Lett., vol. 12, pp. 1210-1211 (2021).

PubChem SID 469710826, available Jul. 28, 2022.

J.G. Kettle, et al., "Structure-Based Design and Pharmacokinetic Optimization of Covalent Allosteric Inhibitors of the Mutant GTPase Kras G12C", J. Med. Chem., vol. 63, pp. 4468-4483 (2020).

Q. Zheng, et al., "Drugging the Next Undruggable KRAS Allele-Gly12Asp", J. Med. Chem, vol. 65, pp. 3119-3122 (2022).

Examination Report in co-pending Chinese Patent Application No. Chinese Patent Application No. 202080087842.9 dated Aug. 3, 2023 (7 pages with English translation).

El-Meligie, Salwa E. M. et al., "New synthetic approaches to thieno[3,2-d]pyrimidine and thieno[3, 4-b]pyridine derivatives", Chemical Papers, vol. 74, pp. 2501-2514 (2020).

El-Kashef, H et al., "Pyridine-Based Heterocycles. Synthesis of New Pyrido[4',3': 4,5]thieno[2,3-d]pyrimidines and Related Heterocycles", Molecules, vol. 15, pp. 2651-2666 (2010).

Szanto, G et al., "New P2X3 receptor antagonists. Part 2: Identification and SAR of quinazolinones," Bioorganic and Medicinal Chemistry Letters, vol. 26, No. 16, pp. 3905-3912, abstract (2016).

Sanad, Smh et al., "Efficient Synthesis and Characterization of Novel Pyrido[3',2': 4,5]thieno[3,2-d]pyrimidines and Their Fused [1,2,4]triazole Derivatives", Journal of Heterocyclic Chemistry, vol. 55, No. 12, pp. 2823-2833, abstract (2018).

Showalter, H.D. Hollis et al., "Tyrosine Kinase Inhibitors. 16. 6,5,6-Tricyclic Benzothieno[3,2-d]pyrimidines and Pyrimido[S,4-b]-and -[4,5-b]indoles as Potent Inhibitors of the Epidermal Growth Factor Receptor Tyrosine Kinase", Journal of Medicinal Chemistry, vol. 42, No. 26, pp. 5464-5474, abstract (1999).

Wang, H. et al., "Annual review of KRAS inhibitors in 2022", European J. of Medicinal Chem., 249, p. 1-14 (2023).

Sanad, SMH et al., "New thieno[2,3-b ]pyridine-fused pyrimidin-4(3H)-ones as potential thymidylate synthase inhibitors: Synthesis, SAR, in vitro and in silica study", Journal of Molecular Structure, vol. 1282, (2023).

* cited by examiner

```
SEQUENCE LISTING

<160> NUMBER OF SEQ ID NOS: 2

<210> SEQ ID NO 1
<211> LENGTH: 170
<212> TYPE: PRT
<213> ORGANISM: Artificial
<220> FEATURE:
<223> OTHER INFORMATION: Synthetic Protein

<400> SEQUENCE: 1

Gly Met Thr Glu Tyr Lys Leu Val Val Val Gly Ala Cys Gly Val Gly
1               5                   10                  15

Lys Ser Ala Leu Thr Ile Gln Leu Ile Gln Asn His Phe Val Asp Glu
            20                  25                  30

Tyr Asp Pro Thr Ile Glu Asp Ser Tyr Arg Lys Gln Val Val Ile Asp
        35                  40                  45

Gly Glu Thr Ser Leu Leu Asp Ile Leu Asp Thr Ala Gly Gln Glu Glu
    50                  55                  60

Tyr Ser Ala Met Arg Asp Gln Tyr Met Arg Thr Gly Glu Gly Phe Leu
65                  70                  75                  80

Leu Val Phe Ala Ile Asn Asn Thr Lys Ser Phe Glu Asp Ile His His
                85                  90                  95

Tyr Arg Glu Gln Ile Lys Arg Val Lys Asp Ser Glu Asp Val Pro Met
            100                 105                 110

Val Leu Val Gly Asn Lys Ser Asp Leu Pro Ser Arg Thr Val Asp Thr
        115                 120                 125

Lys Gln Ala Gln Asp Leu Ala Arg Ser Tyr Gly Ile Pro Phe Ile Glu
    130                 135                 140

Thr Ser Ala Lys Thr Arg Gln Gly Val Asp Asp Ala Phe Tyr Thr Leu
145                 150                 155                 160

Val Arg Glu Ile Arg Lys His Lys Glu Lys
                165                 170
```

-continued

```
<210> SEQ ID NO 2
<211> LENGTH: 188
<212> TYPE: PRT
<213> ORGANISM: Artificial
<220> FEATURE:
<223> OTHER INFORMATION: Synthetic Protein

<400> SEQUENCE: 2

Met Ala Ser Ser His His His His His His Ser Ser Glu Asn Leu Tyr
1               5                   10                  15

Phe Gln Gly Met Thr Glu Tyr Lys Leu Val Val Val Gly Ala Cys Gly
            20                  25                  30

Val Gly Lys Ser Ala Leu Thr Ile Gln Leu Ile Gln Asn His Phe Val
        35                  40                  45

Asp Glu Tyr Asp Pro Thr Ile Glu Asp Ser Tyr Arg Lys Gln Val Val
    50                  55                  60

Ile Asp Gly Glu Thr Cys Leu Leu Asp Ile Leu Asp Thr Ala Gly Gln
65                  70                  75                  80

Glu Glu Tyr Ser Ala Met Arg Asp Gln Tyr Met Arg Thr Gly Glu Gly
                85                  90                  95

Phe Leu Cys Val Phe Ala Ile Asn Asn Thr Lys Ser Phe Glu Asp Ile
            100                 105                 110

His His Tyr Arg Glu Gln Ile Lys Arg Val Lys Asp Ser Glu Asp Val
        115                 120                 125

Pro Met Val Leu Val Gly Asn Lys Cys Asp Leu Pro Ser Arg Thr Val
    130                 135                 140

Asp Thr Lys Gln Ala Gln Asp Leu Ala Arg Ser Tyr Gly Ile Pro Phe
145                 150                 155                 160

Ile Glu Thr Ser Ala Lys Thr Arg Gln Gly Val Asp Asp Ala Phe Tyr
                165                 170                 175

Thr Leu Val Arg Glu Ile Arg Lys His Lys Glu Lys
            180                 185
```

4-AMINOBUT-2-ENAMIDE DERIVATIVES AND SALT THEREOF

CROSS REFERENCE TO RELATED APPLICATIONS

The present application is a national-stage entry under 35 U.S.C. § 371 of International Application No. PCT/JP2020/041642 filed on Oct. 29, 2020, and claims the benefit of priority under 35 U.S.C. § 119(a)-(d) of Japanese Application No. 2019-199140 filed on Oct. 31, 2019, and International Application No. PCT/JP2019/049075 filed on Dec. 6, 2019, the entirety of each of which is incorporated by reference herein.

FIELD OF THE INVENTION

The present invention relates to 4-aminobut-2-enamide derivatives and pharmaceutically acceptable salts thereof having inhibitory activity against active form of KRAS G12C mutation, and relates to a pharmaceutical composition comprising the same as an active ingredient.

BACKGROUND

RAS, which is a small monomeric GTP-binding protein having a molecular weight of about 21 kDa, acts as a molecular on/off switch. RAS can bind to GTP by binding to proteins of a guanine nucleotide exchange factor (GEF) (e.g., SOS1), which forces the release of a bound nucleotide, and releasing GDP. When RAS binds to GTP, it becomes activated (turned on) and recruits and activates proteins necessary for the propagation of other receptors' signals, such as c-Raf and PI 3-kinase. RAS also possesses enzymatic activity with which it cleaves the terminal phosphate of the nucleotide and converts it to GDP. The rate of conversion is usually slow, but can be dramatically sped up by a protein of the GTPase-activating protein (GAP) class, such as RasGAP. When GTP is converted into GDP, RAS is deactivated (turned off).

The mainly known members of the RAS subfamily include HRAS, KRAS, and NRAS. Of these, mutations of KRAS are observed in many malignant tumors: 95% of pancreatic cancers, 45% of colorectal cancers, and 35% of lung cancers. The mutations often occur in the glycine residue at position 12; in pulmonary adenocarcinoma, in particular, the mutation in the glycine residue at position 12 occurs in about 90% of the whole. Among such mutations, the most often occurring mutation (44%) has been reported to be a mutation into cysteine (Non-patent Literature (NPL) 1).

KRAS mutations are historically thought to exist in a constitutively active state (GTP-bound) in cancer cells. However, a recent study indicated that KRAS G12C mutation has basal GTPase activity. K-Ras has a pocket structure to which a medical agent can bind. In part of the pocket, Switch 1 (residue 30 to 40) and Switch 2 (residue 60 to 76) are contained. Switch 1 has threonine-35 and Switch 2 has glycine-60, and these amino acids respectively form a hydrogen bond with γ-phosphoric acid of GTP, and then keep Switch 1 and Switch 2 in an active form. These two regions will be freely loosened by hydrolysis of GTP and liberation of the phosphoric acid to form an inactive GDP form. When GTP bound to K-Ras is replaced with GDP, the three-dimensional conformation of the switch region containing these switches is changed. The change may relate to a bond between K-Ras and a target gene, such as c-Raf.

Actually, it was reported that ARS-853 binds to the cysteine of the G12C mutant of inactive KRAS (GDP), thus preventing conversion of inactive KRAS (GDP) to active KRAS (GTP), inhibiting downstream signaling, and inducing apoptosis in cancer cells with KRAS G12C mutation (Patent Literature (PTL) 1 and NPL 2). It has also been reported that ARS-1620 with a quinazoline backbone exerts antitumor action in tumor-bearing mice expressing KRAS G12C mutation by improving metabolic stability in mice (PTL 2 and NPL 3).

However, because of its mode of action, there is a possibility that the inhibitors which bind to the inactive form of KRAS G12C mutation are not able to exert sufficient effect to KRAS G12C-positive cancer patients in whom active form of KRAS protein (GTP) tends to be increased by activation of an KRAS upstream pathway or deactivation of GTPase activity in clinical settings. In fact, it has been reported that the inhibition of KRAS activity and the anti-proliferative effect of ARS-853 are attenuated by EGFR activation in a KRAS G12C mutation cell line (NPL 2 and NPL 4).

CITATION LIST

Patent Literature

PTL 1: WO 2014/152588
PTL 2: WO 2015/054572

Non-Patent Literature

NPL 1: Nature Reviews Drug Discovery 13 (11), 828-51, 2014
NPL 2: Cancer Discov. 6 (3), 316-29, 2016
NPL 3: Cell. 172 (3), 578-89, 2018
NPL 4: Science. 351 (6273), 604-8, 2016

SUMMARY

It is likely that the specific KRAS upstream inputs to KRAS protein or aberration of GAP function will be cancer-type or patients specific. Thus, appropriate treatment by GDP form KRAS G12C mutation inhibitors such as ARS-853 and ARS-1620 may require a precise understanding of tumor-specific signaling vulnerabilities upstream or downstream of KRAS pathway. Because of that, inhibitors for GDP form KRAS G12C mutation will need to select the effective patient population and likely have to choose the strategies of drug combination, based on the vulnerabilities of KRAS upstream/downstream signaling. On the other hand, inhibitors against active form of KRAS G12C mutation are expected to have therapeutic opportunities toward wider G12C positive patients even as a single agent, with almost no effect from KRAS upstream status.

There is thus a need for a novel compound or a salt thereof that binds to the mutant cysteine of active form of KRAS G12C mutation and a pharmaceutical composition comprising the same.

The present invention relates to the following inventions.

(1) An antitumor agent comprising a compound or a pharmaceutically acceptable salt thereof that covalently binds to GTP-bound KRAS G12C as an active ingredient.

(2) The antitumor agent according to (1), wherein the compound has the formula:

A-L1-L2-G-J wherein,

A is a chemical moiety capable of interacting with a region between Switch 2 and α3-Helix;

L1 is a linker;

L2 is a linker;

G is an electrophilic chemical moiety capable of forming a covalent bond with cysteine 12 of GTP-bound KRAS G12C;

J is a chemical moiety capable of interacting with GTP.

(3) The antitumor agent according to (1) or (2), wherein the agent has a compound having the formula:

A-L1-L2-G-J wherein, G is represented by the following formula:

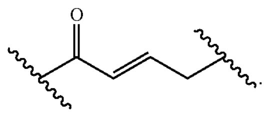 [SMILES: *C/C=C/C(*)=O]

(4) The antitumor agent according to any of (1) to (3), wherein L1 is represented by D with —C(═O)—, L2 is represented by E with —$NR_1$— and J is represented by $NR_2R_3$ in the formula A-L1-L2-G-J, and the compound is represented by Formula (i):

(i)

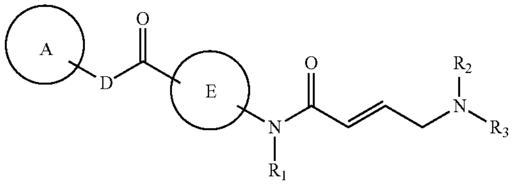

wherein A is a ring system selected from a substituted or unsubstituted single ring or a substituted or unsubstituted fused ring;

D is a single ring having at least one amino group which binds to carbonyl between D and E to form amide, wherein the single ring is unsubstituted or substituted with substituent other than said amino, or D is substituted or unsubstituted fused ring;

E is a ring system selected from a substituted or unsubstituted single ring or a substituted or unsubstituted fused ring;

$R_1$ is hydrogen or substituted or unsubstituted C1-C6 alkyl;

$R_2$ and $R_3$ join together to form a 4- to 10-membered saturated heterocyclic ring which is unsubstituted or substituted with 1-2 substituents independently represented by Ra; or $R_2$ and $R_3$ are independently represented, and $R_2$ is hydrogen; or C1-C10 alkyl, C2-C10 alkenyl, C2-C10 alkynyl, C3-C10 cycloalkyl, C1-C10 alkoxy, C6-C10 aromatic hydrocarbon, a 4- to 10-membered saturated heterocyclic group, a 4- to 10-membered partially saturated heterocyclic group or a 4- to 10-membered unsaturated heterocyclic group, each of which is unsubstituted or substituted with 1-2 substituents independently represented by Ra;

$R_3$ is hydrogen or C1-C6 alkyl which is unsubstituted or substituted with 1-2 substituents independently represented by Ra; Ra represents independently halogen, hydroxy, substituted or unsubstituted C1-C10 alkyl, substituted or unsubstituted C2-C6 alkenyl, substituted or unsubstituted C2-C6 alkynyl, substituted or unsubstituted C3-C10 cycloalkyl, substituted or unsubstituted C1-C10 haloalkyl, substituted or unsubstituted C1-C10 monoalkylamino, substituted or unsubstituted C1-C10 dialkylamino, substituted or unsubstituted C1-C10 alkoxy, substituted or unsubstituted C1-C10 haloalkoxy, substituted or unsubstituted C1-C10 alkylsulfonyl, substituted or unsubstituted C1-C10 acyl, substituted or unsubstituted C1-C10 alkoxycarbonyl or a substituted or unsubstituted 4- to 10-membered saturated heterocyclic group.

(5) The antitumor agent according to (4), wherein the compound is represented by Formula (ii):

(ii)

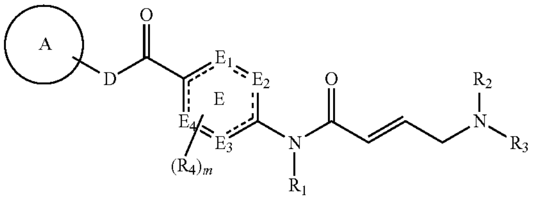

wherein A, D, $R_1$, $R_2$ and $R_3$ are as defined in Formula (i), E is an unsaturated 6-membered ring which is unsubstituted or substituted with $R_4$, wherein $E_1$, $E_2$, $E_3$ and $E_4$ represent independently C, CH, $CH_2$, N or NH;

$R_4$ is halogen, cyano, hydroxy, substituted or unsubstituted C1-C10 alkyl, substituted or unsubstituted C2-C10 alkenyl, substituted or unsubstituted C2-C10 alkynyl, substituted or unsubstituted C3-C10 cycloalkyl, substituted or unsubstituted C1-C10 haloalkyl, substituted or unsubstituted C1-C10 alkoxy, substituted or unsubstituted C1-C10 acyl, substituted or unsubstituted C1-C10 alkoxycarbonyl or substituted or unsubstituted C1-C10 alkylsulfonyl; m is an integer of 0 to 4.

(6) The antitumor agent according to (5), wherein the compound is represented by Formula (iii):

(iii)

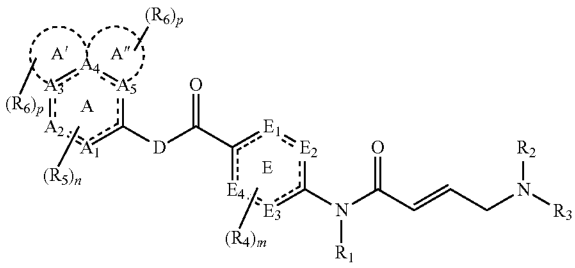

wherein D, $R_1$, $R_2$, and $R_3$ are as defined in Formula (i), and E, $R_4$ and m are as defined in Formula (ii), when A is a single ring, A' and A" are absent, and the single ring is represented by ring A, which is an unsaturated 6-membered ring which is unsubstituted or substituted with $R_8$, wherein $A_1$, $A_2$, $A_3$, $A_4$ and $A_5$ represent independently C, CH, $CH_2$, N or NH;

when A is a fused ring, the fused ring is represented by ring A and ring A' or ring A and ring A", wherein ring A is an unsaturated 6-membered ring which is unsubstituted or substituted with $R_5$, wherein $A_1$, $A_2$, $A_3$, $A_4$ and $A_5$ represent independently C, CH, $CH_2$, N or NH, and ring A' or A" is a saturated or unsaturated ring which is unsubstituted or substituted with $R_6$ and forms a fused ring with ring A containing $A_3$ and $A_4$ or $A_4$ and $A_5$;

$R_5$ is halogen, cyano, amino, hydroxy, substituted or unsubstituted C1-C10 alkyl, substituted or unsubstituted C2-C6 alkenyl, substituted or unsubstituted C2-C6 alkynyl, substituted or unsubstituted C1-C6 haloalkyl, substituted or unsubstituted C1-C10 alkoxy, substituted or unsubstituted C1-C10 acyl, substituted or unsubstituted C1-C10 alkoxycarbonyl, or substituted or unsubstituted C1-C10 alkylsulfonyl; two $R_6$ may join together to form a C3-C10 hydrocarbon ring or a 4- to 10-membered saturated heterocyclic ring sharing two adjacent atoms with ring A' or ring A" when the number of $R_6$ is two or more; or $R_6$ may independently represents halogen, cyano, amino, hydroxy, substituted or unsubstituted C1-C10 alkyl, substituted or unsubstituted C2-C6 alkenyl, substituted or unsubstituted C2-C6 alkynyl, substituted or unsubstituted C1-C6 haloalkyl, substituted or unsubstituted C1-C10 alkoxy, substituted or unsubstituted C1-C10 acyl, substituted or unsubstituted C1-C10 alkoxycarbonyl or substituted or unsubstituted C1-C10 alkylsulfonyl;

n is an integer of 0 to 5; and p is 0, 1, or 2.

(7) The antitumor agent according to (6), wherein the compound is represented by Formula (iv):

(iv)

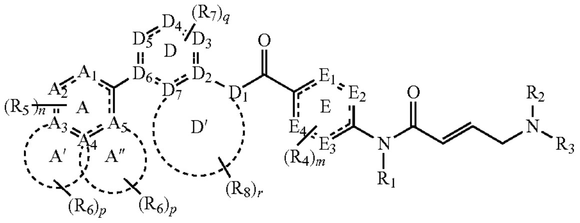

wherein $R_1$, $R_2$, and $R_3$ are as defined in Formula (i), and E, $R_4$ and m are as defined in Formula (ii), and A, $R_5$, $R_6$, n, and p are as defined in Formula (iii);

when D is a single ring, D' is absent, and the single ring is represented by ring D, which is an unsaturated 6-membered ring which is unsubstituted or substituted with $R_7$, wherein $D_1$ represents N or NH, and $D_2$, $D_3$, $D_4$, $D_5$, $D_6$ and $D_7$ represent independently C, CH, $CH_2$, N or NH;

when D is a fused ring, the fused ring is represented by ring D and ring D', wherein ring D is an unsaturated 6-membered ring which is unsubstituted or substituted with $R_7$, wherein $D_1$, $D_2$, $D_3$, $D_4$, $D_5$, $D_6$ and $D_7$ represent independently C, CH, $CH_2$, N or NH, and ring D' is a saturated or unsaturated ring which is unsubstituted or substituted with $R_8$ and forms a fused ring with ring D containing $D_1$, $D_2$ and $D_7$;

$R_7$ is halogen, cyano, hydroxy, amino, carboxamide, substituted or unsubstituted C1-C10 alkyl, substituted or unsubstituted C2-C6 alkenyl, substituted or unsubstituted C2-C6 alkynyl, substituted or unsubstituted C1-C6 haloalkyl, substituted or unsubstituted C1-C10 alkoxy, substituted or unsubstituted C1-C10 acyl, substituted or unsubstituted C1-C10 alkoxycarbonyl or substituted or unsubstituted C1-C10 alkylsulfonyl;

$R_8$ is halogen or substituted or unsubstituted C1-C10 alkyl;

q and r represent independently 0, 1, or 2.

(8) The antitumor agent according to (7), wherein ring A' forms a fused ring with ring A containing $A_3$ and $A_4$, and $A_1$ and $A_5$ are C, CH, or $CH_2$.

(9) The antitumor agent according to (8), wherein $R_1$ is hydrogen.

(10) The antitumor agent according to (9), wherein $R_2$ and $R_3$ are independently represented, and $R_3$ is hydrogen or C1-C3 alkyl.

(11) The antitumor agent according to (10), wherein $D_6$ in ring D is C.

(12) The antitumor agent according to (11), wherein $D_3$, $D_4$ and $D_5$ are C.

(13) The antitumor agent according to (7), wherein the compound is represented by Formula (v):

(v)

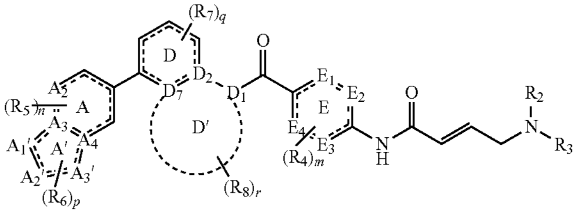

wherein $R_2$ and $R_3$ are as defined in Formula (i), E, $R_4$ and m are as defined in Formula (ii), A, $R_5$, n, and p are as defined in Formula (iii) and D, $R_7$, $R_8$, q, and r are as defined in Formula (iv);

ring A' is a saturated or unsaturated 5-membered ring forming a fused ring containing $A_3$ and $A_4$ with ring A, wherein $A_1'$, $A_2'$, $A_3'$ represent independently C, CH, $CH_2$, N, NH, O or S, two $R_6$ may join together to form a C3-C10 hydrocarbon ring or a 4- to 10-membered saturated heterocyclic ring when the number of $R_6$ is two or more; or $R_6$ may be independently halogen, cyano, hydroxy, substituted or unsubstituted C1-C10 alkyl, substituted or unsubstituted C1-C6 haloalkyl or substituted or unsubstituted C1-C10 alkoxy.

(14) The antitumor agent according to any of (6) to (13), wherein $A_2$ is C.

(15) The antitumor agent according to any of (4) to (14), wherein $R_2$ is C1-C10 alkyl which is unsubstituted or substituted with Ra, C3-C10 cycloalkyl which is unsubstituted or substituted with Ra, or a 4- to 10-membered saturated heterocyclic group which is unsubstituted or substituted with Ra.

(16) The antitumor agent according to any of (1) to (15), wherein $R_3$ is hydrogen.

(17) The antitumor agent according to any of (5) to (16), wherein $R_4$ is halogen, cyano or C1-C6 alkyl.

(18) The antitumor agent according to any of (6) to (17), wherein $R_5$ is hydroxy, halogen, C1-C10 alkyl, C1-C6 haloalkyl or C1-C10 alkoxy.

(19) The antitumor agent according to any of (6) to (18), wherein, two $R_6$ may join together to form a C3-C10 hydrocarbon ring or a 4- to 10-membered saturated heterocyclic ring when the number of $R_6$ is two or more; or each $R_6$ may represent independently substituted or unsubstituted C1-C10 alkyl or substituted or unsubstituted C1-C10 alkoxy.

(20) The antitumor agent according to (13), wherein the compound is represented by Formula (vi):

(vi)

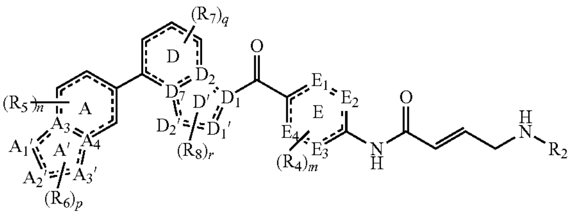

wherein $R_2$ is as defined in Formula (i), E, $R_4$ and m are as defined in Formula (ii), A, $R_5$, n, and p are as defined in Formula (iii) and $R_8$, q and r are as defined in Formula (iv), $R_6$ and A' are as defined in Formula (v);

D is a fused ring represented by ring D and ring D', and ring D' is a saturated or unsaturated 5-membered ring forming a fused ring containing $D_1$, $D_2$ and $D_7$ with ring D, and $D_1'$ and $D_2'$ represent independently C, CH, $CH_2$, N, NH or S, $R_7$ is halogen, cyano, hydroxy, amino, carboxamide, substituted or unsubstituted C1-C10 alkyl, substituted or unsubstituted C1-C10 haloalkyl or substituted or unsubstituted C1-C10 alkoxy.

(21) The antitumor agent according to (20), wherein $R_7$ is halogen or substituted or unsubstituted C1-C10 alkyl.

(22) A compound represented by Formula (i):

(i)

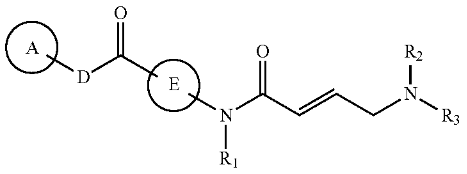

or a pharmaceutically acceptable salt thereof, wherein, A is a ring system selected from a substituted or unsubstituted single ring or a substituted or unsubstituted fused ring;

D is a single ring having at least one amino group which binds to carbonyl between D and E to form amide, wherein the single ring is unsubstituted or substituted with substituent other than said amino, or D is substituted or unsubstituted fused ring;

E is a ring system selected from a substituted or unsubstituted single ring or a substituted or unsubstituted fused ring;

$R_1$ is hydrogen or substituted or unsubstituted C1-C6 alkyl;

$R_2$ and $R_3$ join together to form a 4- to 10-membered saturated heterocyclic ring which is unsubstituted or substituted with 1-2 substituents independently represented by Ra; or $R_2$ and $R_3$ are independently represented, and $R_2$ is hydrogen; or C1-C10 alkyl, C2-C10 alkenyl, C2-C10 alkynyl, C3-C10 cycloalkyl, C1-C10 alkoxy, C6-C10 aromatic hydrocarbon, a 4- to 10-membered saturated heterocyclic group, a 4- to 10-membered partially saturated heterocyclic group or a 4- to 10-membered unsaturated heterocyclic group, each of which is unsubstituted or substituted with 1-2 substituents independently represented by Ra;

$R_3$ is hydrogen or C1-C6 alkyl which is unsubstituted or substituted with 1-2 substituents independently represented by Ra;

Ra represents independently halogen, hydroxy, substituted or unsubstituted C1-C10 alkyl, substituted or unsubstituted C2-C6 alkenyl, substituted or unsubstituted C2-C6 alkynyl, substituted or unsubstituted C3-C10 cycloalkyl, substituted or unsubstituted C1-C10 haloalkyl, substituted or unsubstituted C1-C10 monoalkylamino, substituted or unsubstituted C1-C10 dialkylamino, substituted or unsubstituted C1-C10 alkoxy, substituted or unsubstituted C1-C10 haloalkoxy, substituted or unsubstituted C1-C10 alkylsulfonyl, substituted or unsubstituted C1-C10 acyl, substituted or unsubstituted C1-C10 alkoxycarbonyl or a substituted or unsubstituted 4- to 10-membered saturated heterocyclic group.

(23) The compound according to (22), wherein the compound is represented by Formula (ii):

(ii)

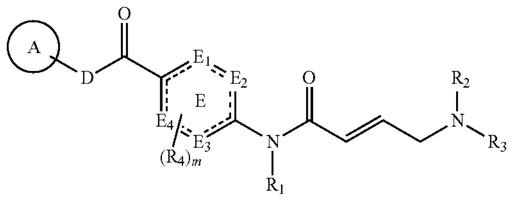

wherein A, D, $R_1$, $R_2$ and $R_3$ are as defined in Formula (i), E is an unsaturated 6-membered ring which is unsubstituted or substituted with $R_4$, wherein $E_1$, $E_2$, $E_3$ and $E_4$ represent independently C, CH, $CH_2$, N or NH;

$R_4$ is halogen, cyano, hydroxy, substituted or unsubstituted C1-C10 alkyl, substituted or unsubstituted C2-C10 alkenyl, substituted or unsubstituted C2-C10 alkynyl, substituted or unsubstituted C3-C10 cycloalkyl, substituted or unsubstituted C1-C10 haloalkyl, substituted or unsubstituted C1-C10 alkoxy, substituted or unsubstituted C1-C10 acyl, substituted or unsubstituted C1-C10 alkoxycarbonyl or substituted or unsubstituted C1-C10 alkylsulfonyl;

m is an integer of 0 to 4; or a pharmaceutically acceptable salt thereof.

(24) The compound according to (24), wherein the compound is represented by Formula (iii):

(iii)

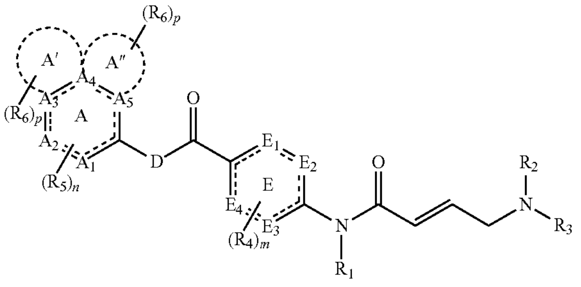

wherein D, $R_1$, $R_2$, and $R_3$ are as defined in Formula (i), and E, $R_4$ and m are as defined in Formula (ii), when A is a single ring, A' and A" are absent, and the single ring is represented by ring A, which is an unsaturated 6-membered ring which is unsubstituted or substituted with $R_5$, wherein $A_1$, $A_2$, $A_3$, $A_4$ and $A_5$ represent independently C, CH, $CH_2$, N or NH;

when A is a fused ring, the fused ring is represented by ring A and ring A' or ring A and ring A", wherein ring A is an unsaturated 6-membered ring which is unsubstituted or substituted with $R_5$, wherein $A_1$, $A_2$, $A_3$, $A_4$ and $A_5$ represent independently C, CH, $CH_2$, N or NH, and ring A' or A" is a saturated or unsaturated ring which is unsubstituted or substituted with $R_6$ and forms a fused ring with ring A containing $A_3$ and $A_4$ or $A_4$ and $A_5$;

$R_5$ is halogen, cyano, amino, hydroxy, substituted or unsubstituted C1-C10 alkyl, substituted or unsubstituted C2-C6 alkenyl, substituted or unsubstituted C2-C6 alkynyl, substituted or unsubstituted C1-C6 haloalkyl, substituted or unsubstituted C1-C10 alkoxy, substituted or unsubstituted C1-C10 acyl, substituted or unsubstituted C1-C10 alkoxycarbonyl, or substituted or unsubstituted C1-C10 alkylsulfonyl; two $R_6$ may join together to form a C3-C10 hydrocarbon ring or a 4- to 10-membered saturated heterocyclic ring sharing two adjacent atoms with ring A' or ring A" when the number of $R_6$ is two or more; or $R_6$ may independently represents halogen, cyano, amino, hydroxy, substituted or unsubstituted C1-C10 alkyl, substituted or unsubstituted C2-C6 alkenyl, substituted or unsubstituted C2-C6 alkynyl, substituted or unsubstituted C1-C6 haloalkyl, substituted or unsubstituted C1-C10 alkoxy, substituted or unsubstituted C1-C10 acyl, substituted or unsubstituted C1-C10 alkoxycarbonyl or substituted or unsubstituted C1-C10 alkylsulfonyl;

n is an integer of 0 to 5; and p is 0, 1, or 2; or a pharmaceutically acceptable salt thereof.

(25) The compound according to (24), wherein the compound is represented by Formula (iv):

(iv)

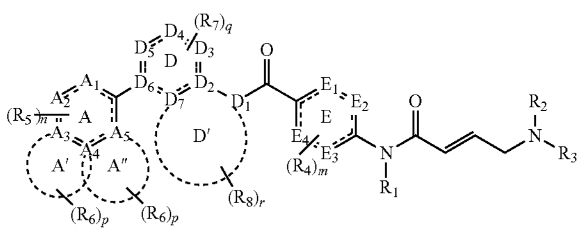

wherein $R_1$, $R_2$, and $R_3$ are as defined in Formula (i), and E, $R_4$ and m are as defined in Formula (ii), and A, $R_5$, $R_6$, n, and p are as defined in Formula (iii);

when D is a single ring, D' is absent, and the single ring is represented by ring D, which is an unsaturated 6-membered ring which is unsubstituted or substituted with $R_7$, wherein $D_1$ represents N or NH, and $D_2$, $D_3$, $D_4$, $D_5$, $D_6$ and $D_7$ represent independently C, CH, $CH_2$, N or NH;

when D is a fused ring, the fused ring is represented by ring D and ring D', wherein ring D is an unsaturated 6-membered ring which is unsubstituted or substituted with $R_7$, wherein $D_1$, $D_2$, $D_3$, $D_4$, $D_5$, $D_6$ and $D_7$ represent independently C, CH, $CH_2$, N or NH, and ring D' is a saturated or unsaturated ring which is unsubstituted or substituted with $R_8$ and forms a fused ring with ring D containing $D_1$, $D_2$ and $D_7$;

$R_7$ is halogen, cyano, hydroxy, amino, carboxamide, substituted or unsubstituted C1-C10 alkyl, substituted or unsubstituted C2-C6 alkenyl, substituted or unsubstituted C2-C6 alkynyl, substituted or unsubstituted C1-C6 haloalkyl, substituted or unsubstituted C1-C10 alkoxy, substituted or unsubstituted C1-C10 acyl, substituted or unsubstituted C1-C10 alkoxycarbonyl or substituted or unsubstituted C1-C10 alkylsulfonyl;

$R_8$ is halogen or substituted or unsubstituted C1-C10 alkyl; q and r represent independently 0, 1, or 2; or a pharmaceutically acceptable salt thereof.

(26) The compound according to (25), wherein ring A' forms a fused ring with ring A containing $A_3$ and $A_4$, and $A_1$ and $A_5$ are C, CH, or $CH_2$; or a pharmaceutically acceptable salt thereof.

(27) The compound according to (26), wherein $R_1$ is hydrogen; or a pharmaceutically acceptable salt thereof.

(28) The compound according to (27), wherein $R_2$ and $R_3$ are independently represented, and $R_3$ is hydrogen or C1-C3 alkyl; or a pharmaceutically acceptable salt thereof.

(29) The compound according to (28), wherein $D_6$ in ring D is C; or a pharmaceutically acceptable salt thereof.

(30) The compound according to (29), wherein $D_3$, $D_4$ and $D_5$ are C; or a pharmaceutically acceptable salt thereof.

(31) The compound according to (25), wherein the compound is represented by Formula (v):

(v)

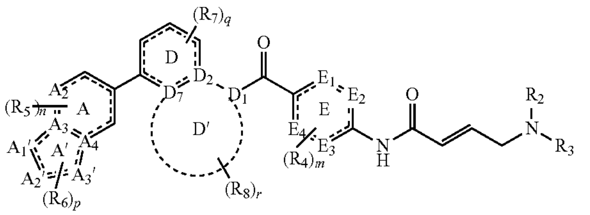

wherein $R_2$ and $R_3$ are as defined in Formula (i), E, $R_4$ and m are as defined in Formula (ii), A, $R_5$, n, and p are as defined in Formula (iii) and D, $R_7$, $R_8$, q, and r are as defined in Formula (iv); ring A' is a saturated or unsaturated 5-membered ring forming a fused ring containing $A_3$ and $A_4$ with ring A, wherein $A_1'$, $A_2'$, $A_3'$ represent independently C, CH, $CH_2$, N, NH, O or S, two $R_6$ may join together to form a C3-C10 hydrocarbon ring or a 4- to 10-membered saturated heterocyclic ring when the number of $R_6$ is two or more; or $R_6$ may be independently halogen, cyano, hydroxy, substituted or unsubstituted C1-C10 alkyl, substituted or unsubstituted C1-C6 haloalkyl or substituted or unsubstituted C1-C10 alkoxy; or a pharmaceutically acceptable salt thereof.

(32) The compound according to any of (24) to (31), wherein $A_2$ is C; or a pharmaceutically acceptable salt thereof.

(33) The compound according to any of (28) to (32), wherein $R_2$ is C1-C10 alkyl which is unsubstituted or substituted with Ra, C3-C10 cycloalkyl which is unsubstituted or substituted with Ra, a 4- to 10-membered saturated heterocyclic group which is unsubstituted or substituted with Ra; or a pharmaceutically acceptable salt thereof.

(34) The compound according to any of (28) to (33), wherein $R_3$ is hydrogen; or a pharmaceutically acceptable salt thereof.

(35) The compound according to any of (23) to (34), wherein $R_4$ is halogen, cyano or C1-C6 alkyl; or a pharmaceutically acceptable salt thereof.

(36) The compound according to any of (24) to (35), wherein $R_5$ is hydroxy, halogen, C1-C10 alkyl, C1-C6 haloalkyl or C1-C10 alkoxy; or a pharmaceutically acceptable salt thereof.

(37) The compound according to any of (24) to (36), wherein, two $R_6$ may join together to form a C3-C10 hydrocarbon ring or a 4- to 10-membered saturated heterocyclic ring when the number of $R_6$ is two or more; or each $R_6$ may represent independently substituted or unsubstituted C1-C10 alkyl or substituted or unsubstituted C1-C10 alkoxy; or a pharmaceutically acceptable salt thereof.

(38) The compound according to (31), wherein the compound is represented by Formula (vi) or a salt thereof:

(vi)

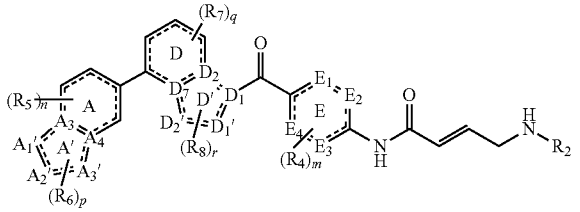

wherein $R_2$ is as defined in Formula (i), E, $R_4$ and m are as defined in Formula (ii), A, $R_5$, n, and p are as defined in Formula (iii) and $R_8$, q and r are as defined in Formula (iv), $R_6$ and A' are as defined in Formula (v);

D is a fused ring represented by ring D and ring D', and ring D' is a saturated or an unsaturated 5-membered ring forming a fused ring containing $D_1$, $D_2$ and $D_7$ with ring D, and $D_1'$ and $D_2'$ represents independently C, CH, $CH_2$, N, NH or S, $R_7$ is halogen, cyano, hydroxy, amino, carboxamide, substituted or unsubstituted C1-C10 alkyl, substituted or unsubstituted C1-C10 haloalkyl or substituted or unsubstituted C1-C10 alkoxy; or a pharmaceutically acceptable salt thereof.

(39) The compound according to (38), wherein $R_7$ is halogen or substituted or unsubstituted C1-C10 alkyl; or a pharmaceutically acceptable salt thereof.

(40) A medicament comprising the compound or pharmaceutically acceptable salt thereof of any of (22) to (39).

(41) A pharmaceutical composition comprising the compound or pharmaceutically acceptable salt thereof of any of (22) to (39).

(42) An antitumor agent, comprising the compound or pharmaceutically acceptable salt thereof of any of (22) to (39) as an active ingredient.

(43) An antitumor agent for oral administration, comprising the compound or pharmaceutically acceptable salt thereof of any of (22) to (39) as an active ingredient.

(44) Use of the compound or a pharmaceutically acceptable salt thereof according to any of (22) to (39) for manufacturing a pharmaceutical composition.

(45) Use of the compound or a pharmaceutically acceptable salt thereof according to any of (22) to (39) for manufacturing an antitumor agent.

(46) Use of the compound or a pharmaceutically acceptable salt thereof according to any of (22) to (39) for manufacturing an antitumor agent for oral administration.

(47) The compound or pharmaceutically acceptable salt thereof of any of (22) to (39) for use as medicament.

(48) The compound or pharmaceutically acceptable salt thereof of any of (22) to (39) for use in the treatment of tumor.

(49) The compound or pharmaceutically acceptable salt thereof of any of (22) to (39) for use in the treatment of tumor by oral administration.

(50) A method for treating tumor, comprising administrating a therapeutically effective amount of the compound or pharmaceutically acceptable salt thereof of any of (22) to (39) to a subject in need thereof.

(51) The antitumor agent of (1), wherein the agent is administered to a subject in need thereof in combination with a pharmaceutically effective amount of one or more other antitumor drugs.

(52) The antitumor agent of (1), wherein the tumor is a cancer.

(53) The antitumor agent of (52), wherein the cancer is one or more selected from the group consisting of a carcinoma, squamous carcinoma, adenocarcinoma, sarcoma, leukemia, neuroma, melanoma, and lymphoma.

(54) The antitumor agent of (53), wherein the squamous carcinoma is a cancer of uterine cervix, tarsus, conjunctiva, vagina, lung, oral cavity, skin, bladder, tongue, larynx or esophagus.

(55) The antitumor agent of (53), wherein the adenocarcinoma is a cancer of prostate, small intestine, endometrium, uterine cervix, large intestine, lung, pancreas, esophagus, rectum, uterus, stomach, breast or ovary.

(56) The method of (51), wherein the tumor is rectal cancer, colon cancer, colorectal cancer, pancreatic cancer, lung cancer, breast cancer or leukemia.

(57) An antitumor agent comprising a compound or a pharmaceutically acceptable salt thereof of any one of (22) to (39), and one or more other antitumor agents as an active ingredient.

(58) An antitumor agent comprising a compound or a pharmaceutically acceptable salt thereof of any one of (22) to (39) as an active ingredient, which is administered in combination with one or more other antitumor agents.

(59) Use of the compound according to any one of (22) to (39) or a salt thereof and one or more other antitumor agents for the manufacture of an antitumor agent.

(60) Use of the compound according to any one of (22) to (39) or a salt thereof for the manufacture of an antitumor agent, which is administered in combination with one or more other antitumor agents.

(61) The combination of a compound according to any one of (22) to (39) or a salt thereof and one or more other antitumor agents for use in the treatment of tumors.

(62) The compound or pharmaceutically acceptable salt thereof of any of (22) to (39) for use in the treatment of tumor, which is administered in combination with one or more other antitumor agents.

(63) A method for treating tumor, comprising administrating a therapeutically effective amount of the compound or pharmaceutically acceptable salt thereof of any of (22) to (39), and one or more other antitumor agents to a subject in need thereof.

(64) A method for treating tumor, comprising administrating a therapeutically effective amount of the compound or pharmaceutically acceptable salt thereof of any of (22) to (39), which is administered in combination with one or more other antitumor agents to a subject in need thereof.

(65) Use of a compound or pharmaceutically acceptable salt thereof that covalently binds to GTP-bound KRAS G12C for manufacturing of an antitumor agent.

(66) A compound or pharmaceutically acceptable salt thereof that covalently binds to GTP-bound KRAS G12C for use in the treatment of tumor.

(67) A method for treating tumor, comprising administrating a therapeutically effective amount of the compound or pharmaceutically acceptable salt thereof that covalently binds to GTP-bound KRAS G12C to a subject in need thereof.

(68) The antitumor agent according to (1) or (2), wherein the agent has a compound having the formula:

A-L1-L2-G-J wherein, G is represented by the following formula:

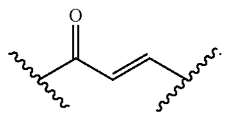 [SMILES: */C=C/C(*)=O]

(69) The antitumor agent according to any of (1), (2) or (68), wherein L1 is represented by D with —C(=O)—, L2 is represented by E with $—NR_1—$ and J is represented by $—CHR_2'—NR_2R_3$ in the formula A-L1-L2-G-J, and the compound is represented by Formula (vii):

(vii)

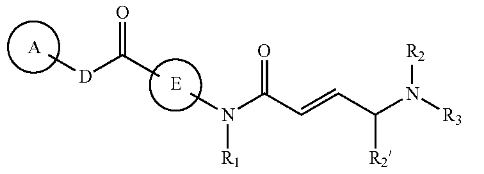

wherein A is a ring system selected from a substituted or unsubstituted single ring or a substituted or unsubstituted fused ring;

D is a single ring having at least one amino group which binds to carbonyl between D and E to form amide, wherein the single ring is unsubstituted or substituted with substituent other than said amino, or D is substituted or unsubstituted fused ring;

E is a ring system selected from a substituted or unsubstituted single ring or a substituted or unsubstituted fused ring;

$R_1$ is hydrogen or substituted or unsubstituted C1-C6 alkyl;

$R_2$ and $R_3$ or $R_2$ and $R_2'$ join together to form a 4- to 10-membered saturated heterocyclic ring which is unsubstituted or substituted with 1-2 substituents independently represented by Ra; or $R_2$, $R_2'$ and $R_3$ are independently represented, and $R_2$ is hydrogen; or C1-C10 alkyl, C2-C10 alkenyl, C2-C10 alkynyl, C3-C10 cycloalkyl, C1-C10 alkoxy, C6-C10 aromatic hydrocarbon, a 4- to 10-membered saturated heterocyclic group, a 4- to 10-membered partially saturated heterocyclic group or a 4- to 10-membered unsaturated heterocyclic group, each of which is unsubstituted or substituted with 1-2 substituents independently represented by Ra;

$R_2'$ is hydrogen or C1-C6 alkyl which is unsubstituted or substituted with 1-2 substituents independently represented by Ra; and $R_3$ is hydrogen or C1-C6 alkyl which is unsubstituted or substituted with 1-2 substituents independently represented by Ra; Ra represents independently halogen, hydroxy, substituted or unsubstituted C1-C10 alkyl, substituted or unsubstituted C2-C6 alkenyl, substituted or unsubstituted C2-C6 alkynyl, substituted or unsubstituted C3-C10 cycloalkyl, substituted or unsubstituted C1-C10 haloalkyl, substituted or unsubstituted C1-C10 monoalkylamino, substituted or unsubstituted C1-C10 dialkylamino, substituted or unsubstituted C1-C10 alkoxy, substituted or unsubstituted C1-C10 haloalkoxy, substituted or unsubstituted C1-C10 alkylsulfonyl, substituted or unsubstituted C1-C10 acyl, substituted or unsubstituted C1-C10 alkoxycarbonyl or a substituted or unsubstituted 4- to 10-membered saturated heterocyclic group.

(70) The antitumor agent according to (69), wherein the compound is represented by Formula (viii):

(viii)

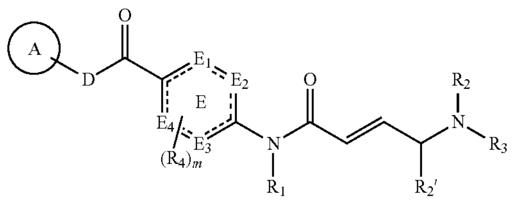

wherein A, D, $R_1$, $R_2$, $R_2$' and $R_3$ are as defined in Formula (vii) in (69), E is an unsaturated 6-membered ring which is unsubstituted or substituted with $R_4$, wherein $E_1$, $E_2$, $E_3$ and $E_4$ represent independently C, CH, $CH_2$, N or NH;

$R_4$ is halogen, cyano, hydroxy, substituted or unsubstituted C1-C10 alkyl, substituted or unsubstituted C2-C10 alkenyl, substituted or unsubstituted C2-C10 alkynyl, substituted or unsubstituted C3-C10 cycloalkyl, substituted or unsubstituted C1-C10 haloalkyl, substituted or unsubstituted C1-C10 alkoxy, substituted or unsubstituted C1-C10 acyl, substituted or unsubstituted C1-C10 alkoxycarbonyl or substituted or unsubstituted C1-C10 alkylsulfonyl;

m is an integer of 0 to 4.

(71) The antitumor agent according to (70), wherein the compound is represented by Formula (ix):

(ix)

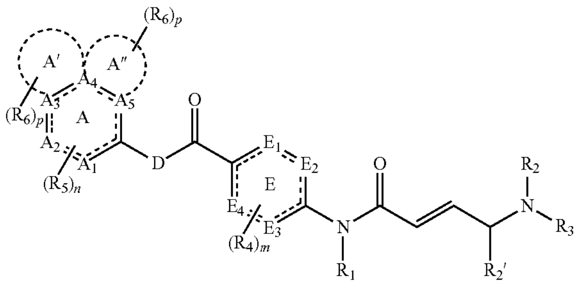

wherein D, $R_1$, $R_2$, $R_2$' and $R_3$ are as defined in Formula (vii) in (69), and E, $R_4$ and m are as defined in Formula (viii) in (70), when A is a single ring, A' and A" are absent, and the single ring is represented by ring A, which is an unsaturated 6-membered ring which is unsubstituted or substituted with $R_5$, wherein $A_1$, $A_2$, $A_3$, $A_4$ and $A_5$ represent independently C, CH, $CH_2$, N or NH;

when A is a fused ring, the fused ring is represented by ring A and ring A' or ring A and ring A", wherein ring A is an unsaturated 6-membered ring which is unsubstituted or substituted with $R_5$, wherein $A_1$, $A_2$, $A_3$, $A_4$ and $A_5$ represent independently C, CH, $CH_2$, N or NH, and ring A' or A" is a saturated or unsaturated ring which is unsubstituted or substituted with $R_6$ and forms a fused ring with ring A containing $A_3$ and $A_4$ or $A_4$ and $A_5$;

$R_5$ is halogen, cyano, amino, hydroxy, substituted or unsubstituted C1-C10 alkyl, substituted or unsubstituted C2-C6 alkenyl, substituted or unsubstituted C2-C6 alkynyl, substituted or unsubstituted C1-C6 haloalkyl, substituted or unsubstituted C1-C10 alkoxy, substituted or unsubstituted C1-C10 acyl, substituted or unsubstituted C1-C10 alkoxycarbonyl, or substituted or unsubstituted C1-C10 alkylsulfonyl; two $R_6$ may join together to form a C3-C10 hydrocarbon ring or a 4- to 10-membered saturated heterocyclic ring sharing two adjacent atoms with ring A' or ring A" when the number of $R_6$ is two or more; or $R_6$ may independently represents halogen, cyano, amino, hydroxy, substituted or unsubstituted C1-C10 alkyl, substituted or unsubstituted C2-C6 alkenyl, substituted or unsubstituted C2-C6 alkynyl, substituted or unsubstituted C1-C6 haloalkyl, substituted or unsubstituted C1-C10 alkoxy, substituted or unsubstituted C1-C10 acyl, substituted or unsubstituted C1-C10 alkoxycarbonyl or substituted or unsubstituted C1-C10 alkylsulfonyl;

n is an integer of 0 to 5; and p is 0, 1, or 2.

(72) The antitumor agent according to (71), wherein the compound is represented by Formula (x):

(x)

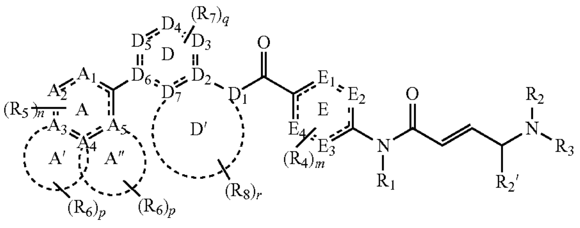

wherein $R_1$, $R_2$, $R_2$' and $R_3$ are as defined in Formula (vii) in (69), and E, $R_4$ and m are as defined in Formula (viii) in (70), and A, $R_5$, $R_6$, n, and p are as defined in Formula (ix) in (71);

when D is a single ring, D' is absent, and the single ring is represented by ring D, which is an unsaturated 6-membered ring which is unsubstituted or substituted with $R_7$, wherein $D_1$ represents N or NH, and $D_2$, $D_3$, $D_4$, $D_5$, $D_6$ and $D_7$ represent independently C, CH, $CH_2$, N or NH;

when D is a fused ring, the fused ring is represented by ring D and ring D', wherein ring D is an unsaturated 6-membered ring which is unsubstituted or substituted with $R_7$, wherein $D_1$, $D_2$, $D_3$, $D_4$, $D_5$, $D_6$ and $D_7$ represent independently C, CH, $CH_2$, N or NH, and ring D' is a saturated or unsaturated ring which is unsubstituted or substituted with $R_8$ and forms a fused ring with ring D containing $D_1$, $D_2$ and $D_7$;

$R_7$ is halogen, cyano, hydroxy, amino, carboxamide, substituted or unsubstituted C1-C10 alkyl, substituted or unsubstituted C2-C6 alkenyl, substituted or unsubstituted C2-C6 alkynyl, substituted or unsubstituted C1-C6 haloalkyl, substituted or unsubstituted C1-C10 alkoxy, substituted or unsubstituted C1-C10 acyl, substituted or unsubstituted C1-C10 alkoxycarbonyl or substituted or unsubstituted C1-C10 alkylsulfonyl;

$R_8$ is halogen or substituted or unsubstituted C1-C10 alkyl; q and r represent independently 0, 1, or 2.

(73) The antitumor agent according to (72), wherein ring A' forms a fused ring with ring A containing $A_3$ and $A_4$, and $A_1$ and $A_5$ are C, CH, or $CH_2$.

(74) The antitumor agent according to (73), wherein $R_1$ is hydrogen.

(75) The antitumor agent according to (74), wherein $R_2$ and $R_3$ are independently represented, and $R_3$ is hydrogen or C1-C3 alkyl.

(76) The antitumor agent according to (75), wherein $D_6$ in ring D is C.

(77) The antitumor agent according to (76), wherein $D_3$, $D_4$ and $D_5$ are C.

(78) The antitumor agent according to any of (72) to (77), wherein the compound is represented by Formula (xi):

(xi)

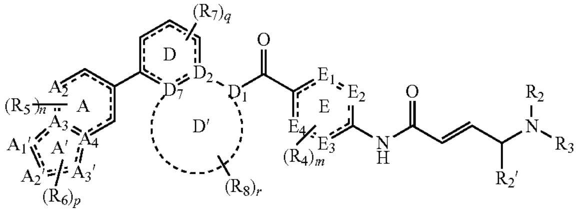

wherein $R_2$ and $R_2$' are as defined in Formula (vii) in (69); $R_2$ and $R_3$ are independently represented and $R_3$ is hydrogen or C1-C3 alkyl; E, $R_4$ and m are as defined in Formula (viii) in (70); A, $R_5$, n, and p are as defined in Formula (ix) in (71) and D, $R_7$, $R_8$, q, and r are as defined in Formula (x) in (72);

ring A' is a saturated or unsaturated 5-membered ring forming a fused ring containing $A_3$ and $A_4$ with ring A, wherein $A_1$', $A_2$', $A_3$' represent independently C, CH, $CH_2$, N, NH, O or S, two $R_6$ may join together to form a C3-C10 hydrocarbon ring or a 4- to 10-membered saturated heterocyclic ring when the number of $R_6$ is two or more; or $R_6$ may be independently halogen, cyano, hydroxy, substituted or unsubstituted C1-C10 alkyl, substituted or unsubstituted C1-C6 haloalkyl or substituted or unsubstituted C1-C10 alkoxy.

(79) The antitumor agent according to any of (71) to (78), wherein $A_2$ is C.

(80) The antitumor agent according to any of (75) to (79), wherein $R_2$ and $R_2$' join together to form a 4- to 6-membered saturated heterocyclic ring which is unsubstituted or substituted with 1-2 substituents independently represented by Ra; or $R_2$, and $R_2$' are independently represented, and $R_2$ is C1-C10 alkyl which is unsubstituted or substituted with Ra, C3-C10 cycloalkyl which is unsubstituted or substituted with Ra, or a 4- to 10-membered saturated heterocyclic group which is unsubstituted or substituted with Ra.

(81) The antitumor agent according to any of (75) to (80), wherein $R_3$ is hydrogen.

(82) The antitumor agent according to any of (70) to (81), wherein $R_4$ is halogen, cyano or C1-C6 alkyl.

(83) The antitumor agent according to any of (71) to (82), wherein $R_5$ is hydroxy, halogen, C1-C10 alkyl, C1-C6 haloalkyl or C1-C10 alkoxy.

(84) The antitumor agent according to any of (71) to (83), wherein, two $R_6$ may join together to form a C3-C10 hydrocarbon ring or a 4- to 10-membered saturated heterocyclic ring when the number of $R_6$ is two or more; or each $R_6$ may represent independently substituted or unsubstituted C1-C10 alkyl or substituted or unsubstituted C1-C10 alkoxy.

(85) The antitumor agent according to any of (78) to (84), wherein the compound is represented by Formula (xii):

(xii)

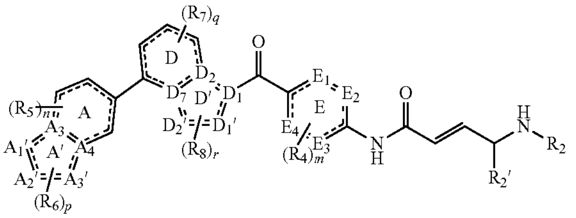

wherein $R_2$ and $R_2$' are as defined in (80), E and m are as defined in Formula (viii) in (70), A, n and p are as defined in Formula (ix) in (71) and $R_8$, q and r are as defined in Formula (x) in (72), A' is as defined in Formula (xi) in (78), $R_4$ is as defined in (82), $R_5$ is as defined in (83), $R_6$ is as defined in (84);

D is a fused ring represented by ring D and ring D', and ring D' is a saturated or unsaturated 5-membered ring forming a fused ring containing $D_1$, $D_2$ and $D_7$ with ring D, and $D_1$' and $D_2$' represent independently C, CH, $CH_2$, N, NH or S, $R_7$ is halogen, cyano, hydroxy, amino, carboxamide, substituted or unsubstituted C1-C10 alkyl, substituted or unsubstituted C1-C10 haloalkyl or substituted or unsubstituted C1-C10 alkoxy.

(86) The antitumor agent according to (85), wherein $R_7$ is halogen or substituted or unsubstituted C1-C10 alkyl.

(87) A compound represented by Formula (vii):

(vii)

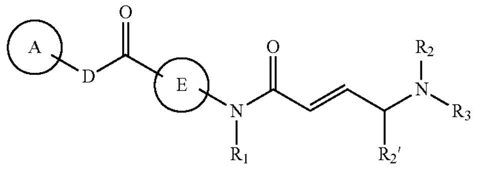

or a pharmaceutically acceptable salt thereof, wherein,

A is a ring system selected from a substituted or unsubstituted single ring or a substituted or unsubstituted fused ring;

D is a single ring having at least one amino group which binds to carbonyl between D and E to form amide, wherein the single ring is unsubstituted or substituted with substituent other than said amino, or D is substituted or unsubstituted fused ring;

E is a ring system selected from a substituted or unsubstituted single ring or a substituted or unsubstituted fused ring;

$R_1$ is hydrogen or substituted or unsubstituted C1-C6 alkyl;

$R_2$ and $R_3$ or $R_2$ and $R_2$'-join together to form a 4- to 10-membered saturated heterocyclic ring which is unsubstituted or substituted with 1-2 substituents independently represented by Ra; or $R_2$, $R_2$' and $R_3$ are independently represented, and $R_2$ is hydrogen; or C1-C10 alkyl, C2-C10 alkenyl, C2-C10 alkynyl, C3-C10 cycloalkyl, C1-C10 alkoxy, C6-C10 aromatic hydrocarbon, a 4- to 10-membered saturated heterocyclic group, a 4- to 10-membered partially saturated heterocyclic group or a 4- to 10-membered unsaturated heterocyclic group, each of which is unsubstituted or substituted with 1-2 substituents independently represented by Ra;

$R_2$' is hydrogen or C1-C6 alkyl which is unsubstituted or substituted with 1-2 substituents independently represented by Ra; and $R_3$ is hydrogen or C1-C6 alkyl which is unsubstituted or substituted with 1-2 substituents independently represented by Ra;

Ra represents independently halogen, hydroxy, substituted or unsubstituted C1-C10 alkyl, substituted or unsubstituted C2-C6 alkenyl, substituted or unsubstituted C2-C6 alkynyl, substituted or unsubstituted C3-C10 cycloalkyl, substituted or unsubstituted C1-C10 haloalkyl, substituted or unsubstituted C1-C10 monoalkylamino, substituted or unsubstituted C1-C10 dialkylamino, substituted or unsubstituted C1-C10 alkoxy, substituted or unsubstituted C1-C10 haloalkoxy, substituted or unsubstituted C1-C10 alkylsulfonyl, substituted or unsubstituted C1-C10 acyl, substituted or unsubstituted C1-C10 alkoxycarbonyl or a substituted or unsubstituted 4- to 10-membered saturated heterocyclic group.

(88) The compound according to (87), wherein the compound is represented by Formula (viii):

(viii)

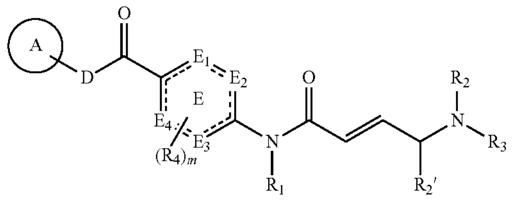

wherein A, D, $R_1$, $R_2$, $R_2$' and $R_3$ are as defined in Formula (vii) in (87), E is an unsaturated 6-membered ring which is unsubstituted or substituted with $R_4$, wherein $E_1$, $E_2$, $E_3$ and $E_4$ represent independently C, CH, $CH_2$, N or NH;

$R_4$ is halogen, cyano, hydroxy, substituted or unsubstituted C1-C10 alkyl, substituted or unsubstituted C2-C10 alkenyl, substituted or unsubstituted C2-C10 alkynyl, substituted or unsubstituted C3-C10 cycloalkyl, substituted or unsubstituted C1-C10 haloalkyl, substituted or unsubstituted C1-C10 alkoxy, substituted or unsubstituted C1-C10 acyl, substituted or unsubstituted C1-C10 alkoxycarbonyl or substituted or unsubstituted C1-C10 alkylsulfonyl; m is an integer of 0 to 4; or a pharmaceutically acceptable salt thereof.

(89) The compound according to (88), wherein the compound is represented by Formula (ix):

(ix)

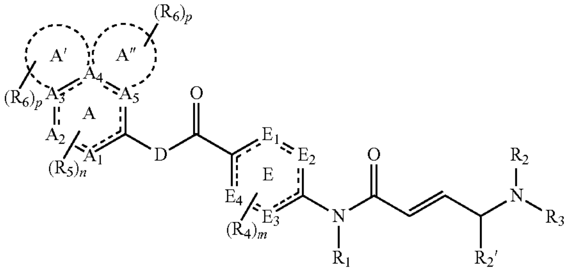

wherein D, $R_1$, $R_2$, $R_2$' and $R_3$ are as defined in Formula (vii) in (87), and E, $R_4$ and m are as defined in Formula (viii) in (88), when A is a single ring, A' and A" are absent, and the single ring is represented by ring A, which is an unsaturated 6-membered ring which is unsubstituted or substituted with $R_5$, wherein $A_1$, $A_2$, $A_3$, $A_4$ and $A_5$ represent independently C, CH, $CH_2$, N or NH;

when A is a fused ring, the fused ring is represented by ring A and ring A' or ring A and ring A", wherein ring A is an unsaturated 6-membered ring which is unsubstituted or substituted with $R_5$, wherein $A_1$, $A_2$, $A_3$, $A_4$ and $A_5$ represent independently C, CH, $CH_2$, N or NH, and ring A' or A" is a saturated or unsaturated ring which is unsubstituted or substituted with $R_6$ and forms a fused ring with ring A containing $A_3$ and $A_4$ or $A_4$ and $A_5$;

$R_5$ is halogen, cyano, amino, hydroxy, substituted or unsubstituted C1-C10 alkyl, substituted or unsubstituted C2-C6 alkenyl, substituted or unsubstituted C2-C6 alkynyl, substituted or unsubstituted C1-C6 haloalkyl, substituted or unsubstituted C1-C10 alkoxy, substituted or unsubstituted C1-C10 acyl, substituted or unsubstituted C1-C10 alkoxycarbonyl, or substituted or unsubstituted C1-C10 alkylsulfonyl; two $R_6$ may join together to form a C3-C10 hydrocarbon ring or a 4- to 10-membered saturated heterocyclic ring sharing two adjacent atoms with ring A' or ring A" when the number of $R_6$ is two or more; or $R_6$ may independently represents halogen, cyano, amino, hydroxy, substituted or unsubstituted C1-C10 alkyl, substituted or unsubstituted C2-C6 alkenyl, substituted or unsubstituted C2-C6 alkynyl, substituted or unsubstituted C1-C6 haloalkyl, substituted or unsubstituted C1-C10 alkoxy, substituted or unsubstituted C1-C10 acyl, substituted or unsubstituted C1-C10 alkoxycarbonyl or substituted or unsubstituted C1-C10 alkylsulfonyl;

n is an integer of 0 to 5; and p is 0, 1, or 2; or a pharmaceutically acceptable salt thereof.

(90) The compound according to (89), wherein the compound is represented by Formula (x):

(x)

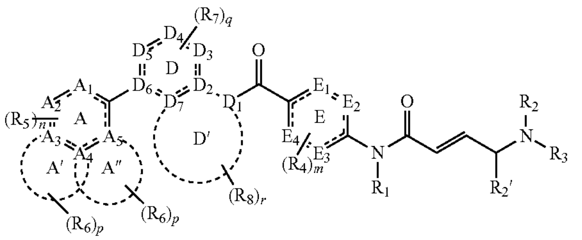

wherein $R_1$, $R_2$, $R_2$' and $R_3$ are as defined in Formula (vii) in (87), and E, $R_4$ and m are as defined in Formula (viii) in (88), and A, $R_5$, $R_6$, n, and p are as defined in Formula (ix) in (89);

when D is a single ring, D' is absent, and the single ring is represented by ring D, which is an unsaturated 6-membered ring which is unsubstituted or substituted with $R_7$, wherein $D_1$ represents N or NH, and $D_2$, $D_3$, $D_4$, $D_5$, $D_6$ and $D_7$ represent independently C, CH, $CH_2$, N or NH;

when D is a fused ring, the fused ring is represented by ring D and ring D', wherein ring D is an unsaturated 6-membered ring which is unsubstituted or substituted with $R_7$, wherein $D_1$, $D_2$, $D_3$, $D_4$, $D_5$, $D_6$ and $D_7$ represent independently C, CH, $CH_2$, N or NH, and ring D' is a saturated or unsaturated ring which is unsubstituted or substituted with $R_8$ and forms a fused ring with ring D containing $D_1$, $D_2$ and $D_7$;

$R_7$ is halogen, cyano, hydroxy, amino, carboxamide, substituted or unsubstituted C1-C10 alkyl, substituted or unsubstituted C2-C6 alkenyl, substituted or unsubstituted C2-C6 alkynyl, substituted or unsubstituted C1-C6 haloalkyl, substituted or unsubstituted C1-C10 alkoxy, substituted or unsubstituted C1-C10 acyl, substituted or unsubstituted C1-C10 alkoxycarbonyl or substituted or unsubstituted C1-C10 alkylsulfonyl;

$R_8$ is halogen or substituted or unsubstituted C1-C10 alkyl; q and r represent independently 0, 1, or 2; or a pharmaceutically acceptable salt thereof.

(91) The compound according to (90), wherein ring A' forms a fused ring with ring A containing $A_3$ and $A_4$, and $A_1$ and $A_5$ are C, CH, or $CH_2$; or a pharmaceutically acceptable salt thereof.

(92) The compound according to (91), wherein $R_1$ is hydrogen; or a pharmaceutically acceptable salt thereof.

(93) The compound according to (92), wherein $R_2$ and $R_3$ are independently represented, and $R_3$ is hydrogen or C1-C3 alkyl; or a pharmaceutically acceptable salt thereof.

(94) The compound according to (93), wherein $D_6$ in ring D is C; or a pharmaceutically acceptable salt thereof.

(95) The compound according to (94), wherein $D_3$, $D_4$ and $D_5$ are C; or a pharmaceutically acceptable salt thereof.

(96) The compound according to any of (90) to (95), wherein the compound is represented by Formula (xi):

(xi)

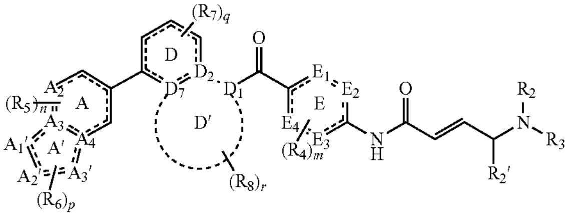

wherein $R_2$ and $R_2$' are as defined in Formula (vii) in (87); $R_2$ and $R_3$ are independently represented and $R_3$ is hydrogen or C1-C3 alkyl; E, $R_4$ and m are as defined in Formula (viii) in (88); A, $R_5$, n, and p are as defined in Formula (ix) in (89) and D, $R_7$, $R_8$, q, and r are as defined in Formula (x) in (90);

ring A' is a saturated or unsaturated 5-membered ring forming a fused ring containing $A_3$ and $A_4$ with ring A, wherein $A_1$', $A_2$', $A_3$' represent independently C, CH, $CH_2$, N, NH, O or S, two $R_6$ may join together to form a C3-C10 hydrocarbon ring or a 4- to 10-membered saturated heterocyclic ring when the number of $R_6$ is two or more; or $R_6$ may be independently halogen, cyano, hydroxy, substituted or unsubstituted C1-C10 alkyl, substituted or unsubstituted C1-C6 haloalkyl or substituted or unsubstituted C1-C10 alkoxy; or a pharmaceutically acceptable salt thereof.

(97) The compound according to any of (89) to (96), wherein $A_2$ is C; or a pharmaceutically acceptable salt thereof.

(98) The compound according to any of (93) to (97), wherein $R_2$ and $R_2$' join together to form a 4- to 6-membered saturated heterocyclic ring which is unsubstituted or substituted with 1-2 substituents independently represented by Ra; or $R_2$, and $R_2$' are independently represented, and $R_2$ is C1-C10 alkyl which is unsubstituted or substituted with Ra, C3-C10 cycloalkyl which is unsubstituted or substituted with Ra, a 4- to 10-membered saturated heterocyclic group which is unsubstituted or substituted with Ra; or a pharmaceutically acceptable salt thereof.

(99) The compound according to any of (93) to (98), wherein $R_3$ is hydrogen; or a pharmaceutically acceptable salt thereof.

(100) The compound according to any of (88) to (99), wherein $R_4$ is halogen, cyano or C1-C6 alkyl; or a pharmaceutically acceptable salt thereof.

(101) The compound according to any of (89) to (100), wherein $R_5$ is hydroxy, halogen, C1-C10 alkyl, C1-C6 haloalkyl or C1-C10 alkoxy; or a pharmaceutically acceptable salt thereof.

(102) The compound according to any of (89) to (101), wherein, two $R_6$ may join together to form a C3-C10 hydrocarbon ring or a 4- to 10-membered saturated heterocyclic ring when the number of $R_6$ is two or more; or each $R_6$ may represent independently substituted or unsubstituted C1-C10 alkyl or substituted or unsubstituted C1-C10 alkoxy; or a pharmaceutically acceptable salt thereof.

(103) The compound according to any of (96) to (102), wherein the compound is represented by Formula (xii) or a salt thereof:

(xii)

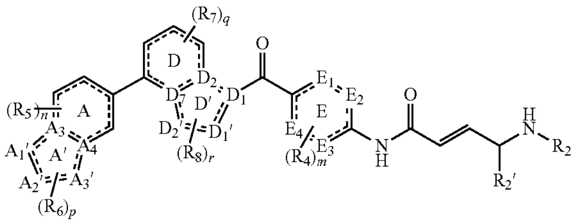

wherein $R_2$ and $R_2$' are as defined in (98), E and m are as defined in Formula (viii) in (88), A, n, and p are as defined in Formula (ix) in (89) and $R_8$, q and r are as defined in Formula (x) in (90), A' is as defined in Formula (xi) in (96), $R_4$ is as defined in (100), $R_5$ is as defined in (101), $R_6$ is as defined in (102);

D is a fused ring represented by ring D and ring D', and ring D' is a saturated or an unsaturated 5-membered ring forming a fused ring containing $D_1$, $D_2$ and $D_7$ with ring D, and $D_1$' and $D_2$' represents independently C, CH, $CH_2$, N, NH or S, $R_7$ is halogen, cyano, hydroxy, amino, carboxamide, substituted or unsubstituted C1-C10 alkyl, substituted or unsubstituted C1-C10 haloalkyl or substituted or unsubstituted C1-C10 alkoxy; or a pharmaceutically acceptable salt thereof.

(104) The compound according to (103), wherein $R_7$ is halogen or substituted or unsubstituted C1-C10 alkyl; or a pharmaceutically acceptable salt thereof.

(105) A medicament comprising the compound or pharmaceutically acceptable salt thereof of any of (87) to (104).

(106) A pharmaceutical composition comprising the compound or pharmaceutically acceptable salt thereof of any of (87) to (104).

(107) An antitumor agent, comprising the compound or pharmaceutically acceptable salt thereof of any of (87) to (104) as an active ingredient.

(108) An antitumor agent for oral administration, comprising the compound or pharmaceutically acceptable salt thereof of any of (87) to (104) as an active ingredient.

(109) Use of the compound or a pharmaceutically acceptable salt thereof according to any of (87) to (104) for manufacturing a pharmaceutical composition.

(110) Use of the compound or a pharmaceutically acceptable salt thereof according to any of (87) to (104) for manufacturing an antitumor agent.

(111) Use of the compound or a pharmaceutically acceptable salt thereof according to any of (87) to (104) for manufacturing an antitumor agent for oral administration.

(112) The compound or pharmaceutically acceptable salt thereof of any of (87) to (104) for use as medicament.

(113) The compound or pharmaceutically acceptable salt thereof of any of (87) to (104) for use in the treatment of tumor.

(114) The compound or pharmaceutically acceptable salt thereof of any of (87) to (104) for use in the treatment of tumor by oral administration.

(115) A method for treating tumor, comprising administrating a therapeutically effective amount of the compound or pharmaceutically acceptable salt thereof of any of (87) to (104) to a subject in need thereof.

(116) An antitumor agent comprising a compound or a pharmaceutically acceptable salt thereof of any one of (87) to (104), and one or more other antitumor agents as an active ingredient.

(117) An antitumor agent comprising a compound or a pharmaceutically acceptable salt thereof of any one of (87) to (104) as an active ingredient, which is administered in combination with one or more other antitumor agents.

(118) Use of the compound according to any one of (87) to (104) or a salt thereof and one or more other antitumor agents for the manufacture of an antitumor agent.

(119) Use of the compound according to any one of (87) to (104) or a salt thereof for the manufacture of an antitumor agent, which is administered in combination with one or more other antitumor agents.

(120) The combination of a compound according to any one of (87) to (104) or a salt thereof and one or more other antitumor agents for use in the treatment of tumors.

(121) The compound or pharmaceutically acceptable salt thereof of any of (87) to (104) for use in the treatment of tumor, which is administered in combination with one or more other antitumor agents.

(122) A method for treating tumor, comprising administrating a therapeutically effective amount of the compound or pharmaceutically acceptable salt thereof of any of (87) to (104), and one or more other antitumor agents to a subject in need thereof.

(123) A method for treating tumor, comprising administrating a therapeutically effective amount of the compound or pharmaceutically acceptable salt thereof of any of (87) to (104), which is administered in combination with one or more other antitumor agents to a subject in need thereof.

A compound or a salt thereof according to an embodiment of the present invention binds to the mutant cysteine (G12C) of active form of KRAS. A compound or a salt thereof according to a preferred embodiment of the present invention impairs the KRAS function in KRAS G12C mutation-positive cancer cells, thereby showing antitumor action; and can be used as an anti-cancer agent.

BRIEF DESCRIPTION OF THE FIGURES

FIG. 1 was generated by the ligand interaction tool within the Molecular Operating Environment (MOE, version 2019.0101) (Molecular Operating Environment; C.C.G., I., 1255 University St., Suite 1600, Montreal, Quebec, Canada, H3B 3X3.).

FIG. 2 was created with the molecular visualization system, PyMOL (version 2.2.0) (Schrödinger).

DETAILED DESCRIPTION

Figure 1:
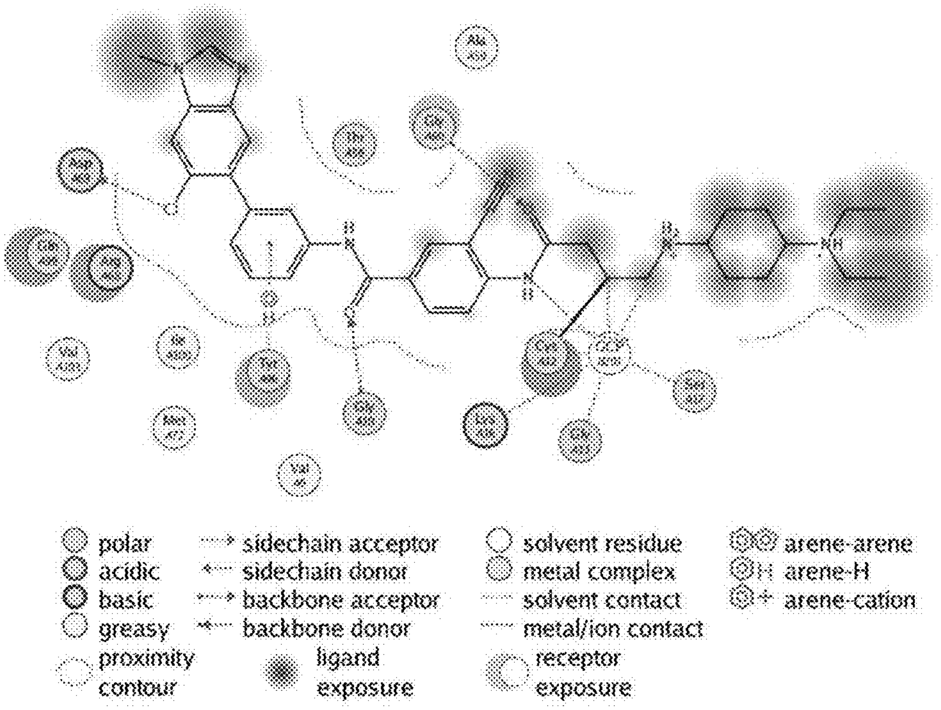
FIG. 1 illustrates 2D interaction diagram for the binding site of the compound of Example 19. Residues are annotated with their 3-letter amino acid code.

The compound represented by Formula (i) above is a novel compound, and is nowhere taught or disclosed in any of the literature cited above.

As used herein, unless otherwise specified, examples of the "substituent" include hydrogen, halogen, cyano, nitro, amino, hydroxy, alkyl, alkenyl, alkynyl, haloalkyl, hydroxyalkyl, cycloalkyl, cycloalkenyl, unsaturated hydrocarbon, alkoxy, haloalkoxy, cycloalkoxy, cycloalkyl-alkoxy, aralkyl, aralkyloxy, alkylthio, cycloalkyl-alkylthio, alkoxyalkyl, mono- or dialkylamino, cycloalkyl-alkylamino, aromatic hydrocarbon, acyl, alkylcarbonyl, acyloxy, arylcarbonyl, oxo, carboxy, alkoxycarbonyl, alkylcarbonyloxy, arylcarbonyloxy, aralkyloxycarbonyl, carbamoyl, sulfonyl, saturated, partially saturated or unsaturated heterocyclic group, aromatic hydrocarbon, and the like. Unless otherwise specified, when a substituent listed above is present, the number of them is typically one, two, or three, preferably one or two, and most preferably one.

As used herein, specific examples of the "halogen" include chlorine, bromine, fluorine, and iodine, with chlorine, fluorine, and bromine being preferable, and chlorine and fluorine being more preferable.

As used herein, the "alkyl" refers to a linear or branched saturated hydrocarbon group. Examples include C1-C10 alkyl, such as methyl, ethyl, n-propyl, isopropyl, n-butyl, isobutyl, sec-butyl, tert-butyl, n-pentyl, isopentyl, and hexyl. The "alkyl" is preferably methyl, ethyl, n-propyl, isopropyl, n-butyl, isobutyl, or tert-butyl.

As used herein, the "alkenyl" refers to a linear or branched unsaturated hydrocarbon group containing at least one double bound (e.g., one to two double bonds, and preferably one double bond). Examples include C2-C6 alkenyl, such as vinyl, allyl, 1-propenyl, 2-methyl-2-propenyl, isopropenyl, 1-, 2-, or 3-butenyl, 2-, 3- or 4-pentenyl, 2-methyl-2-butenyl, 3-methyl-2-butenyl, and 5-hexenyl, with vinyl, allyl, 1-propenyl, and 2-methyl-2-propenyl being preferable.

As used herein, the "alkynyl" refers to linear or branched unsaturated hydrocarbon containing at least one triple bond (e.g., one or two triple bonds, and preferably one triple bond). Examples include C2-C6 alkynyl groups, such as ethynyl, 1- or 2-propynyl, 1-, 2-, or 3-butynyl, and 1-methyl-2-propynyl, with ethynyl and 2-propynyl being preferable.

As used herein, the "haloalkyl" refers to alkyl mentioned above having at least one halogen atom (preferably having 1 to 10, and more preferably 1 to 3 halogen atoms). Examples include C1-C10 haloalkyl, such as fluoromethyl, difluoromethyl, trifluoromethyl, trichloromethyl, 1-fluoroethyl, 1,1-difluoroethyl, 1,1,1-trifluoroethyl, monofluoro-n-propyl, 1,1,1-trifluoro-n-propyl, perfluoro-n-propyl, and perfluoroisopropyl, with trifluoromethyl, difluoromethyl, 1-fluoroethyl, 1,1-difluoroethyl, and 1,1,1-trifluoroethyl being preferable.

As used herein, the "hydroxyalkyl" refers to alkyl mentioned above having at least one hydroxy group (preferably having 1 to 10, and more preferably 1 to 2 hydroxy groups). Examples include C1-C6 hydroxyalkyl, such as hydroxymethyl, hydroxyethyl, 1-hydroxypropyl, 2-hydroxybutyl, and 1,2-dihydroxyisopropyl, with 2-hydroxybutyl and 2-dihydroxyisopropyl being preferable.

As used herein, the "cycloalkyl" refers to monocyclic or polycyclic saturated hydrocarbon, including bicyclic, tricyclic, bridged and spirocyclic hydrocarbon. Examples include C3-C10 cycloalkyl, such as cyclopropyl, cyclobutyl, cyclopentyl, cyclohexyl, cycloheptyl, cyclodecyl, [2.2.0]bicyclohexyl, [2.2.1]bicycloheptanyl, [3.1.1]bicycloheptanyl and [3.2.1] bicyclooctanyl, with cyclopropyl, cyclobutyl, cyclopentyl, cyclohexyl, [2.2.0]bicyclohexyl, [2.2.1]bicycloheptanyl, [3.1.1]bicycloheptanyl and [3.2.1]bicyclooctanyl being preferable, and cyclobutyl and cyclopentyl being particularly preferable.

As used herein, the "cycloalkenyl" refers to monocyclic or polycyclic unsaturated hydrocarbon containing at least one carbon-carbon double bond (e.g., one to two carbon-carbon double bonds, and preferably one carbon-carbon double bond). Examples include C4-C10 cycloalkenyl, such as cyclopropenyl, cyclobutenyl, cyclopentenyl, cyclohexenyl, cycloheptenyl, and cyclodecenyl, with cyclopropenyl, cyclobutenyl, and cyclopentenyl being preferable, and cyclobutenyl and cyclopentenyl being particularly preferable.

As used herein, the "unsaturated hydrocarbon" refers to linear or branched unsaturated hydrocarbon containing at least one carbon-carbon double bond or triple bond. Examples include C2-C10 unsaturated hydrocarbon, such as vinyl, allyl, methylvinyl, 1-propenyl, butenyl, pentenyl, hexenyl, ethynyl, and 2-propynyl, with C2-C4 linear or branched hydrocarbon containing at least one carbon-carbon double bond or triple bond being preferable, and vinyl, allyl, and 1-propenyl being more preferable.

As used herein, the "alkoxy" refers to oxy having alkyl mentioned above. Examples include C1-C10 alkoxy, such as methoxy, ethoxy, n-propoxy, isopropoxy, n-butoxy, isobutoxy, sec-butoxy, tert-butoxy, pentyloxy, isopentyloxy, and hexyloxy, with methoxy, ethoxy and n-propoxy being preferable, and methoxy and ethoxy being more preferable.

As used herein, the "haloalkoxy" refers to alkoxy mentioned above having at least one halogen atom (preferably having 1 to 13, and more preferably 1 to 3 halogen atoms). Examples include C1-C10 haloalkoxy, such as fluoromethoxy, difluoromethoxy, trifluoromethoxy, trichloromethoxy, fluoroethoxy, 1,1,1-trifluoroethoxy, monofluoro-n-propoxy, perfluoro-n-propoxy, and perfluoro-isopropoxy.

As used herein, the "cycloalkoxy" refers to oxy having cycloalkyl mentioned above. Examples include C3-C10 cycloalkoxy, such as cyclopropoxy, cyclobutoxy, cyclopentyloxy, cyclohexyloxy, and cycloheptyloxy, with cyclobutoxy, cyclopentyloxy, and cyclohexyloxy being preferable.

As used herein, the "cycloalkyl-alkoxy" refers to alkoxy mentioned above having at least one cycloalkyl group mentioned above. Examples include C3-C10 cycloalkyl-C1-C10 alkoxy, such as cyclopropylmethoxy, cyclobutylmethoxy, cyclopentylmethoxy, cyclohexylmethoxy, and cycloheptylmethoxy, with cyclohexylmethoxy being preferable.

As used herein, the "aralkyl" refers to alkyl mentioned above substituted with aromatic hydrocarbon mentioned above. Examples include C7-C16 aralkyl, such as benzyl, phenylethyl, phenylpropyl, naphthylmethyl, and naphthylethyl, with benzyl being preferable.

As used herein, the "aralkyloxy" refers to oxy having aralkyl mentioned above. Examples include C7-C20 aralkyloxy, such as benzyloxy, phenethyloxy, naphthylmethyloxy, and fluorenylmethyloxy.

As used herein, the "alkylthio" refers to thioxy having alkyl mentioned above. Examples include C1-C10 alkylthio, such as methylthio, ethylthio, n-propylthio, isopropylthio, n-butylthio, isobutylthio, tert-butylthio, n-pentylthio, isopentylthio, and hexylthio.

As used herein, the "cycloalkyl-alkylthio" refers to alkylthio mentioned above having at least one cycloalkyl group mentioned above. Examples include C3-C10 cycloalkyl-C1-

C10 alkylthio, such as cyclopropylmethylthio, cyclobutylmethylthio, cyclopentylmethylthio, cyclohexylmethylthio, and cycloheptylmethylthio.

As used herein, the "alkoxyalkyl" refers to alkyl mentioned above having at least one alkoxy group mentioned above. Examples include C1-C10 alkoxy-C1-C10 alkyl, such as methoxymethyl, ethoxyethyl, methoxyethyl, and methoxypropyl, with methothymethyl being preferable.

As used herein, the "alkylamino" refers to amino having one or two alkyl groups mentioned above. Specific examples include C1-C10 alkylamino, such as methylamino, ethylamino, dimethylamino, diethylamino, and ethylmethylamino, with methylamino, dimethylamino, and diethylamino being preferable.

As used herein, the "monoalkylamino" refers to amino having one alkyl group mentioned above. Examples include C1-C10 monoalkylamino, such as methylamino, ethylamino, n-propylamino, isopropylamino, n-butylamino, isobutylamino, tert-butylamino, n-pentylamino, isopentylamino, and hexylamino, with methylamino and ethylamino being preferable.

As used herein, the "dialkylamino" refers to amino having two alkyl groups mentioned above. Examples include C1-C10 dialkylamino, which has two alkyls each having 1 to 10 carbon atoms, such as dimethylamino, diethylamino, di(n-propyl)amino, diisopropylamino, di(n-butyl)amino, diisobutylamino, di(tert-butyl)amino, di(n-pentyl)amino, diisopentylamino, dihexylamino, methylethylamino, and methylisopropylamino, with dimethylamino and diethylamino being preferable.

As used herein, the "cycloalkyl-alkylamino" refers to alkylamino mentioned above having cycloalkyl mentioned above in which cycloalkyl is attached to the alkyl moiety of alkylamino. Examples include C3-C10 cycloalkyl-C1-C10 alkylamino, such as cyclopropylmethylamino, cyclobutylmethylamino, cyclopentylmethylamino, cyclohexylmethylamino, cycloheptylmethylamino, and cyclohexyldimethylamino, with cyclohexyldimethylamino being preferable.

As used herein, the "aromatic hydrocarbon" refers to monocyclic or polycyclic aromatic hydrocarbon as being an unsaturated bond-containing ring substituent containing carbon and hydrogen, the monocyclic or polycyclic aromatic hydrocarbon containing 4e+2 number of electrons (e is an integer of 1 or more) in the cyclic $\pi$ electron system. Examples include phenyl, naphthyl, tetrahydronaphthyl, anthracenyl, and the like, and phenyl being preferable.

As used herein, the "acyl" refers to alkylcarbonyl or arylcarbonyl.

As used herein, the "alkylcarbonyl" refers to carbonyl having alkyl mentioned above. Examples include C1-C10 alkylcarbonyl, such as methylcarbonyl, ethylcarbonyl, n-propylcarbonyl, isopropylcarbonyl, n-butylcarbonyl, isobutylcarbonyl, tert-butylcarbonyl, n-pentylcarbonyl, isopentylcarbonyl, and hexylcarbonyl, with methylcarbonyl being preferable. Further, in the present invention, C1-C10 alkylcarbonyl refers to (C1-C10 alkyl)carbonyl.

As used herein, the "acyloxy" refers to acyl having carbonyloxy mentioned above. Examples include C1-C10 acyloxy, such as alkylcarbonyloxy or arylcarbonyloxy.

As used herein, the "arylcarbonyl" refers to carbonyl having aromatic hydrocarbon mentioned above. Examples include (C6-C20 aryl)carbonyl, such as phenylcarbonyl, naphthylcarbonyl, fluorenylcarbonyl, anthrylcarbonyl, biphenylylcarbonyl, tetrahydronaphthylcarbonyl, chromanylcarbonyl, 2,3-dihydro-1,4-dioxanaphthalenylcarbonyl, indanylcarbonyl, and phenanthrylcarbonyl.

As used herein, the "alkoxycarbonyl" refers to carbonyl having alkoxy mentioned above. Examples include (C1-C10 alkoxy)carbonyl, such as methoxycarbonyl, ethoxycarbonyl, propoxycarbonyl, isopropoxycarbonyl, butoxycarbonyl, isobutoxycarbonyl, tert-butoxycarbonyl, pentyloxycarbonyl, isopentyloxycarbonyl, and hexyloxycarbonyl, with tert-butoxycarbonyl being preferable.

As used herein, the "alkylcarbonyloxy" refers to oxy having alkylcarbonyl mentioned above. Examples include (C1-C10 alkyl)carbonyloxy, such as methylcarbonyloxy, ethylcarbonyloxy, n-propylcarbonyloxy, isopropylcarbonyloxy, n-butylcarbonyloxy, isobutylcarbonyloxy, tert-butylcarbonyloxy, n-pentylcarbonyloxy, isopentylcarbonyloxy, and hexylcarbonyloxy, with tert-butylcarbonyloxy being preferable.

As used herein, the "arylcarbonyloxy" refers to oxy having arylcarbonyl mentioned above. Examples include (C6-C13 aryl)carbonyloxy, such as phenylcarbonyloxy, naphthylcarbonyloxy, fluorenylcarbonyloxy, anthrylcarbonyloxy, biphenylylcarbonyloxy, tetrahydronaphthylcarbonyloxy, chromanylcarbonyloxy, 2,3-dihydro-1,4-dioxanaphthalenylcarbonyloxy, indanylcarbonyloxy, and phenanthrylcarbonyloxy.

As used herein, the "aralkyloxycarbonyl" refers to carbonyl having aralkyloxy mentioned above. Examples include (C6-C20 aralkyl)oxycarbonyl, such as benzyloxycarbonyl, phenethyloxycarbonyl, naphthylmethyloxycarbonyl, and fluorenylmethyloxycarbonyl.

As used herein, the "saturated heterocyclic group" refers to a monocyclic or polycyclic saturated heterocyclic group containing at least one heteroatom (preferably having 1 to 5, and more preferably 1 to 3 heteroatoms) selected from nitrogen, oxygen, and sulfur. A monocyclic or polycyclic saturated heterocyclic group includes monocyclic, bicyclic, tricyclic, bridged and spirocyclic saturated heterocyclic group. Examples include aziridinyl, azetidinyl, imidazolidinyl, morpholino, pyrrolidinyl, piperidinyl, piperazinyl, tetrahydrofuranyl, tetrahydropyranyl, tetrahydrothiophenyl, thiazolidinyl, oxazolidinyl, and the like, with azetidinyl, pyrrolidinyl, and piperidinyl being preferable, and azetidinyl and pyrrolidinyl being more preferable.

As used herein, the "partially saturated heterocyclic group" refers to a monocyclic or polycyclic partially saturated heterocyclic group containing at least one heteroatom (preferably having 1 to 5, and more preferably 1 to 3 heteroatoms) selected from nitrogen, oxygen, and sulfur. A monocyclic or polycyclic partially saturated heterocyclic group includes monocyclic, bicyclic, tricyclic, bridged and spirocyclic partially saturated heterocyclic group. Examples include indoline, 1,3-dihydroisobenzofuran, 2,3-dihydro-1H-benzo[d]imidazole, 1,3-benzodioxole and the like, with indoline, 2,3-dihydro-1H-benzo[d]imidazole and 1,3-benzodioxole being preferable, and indoline, 1,3-benzodioxole being more preferable.

As used herein, the "unsaturated heterocyclic group" refers to a monocyclic or polycyclic, completely unsaturated heterocyclic group containing at least one heteroatom (preferably containing 1 to 5, and more preferably 1 to 3 heteroatoms) selected from nitrogen, oxygen, and sulfur. A monocyclic or polycyclic unsaturated heterocyclic group includes monocyclic, bicyclic, tricyclic, bridged and spirocyclic unsaturated heterocyclic group. Examples include imidazolyl, thienyl, pyrrolyl, oxazolyl, isoxazolyl, thiazolyl, isothiazolyl, thiadiazolyl, oxadiazolyl, pyrazolyl, triazolyl, tetrazolyl, pyridyl, pyrazyl, pyrimidinyl, pyridazinyl, indolyl, isoindolyl, indazolyl, triazolopyridyl, benzoimidazolyl, benzoxazolyl, benzothiazolyl, benzothienyl, furanyl, benzofuranyl, purinyl, quinolyl, isoquinolyl, quinazolinyl, quinoxalyl, methylenedioxyphenyl, ethylenedioxyphenyl, dihydrobenzofuranyl, imidazopyridinyl, indazolyl, and the like, with imidazolyl, pyrazolyl, thiazolyl, isoxazolyl, pyridyl, benzoxazolyl, benzothiazolyl, imidazopyridinyl, indazolyl, indolyl, indolyzinyl, and furanyl being preferable, and imidazolyl, pyrazolyl, pyridyl, benzoxazolyl, benzothiazolyl, imidazopyridinyl, indazolyl, indolyl, and indolyzinyl being more preferable, and benzoxazolyl, benzothiazolyl, imidazopyridinyl, indolyl, indazolyl, indolyzinyl being most preferable.

As used herein, the term "CA-CB" used in the description of a group indicates that the group has A to B number of carbon atoms. For example, "C1-C6 alkyl" refers to alkyl having 1 to 6 carbon atoms, and "C6-C14 aromatic hydrocarbon oxy" refers to oxy to which C6-C14 aromatic hydrocarbon is bonded. Further, the term "A- to B-membered" indicates that the number of atoms (number of ring members) that constitute a ring is A to B. More specifically, "4- to 10-membered saturated heterocyclic group" refers to a saturated heterocyclic group containing 4 to 10 ring members.

As used herein, the term C means carbon, N means nitrogen, S means sulfur, and O means oxygen.

As used herein, the term "a linker" in the formula A-L1-L2-G-J refers to a divalent linker. Examples of the linker includes —O—, —S—, —NH—, —$NR_1$—, —C(=O)—, —NHC(=O)—, —$NR_1$C(=O)—, —C(=O)NH—, —C(=O)$NR_1$—, substituted or unsubstituted C1-C6 alkylene (preferably —$CH_2$—, —$CH(CH_3)$—, —$C(CH_3)_2$—), substituted or unsubstituted C2-C6 alkenylene, substituted or unsubstituted C2-C6 alkynylene, a substituted or unsubstituted single ring or a substituted or unsubstituted fused ring and combinations thereof, preferably a linker is selected from a combination of a substituted or unsubstituted single ring or a substituted or unsubstituted fused ring with —C(=O)—; and a combination of a substituted or unsubstituted single ring or a substituted or unsubstituted fused ring with —$NR_1$—.

As used herein, the term "single ring" refers to a substituted or unsubstituted ring having a single cyclic structure, and may refer to a substituted or unsubstituted monocyclic ring. In one embodiment, examples of a single ring include substituted or unsubstituted C3-C10 cycloalkyl, substituted or unsubstituted C6-C10 aromatic hydrocarbon, a substituted or unsubstituted 4- to 10-membered saturated heterocyclic group, a substituted or unsubstituted 4- to 10-membered partially saturated heterocyclic group or a substituted or unsubstituted 4- to 10-membered unsaturated heterocyclic group.

As used herein, the term "fused ring" refers to a substituted or unsubstituted group formed with two or more rings, in which two or more rings share two or more atoms. In one embodiment, examples of a fused ring include a fused ring formed by two or more rings selected from a substituted or unsubstituted C4-C10 hydrocarbon ring, a substituted or unsubstituted C7-C10 aromatic hydrocarbon ring, a substituted or unsubstituted 7- to 10-membered saturated heterocyclic ring, a substituted or unsubstituted 7- to 10-membered partially saturated heterocyclic ring and a substituted or unsubstituted 7- to 10-membered unsaturated heterocyclic ring.

In one embodiment, an antitumor agent of the present invention comprises a compound or a pharmaceutically acceptable salt thereof that covalently binds to GTP-bound KRAS G12C as an active ingredient, and the compound has the following formula:

A-L1-L2-G-J wherein,

A is a chemical moiety capable of interacting with a region between Switch 2 and α3-Helix;

L1 is a linker;

L2 is a linker;

J is a chemical moiety capable of interacting with GTP; and G is an electrophilic chemical moiety capable of forming a covalent bond with cysteine 12 of GTP-bound KRAS G12C.

In a preferred embodiment, G is represented by the following formula:

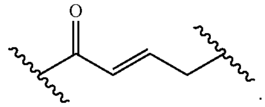 [SMILES: *C/C=C/C(*)=O]

.

In another preferred embodiment, G is represented by the following formula:

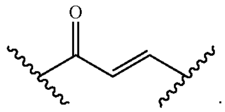 [SMILES: */C=C/C(*)=O]

.

In one embodiment, an antitumor agent of the present invention comprises a compound or a pharmaceutically acceptable salt thereof that covalently binds to GTP-bound KRAS G12C as an active ingredient, and the compound has the following formula:

A-L1-L2-G-J wherein,

A is a chemical moiety capable of interacting with a region between Switch 2 and α3-Helix;

L1 is a linker;

L2 is a linker;

and G-J is represented by the following formula:

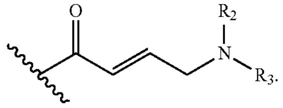

In another preferred embodiment, G-J is represented by the following formula:

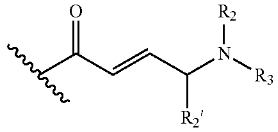

As used herein, the symbol "" refers to the point of attachment of a chemical moiety to the remainder of a molecule or chemical formula.

As used herein, the term "chemical moiety capable of interacting with a region between Switch 2 and α3-Helix" in moiety A refers to a chemical moiety which can interact with a region between Switch 2 (residue 60 to 76) and α3-helix (residue 86 to 103) of K-Ras. In one embodiment, the moiety A interacting with the region via hydrogen bond, van der Waals force, covalent bond, ionic bond or hydrophobic interaction. As used herein, "a region between Switch 2 and α3-Helix" denotes a region formed by one or more amino acids selected from methionine-67, arginine-68, aspartic acid-69, aspartic acid-70, glutamine-71, methionine-72, arginine-73, threonine-75, histidine-95, tyrosine-96, glutamine-99, isoleucine-100, lysine-101, arginine-102 and valine-103, and preferably a region formed by one or more amino acids selected from arginine-68, aspartic acid-69, methionine-72, glutamine-99, isoleucine-100 and valine-103. In one embodiment, K-Ras protein may comprise an amino acid sequence, for example, at least 50%, at least 85%, at least 90%, at least 92%, at least 94%, at least 96%, at least 98%, at least 99%, or 100% identical to one of SEQ ID Nos: 1 and 2.

In one embodiment, the term "a chemical moiety capable of interacting with a region between Switch 2 and α3-Helix" in moiety A of a compound of the present invention can be determined by conducting an X-ray structural analysis on a cocrystal of the compound of the present invention and GTP-bound KRAS G12C and identifying the moiety which interacts with at least one amino acid moiety which exists in a region between Switch 2 and α3-Helix of the GTP-bound KRAS G12C. Such an X-ray structural analysis may be conducted by using the ligand interaction tool within the Molecular Operating Environment. In one embodiment, the at least one amino acid moiety which interacts with the compound is selected from methionine-67, arginine-68, aspartic acid-69, aspartic acid-70, glutamine-71, methionine-72, arginine-73, threonine-75, histidine-95, tyrosine-96, glutamine-99, isoleucine-100, lysine-101, arginine-102 and valine-103, and preferably is selected from arginine-68, aspartic acid-69, methionine-72, glutamine-99, isoleucine-100 and valine-103. In one embodiment, a chemical moiety capable of interacting with a region between Switch 2 and α3-Helix may be a ring system selected from a substituted or unsubstituted single ring or a substituted or unsubstituted fused ring.

As used herein, the term "an electrophilic chemical moiety capable of forming a covalent bond with a GTP-bound K-Ras G12C" in moiety G represents an chemical moiety which can react electrophilically with a mutation at the 12th amino acid (cysteine-12 residue) of GTP-bound K-Ras to form a covalent bond.

As used herein, the term "a chemical moiety capable of interacting with GTP" in moiety J represents a chemical moiety that can interact with GTP bound to K-ras. In one embodiment, the chemical moiety interacts with γ-phosphoric acid placed at a terminal of the GTP, and preferably interacts with the γ-phosphoric acid via hydrogen bond, covalent bond or ionic bond. In a preferred embodiment, moiety J is $—NR_2R_3$ and may directly bind to moiety G or bind to moiety G via $—CH_2—$ or $—CHR_2'—$, and in a more preferred embodiment, moiety J is $—CHR_2'—NR_2R_3$.

In one embodiment, in the compound represented by any one of Formulae (i) to (xii), $R_1$ represents hydrogen or C1-C6 alkyl.

In one embodiment, "C1-C6 alkyl" represented by $R_1$ may be C2-C6 alkyl, C3-C6 alkyl, C4-C6 alkyl, C5-C6 alkyl, C1-C5 alkyl, C1-C4 alkyl, C1-C3 alkyl or C1-C2 alkyl, and is preferably methyl, ethyl, or tert-butyl, more preferably methyl or ethyl, and particularly preferably methyl.

In one embodiment, $R_1$ is hydrogen or substituted or unsubstituted C1-C3 alkyl.

$R_1$ is preferably hydrogen, methyl, ethyl, or tert-butyl.

$R_1$ is more preferably hydrogen or methyl.

$R_1$ is most preferably hydrogen.

In one embodiment, in the compound represented by any one of Formulae (i) to (xi) of the present invention, $R_2$ and $R_3$ may join together to form a 4- to 10-membered saturated heterocyclic ring which is unsubstituted or substituted with 1-2 substituents independently represented by Ra, and $R_2'$ is hydrogen or C1-C6 alkyl which is unsubstituted or substituted with 1-2 substituents independently represented by Ra.

The "4- to 10-membered saturated heterocyclic group" in the "a 4- to 10-membered saturated heterocyclic ring which is unsubstituted or substituted with 1-3 substituents independently represented by Ra" formed with $R_2$ and $R_3$ is preferably a 4- to 8-membered, 5- to 8-membered, 5- to 7-membered or 5- to 6-membered saturated heterocyclic ring which is unsubstituted or substituted with 1-2 substituents, and more preferably pyrrolidinyl, piperidinyl, piperazinyl.

The "substituted with Ra" in the "a 4- to 10-membered saturated heterocyclic ring which is unsubstituted or substituted with 1-2 substituents independently represented by Ra" formed with $R_2$ and $R_3$ preferably means substitution with halogen, hydroxy, substituted or unsubstituted C1-C10 alkyl, substituted or unsubstituted C2-C6 alkenyl, substituted or unsubstituted C2-C6 alkynyl, substituted or unsubstituted C3-C10 cycloalkyl, substituted or unsubstituted C1-C10 haloalkyl, substituted or unsubstituted C1-C10 monoalkylamino, substituted or unsubstituted C1-C10 dialkylamino, substituted or unsubstituted C1-C10 alkoxy, substituted or unsubstituted C1-C10 alkylsulfonyl, substituted or unsubstituted C1-C10 acyl, substituted or unsubstituted C1-C10 alkoxycarbonyl or a substituted or unsubstituted 4- to 10-membered saturated heterocyclic group, more preferably halogen, hydroxy, or C1-C6 alkyl, and most preferably hydroxy.

The "4- to 10-membered saturated heterocyclic ring which is unsubstituted or substituted with 1-2 substituents independently represented by Ra" formed with $R_2$ and $R_3$ is preferably pyrrolidinyl, piperidinyl, or piperazinyl.

The "4- to 10-membered saturated heterocyclic group" in the "a 4- to 10-membered saturated heterocyclic ring which is unsubstituted or substituted with 1-3 substituents independently represented by Ra" formed with $R_2$ and $R_2'$ is preferably a 4- to 8-membered, 5- to 8-membered, 5- to 7-membered or 5- to 6-membered saturated heterocyclic ring which is unsubstituted or substituted with 1-2 substituents, and more preferably pyrrolidinyl, piperidinyl, piperazinyl.

The "substituted with Ra" in the "a 4- to 10-membered saturated heterocyclic ring which is unsubstituted or substituted with 1-2 substituents independently represented by Ra" formed with $R_2$ and $R_2'$ preferably means substitution with halogen, hydroxy, substituted or unsubstituted C1-C10 alkyl, substituted or unsubstituted C2-C6 alkenyl, substituted or unsubstituted C2-C6 alkynyl, substituted or unsubstituted C3-C10 cycloalkyl, substituted or unsubstituted C1-C10 haloalkyl, substituted or unsubstituted C1-C10 monoalkylamino, substituted or unsubstituted C1-C10 dialkylamino, substituted or unsubstituted C1-C10 alkoxy, substituted or unsubstituted C1-C10 alkylsulfonyl, substituted or unsubstituted C1-C10 acyl, substituted or unsubstituted C1-C10 alkoxycarbonyl or a substituted or unsubstituted 4- to 10-membered saturated heterocyclic group, more preferably halogen, hydroxy, or C1-C6 alkyl, and most preferably hydroxy.

The "4- to 10-membered saturated heterocyclic ring which is unsubstituted or substituted with 1-2 substituents independently represented by Ra" formed with $R_2$ and $R_2$' is preferably pyrrolidinyl, piperidinyl, or piperazinyl.

In one embodiment, $R_2$, $R_2$' and $R_3$ may be are independently represented, and in the compound represented by any one of Formula (i) to (xii) of the present invention, $R_2$ is hydrogen; or C1-C10 alkyl, C2-C10 alkenyl, C2-C10 alkynyl, C3-C10 cycloalkyl, C1-C10 alkoxy, C6-C10 aromatic hydrocarbon, a 4- to 10-membered saturated heterocyclic group, a 4- to 10-membered partially saturated heterocyclic group or a 4- to 10-membered unsaturated heterocyclic group, each of which is unsubstituted or substituted with 1-2 substituents independently represented by Ra; $R_2$' is hydrogen or C1-C6 alkyl which is unsubstituted or substituted with 1-2 substituents independently represented by Ra; and $R_3$ is hydrogen or C1-C6 alkyl which is unsubstituted or substituted with 1-2 substituents independently represented by Ra.

The "C1-C10 alkyl" represented by $R_2$ may be C2-C6 alkyl, C3-C6 alkyl, C4-C6 alkyl, C5-C6 alkyl, C1-C5 alkyl, C1-C4 alkyl, C1-C3 alkyl or C1-C2 alkyl, and is preferably methyl, ethyl, n-propyl, isopropyl, n-butyl, tert-butyl, sec-butyl, isobutyl, or n-pentyl, and more preferably methyl, ethyl, n-propyl, isopropyl, n-butyl, tert-butyl, sec-butyl, isobutyl, or n-pentyl (C3-C6 alkyl).

The "Ra" which may substitute "C1-C10 alkyl" represented by $R_2$ may be, for example, the substituents mentioned above, and is preferably halogen, cyano, hydroxy, C3-C7 cycloalkyl, or a 4- to 10-membered saturated heterocyclic group and more preferably hydroxy.

The "C1-C10 alkyl which is unsubstituted or substituted with 1-2 substituents independently represented by Ra" represented by $R_2$ is preferably C1-C6 alkyl, 1,2-dihydroxyisopropyl, 2-hydroxypropyl, more preferably C1-C6 alkyl, still more preferably methyl, ethyl, isopropyl or tert-butyl, and most preferably tert-butyl.

The "C2-C10 alkenyl" represented by $R_2$ may be C2-C6 alkenyl, C3-C6 alkenyl, C4-C6 alkenyl, C5-C6 alkenyl, C2-C5 alkenyl, C2-C4 alkenyl or C2-C3 alkenyl, and is preferably vinyl, 1-propenyl, allyl, or isopropenyl, and more preferably vinyl or isopropenyl.

The "Ra" which may substitute "C2-C10 alkenyl" represented by $R_2$ may be, for example, the substituents mentioned above, and is preferably halogen, cyano, C1-C6 alkyl, or hydroxy, more preferably chlorine, fluorine, or methyl, and more preferably fluorine.

The "C2-C10 alkenyl which is unsubstituted or substituted with 1-2 substituents independently represented by Ra" represented by $R_2$ is preferably C2-C6 alkenyl that may contain halogen, more preferably vinyl, 1-propenyl, 2-methyl-2-propenyl, or 1-(trifluoromethyl)vinyl, and more preferably vinyl or 1-(trifluoromethyl)vinyl.

The "C2-C10 alkynyl" represented by $R_2$ may be C2-C6 alkynyl, C3-C6 alkynyl, C4-C6 alkynyl, C5-C6 alkynyl, C2-C5 alkynyl, C2-C4 alkynyl or C2-C3 alkynyl, and is preferably ethynyl or 1-propynyl.

The "Ra" which may substitute "C2-C10 alkynyl" represented by $R_2$ may be, for example, the substituents mentioned above, and is preferably halogen or hydroxy, and more preferably fluorine or chlorine.

The "C2-C10 alkynyl which is unsubstituted or substituted with 1-2 substituents independently represented by Ra" represented by $R_2$ is preferably ethynyl, 1-chloroethynyl, or 1-propynyl.

The "C3-C10 cycloalkyl" represented by $R_2$ may be C3-C8 cycloalkyl, C4-C8 cycloalkyl, C5-C8 cycloalkyl, C5-C6 cycloalkyl, C3-C6 cycloalkyl or C4-C6 alkynyl, and is preferably monocyclic or bicyclic C3-C10 cycloalkyl, and more preferably cyclopropyl, cyclobutyl, cyclopentyl, cyclohexyl, cycloheptyl, or bicyclo[3.1.0]hexanyl, and more preferably cyclohexyl.

The "Ra" which may substitute "C3-C10 cycloalkyl" represented by $R_2$ may be, the substituents mentioned above, and is preferably hydroxy, halogen, C2-C6 alkyl, C1-C6 haloalkyl, C1-C6 alkoxy, C1-C6 haloalkoxy, C1-C6 monoalkylamino, C1-C6 dialkylamino, saturated heterocyclic group, and more preferably fluorine, chlorine, hydroxy, methyl, ethyl, n-propyl, methoxy, ethoxy, difluoromethoxy, dimethylamino, diethylamino, isopropylamino, trifluoromethyl, dioxolane.

The "C3-C10 cycloalkyl which is unsubstituted or substituted with 1-2 substituents independently represented by Ra" represented by $R_2$ is preferably C3-C10 cycloalkyl that may be substituted with hydroxy, C1-C6 alkyl, C1-C6 haloalkyl, C1-C6 alkoxy, C1-C6 haloalkoxy, C1-C6 monoalkylamino, C1-C6 dialkylamino, saturated heterocyclic group, preferably C3-C6 cycloalkyl that may be substituted with hydroxy, C1-C3 alkyl, C1-C3 haloalkyl, C1-C3 alkoxy, C1-C3 haloalkoxy, C1-C3 monoalkylamino, C1-C3 dialkylamino, saturated heterocyclic group, and more preferably cyclopropyl, cyclobutyl, cyclopentyl, cyclohexyl, 4-hydroxycyclohexyl, 4-methoxycyclohexyl, 4-ethoxycyclohexyl, 4-diethylaminocyclohexyl, 4-dimethylaminocyclohexyl, 4-difluoromethoxycyclohexyl, 4,4-difluorocyclohexyl, difluoro-bicyclo[3.1.0]hexane, 8-methyl-1,4-dioxaspiro{4,5}decane or 4-dioxaspiro{4, 5}decane, and more preferably 4-hydroxycyclohexyl, 4-methoxycyclohexyl, 4-ethoxycyclohexyl, 4-diethylaminocyclohexyl.

The "C1-C10 alkoxy which is unsubstituted or substituted with 1-2 substituents independently represented by Ra" represented by $R_2$ is preferably methoxy, ethoxy.

The "C6-C10 aromatic hydrocarbon which is unsubstituted or substituted with 1-2 substituents independently represented by Ra" represented by $R_2$ is preferably phenyl.

The "4- to 10-membered saturated heterocyclic group" represented by $R_2$ may be 4- to 8-membered, 5- to 8-membered, 5- to 7-membered or 5- to 6-membered saturated heterocyclic group, and is preferably a monocyclic or bicyclic 4- to 10-membered saturated heterocyclic group containing 1 to 5 heteroatoms selected from nitrogen, oxygen, and sulfur, and more preferably a monocyclic 4- to 8-membered saturated heterocyclic group containing 1 to 3 heteroatoms selected from nitrogen, oxygen, and sulfur, and more preferably pyrolidinyl, piperidinyl, piperadinyl, tetrahydrofuranyl, tetrahydropyranyl, 1,4-dioxanyl, 8-oxabicyclo[3,2,1]octanyl, 8-methyl-1,4-dioxaspiro{4,5}decane thianyl, and more preferably, piperidinyl, piperadinyl, 2-ethyltetrahydropyranyl, or tetrahydropyranyl.

The "Ra" which may substitute "4- to 10-membered saturated heterocyclic group" represented by $R_2$ may be the substituents mentioned above, or is preferably halogen, hydroxy, C1-C6 alkyl, C1-C6 haloalkyl, C1-C6 alkoxy, C1-C6 haloalkoxy, C1-C6 monoalkylamino, C1-C6 dialkylamino, C1-C6 alkylsulfonyl, C1-C6 alkylcarbonyl, and more preferably fluorine, chlorine, hydroxy, methyl, ethyl, n-propyl, isopropyl, methoxy, ethoxy, difluoromethoxy, dimethylamino, diethylamino, isopropylamino, trifluoromethyl, dioxolane, methoxycarbonyl, or ethylcarboxyl, and most preferably methyl, dimethylamino, diethylamino, or isopropylamino.

The "4- to 10-membered saturated heterocyclic group which is unsubstituted or substituted with 1-2 substituents independently represented by Ra" represented by $R_2$ is preferably a monocyclic 4- to 8-membered saturated heterocyclic group containing 1 to 3 heteroatoms selected from nitrogen, oxygen, and sulfur, substituted with at least one substituent selected from halogen, hydroxy, C1-C6 alkyl, C1-C6 haloalkyl, C1-C6 alkoxy, C1-C6 haloalkoxy, C1-C6 monoalkylamino, C1-C6 dialkylamino, C1-C6 alkylsulfonyl, and C1-C6 alkylcarbonyl, and more preferably N-isopropyl-4-piperidinyl, N-methylsulfonyl-4-piperidinyl, 2-methyl-4-tetrahydropyranyl, 1-methyl-4-tetrahydropyranyl, 2,2-dimethyl-4-tetrahydropyranyl, 2,4-dimethyl-4-tetrahydropyranyl, 3,3-dimethyl-4-tetrahydropyranyl, 4-isopropyl-4-piperidinyl, 2-ethyltetrahydropyranyl, or tert-butylcarbamatetetrahydropyranyl, and more preferably N-isopropyl-4-pyperidinyl, 1-methyl-4-tetrahydropyranyl, 2-ethyltetrahydropyranyl, or 3,5-dimethyltetrahydropyranyl.

The "4- to 10-membered partially saturated heterocyclic group which is unsubstituted or substituted with 1-2 substituents independently represented by Ra" represented by $R_2$ is preferably a monocyclic or bicyclic 4- to 10-membered, 4- to 8-membered, 5- to 8-membered, 5- to 7-membered or 5- to 6-membered partially saturated heterocyclic group containing 1 to 5 heteroatoms selected from nitrogen, oxygen, and sulfur, more preferably a monocyclic 4- to 7-membered partially saturated heterocyclic group containing 1 to 3 heteroatoms selected from nitrogen, oxygen, and sulfur, and preferably 4H-pyranyl, indoline, 1,3-dihydroisobenzofuran, 2,3-dihydro-1H-benzo[d]imidazole, 1,3-benzodioxole.

The "4- to 10-membered unsaturated heterocyclic group which is unsubstituted or substituted with 1-2 substituents independently represented by Ra" represented by $R_2$ is preferably a monocyclic or bicyclic 4- to 10-membered, 4- to 8-membered, 5- to 8-membered, 5- to 7-membered or 5- to 6-membered unsaturated heterocyclic group containing 1 to 5 heteroatoms selected from nitrogen, oxygen, and sulfur, more preferably a monocyclic 5- to 7-membered unsaturated heterocyclic group containing 1 to 3 heteroatoms selected from nitrogen, oxygen, and sulfur, and more preferably pyridyl, imidazolyl, thienyl, pyrrolyl, oxazolyl, isoxazolyl, thiazolyl, isothiazolyl, thiadiazolyl, oxadiazolyl, pyrazolyl, triazolyl, tetrazolyl, pyrazyl, pyrimidinyl, pyridazinyl, indolyl, isoindolyl, indazolyl, triazolopyridyl, benzoimidazolyl, benzoxazolyl, benzothiazolyl, benzothienyl, furanyl, benzofuranyl, purinyl, quinolyl, isoquinolyl, quinazolinyl, quinoxalyl, methylenedioxyphenyl, ethylenedioxyphenyl, dihydrobenzofuranyl, imidazopyridinyl, indazolyl, and more preferably pyridyl.

$R_2$ is preferably C1-C6 alkyl, C3-C10 cycloalkyl, a 4- to 10-membered saturated heterocyclic group, each of which is unsubstituted or substituted with 1-2 substituents independently represented by Ra.

$R_2$ is more preferably C3-C6 alkyl, cycloalkyl, a 6- to 10-membered saturated heterocyclic group, each of which is unsubstituted or substituted with 1-2 substituents independently represented by Ra.

The Ra which may substitute $R_2$ is preferably halogen, cyano, hydroxy, C1-C10 alkylamino, C1-C10 alkoxy, C1-C10 alkylsulfonyl, C3-C7 cycloalkyl, or a 4- to 10-membered saturated heterocyclic group.

The Ra which may substitute $R_2$ is more preferably hydroxy, dimethylamino, methoxy, methylsulfonyl.

$R_2$ which is unsubstituted or substituted with Ra is preferably methyl, ethyl, isopropyl, tert-butyl, cyclopropyl, cyclobutyl, cyclopentyl, cyclohexyl, 4-hydroxycyclohexyl, 4-methoxycyclohexyl, 4-ethoxycyclohexyl, 4-diethylaminocyclohexyl, 4-dimethylaminocyclohexyl, 4-difluoromethoxycyclohexyl, 4,4-difluorocyclohexyl, difluoro-bicyclo[3.1.0]hexane, 4-dioxaspiro[4.5]decane, N-isopropyl-4-piperidinyl, N-methylsulfonyl-4-piperidinyl, 2-methyl-4-tetrahydropyranyl, 1-methyl-4-tetrahydropyranyl, 2,2-dimethyl-4-tetrahydropyranyl, 2,4-dimethyl-4-tetrahydropyranyl, 3,3-dimethyl-4-tetrahydropyranyl, 4-isopropyl-4-piperidinyl, 2-ethyltetrahydropyranyl, or tert-butylcarbamatetetrahydropyranyl.

$R_2$ is more preferably methyl, ethyl, isopropyl, tert-butyl, cyclohexyl, 4-hydroxycyclohexyl, 4-methoxycyclohexyl, 4-ethoxycyclohexyl, 4-diethylaminocyclohexyl, N-isopropyl-4-pyperidinyl, 1-methyl-4-tetrahydropyranyl, 2-ethyltetrahydropyranyl, or 3,5-dimethyltetrahydropyranyl.

$R_2$ is most preferably tert-butyl, cyclohexyl, 4-hydroxycyclohexyl, 4-methoxycyclohexyl, 4-diethylaminocyclohexyl.

The "C1-C6 alkyl" in the "C1-C6 alkyl which is unsubstituted or substituted with 1-2 substituents independently represented by Ra" in $R_2'$ is preferably methyl, ethyl, isopropyl, or tert-butyl, more preferably methyl or ethyl, and most preferably methyl.

The "C1-C6 alkyl which is unsubstituted or substituted with 1-2 substituents independently represented by Ra" in $R_2'$ is preferably methyl, ethyl, isopropyl, or tert-butyl, more preferably methyl or ethyl, and most preferably methyl.

The "Ra" which may substitute "C1-C10 alkyl" represented by $R_2'$ may be, for example, the substituents mentioned above, and is preferably halogen, cyano, hydroxy, C3-C7 cycloalkyl, or a 4- to 10-membered saturated heterocyclic group and more preferably hydroxy.

$R_2'$ is preferably hydrogen or C1-C6 alkyl.

$R_2'$ is more preferably hydrogen, methyl, ethyl, isopropyl, or tert-butyl.

$R_2'$ is most preferably hydrogen.

The "C1-C6 alkyl" represented by $R_3$ is preferably methyl, ethyl, isopropyl, or tert-butyl, more preferably methyl or ethyl, and most preferably methyl.

The "Ra" which may substitute "C1-C10 alkyl" represented by $R_3$ may be, for example, the substituents mentioned above, and is preferably halogen, cyano, hydroxy, C3-C7 cycloalkyl, or a 4- to 10-membered saturated heterocyclic group and more preferably hydroxy.

$R_3$ is more preferably hydrogen or methyl, ethyl, isopropyl, or tert-butyl.

$R_3$ is more preferably hydrogen or methyl.

$R_3$ is most preferably hydrogen.

In one embodiment, $R_2$ and $R_3$ may be are independently represented, and in the compound represented by any one of Formula (i) to (xii) of the present invention, $R_2$ and $R_2'$ join together to form a 4- to 10-membered saturated heterocyclic ring which is unsubstituted or substituted with 1-2 substituents independently represented by Ra, $R_3$ is hydrogen or C1-C6 alkyl which is unsubstituted or substituted with 1-2 substituents independently represented by Ra.

The "4- to 10-membered saturated heterocyclic group" in the "a 4- to 10-membered saturated heterocyclic ring which is unsubstituted or substituted with 1-3 substituents independently represented by Ra" formed with $R_2$ and $R_{2'}$ is preferably a 4- to 8-membered, 5- to 8-membered, 5- to 7-membered or 5- to 6-membered saturated heterocyclic ring which is unsubstituted or substituted with 1-2 substituents, and more preferably pyrrolidinyl, piperidinyl, piperazinyl.

The "substituted with Ra" in the "a 4- to 10-membered saturated heterocyclic ring which is unsubstituted or substituted with 1-2 substituents independently represented by Ra" formed with $R_2$ and $R_2'$ preferably means substitution with halogen, hydroxy, substituted or unsubstituted C1-C10 alkyl, substituted or unsubstituted C2-C6 alkenyl, substituted or unsubstituted C2-C6 alkynyl, substituted or unsubstituted C3-C10 cycloalkyl, substituted or unsubstituted C1-C10 haloalkyl, substituted or unsubstituted C1-C10 monoalkylamino, substituted or unsubstituted C1-C10 dialkylamino, substituted or unsubstituted C1-C10 alkoxy, substituted or unsubstituted C1-C10 alkylsulfonyl, substituted or unsubstituted C1-C10 acyl, substituted or unsubstituted C1-C10 alkoxycarbonyl or a substituted or unsubstituted 4- to 10-membered saturated heterocyclic group, more preferably halogen, hydroxy, or C1-C6 alkyl, and most preferably hydroxy.

The "4- to 10-membered saturated heterocyclic ring which is unsubstituted or substituted with 1-2 substituents independently represented by Ra" formed with $R_2$ and $R_2'$ is preferably pyrrolidinyl, piperidinyl, or piperazinyl.

The "C1-C6 alkyl" represented by $R_3$ is preferably methyl, ethyl, isopropyl, or tert-butyl, more preferably methyl or ethyl, and most preferably methyl.

The "Ra" which may substitute "C1-C10 alkyl" represented by $R_3$ may be, for example, the substituents mentioned above, and is preferably halogen, cyano, hydroxy, C3-C7 cycloalkyl, or a 4- to 10-membered saturated heterocyclic group and more preferably hydroxy.

$R_3$ is more preferably hydrogen or methyl, ethyl, isopropyl, or tert-butyl.

$R_3$ is more preferably hydrogen or methyl.

$R_3$ is most preferably hydrogen.

In one embodiment, in the compound represented by any one of Formulae (ii) to (xii) of the present invention, $R_4$ represents cyano, hydroxy, halogen, substituted or unsubstituted C1-C10 alkyl, substituted or unsubstituted C2-C10 alkenyl, substituted or unsubstituted C2-C10 alkynyl, substituted or unsubstituted C3-C10 cycloalkyl, substituted or unsubstituted C1-C10 haloalkyl, substituted or unsubstituted C1-C10 alkoxy, substituted or unsubstituted C1-C10 acyl, substituted or unsubstituted C1-C10 alkoxycarbonyl, or substituted or unsubstituted C1-C10 sulfonyl.

The "halogen" represented by $R_4$ is preferably chlorine, bromine, fluorine, and iodine, with chlorine, fluorine, and bromine being preferable, and chlorine and fluorine being more preferable, and fluorine being most preferable.

The "C1-C10 alkyl" in the "substituted or unsubstituted C1-C10 alkyl" represented by $R_4$ is preferably methyl, ethyl, n-propyl, isopropyl, n-butyl, tert-butyl, sec-butyl, isobutyl, or n-pentyl, more preferably methyl, ethyl, n-propyl, isopropyl, n-butyl, tert-butyl, sec-butyl, isobutyl, or n-pentyl (C3-C6 alkyl), and still more preferably methyl.

The "substituent" in the "substituted or unsubstituted C1-C10 alkyl" represented by $R_4$ may be, for example, the substituents mentioned above, and is preferably halogen, cyano, hydroxy or C3-C7 cycloalkyl, and more preferably hydroxy.

The "substituted or unsubstituted C1-C10 alkyl" represented by $R_4$ is preferably C1-C6 alkyl, hydroxymethyl, 2-hydroxyethyl, 1,2-dihydroxyisopropyl, 2-hydroxypropyl, and more preferably C1-C3 alkyl, still more preferably methyl, isopropyl, tert-butyl, hydroxymethyl or 2-hydroxyethyl, and most preferably methyl.

The "C2-C10 alkenyl" in the "substituted or unsubstituted C2-C10 alkenyl" represented by $R_4$ is preferably vinyl, 1-propenyl, allyl, or isopropenyl, and more preferably vinyl or isopropenyl.

The "substituent" in the "substituted or unsubstituted C2-C10 alkenyl" represented by $R_4$ may be, for example, the substituents mentioned above, and is preferably halogen, cyano, or hydroxy, more preferably chlorine or fluorine, and more preferably fluorine.

The "substituted or unsubstituted C2-C10 alkenyl" represented by $R_4$ is preferably C2-C6 alkenyl that may contain halogen, more preferably vinyl, 1-propenyl, 2-methyl-2-propenyl, or 1-(trifluoromethyl)vinyl, and more preferably vinyl or 1-(trifluoromethyl)vinyl.

The "C2-C10 alkynyl" in the "substituted or unsubstituted C2-C10 alkynyl" represented by $R_4$ is preferably ethynyl or 1-propynyl.

The substituent in the "substituted or unsubstituted C2-C10 alkynyl" represented by $R_4$ may be, for example, the substituents mentioned above, and is preferably halogen or hydroxy, and more preferably fluorine or chlorine.

The "substituted or unsubstituted C2-C10 alkynyl" represented by $R_4$ is preferably ethynyl or 1-propynyl.

The "C3-C10 cycloalkyl" in the "substituted or unsubstituted C3-C10 cycloalkyl" represented by $R_4$ is preferably cyclopropyl, cyclobutyl, cyclopentyl, cyclohexyl, cycloheptyl, and more preferably cyclopropyl.

The "substituted or unsubstituted C1-C10 haloalkyl" represented by $R_4$ is preferably fluoromethyl, difluoromethyl, trifluoromethyl.

The "substituted or unsubstituted C1-C10 alkoxyl" represented by $R_4$ is preferably methoxy, ethoxy, 1-fluoromethoxy.

The "substituted or unsubstituted C1-C10 acyl" represented by $R_4$ is preferably formyl, acetyl, propionyl.

The "substituted or unsubstituted C1-C10 alkoxycarbonyl" represented by $R_4$ is preferably methoxycarbonyl, ethoxycarbonyl.

The "substituted or unsubstituted C1-C10 alkylsulfonyl" represented by $R_4$ is preferably methoxysulfonyl, ethoxysulfonyl.

$R_4$ is preferably halogen, cyano or a substituted or unsubstituted C1-C6 alkyl.

$R_4$ is more preferably halogen, cyano or C1-C3 alkyl.

$R_4$ is more preferably halogen, or cyano.

$R_4$ is most preferably fluorine or cyano.

In one embodiment, in the compound represented by any one of Formulae (iii) to (xii) of the present invention, $R_5$ represents cyano, hydroxy, halogen, amino, substituted or unsubstituted C1-C10 alkyl, substituted or unsubstituted C2-C10 or C2-C6 alkenyl, substituted or unsubstituted C2-C10 or C2-C6 alkynyl, substituted or unsubstituted C1-C10 or C2-C6 haloalkyl, substituted or unsubstituted C1-C10 alkoxy, substituted or unsubstituted C1-C10 acyl, substituted or unsubstituted C1-C10 alkoxycarbonyl, or substituted or unsubstituted C1-C10 alkyl sulfonyl.

The "halogen" represented by $R_5$ is preferably chlorine, bromine, fluorine, and iodine, with chlorine, fluorine, and bromine being preferable, and chlorine and fluorine being more preferable, and chlorine being most preferable.

The "C1-C10 alkyl" in the "substituted or unsubstituted C1-C10 alkyl" represented by $R_5$ is preferably methyl, ethyl, n-propyl, isopropyl, n-butyl, tert-butyl, sec-butyl, isobutyl, or n-pentyl, more preferably methyl, ethyl, n-propyl, isopropyl, n-butyl, tert-butyl, sec-butyl, isobutyl, or n-pentyl (C3-C6 alkyl), and still more preferably methyl.

The “substituent” in the “substituted or unsubstituted C1-C10 alkyl” represented by $R_5$ may be, for example, the substituents mentioned above, and is preferably halogen, cyano, hydroxy or C3-C7 cycloalkyl, and more preferably fluorine.

The “substituted or unsubstituted C1-C10 alkyl” represented by $R_5$ is preferably C1-C6 alkyl, more preferably methyl.

The “C2-C10 alkenyl” in the “substituted or unsubstituted C2-C10 alkenyl” represented by $R_5$ is preferably vinyl, 1-propenyl, allyl, or isopropenyl, and more preferably vinyl or isopropenyl.

The “substituent” in the “substituted or unsubstituted C2-C10 alkenyl” represented by $R_5$ may be, for example, the substituents mentioned above, and is preferably halogen, cyano, or hydroxy, more preferably chlorine or fluorine, and more preferably fluorine.

The “substituted or unsubstituted C2-C10 alkenyl” represented by $R_5$ is preferably C2-C6 alkenyl that may contain halogen, more preferably vinyl, 1-propenyl, 2-methyl-2-propenyl, or 1-(trifluoromethyl)vinyl, and more preferably vinyl or 1-(trifluoromethyl)vinyl.

The “C2-C10 alkynyl” in the “substituted or unsubstituted C2-C10 alkynyl” represented by $R_5$ is preferably ethynyl or 1-propynyl.

The substituent in the “substituted or unsubstituted C2-C10 alkynyl” represented by $R_5$ may be, for example, the substituents mentioned above, and is preferably halogen or hydroxy, and more preferably fluorine or chlorine.

The “substituted or unsubstituted C2-C10 alkynyl” represented by $R_5$ is preferably ethynyl or 1-propynyl.

The “substituted or unsubstituted C1-C10 haloalkyl” represented by $R_5$ is preferably fluoromethyl, difluoromethyl, trifluoromethyl, 1-fluoroethyl or 1,1-difluoroethyl, and more preferably fluoromethyl, difluoromethyl or trifluoromethyl.

The “substituted or unsubstituted C1-C10 alkoxyl” represented by $R_5$ is preferably methoxy, ethoxy, 1-fluoromethoxy.

The “substituted or unsubstituted C1-C10 acyl” represented by $R_5$ is preferably formyl, acetyl, propionyl.

The “substituted or unsubstituted C1-C10 alkoxycarbonyl” represented by $R_5$ is preferably methoxycarbonyl, ethoxycarbonyl.

The “substituted or unsubstituted C1-C10 alkyl sulfonyl” represented by $R_5$ is preferably methoxysulfonyl, ethoxysulfonyl.

$R_5$ is more preferably halogen, a substituted or unsubstituted C1-C6 alkyl, a substituted or unsubstituted C1-C6 alkoxy, or substituted or unsubstituted C1-C6 haloalkyl.

$R_5$ is more preferably halogen, C1-C6 alkyl which is unsubstituted or substituted with fluorine, C1-C6 alkoxy which is unsubstituted or substituted with fluorine, or C1-C6 haloalkyl which is unsubstituted or substituted with fluorine.

$R_5$ is more preferably chlorine, fluorine, methyl, tert-butyl, fluoromethyl, fluoroethyl, difluoromethyl, or trifluoromethyl.

$R_5$ is most preferably chlorine or trifluoromethyl.

In the compound represented by any one of Formulae (iii) to (vi) of the present invention, two $R_6$ may join together to form a C3-C10 hydrocarbon ring or a 4- to 10-membered saturated heterocyclic ring sharing two adjacent atoms with ring A' or ring A" when the number of $R_6$ is two or more; or $R_6$ may independently represents cyano, hydroxy, halogen, amino, substituted or unsubstituted C1-C10 alkyl, substituted or unsubstituted C2-C10 or C2-C6 alkenyl, substituted or unsubstituted C2-C10 or C2-C6 alkynyl, substituted or unsubstituted C1-C10 or C1-C6 haloalkyl, substituted or unsubstituted C1-C10 alkoxy, substituted or unsubstituted C1-C10 acyl, substituted or unsubstituted C1-C10 alkoxycarbonyl, or substituted or unsubstituted C1-C10 alkylsulfonyl.

The “C3-C10 hydrocarbon ring” which may be formed with two $R_6$ is preferably cyclopropyl, cyclobutyl, cyclopentyl, or cyclohexyl, and more preferably cyclopentyl.

The “4- to 10-membered saturated heterocyclic ring” which may be formed with two $R_6$ is preferably 4- to 10-membered ring which contains nitrogen, and more preferably pyrrolidinyl, tetrahydrofuranyl, tetrahydrothiophenyl, and more preferably pyrrolidinyl, or tetrahydrofuranyl.

The “halogen” represented by $R_6$ is preferably chlorine, bromine, fluorine, and iodine, with chlorine, fluorine, and bromine being preferable, and chlorine and fluorine being more preferable.

The “C1-C10 alkyl” in the “substituted or unsubstituted C1-C10 alkyl” represented by $R_6$ is preferably methyl, ethyl, n-propyl, isopropyl, n-butyl, tert-butyl, sec-butyl, isobutyl, or n-pentyl, more preferably methyl, ethyl, n-propyl, isopropyl, n-butyl, tert-butyl, sec-butyl, isobutyl, or n-pentyl (C3-C6 alkyl), and still more preferably methyl or ethyl.

The “substituent” in the “substituted or unsubstituted C1-C10 alkyl” represented by $R_6$ may be, for example, the substituents mentioned above, and is preferably halogen, cyano, hydroxy or C1-C6 alkoxy, and more preferably methoxy.

The “substituted or unsubstituted C1-C10 alkyl” represented by $R_6$ is preferably C1-C6 alkyl, 1,2-dihydroxyisopropyl, 2-hydroxypropyl, methoxymethyl, ethoxymethyl, more preferably C1-C3 alkyl, still more preferably methyl, ethyl, methoxymethyl or ethoxymethyl and most preferably methyl, or methoxymethyl.

The “C2-C10 alkenyl” in the “substituted or unsubstituted C2-C10 alkenyl” represented by $R_6$ is preferably vinyl, 1-propenyl, allyl, or isopropenyl, and more preferably vinyl or isopropenyl.

The “substituent” in the “substituted or unsubstituted C2-C10 alkenyl” represented by $R_6$ may be, for example, the substituents mentioned above, and is preferably halogen, cyano, or hydroxy, more preferably chlorine or fluorine, and more preferably fluorine.

The “substituted or unsubstituted C2-C10 alkenyl” represented by $R_6$ is preferably C2-C6 alkenyl that may contain halogen, more preferably vinyl, 1-propenyl, 2-methyl-2-propenyl, or 1-(trifluoromethyl)vinyl, and more preferably vinyl or 1-(trifluoromethyl)vinyl.

The “C2-C10 alkynyl” in the “substituted or unsubstituted C2-C10 alkynyl” represented by $R_6$ is preferably ethynyl or 1-propynyl.

The substituent in the “substituted or unsubstituted C2-C10 alkynyl” represented by $R_6$ may be, for example, the substituents mentioned above, and is preferably halogen or hydroxy, and more preferably fluorine or chlorine.

The “substituted or unsubstituted C2-C10 alkynyl” represented by $R_6$ is preferably ethynyl or 1-propynyl.

The “substituted or unsubstituted C1-C10 haloalkyl” represented by $R_6$ is preferably C1-C6 haloalkyl, and more preferably, fluoromethyl, difluoromethyl, trifluoromethyl.

The “substituted or unsubstituted C1-C10 alkoxyl” represented by $R_6$ is preferably methoxy, ethoxy, 1-fluoromethoxy.

The “substituted or unsubstituted C1-C10 acyl” represented by $R_6$ is preferably formyl, acetyl, propionyl.

The "substituted or unsubstituted C1-C10 alkoxycarbonyl" represented by $R_6$ is preferably methoxycarbonyl, ethoxycarbonyl.

The "substituted or unsubstituted C1-C10 alkylsulfonyl" represented by $R_6$ is preferably methoxysulfonyl, ethoxysulfonyl.

$R_6$ is more preferably halogen or substituted or unsubstituted C1-C6alkyl, or two $R_6$ may join together to form a C3-C10 hydrocarbon ring, a 4- to 10-membered saturated heterocyclic ring.

$R_6$ is more preferably halogen or methyl, ethyl, methoxymethyl, may join together to form cyclopentyl, pyrrolidinyl, tetrahydrofuranyl, tetrahydrothiophenyl.

$R_6$ is most preferably methyl, ethyl, may join together to form cyclopentyl, pyrrolidinyl.

In the compound represented by any one of Formula (iv) to (vi) and (x) to (xii) of the present invention, $R_7$ represents cyano, hydroxy, halogen, amino, substituted or unsubstituted C1-C10 alkyl, substituted or unsubstituted C2-C10 or C2-C6 alkenyl, substituted or unsubstituted C2-C10 or C2-C6 alkynyl, substituted or unsubstituted C1-C10 or C1-C6 haloalkyl, substituted or unsubstituted C1-C10 alkoxy, substituted or unsubstituted C1-C10 acyl, substituted or unsubstituted C1-C10 alkoxycarbonyl, or substituted or unsubstituted C1-C10 alkylsulfonyl.

The "halogen" represented by $R_7$ is preferably chlorine, bromine, fluorine, and iodine, with chlorine, fluorine, and bromine being preferable, and chlorine and fluorine being more preferable.

The "C1-C10 alkyl" in the "substituted or unsubstituted C1-C10 alkyl" represented by $R_7$ is preferably methyl, ethyl, n-propyl, isopropyl, n-butyl, tert-butyl, sec-butyl, isobutyl, or n-pentyl, more preferably methyl, ethyl, n-propyl, isopropyl, n-butyl, tert-butyl, sec-butyl, isobutyl, or n-pentyl (C3-C6 alkyl), and still more preferably methyl, ethyl, or tert-butyl.

The "substituent" in the "substituted or unsubstituted C1-C10 alkyl" represented by $R_7$ may be, for example, the substituents mentioned above, and is preferably halogen, cyano, hydroxy or C3-C7 cycloalkyl, and more preferably hydroxy.

The "substituted or unsubstituted C1-C10 alkyl" represented by $R_7$ is preferably C1-C6 alkyl, 1,2-dihydroxyisopropyl, 2-hydroxypropyl, more preferably C3-C6 alkyl, still more preferably methyl, ethyl, isopropyl or tert-butyl, and most preferably methyl.

The "C2-C10 alkenyl" in the "substituted or unsubstituted C2-C10 alkenyl" represented by $R_7$ is preferably vinyl, 1-propenyl, allyl, or isopropenyl, and more preferably vinyl or isopropenyl.

The "substituent" in the "substituted or unsubstituted C2-C10 alkenyl" represented by $R_7$ may be, for example, the substituents mentioned above, and is preferably halogen, cyano, or hydroxy, more preferably chlorine or fluorine, and more preferably fluorine.

The "substituted or unsubstituted C2-C10 alkenyl" represented by $R_7$ is preferably C2-C6 alkenyl that may contain halogen, more preferably vinyl, 1-propenyl, 2-methyl-2-propenyl, or 1-(trifluoromethyl)vinyl, and more preferably vinyl or 1-(trifluoromethyl)vinyl.

The "C2-C10 alkynyl" in the "substituted or unsubstituted C2-C10 alkynyl" represented by $R_7$ is preferably ethynyl or 1-propynyl.

The substituent in the "substituted or unsubstituted C2-C10 alkynyl" represented by $R_7$ may be, for example, the substituents mentioned above, and is preferably halogen or hydroxy, and more preferably fluorine or chlorine.

The "substituted or unsubstituted C2-C10 alkynyl" represented by $R_7$ is preferably ethynyl or 1-propynyl.

The "C3-C10 cycloalkyl" in the "substituted or unsubstituted C3-C10 cycloalkyl" represented by $R_7$ is preferably cyclopropyl, cyclobutyl, cyclopentyl, cyclohexyl, cycloheptyl, and more preferably cyclohexyl.

The "substituted or unsubstituted C1-C10 haloalkyl" represented by $R_7$ is preferably fluoromethyl, difluoromethyl, trifluoromethyl.

The "substituted or unsubstituted C1-C10 alkoxyl" represented by $R_7$ is preferably methoxy, ethoxy, 1-fluoromethoxy.

The "substituted or unsubstituted C1-C10 acyl" represented by $R_7$ is preferably formyl, acetyl, propionyl.

The "substituted or unsubstituted C1-C10 alkoxycarbonyl" represented by $R_7$ is preferably methoxycarbonyl, ethoxycarbonyl.

The "substituted or unsubstituted C1-C10 sulfonyl" represented by $R_7$ is preferably methoxysulfonyl, ethoxysulfonyl.

$R_7$ is preferably halogen or a substituted or unsubstituted C1-C6 alkyl.

$R_7$ is more preferably halogen or C1-C3 alkyl.

$R_7$ is most preferably fluorine or methyl.

In one embodiment, in the compound represented by any one of Formulae (iv) to (vi) and (X) to (xii) of the present invention, $R_8$ represents halogen or substituted or unsubstituted C1-C6 alkyl.

The "halogen" represented by $R_8$ is preferably chlorine, bromine, fluorine, and iodine, with chlorine, fluorine, and bromine being preferable, and chlorine and fluorine being more preferable.

The "C1-C6 alkyl" in the "substituted or unsubstituted C1-C6 alkyl" represented by $R_8$ is preferably methyl, ethyl, n-propyl, or isopropyl, more preferably methyl or ethyl, and particularly preferably methyl.

The substituent in the "substituted or unsubstituted C1-C6 alkyl" represented by $R_8$ may be, for example, the substituents mentioned above, and is preferably, halogen, cyano, or hydroxy, and more preferably fluorine, chlorine, cyano, or hydroxy.

The "substituted or unsubstituted C1-C6 alkyl" represented by $R_8$ is preferably C1-C6 alkyl, more preferably methyl, ethyl, or tert-butyl, more preferably methyl or ethyl, and particularly preferably methyl.

$R_8$ is preferably halogen, or substituted or unsubstituted C1-C6 alkyl.

$R_8$ is more preferably halogen or C1-C6 alkyl.

$R_8$ is most preferably fluorine or methyl.

In one embodiment of the present invention, in the compound represented by Formula A-L1-L2-G-J, (i), (ii), (vii) or (viii) of the present invention, A represents a chemical moiety capable of interacting with a region between Switch 2 and α3-Helix, and more preferably A represents ring system, ring A which is a substituted or unsubstituted single ring or a substituted or unsubstituted fused ring, more preferably A represents ring A which is a substituted or unsubstituted C3-C10 cycloalkyl, a substituted or unsubstituted C6-C10 aromatic hydrocarbon, a substituted or unsubstituted 4- to 10-membered saturated heterocyclic group, or a substituted or unsubstituted 4- to 10-membered partially saturated heterocyclic group or a substituted or unsubstituted 4- to 10-membered unsaturated heterocyclic group.

In one embodiment of the present invention, in the compound represented by Formula (iii), (iv), (ix) or (x) of the present invention, when A is a single ring, A' and A" are absent, and the single ring is represented by ring A, which is an unsaturated 6-membered ring which is unsubstituted or substituted with $R_5$, wherein $A_1$, $A_2$, $A_3$, $A_4$ and $A_5$ represent independently C, CH, $CH_2$, N or NH; when A is a fused ring, the fused ring is represented by ring A and ring A' or ring A and ring A", wherein ring A is an unsaturated 6-membered ring which is unsubstituted or substituted with $R_5$, wherein $A_1$, $A_2$, $A_3$, $A_4$ and $A_5$ represent independently C, CH, $CH_2$, N or NH, and ring A' or A" is a saturated or unsaturated ring which is unsubstituted or substituted with $R_6$ and forms a fused ring with ring A containing $A_3$ and $A_4$ or $A_4$ and $A_5$.

In a preferred embodiment, in the compound represented by Formula (iii), (iv), (ix) or (x) of the present invention, ring A' forms a fused ring with ring A containing $A_3$ and $A_4$, and $A_1$ and $A_5$ are C, CH, or $CH_2$.

More preferably, in the compound represented by Formula (iii), (iv), (ix) or (x) of the present invention, $A_2$ in ring A represents C.

More preferably, in the compound represented by Formula (iii), (iv), (ix) or (x) of the present invention, ring A and ring A' jointly represent benzimidazolyl, benzothiazolyl, indazolyl, benzodioxanyl, imidazopyridinyl, and more preferably, benzoimidazolyl.

In one embodiment, in the compound represented by Formula A-L1-L2-G-J of the present invention, L1 represents a linker. More preferably, L1 is a combination of a substituted or unsubstituted single ring or a substituted or unsubstituted fused ring with —C(═O)—. More preferably, L1 is

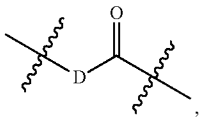

, wherein D is a single ring having at least one amino group which binds to carbonyl between D and E to form amide, wherein the single ring is unsubstituted or substituted with substituent other than said amino, or D is substituted or unsubstituted fused ring, more preferably a substituted or unsubstituted C6-C10 aromatic hydrocarbon, or a substituted or unsubstituted 4- to 10-membered partially saturated heterocyclic group, or a substituted or unsubstituted 4- to 10-membered unsaturated heterocyclic group.

In one embodiment, in the compound represented by Formula (i), (ii), (iii), (vii), (viii) or (ix) of the present invention, D represents a single ring having at least one amino group which binds to carbonyl between D and E to form amide, wherein the single ring is unsubstituted or substituted with substituent other than said amino, or D is substituted or unsubstituted fused ring, more preferably a substituted or unsubstituted C6-C10 aromatic hydrocarbon, or a substituted or unsubstituted 4- to 10-membered partially saturated heterocyclic group, or a substituted or unsubstituted 4- to 10-membered unsaturated heterocyclic group.

More preferably, in the compound represented by Formula (iv) or (x) of the present invention, when D is a single ring, D' is absent, and the single ring is represented by ring D, which is an unsaturated 6-membered ring which is unsubstituted or substituted with $R_7$, wherein $D_1$ represents N or NH, and $D_2$, $D_3$, $D_4$, $D_5$, $D_6$ and $D_7$ represent independently C, CH, $CH_2$, N or NH;

when D is a fused ring, the fused ring is represented by ring D and ring D', wherein ring D is an unsaturated 6-membered ring which is unsubstituted or substituted with $R_7$, wherein $D_1$, $D_2$, $D_3$, $D_4$, $D_5$, $D_6$ and $D_7$ represent independently C, CH, $CH_2$, N or NH, and ring D' is a saturated or unsaturated ring which is unsubstituted or substituted with $R_8$ and forms a fused ring with ring D containing $D_1$, $D_2$ and $D_7$.

More preferably, in the compound represented by Formula (iv) or (x) of the present invention, $D_6$ in ring D is C.

More preferably, in the compound represented by Formula (iv) or (x) of the present invention, $D_3$, $D_4$ and $D_5$ are C.

More preferably, in the compound represented by Formula (iv), (v), (vi), (x), (xi) or (xii) of the present invention, D is fused ring represented by ring D and ring D', and ring D' is a saturated or an unsaturated 5-membered ring forming a fused ring containing $D_1$, $D_2$ and $D_7$ with ring D, and $D_1$' and $D_2$' represent independently C, CH, $CH_2$, N, NH or S. More preferably, $D_1$' and $D_2$' represent independently C, CH, $CH_2$, N or NH.

More preferably, in the compound represented by Formula (iv), (v), (vi), (x), (xi) or (xii) of the present invention, ring D and ring D' jointly represents indole, indolizine, imidazopyridine, indoline or benzothiophene, still more preferably indole, indolizine, imidazopyridine or indoline.

In the compound represented by Formula A-L1-L2-G-J of the present invention, L2 represents a linker, and more preferably a combination of a substituted or unsubstituted single ring or a substituted or unsubstituted fused ring with —$NR_1$—, more preferably

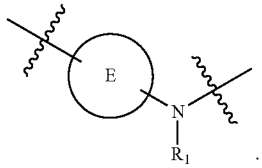

.

In the compound represented by Formula (i) or (vii) of the present invention, E represents a ring system, and more preferably a ring system selected from a substituted or unsubstituted single ring or a substituted or unsubstituted fused ring.

More preferably, in the compound represented by any of Formulae (i) to (xii) of the present invention, E represents 6-membered ring, more preferably a substituted or unsubstituted C6-C10 aromatic hydrocarbon, a substituted or unsubstituted 4- to 10-membered partially saturated heterocyclic group, or a substituted or unsubstituted 4- to 10-membered unsaturated heterocyclic group.

More preferably, in the compound represented by any of Formulae (ii) to (vi) and (viii) to (xii) of the present invention, $E_1$, $E_2$, $E_3$, $E_4$ in E represent independently C, CH, $CH_2$, N or NH, and E is a saturated or unsaturated 6-membered ring.

More preferably, in the compound represented by any of Formulae (i) to (xii) of the present invention, E represents phenyl, pyridinyl, pyrimidinyl, pyridazinyl, pyrazinyl or triazinyl, and preferably phenyl or pyridinyl.

In one embodiment, in the compound represented by Formula (ii), (iv), (v), (vi), (viii), (x), (xi) or (xii) of the present invention, m represents an integer of 0 to 4 and more preferably 0, 1 or 2, and more preferably 1.

In one embodiment, in the compound represented by Formula (iii), (iv), (v), (ix), (x), (xi) or (xii) of the present invention, n represents an integer of 0 to 5 and more preferably 1, 2 or 3, and more preferably 1.

In one embodiment, in the compound represented by Formula (iii), (iv), (v), (ix), (x), (xi) or (xii) of the present invention, p represents 0, 1 or 2

In one embodiment, in the compound represented by Formula (iv), (v), (vi), (x), (xi) or (xii) of the present invention, q represents 0, 1 or 2 and more preferably 0.

In one embodiment, in the compound represented by Formula (iv), (v), (vi), (x), (xi) or (xii) of the present invention, r represents 0, 1 or 2 and more preferably 0.

In one embodiment, in the compound represented by Formula A-L1-L2-G-J of the present invention, G represents an electrophilic chemical moiety capable of forming a covalent bond with cysteine 12 of GTP-bound KRAS G12C and more preferably

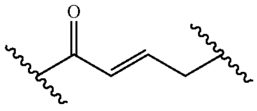

or

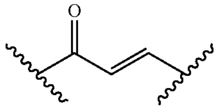

.

In one embodiment, in the compound represented by Formula A-L1-L2-G-J of the present invention, J represents a chemical moiety capable of interacting with GTP and more preferably

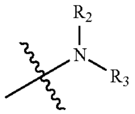

or

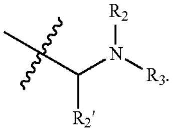

In one embodiment, in the compound represented by Formula (i) of the present invention, A is selected from:

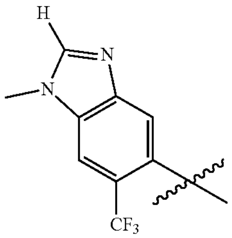

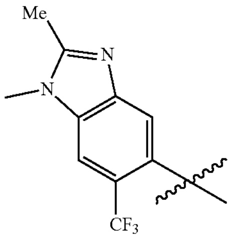

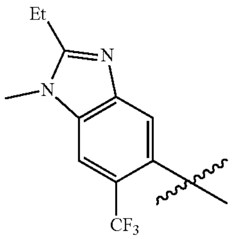

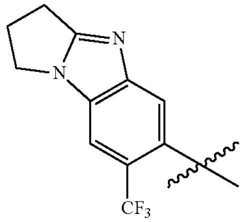

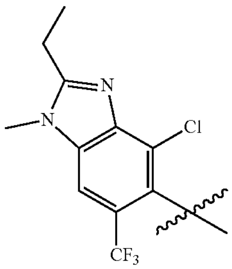

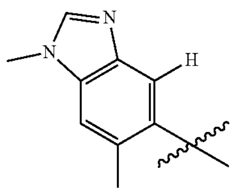

-continued

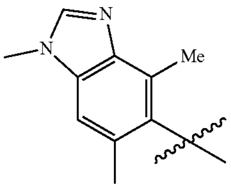

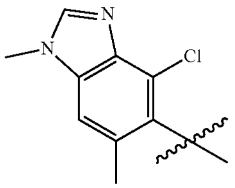

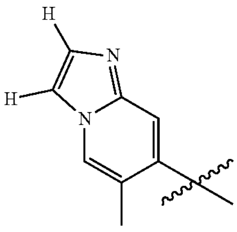

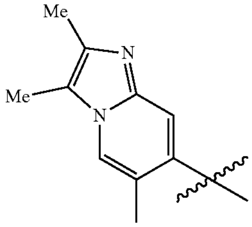

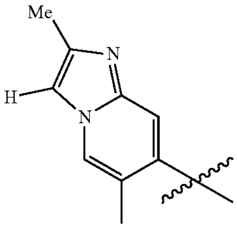

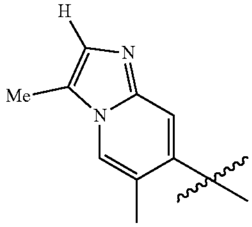

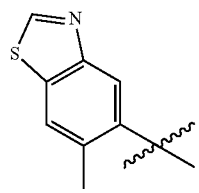

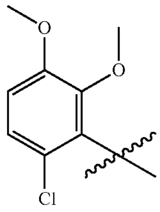

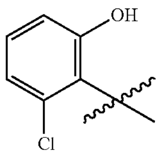

.

In one embodiment, in the compound represented by Formula (i) of the present invention, D is selected from:

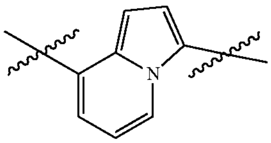

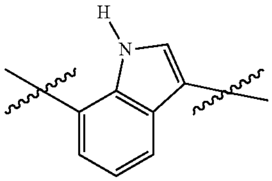

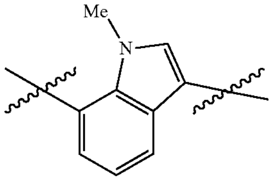

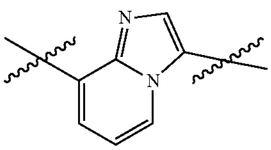

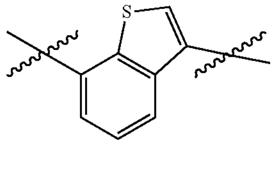

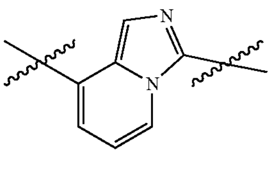

-continued

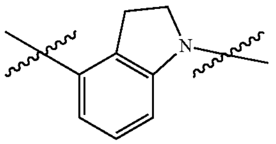
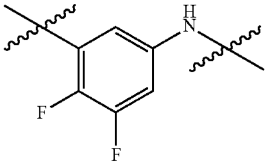
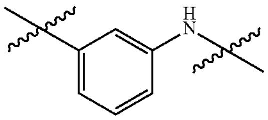
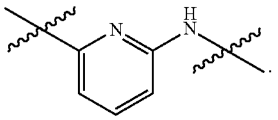

In one embodiment, in the compound represented by Formula (i) of the present invention, E is selected from:

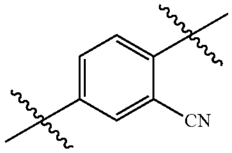
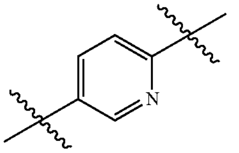
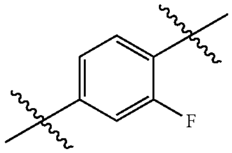
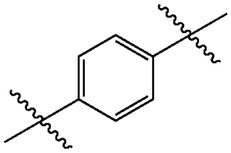
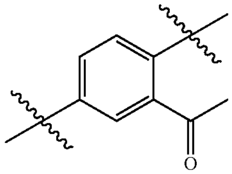
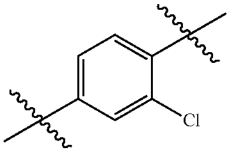
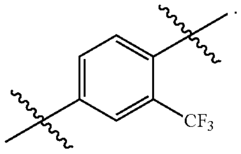

In one embodiment, in the compound represented by Formula (i) of the present invention, —$NR_2R_3$ is selected from:

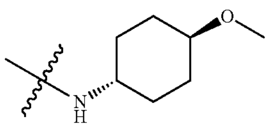
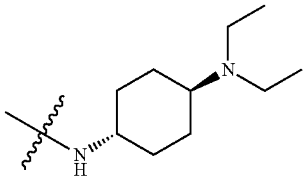
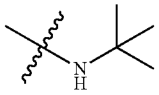
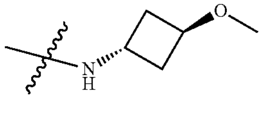
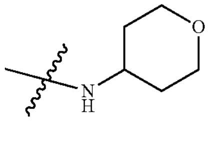

-continued

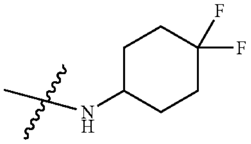
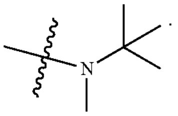

Embodiment A

In one embodiment, the compound represented by Formula (iv) or a pharmaceutically acceptable salt thereof is provided, where when A is a single ring, A' and A" are absent, and the single ring is represented by ring A, which is an unsaturated 6-membered ring which is unsubstituted or substituted with $R_5$, wherein $A_1$, $A_2$, $A_3$, $A_4$ and $A_5$ represent independently C, CH, $CH_2$, N or NH;

when A is a fused ring, the fused ring is represented by ring A and ring A' or ring A and ring A", wherein ring A is an unsaturated 6-membered ring which is unsubstituted or substituted with $R_5$, wherein $A_1$, $A_2$, $A_3$, $A_4$ and $A_5$ represent independently C, CH, $CH_2$, N or NH, and ring A' or A" is a saturated or unsaturated ring which is unsubstituted or substituted with $R_6$ and forms a fused ring with ring A containing $A_3$ and $A_4$ or $A_4$ and $A_5$;

when D is a single ring, D' is absent, and the single ring is represented by ring D, which is an unsaturated 6-membered ring which is unsubstituted or substituted with $R_7$, wherein $D_1$ represents N or NH, and $D_2$, $D_3$, $D_4$, $D_5$, $D_6$ and $D_7$ represent independently C, CH, $CH_2$, N or NH;

when D is a fused ring, the fused ring is represented by ring D and ring D', wherein ring D is an unsaturated 6-membered ring which is unsubstituted or substituted with $R_7$, wherein $D_1$, $D_2$, $D_3$, $D_4$, $D_5$, $D_6$ and $D_7$ represent independently C, CH, $CH_2$, N or NH, and ring D' is a saturated or unsaturated ring which is unsubstituted or substituted with $R_8$ and forms a fused ring with ring D containing $D_1$, $D_2$ and $D_7$; E is an unsaturated 6-membered ring which is unsubstituted or substituted with $R_4$, wherein $E_1$, $E_2$, $E_3$ and $E_4$ represent independently C, CH, $CH_2$, N or NH;

$R_1$ is hydrogen or substituted or unsubstituted C1-C6 alkyl;

$R_2$ and $R_3$ may join together to form a 4- to 10-membered saturated heterocyclic ring which is unsubstituted or substituted with 1-2 substituents independently represented by Ra; or $R_2$ and $R_3$ may be independently represented, and $R_2$ is hydrogen; or C1-C10 alkyl, C2-C10 or C2-C6 alkenyl, C2-C10 or C2-C6 alkynyl, C3-C10 cycloalkyl, C1-C10 alkoxy, C6-C10 aromatic hydrocarbon, a 4- to 10-membered saturated heterocyclic group, a 4- to 10-membered partially saturated heterocyclic group or a 4- to 10-membered unsaturated heterocyclic group, each of which is unsubstituted or substituted with 1-2 substituents independently represented by Ra;

$R_3$ is hydrogen or C1-C6 alkyl which is unsubstituted or substituted with 1-2 substituents independently represented by Ra;

$R_4$ is halogen, cyano, hydroxy, substituted or unsubstituted C1-C10 or C1-C6 alkyl, substituted or unsubstituted C2-C10 or C2-C6 alkenyl, substituted or unsubstituted C2-C10 or C2-C6 alkynyl, substituted or unsubstituted C3-C10 cycloalkyl, substituted or unsubstituted C1-C10 haloalkyl, substituted or unsubstituted C1-C10 alkoxy, substituted or unsubstituted C1-C10 acyl, substituted or unsubstituted C1-C10 alkoxycarbonyl or substituted or unsubstituted C1-C10 alkylsulfonyl; $R_5$ is halogen, cyano, amino, hydroxy, substituted or unsubstituted C1-C10 alkyl, substituted or unsubstituted C2-C6 alkenyl, substituted or unsubstituted C2-C6 alkynyl, substituted or unsubstituted C1-C6 haloalkyl, substituted or unsubstituted C1-C10 alkoxy, substituted or unsubstituted C1-C10 acyl, substituted or unsubstituted C1-C10 alkoxycarbonyl, or substituted or unsubstituted C1-C10 alkylsulfonyl; two $R_6$ may join together to form a C3-C10 hydrocarbon ring or a 4- to 10-membered saturated heterocyclic ring sharing two adjacent atoms with ring A' or ring A" when the number of $R_6$ is two or more;

$R_6$ may independently represents halogen, cyano, amino, hydroxy, substituted or unsubstituted C1-C10 alkyl, substituted or unsubstituted C2-C6 alkenyl, substituted or unsubstituted C2-C6 alkynyl, substituted or unsubstituted C1-C6 haloalkyl, substituted or unsubstituted C1-C10 alkoxy, substituted or unsubstituted C1-C10 acyl, substituted or unsubstituted C1-C10 alkoxycarbonyl or substituted or unsubstituted C1-C10 alkylsulfonyl;

$R_7$ is halogen, cyano, hydroxy, amino, carboxamide, substituted or unsubstituted C1-C10 alkyl, substituted or unsubstituted C2-C6 alkenyl, substituted or unsubstituted C2-C6 alkynyl, substituted or unsubstituted C1-C10 or C1-C6 haloalkyl, substituted or unsubstituted C1-C10 alkoxy, substituted or unsubstituted C1-C10 acyl, substituted or unsubstituted C1-C10 alkoxycarbonyl or substituted or unsubstituted C1-C10 alkylsulfonyl;

$R_8$ is halogen or substituted or unsubstituted C1-C10 alkyl;

Ra represents independently halogen, hydroxy, substituted or unsubstituted C1-C10 alkyl, substituted or unsubstituted C2-C6 alkenyl, substituted or unsubstituted C2-C6 alkynyl, substituted or unsubstituted C3-C10 cycloalkyl, substituted or unsubstituted C1-C10 haloalkyl, substituted or unsubstituted C1-C10 monoalkylamino, substituted or unsubstituted C1-C10 dialkylamino, substituted or unsubstituted C1-C10 alkoxy, substituted or unsubstituted C1-C10 haloalkoxy, substituted or unsubstituted C1-C10 alkylsulfonyl, substituted or unsubstituted C1-C10 acyl, substituted or unsubstituted C1-C10 alkoxycarbonyl or a substituted or unsubstituted 4- to 10-membered saturated heterocyclic group;

m is an integer of 0 to 4;

n is an integer of 0 to 5; and p, q and r represent independently 0, 1, or 2.

In a preferred embodiment, the compound represented by Formula (iv) or a pharmaceutically acceptable salt thereof is provided, where when A is a single ring, A' and A" are absent, and the single ring is represented by ring A, which is an unsaturated 6-membered ring which is unsubstituted or substituted with $R_5$, wherein $A_1$ and $A_5$ represent C, CH, or $CH_2$, and $A_2$, $A_3$ and $A_4$ represent independently C, CH, $CH_2$, N or NH;

when A is a fused ring, the fused ring is represented by ring A and ring A' or ring A and ring A", wherein ring A is an unsaturated 6-membered ring which is unsubstituted or substituted with $R_5$, wherein $A_1$ and $A_5$ represent C, CH, or $CH_2$, and $A_2$, $A_3$ and $A_4$ represent independently C, CH, $CH_2$, N or NH, and ring A' or A" is a saturated or unsaturated ring which is unsubstituted or substituted with $R_6$ and forms a fused ring with ring A containing $A_3$ and $A_4$ or $A_4$ and $A_5$; when D is a single ring, D' is absent, and the single ring is represented by ring D, which is an unsaturated 6-membered ring which is unsubstituted or substituted with $R_7$, wherein $D_1$ represents N or NH, $D_6$ represents C, CH, or $CH_2$, and $D_2$, $D_3$, $D_4$, $D_5$ and $D_7$ represent independently C, CH, $CH_2$, N or NH;

when D is a fused ring, the fused ring is represented by ring D and ring D', wherein ring D is an unsaturated 6-membered ring which is unsubstituted or substituted with $R_7$, wherein $D_1$, $D_2$, $D_3$, $D_4$, $D_5$, $D_6$ and $D_7$ represent independently C, CH, $CH_2$, N or NH, and ring D' is a saturated or unsaturated ring which is unsubstituted or substituted with $R_8$ and forms a fused ring with ring D containing $D_1$, $D_2$ and $D_7$; E is an unsaturated 6-membered ring which is unsubstituted or substituted with $R_4$, wherein $E_1$, $E_2$, $E_3$ and $E_4$ represent independently C, CH, $CH_2$, N or NH;

$R_1$ is hydrogen;

$R_2$ and $R_3$ are independently represented, and $R_2$ is hydrogen; or C1-C10 alkyl, C2-C10 or C2-C6 alkenyl, C2-C10 or C2-C6 alkynyl, C3-C10 cycloalkyl, C1-C10 alkoxy, C6-C10 aromatic hydrocarbon, a 4- to 10-membered saturated heterocyclic group, a 4- to 10-membered partially saturated heterocyclic group or a 4- to 10-membered unsaturated heterocyclic group, each of which is unsubstituted or substituted with 1-2 substituents independently represented by Ra;

$R_3$ is hydrogen or C1-C6 alkyl which is unsubstituted or substituted with 1-2 substituents independently represented by Ra;

$R_4$ is halogen, cyano, hydroxy, substituted or unsubstituted C1-C10 or C1-C6 alkyl, substituted or unsubstituted C2-C10 or C2-C6 alkenyl, substituted or unsubstituted C2-C10 or C2-C6 alkynyl, substituted or unsubstituted C3-C10 cycloalkyl, substituted or unsubstituted C1-C10 haloalkyl, substituted or unsubstituted C1-C10 alkoxy, substituted or unsubstituted C1-C10 acyl, substituted or unsubstituted C1-C10 alkoxycarbonyl or substituted or unsubstituted C1-C10 alkylsulfonyl; $R_5$ is halogen, cyano, amino, hydroxy, substituted or unsubstituted C1-C10 alkyl, substituted or unsubstituted C2-C6 alkenyl, substituted or unsubstituted C2-C6 alkynyl, substituted or unsubstituted C1-C6 haloalkyl, substituted or unsubstituted C1-C10 alkoxy, substituted or unsubstituted C1-C10 acyl, substituted or unsubstituted C1-C10 alkoxycarbonyl, or substituted or unsubstituted C1-C10 alkylsulfonyl; two $R_6$ may join together to form a C3-C10 hydrocarbon ring or a 4- to 10-membered saturated heterocyclic ring sharing two adjacent atoms with ring A' or ring A" when the number of $R_6$ is two or more;

$R_6$ may independently represent halogen, cyano, amino, hydroxy, substituted or unsubstituted C1-C10 alkyl, substituted or unsubstituted C2-C6 alkenyl, substituted or unsubstituted C2-C6 alkynyl, substituted or unsubstituted C1-C6 haloalkyl, substituted or unsubstituted C1-C10 alkoxy, substituted or unsubstituted C1-C10 acyl, substituted or unsubstituted C1-C10 alkoxycarbonyl or substituted or unsubstituted C1-C10 alkylsulfonyl;

$R_7$ is halogen, cyano, hydroxy, amino, carboxamide, substituted or unsubstituted C1-C10 alkyl, substituted or unsubstituted C2-C6 alkenyl, substituted or unsubstituted C2-C6 alkynyl, substituted or unsubstituted C1-C10 or C1-C6 haloalkyl, substituted or unsubstituted C1-C10 alkoxy, substituted or unsubstituted C1-C10 acyl, substituted or unsubstituted C1-C10 alkoxycarbonyl or substituted or unsubstituted C1-C10 alkylsulfonyl;

$R_8$ is halogen or substituted or unsubstituted C1-C10 alkyl;

Ra represents independently halogen, hydroxy, substituted or unsubstituted C1-C10 alkyl, substituted or unsubstituted C2-C6 alkenyl, substituted or unsubstituted C2-C6 alkynyl, substituted or unsubstituted C3-C10 cycloalkyl, substituted or unsubstituted C1-C10 haloalkyl, substituted or unsubstituted C1-C10 monoalkylamino, substituted or unsubstituted C1-C10 dialkylamino, substituted or unsubstituted C1-C10 alkoxy, substituted or unsubstituted C1-C10 haloalkoxy, substituted or unsubstituted C1-C10 alkylsulfonyl, substituted or unsubstituted C1-C10 acyl, substituted or unsubstituted C1-C10 alkoxycarbonyl or a substituted or unsubstituted 4- to 10-membered saturated heterocyclic group;

m is an integer of 0 to 3;

n is an integer of 0 to 4; and p, q and r represent independently 0, 1, or 2.

In a more preferred embodiment, the compound represented by Formula (iv) or a pharmaceutically acceptable salt thereof is provided, where A is a fused ring, and the fused ring is represented by ring A and ring A' or ring A and ring A", wherein ring A is an unsaturated 6-membered ring which is unsubstituted or substituted with $R_5$, wherein $A_1$ and $A_5$ represent C, CH, or $CH_2$, and $A_2$, $A_3$ and $A_4$ represent independently C, CH, $CH_2$, N or NH, and ring A' or A" is an unsaturated 5-membered ring which is unsubstituted or substituted with $R_6$ and forms a fused ring with ring A containing $A_3$ and $A_4$ or $A_4$ and $A_5$, and $A_1'$, $A_2'$ and $A_3'$ represent independently C, CH, $CH_2$, N, NH, O or S;

when D is a single ring, D' is absent, and the single ring is represented by ring D, which is an unsaturated 6-membered ring which is unsubstituted or substituted with $R_7$, wherein $D_1$ represents N or NH, $D_6$ represents C, CH, or $CH_2$, and $D_2$, $D_3$, $D_4$, $D_5$ and $D_7$ represent independently C, CH, $CH_2$, N or NH;

when D is a fused ring, the fused ring is represented by ring D and ring D', wherein ring D is an unsaturated 6-membered ring which is unsubstituted or substituted with $R_7$, wherein $D_1$, $D_2$, $D_3$, $D_4$, $D_5$, $D_6$ and $D_7$ represent independently C, CH, $CH_2$, N or NH, and ring D' is a saturated or unsaturated ring which is unsubstituted or substituted with $R_8$ and forms a fused ring with ring D containing $D_1$, $D_2$ and $D_7$; E is an unsaturated 6-membered ring which is unsubstituted or substituted with $R_4$, wherein $E_1$, $E_2$, $E_3$ and $E_4$ represent independently C, CH, $CH_2$, N or NH;

$R_1$ is hydrogen;

$R_2$ and $R_3$ are independently represented, and $R_2$ is C1-C10 alkyl, C3-C10 cycloalkyl or a 4- to 10-membered saturated heterocyclic group, each of which is unsubstituted or substituted with 1-2 substituents independently represented by Ra;

$R_3$ is hydrogen or C1-C6 alkyl which is unsubstituted or substituted with 1-2 substituents independently represented by Ra;

$R_4$ is halogen, cyano or substituted or unsubstituted C1-C10 alkyl;

$R_5$ is halogen, substituted or unsubstituted C1-C10 alkyl, substituted or unsubstituted C1-C6 haloalkyl or substituted or unsubstituted C1-C10 alkoxy;

two $R_6$ may join together to form a C3-C10 hydrocarbon ring or a 4- to 10-membered saturated heterocyclic ring sharing two adjacent atoms with ring A' or ring A" when the number of $R_6$ is two or more;

$R_6$ may independently represent halogen, cyano, amino, hydroxy, substituted or unsubstituted C1-C10 alkyl, substituted or unsubstituted C1-C6 haloalkyl or substituted or unsubstituted C1-C10 alkoxy;

$R_7$ is halogen;

$R_8$ is halogen or substituted or unsubstituted C1-C10 alkyl;

Ra represents independently halogen, hydroxy, substituted or unsubstituted C1-C10 monoalkylamino, substituted or unsubstituted C1-C10 dialkylamino, substituted or unsubstituted C1-C10 alkoxy or substituted or unsubstituted C1-C10 alkylsulfonyl;

m is an integer of 0 to 2;

n is an integer of 0 to 3; and p, q and r represent independently 0, 1, or 2.

In a still more preferred embodiment, the compound represented by Formula (iv) or a pharmaceutically acceptable salt thereof is provided, where A is a fused ring, and the fused ring is represented by ring A and ring A' or ring A and ring A", wherein ring A is an unsaturated 6-membered ring which is unsubstituted or substituted with $R_5$, wherein $A_1$, $A_2$ and $A_5$ represent C, CH, or $CH_2$, and $A_3$ and $A_4$ represent independently C, CH, $CH_2$, N or NH, and ring A' or A" is an unsaturated 5-membered ring which is unsubstituted or substituted with $R_6$ and forms a fused ring with ring A containing $A_3$ and $A_4$ or $A_4$ and $A_5$, and $A_1'$ and $A_3'$ represent independently C, CH, $CH_2$, N, NH, O or S, and $A_2'$ represents C;

when D is a single ring, D' is absent, and the single ring is represented by ring D, which is an unsaturated 6-membered ring which is unsubstituted or substituted with $R_7$, wherein $D_1$ represents N or NH, $D_6$ represents C, CH, or $CH_2$, and $D_2$, $D_3$, $D_4$, $D_5$ and $D_7$ represent independently C, CH, $CH_2$, N or NH;

when D is a fused ring, the fused ring is represented by ring D and ring D', wherein ring D is an unsaturated 6-membered ring which is unsubstituted or substituted with $R_7$, wherein $D_1$, $D_2$, $D_3$, $D_4$, $D_5$, $D_6$ and $D_7$ represent independently C, CH, $CH_2$, N or NH, and ring D' is a saturated or unsaturated ring which is unsubstituted or substituted with $R_8$ and forms a fused ring with ring D containing $D_1$, $D_2$ and $D_7$;

E is an unsaturated 6-membered ring which is unsubstituted or substituted with $R_4$, wherein $E_1$, $E_2$, $E_3$ and $E_4$ represent independently C, CH, $CH_2$, N or NH;

$R_1$ is hydrogen;

$R_2$ and $R_3$ are independently represented, and $R_2$ is C3-C10 cycloalkyl or a 4- to 10-membered saturated heterocyclic group, each of which is unsubstituted or substituted with 1-2 substituents independently represented by Ra;

$R_3$ is hydrogen;

$R_4$ is halogen, cyano or substituted or unsubstituted C1-C10 alkyl;

$R_5$ is halogen, substituted or unsubstituted C1-C10 alkyl, substituted or unsubstituted C1-C6 haloalkyl or substituted or unsubstituted C1-C10 alkoxy;

two $R_6$ may join together to form a C3-C10 hydrocarbon ring or a 4- to 10-membered saturated heterocyclic ring sharing two adjacent atoms with ring A' or ring A" when the number of $R_6$ is two or more;

$R_6$ may independently represent substituted or unsubstituted C1-C10 alkyl, substituted or unsubstituted C1-C6 haloalkyl or substituted or unsubstituted C1-C10 alkoxy;

$R_7$ is halogen;

$R_8$ is halogen or substituted or unsubstituted C1-C6 alkyl;

Ra represents independently halogen, hydroxy, substituted or unsubstituted C1-C10 monoalkylamino, substituted or unsubstituted C1-C10 dialkylamino, substituted or unsubstituted C1-C10 alkoxy or substituted or unsubstituted C1-C10 alkylsulfonyl;

m is an integer of 0 to 1;

n is an integer of 0 to 2; and p, q and r represent independently 0, 1, or 2.

In a most preferred embodiment, the compound represented by Formula (iv) or a pharmaceutically acceptable salt thereof is provided, where A is a fused ring, and the fused ring is represented by ring A and ring A' or ring A and ring A", wherein ring A is an unsaturated 6-membered ring which is unsubstituted or substituted with $R_5$, wherein $A_1$, $A_2$ and $A_5$ represent C, CH, or $CH_2$, and $A_3$ and $A_4$ represent independently C, CH, $CH_2$, N or NH, and ring A' or A" is an unsaturated 5-membered ring which is unsubstituted or substituted with $R_6$ and forms a fused ring with ring A containing $A_3$ and $A_4$ or $A_4$ and $A_5$, and $A_1$' and $A_3$' represent independently C, CH, $CH_2$, N, NH, O or S, and $A_2$' represents C;

D is a fused ring, and the fused ring is represented by ring D and ring D', wherein ring D is an unsaturated 6-membered ring which is unsubstituted or substituted with $R_7$, wherein $D_1$, $D_2$, $D_3$, $D_4$, $D_5$, $D_6$ and $D_7$ represent independently C, CH, $CH_2$, N or NH, and ring D' is a saturated or unsaturated 5-membered ring which is unsubstituted or substituted with $R_8$ and forms a fused ring with ring D containing $D_1$, $D_2$ and $D_7$ and $D_1$' and $D_2$' represent independently C, CH, $CH_2$, N, NH or S;

E is an unsaturated 6-membered ring which is unsubstituted or substituted with $R_4$, wherein $E_1$, $E_2$, $E_3$ and $E_4$ represent independently C, CH, $CH_2$, N or NH;

$R_1$ is hydrogen; $R_2$ and $R_3$ are independently represented, and $R_2$ is C3-C10 cycloalkyl or a 4- to 10-membered saturated heterocyclic group, each of which is unsubstituted or substituted with 1-2 substituents independently represented by Ra; $R_3$ is hydrogen;

$R_4$ is halogen, cyano or substituted or unsubstituted C1-C10 alkyl;

$R_5$ is halogen, substituted or unsubstituted C1-C10 alkyl, substituted or unsubstituted C1-C6 haloalkyl or substituted or unsubstituted C1-C10 alkoxy;

two $R_6$ may join together to form a C3-C10 hydrocarbon ring or a 4- to 10-membered saturated heterocyclic ring sharing two adjacent atoms with ring A' or ring A" when the number of $R_6$ is two or more;

$R_6$ may independently represents substituted or unsubstituted C1-C10 alkyl, substituted or unsubstituted C1-C6 haloalkyl or substituted or unsubstituted C1-C10 alkoxy;

$R_7$ is halogen;

$R_8$ is halogen or substituted or unsubstituted C1-C6 alkyl; the number of Ra is one or two and each Ra represents independently halogen, hydroxy, substituted or unsubstituted C1-C10 monoalkylamino, substituted or unsubstituted C1-C10 dialkylamino, substituted or unsubstituted C1-C10 alkoxy or substituted or unsubstituted C1-C10 alkylsulfonyl;

m is an integer of 0 to 1;

n is an integer of 0 to 2; and p, q and r represent independently 0, 1, or 2.

In one embodiment, the compound represented by Formula (x) or a pharmaceutically acceptable salt thereof is provided, where when A is a single ring, A' and A" are absent, and the single ring is represented by ring A, which is an unsaturated 6-membered ring which is unsubstituted or substituted with $R_5$, wherein $A_1$, $A_2$, $A_3$, $A_4$ and $A_5$ represent independently C, CH, $CH_2$, N or NH;

when A is a fused ring, the fused ring is represented by ring A and ring A' or ring A and ring A", wherein ring A is an unsaturated 6-membered ring which is unsubstituted or substituted with $R_5$, wherein $A_1$, $A_2$, $A_3$, $A_4$ and $A_5$ represent independently C, CH, $CH_2$, N or NH, and ring A' or A" is a saturated or unsaturated ring which is unsubstituted or substituted with $R_6$ and forms a fused ring with ring A containing $A_3$ and $A_4$ or $A_4$ and $A_5$;

when D is a single ring, D' is absent, and the single ring is represented by ring D, which is an unsaturated 6-membered ring which is unsubstituted or substituted with $R_7$, wherein $D_1$ represents N or NH, and $D_2$, $D_3$, $D_4$, $D_5$, $D_6$ and $D_7$ represent independently C, CH, $CH_2$, N or NH;

when D is a fused ring, the fused ring is represented by ring D and ring D', wherein ring D is an unsaturated 6-membered ring which is unsubstituted or substituted with $R_7$, wherein $D_1$, $D_2$, $D_3$, $D_4$, $D_5$, $D_6$ and $D_7$ represent independently C, CH, $CH_2$, N or NH, and ring D' is a saturated or unsaturated ring which is unsubstituted or substituted with $R_8$ and forms a fused ring with ring D containing $D_1$, $D_2$ and $D_7$; E is an unsaturated 6-membered ring which is unsubstituted or substituted with $R_4$, wherein $E_1$, $E_2$, $E_3$ and $E_4$ represent independently C, CH, $CH_2$, N or NH;

$R_1$ is hydrogen or substituted or unsubstituted C1-C6 alkyl;

$R_2$ and $R_3$ or $R_2$ and $R_2$' may join together to form a 4- to 10-membered saturated heterocyclic ring which is unsubstituted or substituted with 1-2 substituents independently represented by Ra; or $R_2$, $R_2$' and $R_3$ may be independently represented, and $R_2$ is hydrogen; or C1-C10 alkyl, C2-C10 or C2-C6 alkenyl, C2-C10 or C2-C6 alkynyl, C3-C10 cycloalkyl, C1-C10 alkoxy, C6-C10 aromatic hydrocarbon, a 4- to 10-membered saturated heterocyclic group, a 4- to 10-membered partially saturated heterocyclic group or a 4- to 10-membered unsaturated heterocyclic group, each of which is unsubstituted or substituted with 1-2 substituents independently represented by Ra;

$R_2$' is hydrogen or C1-C6 alkyl which is unsubstituted or substituted with 1-2 substituents independently represented by Ra; and $R_3$ is hydrogen or C1-C6 alkyl which is unsubstituted or substituted with 1-2 substituents independently represented by Ra;

$R_4$ is halogen, cyano, hydroxy, substituted or unsubstituted C1-C10 or C1-C6 alkyl, substituted or unsubstituted C2-C10 or C2-C6 alkenyl, substituted or unsubstituted C2-C10 or C2-C6 alkynyl, substituted or unsubstituted C3-C10 cycloalkyl, substituted or unsubstituted C1-C10 haloalkyl, substituted or unsubstituted C1-C10 alkoxy, substituted or unsubstituted C1-C10 acyl, substituted or unsubstituted C1-C10 alkoxycarbonyl or substituted or unsubstituted C1-C10 alkylsulfonyl;

$R_5$ is halogen, cyano, amino, hydroxy, substituted or unsubstituted C1-C10 alkyl, substituted or unsubstituted C2-C6 alkenyl, substituted or unsubstituted C2-C6 alkynyl, substituted or unsubstituted C1-C6 haloalkyl, substituted or unsubstituted C1-C10 alkoxy, substituted or unsubstituted C1-C10 acyl, substituted or unsubstituted C1-C10 alkoxycarbonyl, or substituted or unsubstituted C1-C10 alkylsulfonyl; two $R_6$ may join together to form a C3-C10 hydrocarbon ring or a 4- to 10-membered saturated heterocyclic ring sharing two adjacent atoms 5 with ring A' or ring A" when the number of $R_6$ is two or more;

$R_6$ may independently represents halogen, cyano, amino, hydroxy, substituted or unsubstituted C1-C10 alkyl, substituted or unsubstituted C2-C6 alkenyl, substituted or unsubstituted C2-C6 alkynyl, substituted or unsubstituted C1-C6 haloalkyl, substituted or unsubstituted C1-C10 alkoxy, substituted or unsubstituted C1-C10 acyl, substituted or unsubstituted C1-C10 alkoxycarbonyl or substituted or unsubstituted C1-C10 alkylsulfonyl;

$R_7$ is halogen, cyano, hydroxy, amino, carboxamide, substituted or unsubstituted C1-C10 alkyl, substituted or unsubstituted C2-C6 alkenyl, substituted or unsubstituted C2-C6 alkynyl, substituted or unsubstituted C1-C10 or C1-C6 haloalkyl, substituted or unsubstituted C1-C10 alkoxy, substituted or unsubstituted C1-C10 acyl, substituted or unsubstituted C1-C10 alkoxycarbonyl or substituted or unsubstituted C1-C10 alkylsulfonyl;

$R_8$ is halogen or substituted or unsubstituted C1-C10 alkyl;

Ra represents independently halogen, hydroxy, substituted or unsubstituted C1-C10 alkyl, substituted or unsubstituted C2-C6 alkenyl, substituted or unsubstituted C2-C6 alkynyl, substituted or unsubstituted C3-C10 cycloalkyl, substituted or unsubstituted C1-C10 haloalkyl, substituted or unsubstituted C1-C10 monoalkylamino, substituted or unsubstituted C1-C10 dialkylamino, substituted or unsubstituted C1-C10 alkoxy, substituted or unsubstituted C1-C10 haloalkoxy, substituted or unsubstituted C1-C10 alkylsulfonyl, substituted or unsubstituted C1-C10 acyl, substituted or unsubstituted C1-C10 alkoxycarbonyl or a substituted or unsubstituted 4- to 10-membered saturated heterocyclic group;

m is an integer of 0 to 4:

n is an integer of 0 to 5; and p, q and r represent independently 0, 1, or 2.

In a preferred embodiment, the compound represented by Formula (x) or a pharmaceutically acceptable salt thereof is provided, where when A is a single ring, A' and A" are absent, and the single ring is represented by ring A, which is an unsaturated 6-membered ring which is unsubstituted or substituted with $R_5$, wherein $A_1$ and $A_5$ represent C, CH, or $CH_2$, and $A_2$, $A_3$ and $A_4$ represent independently C, CH, $CH_2$, N or NH;

when A is a fused ring, the fused ring is represented by ring A and ring A' or ring A and ring A", wherein ring A is an unsaturated 6-membered ring which is unsubstituted or substituted with $R_5$, wherein $A_1$ and $A_5$ represent C, CH, or $CH_2$, and $A_2$, $A_3$ and $A_4$ represent independently C, CH, $CH_2$, N or NH, and ring A' or A" is a saturated or unsaturated ring which is unsubstituted or substituted with $R_6$ and forms a fused ring with ring A containing $A_3$ and $A_4$ or $A_4$ and $A_5$;

when D is a single ring, D' is absent, and the single ring is represented by ring D, which is an unsaturated 6-membered ring which is unsubstituted or substituted with $R_7$, wherein $D_1$ represents N or NH, $D_6$ represents C, CH, or $CH_2$, and $D_2$, $D_3$, $D_4$, $D_5$ and $D_7$ represent independently C, CH, $CH_2$, N or NH;

when D is a fused ring, the fused ring is represented by ring D and ring D', wherein ring D is an unsaturated 6-membered ring which is unsubstituted or substituted with $R_7$, wherein $D_1$, $D_2$, $D_3$, $D_4$, $D_5$, $D_6$ and $D_7$ represent independently C, CH, $CH_2$, N or NH, and ring D' is a saturated or unsaturated ring which is unsubstituted or substituted with $R_8$ and forms a fused ring with ring D containing $D_1$, $D_2$ and $D_7$;

E is an unsaturated 6-membered ring which is unsubstituted or substituted with $R_4$, wherein $E_1$, $E_2$, $E_3$ and $E_4$ represent independently C, CH, $CH_2$, N or NH;

$R_1$ is hydrogen;

$R_2$ and $R_2'$ may join together to form a 4- to 10-membered saturated heterocyclic ring which is unsubstituted or substituted with 1-2 substituents independently represented by Ra; or $R_2$, $R_2'$ and $R_3$ are independently represented, and $R_2$ is hydrogen; or C1-C10 alkyl, C2-C10 or C2-C6 alkenyl, C2-C10 or C2-C6 alkynyl, C3-C10 cycloalkyl, C1-C10 alkoxy, C6-C10 aromatic hydrocarbon, a 4- to 10-membered saturated heterocyclic group, a 4- to 10-membered partially saturated heterocyclic group or a 4- to 10-membered unsaturated heterocyclic group, each of which is unsubstituted or substituted with 1-2 substituents independently represented by Ra;

$R_2'$ is hydrogen or C1-C6 alkyl which is unsubstituted or substituted with 1-2 substituents independently represented by Ra; and $R_3$ is hydrogen or C1-C6 alkyl which is unsubstituted or substituted with 1-2 substituents independently represented by Ra;

$R_4$ is halogen, cyano, hydroxy, substituted or unsubstituted C1-C10 or C1-C6 alkyl, substituted or unsubstituted C2-C10 or C2-C6 alkenyl, substituted or unsubstituted C2-C10 or C2-C6 alkynyl, substituted or unsubstituted C3-C10 cycloalkyl, substituted or unsubstituted C1-C10 haloalkyl, substituted or unsubstituted C1-C10 alkoxy, substituted or unsubstituted C1-C10 acyl, substituted or unsubstituted C1-C10 alkoxycarbonyl or substituted or unsubstituted C1-C10 alkylsulfonyl;

$R_5$ is halogen, cyano, amino, hydroxy, substituted or unsubstituted C1-C10 alkyl, substituted or unsubstituted C2-C6 alkenyl, substituted or unsubstituted C2-C6 alkynyl, substituted or unsubstituted C1-C6 haloalkyl, substituted or unsubstituted C1-C10 alkoxy, substituted or unsubstituted C1-C10 acyl, substituted or unsubstituted C1-C10 alkoxycarbonyl, or substituted or unsubstituted C1-C10 alkylsulfonyl; two $R_6$ may join together to form a C3-C10 hydrocarbon ring or a 4- to 10-membered saturated heterocyclic ring sharing two adjacent atoms with ring A' or ring A" when the number of $R_6$ is two or more;

$R_6$ may independently represent halogen, cyano, amino, hydroxy, substituted or unsubstituted C1-C10 alkyl, substituted or unsubstituted C2-C6 alkenyl, substituted or unsubstituted C2-C6 alkynyl, substituted or unsubstituted C1-C6 haloalkyl, substituted or unsubstituted C1-C10 alkoxy, substituted or unsubstituted C1-C10 acyl, substituted or unsubstituted C1-C10 alkoxycarbonyl or substituted or unsubstituted C1-C10 alkylsulfonyl;

$R_7$ is halogen, cyano, hydroxy, amino, carboxamide, substituted or unsubstituted C1-C10 alkyl, substituted or unsubstituted C2-C6 alkenyl, substituted or unsubstituted C2-C6 alkynyl, substituted or unsubstituted C1-C10 or C1-C6 haloalkyl, substituted or unsubstituted C1-C10 alkoxy, substituted or unsubstituted C1-C10 acyl, substituted or unsubstituted C1-C10 alkoxycarbonyl or substituted or unsubstituted C1-C10 alkylsulfonyl;

$R_8$ is halogen or substituted or unsubstituted C1-C10 alkyl;

Ra represents independently halogen, hydroxy, substituted or unsubstituted C1-C10 alkyl, substituted or unsubstituted C2-C6 alkenyl, substituted or unsubstituted C2-C6 alkynyl, substituted or unsubstituted C3-C10 cycloalkyl, substituted or unsubstituted C1-C10 haloalkyl, substituted or unsubstituted C1-C10 monoalkylamino, substituted or unsubstituted C1-C10 dialkylamino, substituted or unsubstituted C1-C10 alkoxy, substituted or unsubstituted C1-C10 haloalkoxy, substituted or unsubstituted C1-C10 alkylsulfonyl, substituted or unsubstituted C1-C10 acyl, substituted or unsubstituted C1-C10 alkoxycarbonyl or a substituted or unsubstituted 4- to 10-membered saturated heterocyclic group;

m is an integer of 0 to 3;

n is an integer of 0 to 4; and p, q and r represent independently 0, 1, or 2.

In a more preferred embodiment, the compound represented by Formula (x) or a pharmaceutically acceptable salt thereof is provided, where A is a fused ring, and the fused ring is represented by ring A and ring A' or ring A and ring A", wherein ring A is an unsaturated 6-membered ring which is unsubstituted or substituted with $R_5$, wherein $A_1$ and $A_5$ represent C, CH, or $CH_2$, and $A_2$, $A_3$ and $A_4$ represent independently C, CH, $CH_2$, N or NH, and ring A' or A" is an unsaturated 5-membered ring which is unsubstituted or substituted with $R_6$ and forms a fused ring with ring A containing $A_3$ and $A_4$ or $A_4$ and $A_5$, and $A_1$', $A_2$' and $A_3$' represent independently C, CH, $CH_2$, N, NH, O or S;

when D is a single ring, D' is absent, and the single ring is represented by ring D, which is an unsaturated 6-membered ring which is unsubstituted or substituted with $R_7$, wherein $D_1$ represents N or NH, $D_6$ represents C, CH, or $CH_2$, and $D_2$, $D_3$, $D_4$, $D_5$ and $D_7$ represent independently C, CH, $CH_2$, N or NH;

when D is a fused ring, the fused ring is represented by ring D and ring D', wherein ring D is an unsaturated 6-membered ring which is unsubstituted or substituted with $R_7$, wherein $D_1$, $D_2$, $D_3$, $D_4$, $D_5$, $D_6$ and $D_7$ represent independently C, CH, $CH_2$, N or NH, and ring D' is a saturated or unsaturated ring which is unsubstituted or substituted with $R_8$ and forms a fused ring with ring D containing $D_1$, $D_2$ and $D_7$;

E is an unsaturated 6-membered ring which is unsubstituted or substituted with $R_4$, wherein $E_1$, $E_2$, $E_3$ and $E_4$ represent independently C, CH, $CH_2$, N or NH;

$R_1$ is hydrogen;

$R_2$ and $R_2$' join together to form a 4- to 6-membered saturated heterocyclic ring which is unsubstituted or substituted with 1-2 substituents independently represented by Ra, or $R_2$, $R_2$' and $R_3$ are independently represented, and $R_2$ is C1-C10 alkyl which is unsubstituted or substituted with Ra, C3-C10 cycloalkyl which is unsubstituted or substituted with Ra, or a 4- to 10-membered saturated heterocyclic group which is unsubstituted or substituted with Ra;

$R_2$' is hydrogen or C1-C3 alkyl;

$R_3$ is hydrogen or C1-C3 alkyl;

$R_4$ is halogen, cyano or substituted or unsubstituted C1-C10 alkyl;

$R_5$ is halogen, substituted or unsubstituted C1-C10 alkyl, substituted or unsubstituted C1-C6 haloalkyl or substituted or unsubstituted C1-C10 alkoxy;

two $R_6$ may join together to form a C3-C10 hydrocarbon ring or a 4- to 10-membered saturated heterocyclic ring sharing two adjacent atoms with ring A' or ring A" when the number of $R_6$ is two or more;

$R_6$ may independently represent halogen, cyano, amino, hydroxy, substituted or unsubstituted C1-C10 alkyl, substituted or unsubstituted C1-C6 haloalkyl or substituted or unsubstituted C1-C10 alkoxy;

$R_7$ is halogen;

$R_8$ is halogen or substituted or unsubstituted C1-C10 alkyl;

Ra represents independently halogen, hydroxy, substituted or unsubstituted C1-C10 monoalkylamino, substituted or unsubstituted C1-C10 dialkylamino, substituted or unsubstituted C1-C10 alkoxy or substituted or unsubstituted C1-C10 alkylsulfonyl;

m is an integer of 0 to 2;

n is an integer of 0 to 3; and p, q and r represent independently 0, 1, or 2.

In a still more preferred embodiment, the compound represented by Formula (x) or a pharmaceutically acceptable salt thereof is provided, where A is a fused ring, and the fused ring is represented by ring A and ring A' or ring A and ring A", wherein ring A is an unsaturated 6-membered ring which is unsubstituted or substituted with $R_5$, wherein $A_1$, $A_2$ and $A_5$ represent C, CH, or $CH_2$, and $A_3$ and $A_4$ represent independently C, CH, $CH_2$, N or NH, and ring A' or A" is an unsaturated 5-membered ring which is unsubstituted or substituted with $R_6$ and forms a fused ring with ring A containing $A_3$ and $A_4$ or $A_4$ and $A_5$, and $A_1$' and $A_3$' represent independently C, CH, $CH_2$, N, NH, O or S, and $A_2$' represents C;

when D is a single ring, D' is absent, and the single ring is represented by ring D, which is an unsaturated 6-membered ring which is unsubstituted or substituted with $R_7$, wherein $D_1$ represents N or NH, $D_6$ represents C, CH, or $CH_2$, and $D_2$, $D_3$, $D_4$, $D_5$ and $D_7$ represent independently C, CH, $CH_2$, N or NH;

when D is a fused ring, the fused ring is represented by ring D and ring D', wherein ring D is an unsaturated 6-membered ring which is unsubstituted or substituted with $R_7$, wherein $D_1$, $D_2$, $D_3$, $D_4$, $D_5$, $D_6$ and $D_7$ represent independently C, CH, $CH_2$, N or NH, and ring D' is a saturated or unsaturated ring which is unsubstituted or substituted with $R_8$ and forms a fused ring with ring D containing $D_1$, $D_2$ and $D_7$;

E is an unsaturated 6-membered ring which is unsubstituted or substituted with $R_4$, wherein $E_1$, $E_2$, $E_3$ and $E_4$ represent independently C, CH, $CH_2$, N or NH;

$R_1$ is hydrogen;

$R_2$ and $R_2$' join together to form a 4- to 6-membered saturated heterocyclic ring which is unsubstituted or substituted with 1-2 substituents independently represented by Ra, or $R_2$, $R_2$' and $R_3$ are independently represented, and $R_2$ is C3-C10 cycloalkyl or a 4- to 10-membered saturated heterocyclic group, each of which is unsubstituted or substituted with 1-2 substituents independently represented by Ra;

$R_2$' is hydrogen or C1-C3 alkyl;

$R_3$ is hydrogen;

$R_4$ is halogen, cyano or substituted or unsubstituted C1-C10 alkyl;

$R_5$ is halogen, substituted or unsubstituted C1-C10 alkyl, substituted or unsubstituted C1-C6 haloalkyl or substituted or unsubstituted C1-C10 alkoxy;

two $R_6$ may join together to form a C3-C10 hydrocarbon ring or a 4- to 10-membered saturated heterocyclic ring sharing two adjacent atoms with ring A' or ring A" when the number of $R_6$ is two or more;

$R_6$ may independently represent substituted or unsubstituted C1-C10 alkyl, substituted or unsubstituted C1-C6 haloalkyl or substituted or unsubstituted C1-C10 alkoxy;

$R_7$ is halogen;

$R_8$ is halogen or substituted or unsubstituted C1-C6 alkyl;

Ra represents independently halogen, hydroxy, substituted or unsubstituted C1-C10 monoalkylamino, substituted or unsubstituted C1-C10 dialkylamino, substituted or unsubstituted C1-C10 alkoxy or substituted or unsubstituted C1-C10 alkylsulfonyl;

m is an integer of 0 to 1;

n is an integer of 0 to 2; and p, q and r represent independently 0, 1, or 2.

In a most preferred embodiment, the compound represented by Formula (x) or a pharmaceutically acceptable salt thereof is provided, where A is a fused ring, and the fused ring is represented by ring A and ring A' or ring A and ring A", wherein ring A is an unsaturated 6-membered ring which is unsubstituted or substituted with $R_5$, wherein $A_1$, $A_2$ and $A_5$ represent C, CH, or $CH_2$, and $A_3$ and $A_4$ represent independently C, CH, $CH_2$, N or NH, and ring A' or A" is an unsaturated 5-membered ring which is unsubstituted or substituted with $R_6$ and forms a fused ring with ring A containing $A_3$ and $A_4$ or $A_4$ and $A_5$, and $A_1$' and $A_3$' represent independently C, CH, $CH_2$, N, NH, O or S, and $A_2$' represents C;

D is a fused ring, and the fused ring is represented by ring D and ring D', wherein ring D is an unsaturated 6-membered ring which is unsubstituted or substituted with $R_7$, wherein $D_1$, $D_2$, $D_3$, $D_4$, $D_5$, $D_6$ and $D_7$ represent independently C, CH, $CH_2$, N or NH, and ring D' is a saturated or unsaturated 5-membered ring which is unsubstituted or substituted with $R_8$ and forms a fused ring with ring D containing $D_1$, $D_2$ and $D_7$ and $D_1$' and $D_2$' represent independently C, CH, $CH_2$, N, NH or S;

E is an unsaturated 6-membered ring which is unsubstituted or substituted with $R_4$, wherein $E_1$, $E_2$, $E_3$ and $E_4$ represent independently C, CH, $CH_2$, N or NH;

$R_1$ is hydrogen;

$R_2$ and $R_2$' join together to form a 4- to 6-membered saturated heterocyclic ring, or $R_3$ is hydrogen;

$R_4$ is halogen, cyano or substituted or unsubstituted C1-C10 alkyl;

$R_5$ is halogen, substituted or unsubstituted C1-C10 alkyl, substituted or unsubstituted C1-C6 haloalkyl or substituted or unsubstituted C1-C10 alkoxy;

two $R_6$ may join together to form a C3-C10 hydrocarbon ring or a 4- to 10-membered saturated heterocyclic ring sharing two adjacent atoms with ring A' or ring A" when the number of $R_6$ is two or more;

$R_6$ may independently represents substituted or unsubstituted C1-C10 alkyl, substituted or unsubstituted C1-C6 haloalkyl or substituted or unsubstituted C1-C10 alkoxy;

$R_7$ is halogen;

$R_8$ is halogen or substituted or unsubstituted C1-C6 alkyl;

the number of Ra is one or two and each Ra represents independently halogen, hydroxy, substituted or unsubstituted C1-C10 monoalkylamino, substituted or unsubstituted C1-C10 dialkylamino, substituted or unsubstituted C1-C10 alkoxy or substituted or unsubstituted C1-C10 alkylsulfonyl;

m is an integer of 0 to 1;

n is an integer of 0 to 2; and p, q and r represent independently 0, 1, or 2.

In the most preferred embodiments, a compound of the invention is selected from the followings:

(1) 3-cyano-N-(3-(2-ethyl-1-methyl-6-(trifluoromethyl)-1H-benzo[d]imidazol-5-yl)phenyl)-4-((E)-4-(((1r, 4r)-4-methoxycyclohexyl)amino)but-2-enamido)benzamide (2) (E)-4-(4-(tert-butyl(methyl)amino)but-2-enamido)-3-cyano-N-(3-(2-ethyl-1-methyl-6-(trifluoromethyl)-1H-benzo[d]imidazol-5-yl)phenyl)benzamide (3) 3-cyano-4-((E)-4-(((1r,4r)-4-methoxycyclohexyl)amino)but-2-enamido)-N-(6-(7-methyl-2,3-dihydro-1H-benzo[d]pyrrolo[1,2-a]imidazol-6-yl)pyridin-2-yl)benzamide (4) (E)-N-(2-cyano-4-(8-(1,6-dimethyl-1H-benzo[d]imidazol-5-yl)indolizine-3-carbonyl)phenyl)-4-(((1r,4r)-4-methoxycyclohexyl)amino)but-2-enamide (5) (E)-4-(tert-butylamino)-N-(2-cyano-4-(8-(1,6-dimethyl-1H-benzo[d]imidazol-5-yl)indolizine-3-carbonyl)phenyl)but-2-enamide (6) (E)-N-(2-cyano-4-(8-(1-methyl-6-(trifluoromethyl)-1H-benzo[d]imidazol-5-yl)indolizine-3-carbonyl)phenyl)-4-(((1r,4r)-4-methoxycyclohexyl)amino)but-2-enamide (7) (E)-N-(2-cyano-4-(8-(1,2-dimethyl-6-(trifluoromethyl)-1H-benzo[d]imidazol-5-yl)indolizine-3-carbonyl)phenyl)-4-(((1r,4r)-4-methoxycyclohexyl)amino)but-2-enamide (8) (E)-N-(2-cyano-4-(7-(1-methyl-6-(trifluoromethyl)-1H-benzo[d]imidazol-5-yl)-1H-indole-3-carbonyl)phenyl)-4-(((1r,4r)-4-methoxycyclohexyl)amino)but-2-enamide (9) (E)-N-(2-cyano-4-(8-(1,6-dimethyl-1H-benzo[d]imidazol-5-yl)imidazo[1,2-a]pyridine-3-carbonyl)phenyl)-4-(((1r,4r)-4-methoxycyclohexyl)amino)but-2-enamide

(10) (E)-N-(2-cyano-4-(4-(2-ethyl-1-methyl-6-(trifluoromethyl)-1H-benzo[d]imidazol-5-yl)indoline-1-carbonyl)phenyl)-4-(((1r,4r)-4-methoxycyclohexyl)amino)but-2-enamide

(11) (E)-N-(6'-chloro-2',3'-dimethoxy-[1,1'-biphenyl]-3-yl)-3-cyano-4-(4-((1-(methylsulfonyl)piperidin-4-yl)amino)but-2-enamido)benzamide

(12) N-(3-(5-chloro-1-methyl-1H-indazol-4-yl)phenyl)-3-cyano-4-((E)-4-(((1r,4r)-4-(diethylamino)cyclohexyl)amino)but-2-enamido)benzamide

(13) N-(3-(6-chloro-1,2-dimethyl-1H-benzo[d]imidazol-5-yl)phenyl)-4-((E)-4-(((1r,4r)-4-(diethylamino)cyclohexyl)amino)but-2-enamido)-3-fluorobenzamide

(14) N-(3-(6-chloro-1H-benzo[d]imidazol-5-yl)phenyl)-6-((E)-4-(((1r,4r)-4-hydroxycyclohexyl)amino)but-2-enamido)nicotinamide

(15) N-(3-(4-chloro-2-ethyl-1-methyl-6-(trifluoromethyl)-1H-benzo[d]imidazol-5-yl)phenyl)-3-cyano-4-((E)-4-(((1r,4r)-4-methoxycyclohexyl)amino)but-2-enamido)benzamide

(16) 3-cyano-4-((E)-4-(((1r,4r)-4-methoxycyclohexyl)amino)but-2-enamido)-N-(3-(6-methylbenzo[d]thiazol-5-yl)phenyl)benzamide

(17) (E)-N-(3-(6-chloroimidazo[1,2-a]pyridin-7-yl)phenyl)-3-cyano-4-(4-((1-(methylsulfonyl)piperidin-4-yl)amino)but-2-enamido)benzamide

(18) 3-cyano-N-(3-(1,6-dimethyl-1H-benzo[d]imidazol-5-yl)-4,5-difluorophenyl)-4-((E)-4-(((1r,4r)-4-methoxycyclohexyl)amino)but-2-enamido)benzamide

(19) N-(3-(6-chloro-1-methyl-1H-benzo[d]imidazol-5-yl)phenyl)-3-cyano-4-((E)-4-(((1r,4r)-4-(diethylamino)cyclohexyl)amino)but-2-enamido)benzamide

(20) (E)-3-cyano-N-(3-(4,6-dichloro-1,2-dimethyl-1H-benzo[d]imidazol-5-yl)phenyl)-4-(4-((4,4-difluorocyclohexyl)amino)but-2-enamido)benzamide

(21) 3-cyano-4-((E)-4-(((1r,4r)-4-methoxycyclohexyl)amino)but-2-enamido)-N-(3-(2-(methoxymethyl)-1-methyl-6-(trifluoromethyl)-1H-benzo[d]imidazol-5-yl)phenyl)benzamide

(22) 4-((E)-4-(((1R,5S)-8-oxabicyclo[3.2.1]octan-3-yl)amino)but-2-enamido)-3-cyano-N-(3-(2-(methoxymethyl)-1-methyl-6-(trifluoromethyl)-1H-benzo[d]imidazol-5-yl)phenyl)benzamide

(23) 3-cyano-4-((E)-4-(((1r,4r)-4-methoxycyclohexyl)amino)but-2-enamido)-N-(3-(2-((R)-1-methoxyethyl)-1-methyl-6-(trifluoromethyl)-1H-benzo[d]imidazol-5-yl)phenyl)benzamide

(24) (E)-3-cyano-N-(3-(2-(methoxymethyl)-1-methyl-6-(trifluoromethyl)-1H-benzo[d]imidazol-5-yl)phenyl)-4-(4-((8-methyl-1,4-dioxaspiro[4.5]decan-8-yl)amino)but-2-enamido)benzamide

(25) (E)-3-cyano-4-(4-((6,6-difluorobicyclo[3.1.0]hexan-3-yl)amino)but-2-enamido)-N-(3-(2-(methoxymethyl)-1-methyl-6-(trifluoromethyl)-1H-benzo[d]imidazol-5-yl)phenyl)benzamide

(26) (E)-3-cyano-4-(4-(cyclobutylamino)but-2-enamido)-N-(3-(2-(methoxymethyl)-1-methyl-6-(trifluoromethyl)-1H-benzo[d]imidazol-5-yl)phenyl)benzamide

(27) (E)-3-cyano-4-(4-(cyclohexylamino)but-2-enamido)-N-(3-(2-(methoxymethyl)-1-methyl-6-(trifluoromethyl)-1H-benzo[d]imidazol-5-yl)phenyl)benzamide

(28) 3-cyano-4-((E)-4-(((1r,3r)-3-methoxycyclobutyl)amino)but-2-enamido)-N-(3-(7-(trifluoromethyl)-2,3-dihydro-1H-benzo[d]pyrrolo[1,2-a]imidazol-6-yl)phenyl)benzamide

(29) (E)-N-(2-cyano-4-(4-(2-ethyl-1-methyl-6-(trifluoromethyl)-1H-benzo[d]imidazol-5-yl)indoline-1-carbonyl)phenyl)-4-(((1r,4r)-4-(pyrrolidin-1-yl)cyclohexyl)amino)but-2-enamide

(30) (E)-N-(2-cyano-4-(4-(2-ethyl-1-methyl-6-(trifluoromethyl)-1H-benzo[d]imidazol-5-yl)indoline-1-carbonyl)phenyl)-4-((1-isopropylpiperidin-4-yl)amino)but-2-enamide

(31) (E)-N-(2-cyano-4-(8-(7-(trifluoromethyl)-2,3-dihydro-1H-benzo[d]pyrrolo[1,2-a]imidazol-6-yl)indolizine-3-carbonyl)phenyl)-4-(((1r,4r)-4-methoxycyclohexyl)amino)but-2-enamide

(32) 3-cyano-N-(3-(7-ethyl-2,3-dihydro-1H-benzo[d]pyrrolo[1,2-a]imidazol-6-yl)phenyl)-4-((E)-4-(((1r,4r)-4-methoxycyclohexyl)amino)but-2-enamido)benzamide

(33) (E)-N-(2-cyano-4-(8-(2-ethyl-1-methyl-6-(trifluoromethyl)-1H-benzo[d]imidazol-5-yl)indolizine-3-carbonyl)phenyl)-4-(((1r,4r)-4-methoxycyclohexyl)amino)but-2-enamide

(34) 3-cyano-4-((E)-4-(((1r,4r)-4-methoxycyclohexyl)amino)but-2-enamido)-N-(6-(7-(trifluoromethyl)-2,3-dihydro-1H-benzo[d]pyrrolo[1,2-a]imidazol-6-yl)pyridin-2-yl)benzamide

(35) (E)-N-(2-cyano-4-(7-(7-(trifluoromethyl)-2,3-dihydro-1H-benzo[d]pyrrolo[1,2-a]imidazol-6-yl)-1H-indole-3-carbonyl)phenyl)-4-(((1r,4r)-4-methoxycyclohexyl)amino)but-2-enamide

(36) (E)-N-(2-cyano-4-(8-(6-(difluoromethyl)-1-methyl-1H-benzo[d]imidazol-5-yl)indolizine-3-carbonyl)phenyl)-4-(((1r,4r)-4-methoxycyclohexyl)amino)but-2-enamide

(37) 3-cyano-4-((E)-4-(((1r,4r)-4-(diethylamino)cyclohexyl)amino)but-2-enamido)-N-(6-(7-(trifluoromethyl)-2,3-dihydro-1H-benzo[d]pyrrolo[1,2-a]imidazol-6-yl)pyridin-2-yl)benzamide

(38) (E)-N-(2-cyano-4-(1-methyl-7-(1-methyl-6-(trifluoromethyl)-1H-benzo[d]imidazol-5-yl)-1H-indole-3-carbonyl)phenyl)-4-(((1r,4r)-4-methoxycyclohexyl)amino)but-2-enamide

(39) (E)-4-(((1r,4r)-4-methoxycyclohexyl)amino)-N-(4-(8-(1-methyl-6-(trifluoromethyl)-1H-benzo[d]imidazol-5-yl)indolizine-3-carbonyl)phenyl)but-2-enamide

(40) (E)-N-(2-cyano-4-(8-(2-methoxyphenyl)indolizine-3-carbonyl)phenyl)-4-(((1r,4r)-4-methoxycyclohexyl)amino)but-2-enamide

(41) (E)-N-(4-(8-(2-chloro-6-methoxyphenyl)indolizine-3-carbonyl)-2-cyanophenyl)-4-(((1r,4r)-4-methoxycyclohexyl)amino)but-2-enamide

(42) (R,E)-N-(2-cyano-4-(8-(1-methyl-6-(trifluoromethyl)-1H-benzo[d]imidazol-5-yl)indolizine-3-carbonyl)phenyl)-3-(pyrrolidin-2-yl)acrylamide

(43) (E)-N-(2-cyano-4-(8-(2-fluoro-6-methoxyphenyl)indolizine-3-carbonyl)phenyl)-4-(((1r,4r)-4-methoxycyclohexyl)amino)but-2-enamide

(44) (S,E)-N-(2-cyano-4-(8-(1-methyl-6-(trifluoromethyl)-1H-benzo[d]imidazol-5-yl)indolizine-3-carbonyl)phenyl)-3-(pyrrolidin-2-yl)acrylamide

(45) (E)-N-(4-(8-(2-chlorophenyl)indolizine-3-carbonyl)-2-cyanophenyl)-4-(((1r,4r)-4-methoxycyclohexyl)amino)but-2-enamide

(46) (E)-N-(2-cyano-4-(8-(2-fluoro-6-hydroxyphenyl)indolizine-3-carbonyl)phenyl)-4-(((1r,4r)-4-methoxycyclohexyl)amino)but-2-enamide

(47) (E)-N-(4-(5-chloro-7-(1-methyl-6-(trifluoromethyl)-1H-benzo[d]imidazol-5-yl)-1H-indole-3-carbonyl)-2-cyanophenyl)-4-(((1r,4r)-4-methoxycyclohexyl)amino)but-2-enamide

(48) (2E)-N-{1-[8-(1,6-dimethyl-1H-1,3-benzodiazol-5-yl)indolizine-3-carbonyl]piperidin-4-yl}-4-{[trans-4-methoxycyclohexyl]amino}but-2-enamide

(49) (2E)-4-(tert-Butylamino)-N-(2,6-difluoro-4-{8-[1-methyl-6-(trifluoromethyl)-1H-1,3-benzodiazol-5-yl]indolizine-3-carbonyl}phenyl)but-2-enamide

(50) (2E)-4-(tert-Butylamino)-N-(2-cyano-6-methyl-4-{8-[1-methyl-6-(trifluoromethyl)-1H-1,3-benzodiazol-5-yl]indolizine-3-carbonyl}phenyl)but-2-enamide

(51) (2E)-4-(tert-Butylamino)-N-(2-fluoro-4-{8-[1-methyl-6-(trifluoromethyl)-1H-1,3-benzodiazol-5-yl]indolizine-3-carbonyl}phenyl)but-2-enamide

(52) (2E)-4-(tert-Butylamino)-N-{4-[8-(4-chloro-2-methyl-2H-indazol-5-yl)indolizine-3-carbonyl]-2-cyanophenyl}but-2-enamide

(53) (2E)-4-(tert-Butylamino)-N-{2-cyano-4-[8-(1,5-dimethyl-1H-indazol-4-yl)indolizine-3-carbonyl]phenyl}but-2-enamide

(54) (2E)-4-(tert-Butylamino)-N-{2-cyano-4-[8-(1,6-dimethyl-1H-indazol-5-yl)indolizine-3-carbonyl]phenyl}but-2-enamide

(55) (E)-4-(tert-butylamino)-N-(2-cyano-4-(8-(4,6-dichloro-1-methyl-1H-benzo[d]imidazol-5-yl)indolizine-3-carbonyl)phenyl)but-2-enamide

(56) (E)-N-(2-cyano-4-(7-(1,6-dimethyl-1H-benzo[d]imidazol-5-yl)benzo[b]thiophene-3-carbonyl)phenyl)-4-(((1r, 4r)-4-methoxycyclohexyl)amino)but-2-enamide

(57) (E)-N-(2-cyano-4-(8-(1,6-dimethyl-1H-benzo[d]imidazol-5-yl)imidazo[1,5-a]pyridine-3-carbonyl)phenyl)-4-(((1r,4r)-4-methoxycyclohexyl)amino)but-2-enamide

(58) (E)-N-(2-cyano-4-(7-(1,6-dimethyl-1H-benzo[d]imidazol-5-yl)-1-methyl-1H-indazole-3-carbonyl)phenyl)-4-(((1r,4r)-4-methoxycyclohexyl)amino)but-2-enamide

(59) (E)-4-(tert-butylamino)-N-(4-(8-(4-chloro-1,6-dimethyl-1H-benzo[d]imidazol-5-yl)indolizine-3-carbonyl)-2-cyanophenyl)but-2-enamide

(60) (E)-N-(4-(8-(4-chloro-1,6-dimethyl-1H-benzo[d]imidazol-5-yl)indolizine-3-carbonyl)-2-cyanophenyl)-4-(((1r,4r)-4-methoxycyclohexyl)amino)but-2-enamide

(61) (E)-4-(tert-butylamino)-N-(2-cyano-4-(8-(1,6-dimethyl-4-(prop-1-en-2-yl)-1H-benzo[d]imidazol-5-yl)indolizine-3-carbonyl)phenyl)but-2-enamide

(62) (E)-N-(2-cyano-4-(8-(4,6-dichloro-1-methyl-1H-benzo[d]imidazol-5-yl)indolizine-3-carbonyl)phenyl)-4-(((1r, 4r)-4-methoxycyclohexyl)amino)but-2-enamide

(63) (E)-N-(2-cyano-4-(8-(4,6-dichloro-1-methyl-1H-benzo[d]imidazol-5-yl)indolizine-3-carbonyl)phenyl)-4-(((1r, 4r)-4-methoxycyclohexyl)amino)but-2-enamide

(64) (E)-N-(2-cyano-4-(8-(4-isopropyl-1,6-dimethyl-1H-benzo[d]imidazol-5-yl)indolizine-3-carbonyl)phenyl)-4-(((1r,4r)-4-methoxycyclohexyl)amino)but-2-enamide

(65) (E)-N-(4-(1-chloro-8-(1,6-dimethyl-1H-benzo[d]imidazol-5-yl)indolizine-3-carbonyl)-2-cyanophenyl)-4-(((1r,4r)-4-methoxycyclohexyl)amino)but-2-enamide

(66) (E)-N-(2-cyano-4-(8-(1-methyl-6-(trifluoromethyl)-1H-benzo[d]imidazol-5-yl)indolizine-3-carbonyl)phenyl)-4-(dimethylamino)but-2-enamide

(67) (E)-4-(tert-butylamino)-N-(2,6-difluoro-4-(8-(1-methyl-6-(trifluoromethyl)-1H-benzo[d]imidazol-5-yl)imidazo[1,2-a]pyridine-3-carbonyl)phenyl)but-2-enamide

(68) (E)-N-(2,6-difluoro-4-(8-(1-methyl-6-(trifluoromethyl)-1H-benzo[d]imidazol-5-yl)imidazo[1,2-a]pyridine-3-carbonyl)phenyl)-4-(((1r,4r)-4-methoxycyclohexyl)amino)but-2-enamide

(69) (E)-N-(2-cyano-4-(8-(1,6-dimethyl-4-(pyrimidin-5-yl)-1H-benzo[d]imidazol-5-yl)indolizine-3-carbonyl)phenyl)-4-(((1r,4r)-4-methoxycyclohexyl)amino)but-2-enamide

(70) (E)-N-(2,6-difluoro-4-(8-(1-methyl-6-(trifluoromethyl)-1H-benzo[d]imidazol-5-yl)indolizine-3-carbonyl)phenyl)-4-(((1r,4r)-4-methoxycyclohexyl)amino)but-2-enamide

(71) (E)-N-(4-(8-(4-chloro-2-methyl-2H-indazol-5-yl)indolizine-3-carbonyl)-2-cyanophenyl)-4-(((1r,4r)-4-methoxycyclohexyl)amino)but-2-enamide

(72) (E)-4-(tert-butylamino)-N-(4-(8-(1,6-dimethyl-1H-benzo[d]imidazol-5-yl)indolizine-3-carbonyl)-2,6-difluorophenyl)but-2-enamide

(73) (E)-N-(4-(8-(1,6-dimethyl-1H-benzo[d]imidazol-5-yl)indolizine-3-carbonyl)-2,6-difluorophenyl)-4-(((1r,4r)-4-methoxycyclohexyl)amino)but-2-enamide

(74) (E)-N-(4-(8-(4-chloro-1-isopropyl-1H-imidazol-5-yl)indolizine-3-carbonyl)-2-cyanophenyl)-4-(((1r,4r)-4-methoxycyclohexyl)amino)but-2-enamide

(75) (E)-N-(2-cyano-4-(8-(2,5-dimethyl-2H-indazol-6-yl)indolizine-3-carbonyl)phenyl)-4-(((1r,4r)-4-methoxycyclohexyl)amino)but-2-enamide

(76) (E)-N-(2-cyano-4-(8-(2,6-dimethyl-2H-indazol-5-yl)indolizine-3-carbonyl)phenyl)-4-(((1r,4r)-4-methoxycyclohexyl)amino)but-2-enamide

(77) (E)-4-(tert-butylamino)-N-(2-chloro-4-(8-(1-methyl-6-(trifluoromethyl)-1H-benzo[d]imidazol-5-yl)indolizine-3-carbonyl)phenyl)but-2-enamide

(78) (E)-N-(2-cyano-4-(8-(1-methyl-6-(trifluoromethyl)-1H-benzo[d]imidazol-5-yl)indolizine-3-carbonyl)phenyl)-4-(((1r,4r)-4-methoxycyclohexyl)(methyl)amino) but-2-enamide

(79) (E)-N-(2-cyano-4-(8-(3,4-dichloro-2-methyl-2H-indazol-5-yl)indolizine-3-carbonyl)phenyl)-4-(((1r,4r)-4-methoxycyclohexyl)amino)but-2-enamide

(80) (E)-N-(2-cyano-4-(8-(1-methyl-6-(trifluoromethyl)-1H-benzo[d]imidazol-5-yl)imidazo[1,2-a]pyridine-3-carbonyl)phenyl)-4-(((1r,4r)-4-methoxycyclohexyl)amino) but-2-enamide

(81) (E)-N-(2-cyano-4-(8-(6-methoxy-1-methyl-1H-benzo[d]imidazol-5-yl)indolizine-3-carbonyl)phenyl)-4-(((1r, 4r)-4-methoxycyclohexyl)amino)but-2-enamide

(82) (E)-N-(2-cyano-4-(8-(1,6-dimethyl-4-(pyridin-3-yl)-1H-benzo[d]imidazol-5-yl)indolizine-3-carbonyl)phenyl)-4-(((1r,4r)-4-methoxycyclohexyl)amino)but-2-enamide

(83) (E)-N-(3-fluoro-4-(7-(1-methyl-6-(trifluoromethyl)-1H-benzo[d]imidazol-5-yl)-1H-indole-3-carbonyl)phenyl)-4-(((1r, 4r)-4-methoxycyclohexyl)amino)but-2-enamide The following are details of the method for producing the compound of the present invention. The compound represented by Formula (I) or (vii) of the present invention can be produced, for example, through the following production methods or the methods described in the Examples. However, the production methods for the compound represented by Formula (I), (I'), (i) or (vii) of the present invention are not limited to these reaction examples. The reaction product obtained in each step can be subjected to the subsequent step after, or without, isolation and purification by known separation and purification methods, such as concentration, vacuum concentration, crystallization, solvent extraction, reprecipitation, and chromatography.

To the reaction product obtained in each step and the starting material, a protecting group that can be easily converted to the functional group can be introduced if it is effective in each step, or so as to change the order of the steps. Examples of the protecting group used here may be the protecting groups etc. used in the method disclosed in the document "Protective Groups in Organic Synthesis," 5th edition, Greene and Wuts, John Wiley & Sons Inc., 2014. The protecting group may be appropriately selected according to the reaction conditions of each step. After introducing a protecting group and performing reaction, the protecting group is optionally removed to thus yield a desired compound.

As used herein, the "mole" refers to a unit denoting $6.02\times10^{23}$ molecules of a compound, which is also known as Avogadro constant.

Production Method 1

Scheme 1

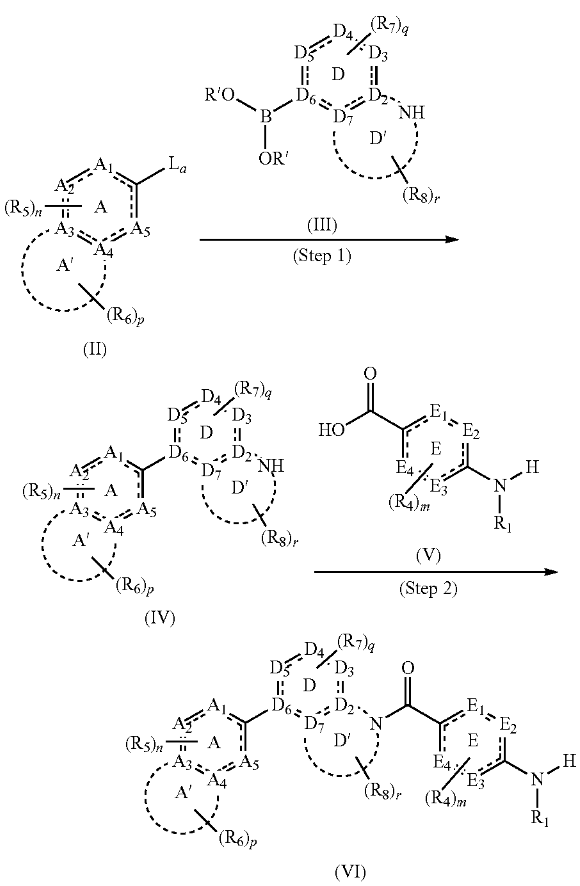

Scheme 1, $L_a$ represents halogen, each R' independently represents hydrogen or substituted or unsubstituted alkyl, two R' may together form a 5- to 10-membered ring and other symbols are as defined in embodiment A.

(Step 1)

This step is a step of obtaining a compound represented by the general formula (IV) by a cross-coupling reaction of a compound represented by the general formula (II) with an arylboronic acid or arylboronic acid ester, or unsaturated heterocyclic boronic acid or unsaturated heterocyclic boronic acid ester (III), each of which may be a commercially available product or can be produced by a known method, when $L_a$ in the compound represented by the general formula (II) has a leaving group such as halogen. The compound represented by the general formula (II) may be a commercially available product or can be produced in accordance with a known method.

This step can be usually carried out in accordance with a known method (e.g., Chemical Reviews, Vol. 95, p. 2457, 1995), and can be carried out, for example, in the presence of a transition metal catalyst and a base, in a solvent which does not adversely affect the reaction.

The arylboronic acid or arylboronic acid ester, or unsaturated heterocyclic boronic acid or unsaturated heterocyclic boronic acid ester can be used in an amount of 1 to 10 moles, and preferably of the order of 1 to 3 moles, based on 1 mole of the compound of the general formula (II).

As the transition metal catalyst, a palladium catalyst (e.g., palladium acetate, palladium chloride, tetrakis(triphenylphosphine)palladium, and dichlorobis(triphenylphosphine)palladium), a nickel catalyst (e.g., nickel chloride), or the like is used for example. A ligand (e.g., triphenylphosphine and tri-tert-butylphosphine) is added to the catalyst, as required, and a metal oxide (e.g., copper oxide and silver oxide) or the like may be used as a co-catalyst. The amount of the transition metal catalyst to be used, which depends on the type of the catalyst, is usually about 0.0001 to 1 mole, and preferably of the order of 0.01 to 0.5 moles, based on 1 mole of the compound of the general formula (II). The amount of the ligand to be used is usually about 0.0001 to 4 moles, and preferably of the order of 0.01 to 2 moles, based on 1 mole of the compound of the general formula (II). The amount of the co-catalyst to be used is usually about 0.0001 to 4 moles, and preferably of the order of 0.01 to 2 moles, based on 1 mole of the compound of the general formula (II).

Examples of the base include organic amines (e.g., trimethylamine, triethylamine, N,N-diisopropylethylamine, N-methylmorpholine, 1,8-diazabicyclo[5,4,0]undec-7-ene, pyridine, and N,N-dimethylaniline), alkaline metal salts (e.g., sodium hydrogen carbonate, potassium hydrogen carbonate, sodium carbonate, potassium carbonate, cesium carbonate, sodium phosphate, potassium phosphate, sodium hydroxide, and potassium hydroxide), metal hydrides (e.g., potassium hydride and sodium hydride), alkaline metal alkoxides (e.g., sodium methoxide, sodium ethoxide, sodium tert-butoxide, and potassium tert-butoxide), and alkaline metal disilazides (e.g., lithium disilazide, sodium disilazide, and potassium disilazide). The amount of the base to be used is usually 0.1 to 10 moles, and preferably of the order of 1 to 5 moles, based on 1 mole of the compound represented by the general formula (II).

The solvent is only required not to adversely affect the reaction. Examples of the solvent include hydrocarbons (e.g., benzene, toluene, and xylene), halogenated hydrocarbons (e.g., chloroform and 1,2-dichloroethane), nitriles (e.g., acetonitrile), ethers (e.g., 1,2-dimethoxyethane and THF), alcohols (e.g., methanol and ethanol), aprotic polar solvents (e.g., DMF, dimethyl sulfoxide, and hexamethylphosphoramide), water, and mixtures thereof.

The reaction time is 0.1 to 100 hours, and preferably 0.5 to 24 hours. The reaction temperature is 0° C. to the boiling point of the solvent, and preferably 0° C. to 150° C.

The compound of the general formula (IV) thus obtained may be isolated and purified by a known separation purification means, or may be subjected to the subsequent step without such isolation and purification.

(Step 2)

This step is a step of obtaining a compound represented by the general formula (VI) by an amidation reaction between the amine represented by the general formula (IV) and a carboxylic acid (V), which may be a commercially available product or can be produced by a known method.

This step is carried out using 0.5 to 10 moles of, and preferably 1 to 3 moles of the carboxylic acid (V), based on 1 mole of the compound represented by the general formula (IV). In a solvent inert to the reaction, an appropriate condensing agent as an amidation reagent is added, and the mixture is stirred under cooling to under heating, preferably −20° C. to 80° C., usually for 1 minute to 1 week.

Examples of the condensing agent include, but are not particularly limited to, N,N'-dicyclohexylcarbodiimide, N,N'-diisopropylcarbodiimide, 1-(3-dimethylaminopropyl)-3-ethylcarbodiimide, 1-(3-dimethylaminopropyl)-3-ethylcarbodiimide hydrochloride, benzotriazol-1-yloxy-tris-(dimethylamino)phosphonium hexafluorophosphate, benzotriazol-1-yloxy-tris-pyrrolidinophosphonium hexafluorophosphate, bromo tris-(dimethylamino)phosphonium hexafluorophosphate, diphenylphosphoryl azide, 1,1'-carbonyldiimidazole, and propylphosphonic acid anhydride (cyclic trimer).

Examples of the solvent include, but are not particularly limited to, toluene, methylene chloride, chloroform, THF, 1,4-dioxane, DMF, N,N-dimethylacetamide, NMP, 2-propanol, ethanol, methanol, water, and mixtures thereof.

An additive, such as 1-hydroxybenzotriazole and a base also may be added, as required. Examples of the base include, but are not particularly limited to, inorganic bases, such as sodium carbonate, potassium carbonate, and sodium hydrogen carbonate, or organic bases, such as triethylamine, N,N-diisopropylethylamine, and 4-dimethylaminopyridine, or mixtures thereof.

The compound represented by the general formula (VI) thus obtained may be used for production of a compound represented by the general formula (I) after or without isolation and purification by a known separation and purification means, such as concentration, vacuum concentration, crystallization, solvent extraction, reprecipitation, and chromatography.

Production Method 2

Scheme 2

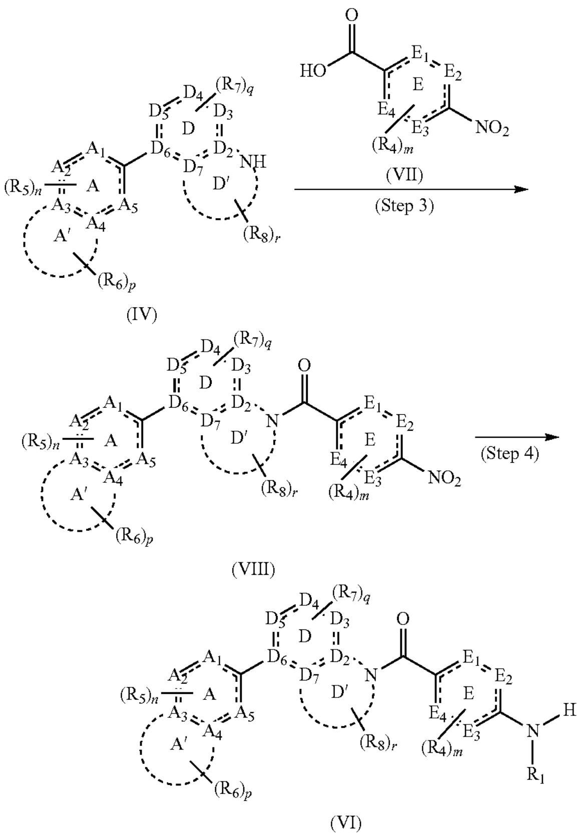

Scheme 2, $R_1$ represents hydrogen, and other symbols are as defined in embodiment A.

(Step 3)

This step is a step of obtaining a compound represented by the general formula (VIII) by subjecting the compound represented by the general formula (IV) and a carboxylic acid represented by the general formula (VII), which may be a commercially available product or can be produced by a known method, to an amidation reaction.

This step can be carried out in the same manner as Step 2.

(Step 4)

This step is a step of producing a compound represented by the general formula (VI) by reducing the compound represented by the general formula (VIII).

This step can be carried out in a solvent that does not adversely affect the reaction, for example, acetonitrile, ethyl acetate, THF, methanol, ethanol, DMF, DMA, or NMP by use of a hydrogen source, such as hydrogen, formic acid, ammonium formate, or cyclohexadiene, and with palladium/carbon or palladium hydroxide/carbon as a catalyst. This step is usually carried out using 0.01 to 5 moles of, and preferably 0.05 to 1 mole of the catalyst, based on 1 mole of the compound represented by the general formula (VIII). The reaction temperature is usually room temperature to the reflux temperature of the solvent. The reaction time is usually 1 hour to 24 hours.

The compound represented by the general formula (VI) thus obtained may be used for production of the compound represented by the general formula (I) after or without isolation and purification by a known separation and purification means, such as concentration, vacuum concentration, crystallization, solvent extraction, reprecipitation, and chromatography.

Production Method 3

Scheme 3

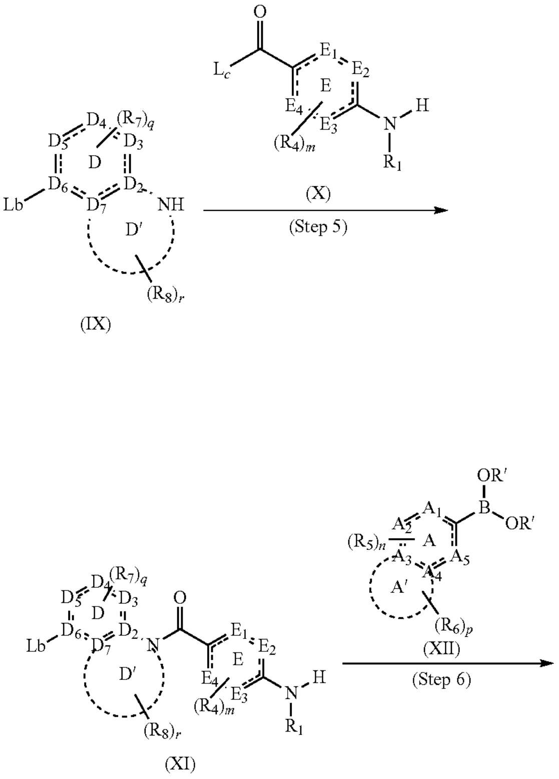

-continued

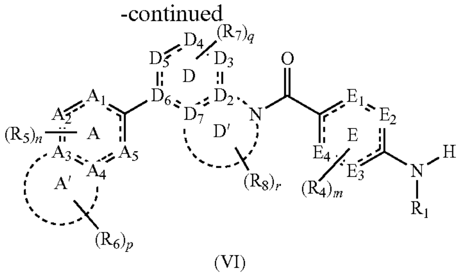

(VI)

Scheme 3, $L_b$ represents halogen, $L_e$ represents a hydroxy group or chlorine atom or bromine atom, and other symbols are as defined in embodiment A.

(Step 5)

This step is a step of obtaining a compound represented by the general formula (XI) by means of an amidation reaction between the compound represented by the general formula (IX) and a carboxylic acid ($L_c$=OH) or acid halide ($L_c$=Cl, Br) represented by the general formula (X).

When the carboxylic acid ($L_c$=OH) represented by the general formula (X) is used, this step can be carried out in the same manner as Step 2.

When the acid halide ($L_c$=Cl, Br) represented by the general formula (X) is used, usually 0.5 to 10 moles of, and preferably about 1 to 5 moles of the acid halide is used, based on 1 mole of the compound represented by the general formula (IX). The acid halide may be a commercially available product or can be produced in accordance with a known method.

A base also may be added, as required. Examples of the base include organic amines (e.g., trimethylamine, triethylamine, N,N-diisopropylethylamine, N-methylmorpholine, 1,8-diazabicyclo[5,4,0]undec-7-ene, pyridine, and N,N-dimethylaniline), alkaline metal salts (e.g., sodium hydrogen carbonate, potassium hydrogen carbonate, sodium carbonate, potassium carbonate, cesium carbonate, sodium phosphate, potassium phosphate, sodium hydroxide, and potassium hydroxide), metal hydrides (e.g., potassium hydride and sodium hydride), and alkaline metal alkoxides (e.g., sodium methoxide, sodium ethoxide, sodium tert-butoxide, and potassium tert-butoxide). The amount of the base to be used is usually 1 to 100 moles, and preferably of the order of 1 to 10 moles, based on 1 mole of the compound represented by the general formula (IX).

The solvent to be used in the reaction is only required not to adversely affect the reaction. Examples of the solvent include alcohols (e.g., methanol), hydrocarbons (e.g., benzene, toluene, and xylene), halogenated hydrocarbons (e.g., methylene chloride, chloroform, and 1,2-dichloroethane), nitriles (e.g., acetonitrile), ethers (e.g., 1,2-dimethoxyethane and THF), aprotic polar solvents (e.g., DMF, dimethyl sulfoxide, and hexamethylphosphoramide), and mixtures thereof. The reaction time is 0.1 to 100 hours, and preferably 0.5 to 24 hours. The reaction temperature is 0° C. to the boiling point of the solvent, and preferably 0° C. to 100° C.

The compound of the general formula (XI) thus obtained may be subjected to the subsequent step after or without isolation and purification by a known separation and purification means.

(Step 6)

This step is a step of obtaining a compound represented by the general formula (VI) by a coupling reaction of the compound represented by the general formula (XI) with an arylboronic acid or arylboronic acid ester, or with unsaturated heterocyclic boronic acid or unsaturated heterocyclic boronic acid ester (XII), each of which may be a commercially available product or can be produced by a known method, when $L_b$ in the compound represented by the general formula (XI) has a leaving group such as halogen.

This step can be carried out in the same manner as Step 1.

Production Method 4

Scheme 4

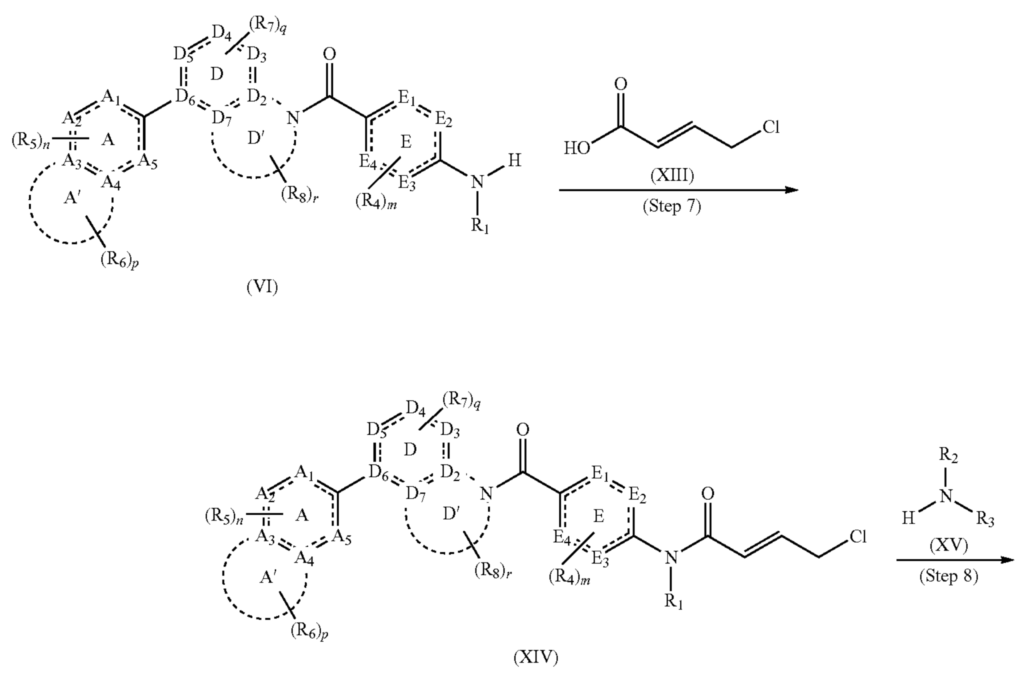

-continued

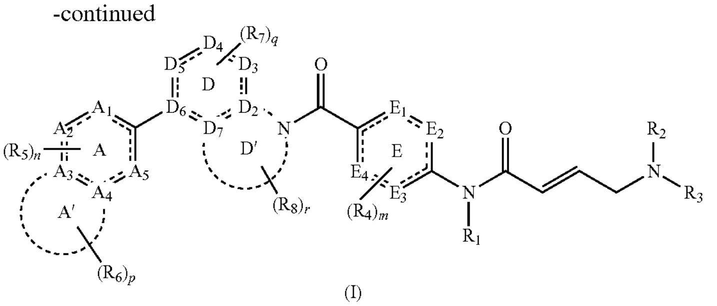

(I)

Scheme 4, the symbols are as defined in embodiment A.

(Step 7)

This step is a step of obtaining a compound represented by the general formula (XIV) by means of an amidation reaction between the compound represented by the general formula (VI) and a carboxylic acid (XIII).

This step can be carried out in the same manner as Step 2.

(Step 8)

This step is a step of producing the compound of the present invention represented by the general formula (I) by allowing the compound represented by the general formula (XIV) to react with an amine represented by the general formula (XV).

The amine represented by the general formula (XV) may be used in an amount of 1 to 20 moles, and preferably of 1 to 10 moles, based on 1 mole of the compound represented by the general formula (XIV).

A base may be added to the reaction described above, as required. Examples of the base include organic bases, such as triethylamine, N,N-diisopropylethylamine, pyridine, lutidine, collidine, 4-dimethylaminopyridine, potassium tert-butoxide, sodium tert-butoxide, sodium methoxide, sodium ethoxide, lithium hexamethyldisilazide, sodium hexamethyldisilazide, potassium hexamethyldisilazide, and butyl lithium or inorganic bases, such as sodium hydrogen carbonate, sodium carbonate, potassium carbonate, cesium carbonate, sodium hydroxide, sodium hydride, and potassium phosphate. As the amount of the base to be added, 1 to 100 moles, and preferably 1 to 20 moles may be used, based on 1 mole of the compound represented by the general formula (XIV).

An inorganic salt also may be added, as required. Examples of the inorganic salt include sodium iodide and potassium iodide. The amount of the inorganic salt to be used is usually 1 to 100 moles, and preferably of the order of 1 to 10 moles, based on 1 mole of the compound represented by the general formula (XIV).

The reaction solvent is not particularly limited as long as the solvent does not adversely affect the reaction. For example, DMF, N,N-dimethylacetamide, dimethyl sulfoxide, THF, 1,4-dioxane, N-methylpyrrolidine-2-one, and acetonitrile may be used singly or in admixture. The reaction time is 0.1 to 100 hours, and preferably 0.5 to 24 hours. The reaction temperature is 0° C. to the boiling point of the solvent, and preferably 0 to 100° C.

The compound of the present invention represented by the general formula (I) thus obtained may be isolated and purified by a known separation and purification means, such as concentration, vacuum concentration, crystallization, solvent extraction, reprecipitation, and chromatography.

Production Method 5

Scheme 5

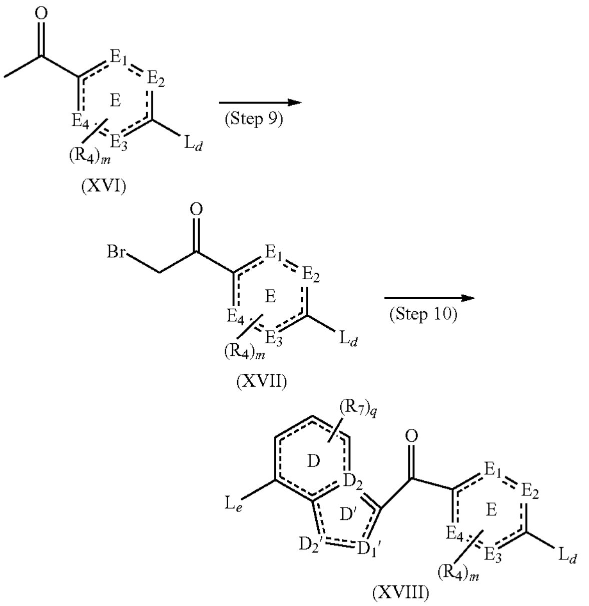

Scheme 5, $L_d$ represents a fluorine atom or amino group or $NHR_1$, $L_c$ represents halogen, and other symbols are as defined in embodiment A.

(Step 9)

This step is a method of obtaining a compound represented by the general formula (XVII) by means of a bromination reaction of a compound represented by the general formula (XVI), which may be a commercially available product or can be produced by a known method.

This step may be carried out in a solvent that does not adversely affect the reaction, for example, acetonitrile, ethyl acetate, dichloromethane, chloroform, 1,4-dioxane, or ethanol by use of a bromine source, such as bromine or copper (II) bromide. Iodine as an additive also may be used, as required. In this step, usually 1 to 100 moles of, and preferably of the order of 1 to 10 moles of a bromine source may be usually used, based on 1 mole of the compound represented by the general formula (XVI). The reaction temperature is usually room temperature to the reflux temperature of the solvent. The reaction time is usually 1 hour to 24 hours.

The compound represented by the general formula (XVII) thus obtained may be subjected to the subsequent step after or without isolation and purification by a known separation and purification means.

(Step 10)

This step is a step of obtaining a compound represented by the general formula (XVIII) by means of a nucleophilic substitution reaction of a substituted pyridine, which may be a commercially available product or can be produced by a known method, with the compound represented by the general formula (XVII), followed by an intramolecular cyclization reaction.

When $D_2$ is N, $D_1'$ and $D_2'$ are C, CH or $CH_2$, and $L_d$ is a fluorine atom, in a solvent that does not adversely affect the reaction, such as THF and ethanol, 0.5 to 10 moles of, and preferably of the order of 1 to 5 moles of 2-methylpyridine having substituents $L_e$ and $R_7$ may be usually used, based on 1 mole of the compound represented by the general formula (XVII). The 2-methylpyridine may be a commercially available product or can be produced in accordance with a known method. The reaction temperature is usually room temperature to the reflux temperature of the solvent. The reaction time is usually 1 hour to of the order of 4 days.

The pyridinium salt thus obtained may be subjected to the subsequent reaction after or without isolation and purification by a known separation and purification means.

Based on 1 mole of the pyridinium salt obtained above, usually 1 to 100 moles of, and preferably of the order of 1 to 20 moles of (methoxymethylene)dimethylammonium methyl sulfate, which may be a commercially available product or can be produced by a known method, may be used, and a base also may be added, as required. Examples of the base include organic amines (e.g., trimethylamine, triethylamine, N,N-diisopropylethylamine, N-methylmorpholine, 1,8-diazabicyclo[5,4,0]undec-7-ene, pyridine, and N,N-dimethylaniline), alkaline metal salts (e.g., sodium hydrogen carbonate, potassium hydrogen carbonate, sodium carbonate, potassium carbonate, cesium carbonate, sodium phosphate, potassium phosphate, sodium hydroxide, and potassium hydroxide), metal hydrides (e.g., potassium hydride and sodium hydride), and alkaline metal alkoxides (e.g., sodium methoxide, sodium ethoxide, sodium tert-butoxide, and potassium tert-butoxide). The amount of the base to be used is usually 1 to 100 moles, and preferably of the order of 1 to 10 moles, based on 1 mole of the pyridinium salt.

The solvent to be used in the reaction is only required not to adversely affect the reaction. Examples of the solvent include aprotic polar solvents (e.g., DMF, dimethyl sulfoxide, and hexamethylphosphoramide). The reaction time is 0.1 to 100 hours, and preferably 0.5 to 24 hours. The reaction temperature is 0° C. to the boiling point of the solvent, and preferably 0° C. to 100° C.

The compound represented by the general formula (XVIII) thus obtained may be used for production of the compound (I') of the present invention after or without isolation and purification by a known separation and purification means, such as concentration, vacuum concentration, crystallization, solvent extraction, reprecipitation, and chromatography.

When $D_2$ and $D_2'$ are N or NH and $D_1'$ is C, CH, or $CH_2$, in a solvent that does not adversely affect the reaction, such as DMF and ethanol, usually 0.5 to 10 moles of, and preferably of the order of 1 to 5 moles of (E)-N,N-dimethyl-N'-(pyridin-2-yl)formimidamide having substituents $L_e$ and $R_7$ can be used, based on 1 mole of the compound represented by the general formula (XVII). The (E)-N,N-dimethyl-N'-(pyridin-2-yl)formimidamide may be a commercially available product or can be produced in accordance with a known method. A base also may be added, as required. Examples of the base include organic amines (e.g., trimethylamine, triethylamine, N,N-diisopropylethylamine, N-methylmorpholine, 1,8-diazabicyclo[5,4,0]undec-7-ene, pyridine, and N,N-dimethylaniline) and alkaline metal salts (e.g., sodium hydrogen carbonate, potassium hydrogen carbonate, sodium carbonate, potassium carbonate, cesium carbonate, sodium phosphate, potassium phosphate, sodium hydroxide, and potassium hydroxide). The reaction temperature is usually room temperature to the reflux temperature of the solvent. The reaction time is usually 1 hour to 24 hours.

The compound represented by the general formula (XVIII) thus obtained may be used for production of the compound (I') of the present invention after or without isolation and purification by a known separation and purification means, such as concentration, vacuum concentration, crystallization, solvent extraction, reprecipitation, and chromatography.

Production Method 6

Scheme 6

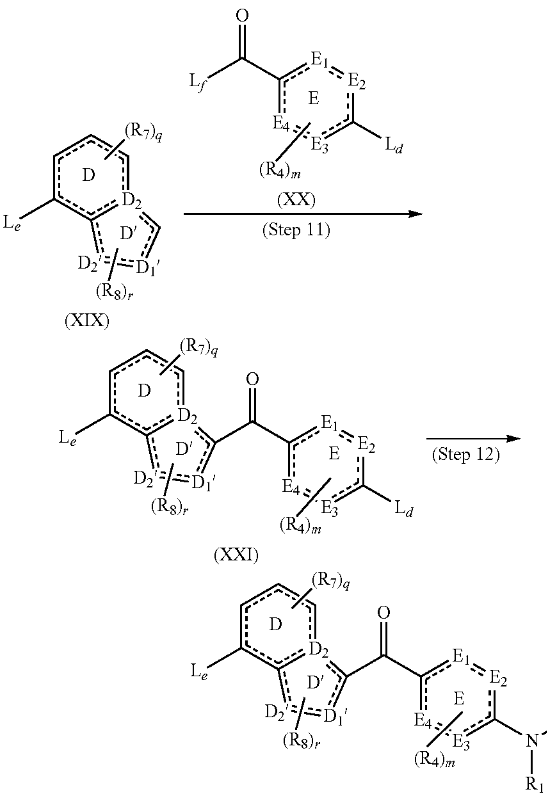

(XX) (XIX) (XXI) (XXII)

Scheme 6, $L_f$ represents a hydroxy group, chlorine atom, or bromine atom, and other symbols are as defined in embodiment A.

(Step 11)

This step is a step of obtaining a compound represented by the general formula (XXI) by a Friedel-Crafts reaction between a compound represented by the general formula (XIX), which may be a commercially available product or can be produced by a known method, and a compound represented by the general formula (XX).

When the carboxylic acid ($L_f$=OH) represented by the general formula (XX) is used, this step can be carried out in a solvent that does not adversely affect the reaction, such as dichloromethane, THF, and 1,4-dioxane by use of trifluoroacetic anhydride, phosphoric acid or the like. A base also may be added, as required. Examples of the base include organic amines (e.g., trimethylamine, triethylamine, N,N-diisopropylethylamine, N-methylmorpholine, 1,8-diazabicyclo[5,4,0]undec-7-ene, pyridine, and N,N-dimethylaniline). In this step, usually 1 to 100 moles of, and preferably of the order of 1 to 10 moles of an acid can be usually used, based on 1 mole of the compound represented by the general formula (XIX). The reaction temperature is usually room temperature to the reflux temperature of the solvent. The reaction time is usually 1 hour to 3 days.

When the acid halide ($L_f$=Cl, Br) represented by the general formula (XX) is used, this step can be carried out in a solvent that does not adversely affect the reaction, such as dichloromethane, THF, and 1,4-dioxane, in the presence of a Lewis acid such as aluminum chloride or an organic amine (e.g., trimethylamine, triethylamine, N,N-diisopropylethylamine, N-methylmorpholine, 1,8-diazabicyclo[5,4,0]undec-7-ene, pyridine, and N,N-dimethylaniline). In this step, usually 1 to 100 moles of, and preferably of the order of 1 to 10 moles of the Lewis acid or base can be usually used, based on 1 mole of the compound represented by the general formula (XIX). The reaction temperature is usually 0° C. to the reflux temperature of the solvent. The reaction time is usually 1 hour to 24 hours.

The compound represented by the general formula (XXI) thus obtained can be subjected to the subsequent reaction after or without isolation and purification by a known separation and purification means.

(Step 12)

This step is a method of obtaining a compound represented by the general formula (XXII) by an aromatic electrophilic substitution reaction of an amine, when $L_d$ is a fluorine atom.

This step can be carried out in a solvent that does not adversely affect the reaction, such as THF, 1,4-dioxane, and 1,2-dimethoxyethane, by use of an ammonia aqueous solution ($R_1$=H), alkylamine ($R_1$—$NH_2$), or the like. In this step, usually 1 to 100 moles, and preferably of the order of 1 to 50 moles of an amine can be usually used, based on 1 mole of the compound represented by the general formula (XXI). The reaction temperature is usually room temperature to the reflux temperature of the solvent. The reaction time is usually 1 hour to 24 hours.

Production Method 7

Scheme 7

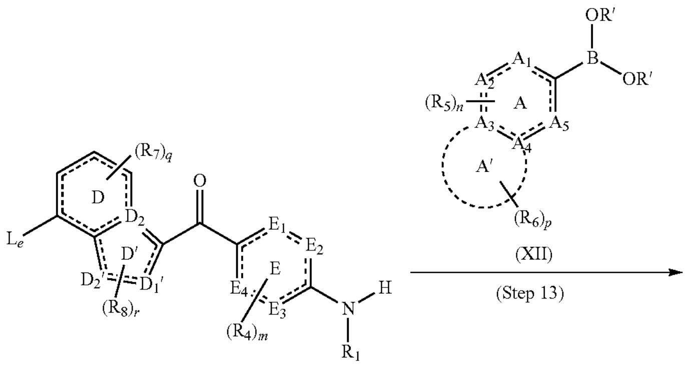

(XXII)

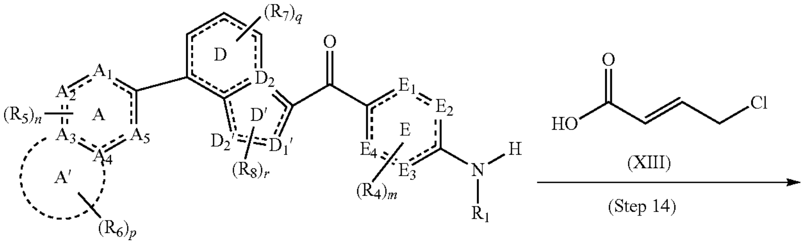

(XXIII)

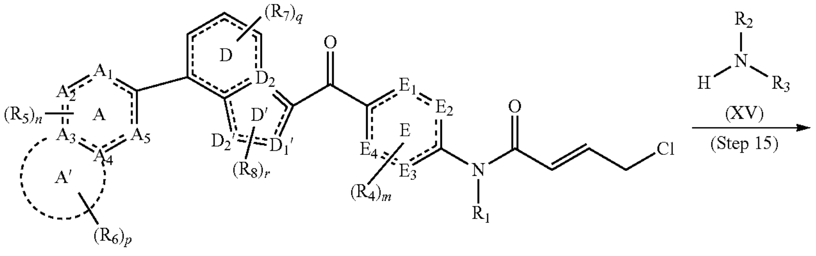

(XXIV)

-continued

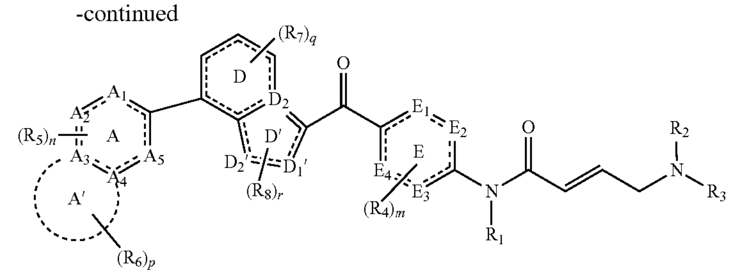

(I')

In Scheme 7, the symbols are as defined in embodiment A.

(Step 13)

This step is a step of obtaining a compound represented by the general formula (XXIII) by a cross-coupling reaction of a compound represented by the general formula (XXII) with an arylboronic acid or arylboronic acid ester, or with unsaturated heterocyclic boronic acid or unsaturated heterocyclic boronic acid ester (XII), each of which may be a commercially available product or can be produced by a known method, when $L_e$ in the compound represented by the general formula (XXII) has a leaving group such as halogen.

This step can be carried out in the same manner as Step 1.

(Step 14)

This step is a step of obtaining a compound represented by the general formula (XXIV) by an amidation reaction between the compound represented by the general formula (XXIII) and a carboxylic acid (XIII).

This step can be carried out in the same manner as Step 2.

(Step 15)

This step is a step of producing a compound of the present invention represented by the general formula (I') by allowing the compound represented by the general formula (XXIV) to react with an amine represented by the general formula (XV).

This step can be carried out in the same manner as Step 8.

Production Method 8

Scheme 8

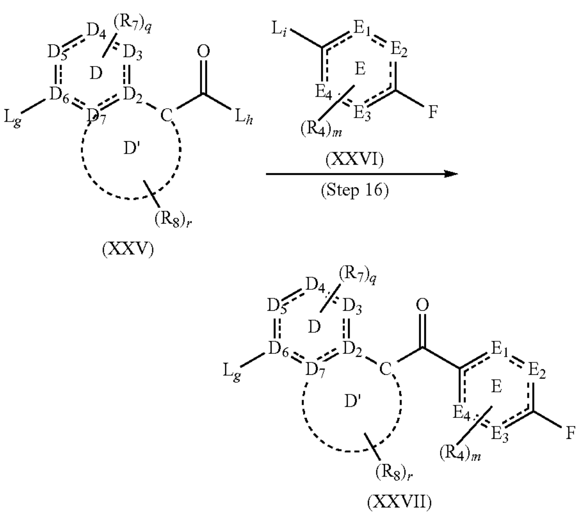

In Scheme 8, $L_g$ represents halogen, $L_h$ represents chlorine or bromine, L1 represents halogen, and other symbols are as defined in embodiment A.

(Step 16)

This step is a step of obtaining a compound represented by the general formula (XXVII) by an electrophilic addition reaction in which a strong base is added to a halogenated aryl (XXVI) to generate an anion to be reacted with an acid halide ($L_h$=Cl, Br) represented by the general formula (XXV), which may be a commercially available product or can be produced by a known method.

This reaction can be carried out by, for example, adding a strong base in an appropriate solvent, stirring the mixture in the range of −78° C. to room temperature, usually for 10 minutes to 12 hours to generate an anion, and adding the acid halide ($L_h$=Cl, Br) represented by the general formula (XXV) thereto. The reaction solvent that may be used is not particularly limited as long as the solvent does not participate the reaction. Examples of the solvent include ethers, such as THF and 1,4-dioxane, hydrocarbons such as benzene and toluene, and mixtures thereof. Examples of the strong base which may be used include, but are not particularly limited to, butyl lithium, lithium diisopropylamide, lithium 2,2,6,6-tetramethylpiperidide, 2,2,6,6-tetramethylpiperidinylmagnesium chloride lithium chloride complex, and isopropylmagnesium chloride lithium chloride complex.

The compound represented by the general formula (XXVII) thus obtained can be used for production of the compound of the present invention after or without isolation and purification by a known separation and purification means, such as concentration, vacuum concentration, crystallization, solvent extraction, reprecipitation, and chromatography.

When the compound according to one embodiment of the present invention has isomers such as optical isomers, stereoisomers, rotational isomers, and tautomers, any of the isomers and mixtures thereof are included within the scope of the compound of the present invention unless otherwise specified. For example, when the compound of the present invention has optical isomers, racemic mixtures and the optical isomers separated from a racemic mixture are also included within the scope of the compound of the present invention unless otherwise specified.

The compound or a salt thereof according to one embodiment of the present invention may be in the form of amorphous or crystals. Single crystals and polymorphic mixtures are included within the scope of the compound or a salt thereof of the present invention. Such crystals can be produced by crystallization according to a crystallization method known in the art. The compound or a salt thereof of the present invention may be a solvate (e.g., a hydrate) or a non-solvate. Any of such forms are included within the scope of the compound or a salt thereof of the present invention. Compounds labeled with an isotope (e.g., $^{2}H$, $^{3}H$, $^{13}C$, $^{14}C$, $^{35}S$, $^{125}I$) are also included within the scope of the compound or a salt thereof of the present invention.

The salts of the compound according to one embodiment of the present invention refer to any pharmaceutically acceptable salts; examples include base addition salts and acid addition salts.

The compound or a salt thereof according to one embodiment of the present invention also encompass prodrugs thereof. A prodrug refers to a compound that can be converted to the compound or a salt thereof of the present invention through a reaction with an enzyme, gastric acid, or the like under physiological conditions in vivo, i.e., a compound that can be converted to the compound or a salt thereof of the present invention by enzymatic oxidation, reduction, hydrolysis, or the like; or a compound that can be converted to the compound or a salt thereof of the present invention by hydrolysis or the like with gastric acid or the like. Further, the prodrug may be compounds that can be converted to the compound or a salt thereof of the present invention under physiological conditions, such as those described in *Iyakuhin no Kaihatsu*, "Development of Pharmaceuticals," Vol. 7, Molecular Design, published in 1990 by Hirokawa Shoten Co., pp. 163-198.

As used herein, the "effective amount" of the compound according to an embodiment of the present invention refers to an amount of the compound which is sufficient to achieve a biological response or therapeutic response of a subject, such as causing reduction or prevention of an activity of enzyme or protein; or improving a symptom, alleviating a medical state, delaying or retarding progression of disorder, or preventing a disease (therapeutically effective amount).

As used herein, the "subject" includes a mammal and a nonmammal. Examples of a mammal include, but not limited to, a human, a chimpanzee, an anthropoid, a monkey, a cow, a horse, a sheep, a goat, a pig, a rabbit, a dog, a cat, a rat, a mouse, a *Cavia porcellus*, a hedgehog, a kangaroo, a mole, a boar, a bear, a tiger and a lion. Examples of a nonmammal include, but not limited to, birds, fishes and reptiles. In one embodiment, the subject is a human, and may be a human who has been diagnosed to need a treatment for the symptom, the medical state or disease as disclosed herein.

In one embodiment, a medicament, a pharmaceutical composition or a pharmaceutical preparation comprising the compound or pharmaceutically acceptable salt thereof of the present invention may be provided. In another embodiment, an antitumor agent comprising the compound or pharmaceutically acceptable salt thereof of the present invention as an active ingredient may be provided.

When the compound or a salt thereof according to one embodiment of the present invention is used as a pharmaceutical preparation, a medicament, or a pharmaceutical composition, a pharmaceutically acceptable carrier can be added, if required, thereby forming a suitable dosage form according to prevention and treatment purposes. Examples of the dosage form include oral preparations, injections, suppositories, ointments, inhalations, patches, and the like. Such dosage forms can be formed by methods conventionally known to a person skilled in the art.

As the pharmaceutically acceptable carrier, various conventional organic or inorganic carrier materials used as preparation materials may be blended as an excipient, binder, disintegrant, lubricant, or colorant in solid preparations; or as a solvent, solubilizing agent, suspending agent, isotonizing agent, buffer, or soothing agent in liquid preparations. Moreover, pharmaceutical preparation additives, such as antiseptics, antioxidants, colorants, sweeteners, and stabilizers, may also be used, if required.

In one embodiment, a medicament, a pharmaceutical composition or a pharmaceutical preparation for oral administration or an oral solid preparation comprising the compound or pharmaceutically acceptable salt thereof of the present invention may be provided. In other embodiment, an antitumor agent for oral administration comprising the compound or pharmaceutically acceptable salt thereof of the present invention as an active ingredient may be provided. Oral solid preparations or a medicament, a pharmaceutical composition, an antitumor agent or a pharmaceutical preparation for oral administration are prepared as follows. After an excipient is added optionally with a binder, disintegrant, lubricant, colorant, taste-masking or flavoring agent, etc. to the compound or a salt thereof of the present invention, the resulting mixture is formulated into tablets, coated tablets, granules, powders, capsules, or the like by ordinary methods.

When an injection agent is prepared, a pH regulator, a buffer, a stabilizer, an isotonizing agent, a local anesthetic, and the like may be added to the compound of the present invention; and the mixture may be formulated into a subcutaneous, intramuscular, or intravenous injection according to an ordinary method.

The amount of the compound according to one embodiment of the present invention to be incorporated in each of such dosage unit forms depends on the condition of the patient to whom the compound is administered, the dosage form, etc. In general, for an oral agent, the amount of the compound is preferably about 0.05 to 1000 mg per dosage unit form. For an injection, the amount of the compound is preferably about 0.01 to 500 mg per dosage unit form, and for a suppository, the amount of the compound is preferably about 1 to 1000 mg per dosage unit form.

Further, the daily dose of the medicine in such a dosage form varies depending on the condition, body weight, age, sex, etc. of the patient, and cannot be unconditionally determined. For example, the daily dose for an adult (body weight: 50 kg) of the compound of the present invention may be generally about 0.05 to 5000 mg, and preferably 0.1 to 1000 mg.

The compound or a salt thereof according to one embodiment of the present invention has excellent KRAS inhibitory activity against KRAS G12C mutation-positive cancer cells. Therefore, the compound or a salt thereof according to one embodiment of the present invention is useful as an antitumor agent against KRAS G12C mutation-positive cancer cells, and has the advantage of having fewer side effects.

Due to its excellent KRAS G12C inhibitory activity, the compound or a salt thereof according to one embodiment of the present invention inhibits the KRAS function and is useful as a pharmaceutical preparation for preventing and treating KRAS-associated signaling-related diseases.

In one embodiment, use of a compound or pharmaceutically acceptable salt thereof of the present invention for manufacturing a pharmaceutical composition may be provided. In one embodiment, use of a compound or pharmaceutically acceptable salt thereof of the present invention for manufacturing an antitumor agent may be provided. In one embodiment, use of a compound or pharmaceutically acceptable salt thereof of the present invention for manufacturing an antitumor agent for oral administration may be provided. In one embodiment, a compound or pharmaceutically acceptable salt thereof of the present invention for use as medicament may be provided. In one embodiment, a compound or pharmaceutically acceptable salt thereof of the present invention for use in the prevention and/or treatment of tumor may be provided. In one embodiment, a compound or pharmaceutically acceptable salt thereof of the present invention for use in the prevention and/or treatment of tumor by oral administration may be provided.

In one embodiment, there is provided a method for preventing and/or treating tumor, comprising administrating a therapeutically effective amount of the compound or pharmaceutically acceptable salt thereof of the present invention to a subject in need thereof. In one embodiment, an antitumor agent which is administered to a subject in need thereof in combination with a pharmaceutically effective amount of one or more other antitumor drugs may be provided.

In terms of RAS-associated signaling in the KRAS-associated signaling-related diseases, KRAS is involved in various signaling transduction as RAS-associated signaling; KRAS mainly activates, but is not limited to, RAF, PI3K, RAL-GEF, and the like. Examples of the diseases include diseases whose incidence can be reduced, and whose symptoms can be remitted, relieved, and/or completely cured by deleting, suppressing, and/or inhibiting their functions. Examples of such diseases include, but are not limited to, tumors, cancers, autoimmune diseases, macroglobulinemia, and the like. Cancer or tumor, in accordance with the present disclosure includes, but is not limited to, glandular tumors, carcinoid tumors, undifferentiated carcinomas, angiosarcoma, adenocarcinoma, sarcoma, neuroma, gastrointestinal cancers (e.g., colorectal cancers ("CRC") including colon cancer and rectal cancer, biliary cancers including gall bladder cancer and bile duct cancer, anal cancer, esophageal cancer, gastric (stomach) cancer, gastrointestinal carcinoid tumor(s), gastrointestinal stromal tumor(s) ("GIST"), liver cancer, duodenal cancer and small intestine cancer), digestive organ cancer, lung cancers (e.g., non-small cell lung cancer ("NSCLC"), squamous-cell lung carcinoma, large-cell lung carcinoma, small cell lung carcinoma, mesothelioma and other lung cancers such as bronchial tumors and pleuropulmonary blastoma), urological cancers (e.g., kidney (renal) cancer, transitional cell cancer ("TCC") of kidney, TCC of the renal pelvis and ureter ("PDQ"), bladder cancer, urethral cancer and prostate cancer), head and neck cancers (e.g., eye cancer, retinoblastoma, intraocular melanoma, hypopharyngeal cancer, pharyngeal cancer, laryngeal cancer, laryngeal papillomatosis, metastatic squamous neck cancer with occult primary, oral (mouth) cancer, lip cancer, throat cancer, oropharyngeal cancer, esthesioneuroblastoma, nasal cavity and paranasal sinus cancer, nasopharyngeal cancer, and salivary gland cancer), endocrine cancers (e.g., thyroid cancer, parathyroid cancer, multiple endocrine neoplasia syndromes, thymoma and thymic carcinoma, pancreatic cancers including pancreatic ductal adenocarcinoma ("PDAC"), pancreatic neuroendocrine tumors and islet cell tumors), breast cancers (extrahepatic ductal carcinoma in situ ("DCIS"), lobular carcinoma in situ ("LCIS"), triple negative breast cancer, and inflammatory breast cancer), male and female reproductive and/or genital cancers (e.g., cervical cancer, ovarian cancer, endometrial cancer, uterine sarcoma, uterine cancer, vaginal cancer, vulvar cancer, gestational trophoblastic tumor ("GTD"), extragonadal germ cell tumor, extracranial germ cell tumor, germ cell tumor, testicular cancer and penile cancer), brain and nervous system cancers (e.g., astrocytomas, brain stem glioma, brain tumor, craniopharyngioma, central nervous system ("CNS") cancer, chordomas, ependymoma, embryonal tumors, neuroblastoma, paraganglioma and atypical teratoid), skin cancers (e.g., basal cell carcinoma ("BCC"), squamous cell skin carcinoma ("SCC"), Merkel cell carcinoma and melanoma), tissue and bone cancers (e.g., soft-tissue sarcoma, rhabdomyosarcoma, fibrous histiocytoma of bone, Ewing sarcoma, malignant fibrous histiocytoma of bone ("MFH"), osteosarcoma and chondrosarcoma), cardiovascular cancers (e.g., heart cancer and cardiac tumors), appendix cancers, childhood and adolescent cancers (e.g., adrenocortical carcinoma childhood, midline tract carcinoma, hepatocellular carcinoma ("HCC"), hepatoblastoma and Wilms' tumor) and viral-induced cancers (e.g., HHV-8 related cancers (Kaposi sarcoma) and HIV/AIDS related cancers). In some embodiments, the cancer is lung cancer, pancreatic cancer, rectal cancer, colon cancer, or colorectal cancer. In one embodiment, squamous carcinoma is a cancer of uterine cervix, tarsus, conjunctiva, vagina, lung, oral cavity, skin, bladder, tongue, larynx or esophagus. In one embodiment, adenocarcinoma is a cancer of prostate, small intestine, endometrium, uterine cervix, large intestine, lung, pancreas, esophagus, rectum, uterus, stomach, breast or ovary. In one embodiment, tumor is rectal cancer, colon cancer, colorectal cancer, pancreatic cancer, lung cancer, breast cancer or leukemia. In one embodiment, a subject suffering from any of the diseases selected from the above does not have to have K-Ras G12C mutant protein. In a preferred embodiment, a subject suffering from any of the diseases selected from the above has K-Ras G12C mutant protein.

Cancer, in accordance with the present disclosure also includes, but is not limited to, hematological and plasma cell malignancies and hematopoietic tumors (e.g., cancers that affect blood, bone marrow and/or lymph nodes) such as multiple myeloma, leukemias and lymphomas, myelodysplastic syndromes and myeloproliferative disorders. Leukemias include, without limitation, acute lymphoblastic leukemia ("ALL"), acute myelogenous (myeloid) leukemia ("AML"), chronic lymphocytic leukemia ("CLL"), chronic myelogenous leukemia ("CML"), acute monocytic leukemia ("AMoL"), hairy cell leukemia, and/or other leukemias. Lymphomas include, without limitation, Hodgkin's lymphoma and non-Hodgkin's lymphoma ("NHL"). In some embodiments, NHL is B-cell lymphomas and/or T-cell lymphomas. In some embodiments, NHL includes, without limitation, diffuse large B-cell lymphoma ("DLBCL"), small lymphocytic lymphoma ("SLL"), chronic lymphocytic leukemia ("CLL"), mantle cell lymphoma ("MCL"), Burkitt's lymphoma, cutaneous T-cell lymphoma including mycosis fungoides and Sézary syndrome, AIDS-related lymphoma, follicular lymphoma, lymphoplasmacytic lymphoma (Waldenstrom's macroglobulinemia ("WM")), primary central nervous system (CNS) lymphoma and/or other lymphomas.

In one embodiment, an antitumor agent comprising a compound or a pharmaceutically acceptable salt thereof of the present invention, and one or more other antitumor agents as an active ingredient may be provided. In one embodiment, an antitumor agent comprising a compound or a pharmaceutically acceptable salt thereof of the present invention as an active ingredient, which is administered in combination with one or more other antitumor agents may be provided. In one embodiment, use of the compound of the present invention or a salt thereof and one or more other antitumor agents for the manufacture of an antitumor agent may be provided. In one embodiment, use of the compound of the present invention or a salt thereof for the manufacture of an antitumor agent, which is administered in combination with one or more other antitumor agents may be provided. In one embodiment, the combination of a compound of the present invention or a salt thereof and one or more other antitumor agents for use in the treatment of tumors may be provided. In one embodiment, the compound or pharmaceutically acceptable salt thereof of the present invention for use in the treatment of tumor, which is administered in combination with one or more other antitumor agents may be provided. In one embodiment, a method for treating tumor, comprising administrating a therapeutically effective amount of the compound or pharmaceutically acceptable salt thereof of the present invention, and one or more other antitumor agents to a subject in need thereof may be provided. In one embodiment, a method for treating tumor, comprising administrating a therapeutically effective amount of the compound or pharmaceutically acceptable salt thereof of the present invention, which is administered in combination with one or more other antitumor agents to a subject in need thereof may be provided.

The compound or pharmaceutically acceptable salt thereof of the present invention can be used to treat cancer in combination with one or more other antitumor agents. In other words, a single compound or pharmaceutically acceptable salt thereof of the present invention or more than one compound or pharmaceutically acceptable salt thereof of the present invention may be used in combination with a single other antitumor agent or more than one other antitumor agents.

As used herein, an "other antitumor agent" can be any pharmaceutically active agent (or pharmaceutically acceptable salt thereof) that is active in the body and that is different from the compound or pharmaceutically acceptable salt thereof of the present invention. The other antitumor agents include prodrugs, free-acid, free-base and pharmaceutically acceptable salts of the additional active agents. Generally any suitable other antitumor agent, including chemotherapeutic agents or therapeutic antibodies, may be used in any combination with a compound or pharmaceutically acceptable salt thereof of the present invention in a single dosage formulation (e.g., a fixed dose drug combination) or in one or more separate dosage formulations which allow for concurrent or sequential administration of the pharmaceutically active agents (co-administration of the separate active agents) to subjects. In certain embodiments, a compound or pharmaceutically acceptable salt thereof of the present invention and an other antitumor agent are administered a few minutes apart, or a few hours apart, or a few days apart. In addition, the compound or pharmaceutically acceptable salt thereof of the present invention can be administered in combination with radiation therapy, hormone therapy, targeted therapy, surgery or immunotherapy. In one embodiment, the one or more other antitumor agents are included in a pharmaceutical composition as described above.

In one embodiment, the other antitumor agent(s) is an additional anti-cancer agent (also known as an antineoplastic agent). As used herein, an "anti-cancer agent" is any pharmaceutically active agent (or pharmaceutically active salt thereof) that is active in the body against cancer. Examples of anti-cancer agents include chemotherapeutic agents (e.g., cytotoxic agents), immunotherapeutic agents, hormonal and anti-hormonal agents, targeted therapy agents, and anti-angiogenesis agents. Many anti-cancer agents can be classified within one or more of these groups. While certain anti-cancer agents have been categorized within a specific group(s) or subgroup(s) herein, many of these agents can also be listed within one or more other group(s) or subgroup(s), as would be presently understood in the art. It is to be understood that the classification herein of a particular agent into a particular group is not intended to be limiting. Many anti-cancer agents are presently known in the art and can be used in combination with the compound or pharmaceutically acceptable salt thereof of the present invention.

Further, an agent can be an agonist, antagonist, allosteric modulator, toxin or, more generally, may act to inhibit or stimulate its target (e.g., receptor or enzyme activation or inhibition). For example, suitable for use are one or more agents (e.g., antibodies, antigen binding regions, or soluble receptors) that specifically bind and inhibit the activity of growth factors, such as antagonists of hepatocyte growth factor (HGF, also known as Scatter Factor), and antibodies or antigen binding regions that specifically bind its receptor "c-met".

In an embodiment, the additional anti-cancer agent is a chemotherapeutic agent, an immunotherapeutic agent, a hormonal agent, an anti-hormonal agent, a targeted therapy agent, or an anti-angiogenesis agent (or angiogenesis inhibitor). In an embodiment, the additional anti-cancer agent is selected from the group consisting of a chemotherapeutic agent, a mitotic inhibitor, a plant alkaloid, an alkylating agent, an anti-metabolite, a platinum analog, an enzyme, a topoisomerase inhibitor, a retinoid, an aziridine, an antibiotic, a hormonal agent, an anti-hormonal agent, an anti-estrogen, an anti-androgen, an anti-adrenal, an androgen, a targeted therapy agent, an immunotherapeutic agent, a biological response modifier, a cytokine inhibitor, a tumor vaccine, a monoclonal antibody, an immune checkpoint inhibitor, an anti-PD-1 agent, an anti-PD-L1 agent, a colony-stimulating factor, an immunomodulator, an immunomodulatory imide (IMiD), an anti-CTLA4 agent, an anti-LAG1 agent, an anti-OX40 agent, a GITR agonist, a CAR-T cell, a BiTE, a signal transduction inhibitor, a growth factor inhibitor, a tyrosine kinase inhibitor, an EGFR inhibitor, a histone deacetylase (HDAC) inhibitor, a proteasome inhibitor, a cell-cycle inhibitor, an anti-angiogenesis agent, a matrix-metalloproteinase (MMP) inhibitor, a hepatocyte growth factor inhibitor, a TOR inhibitor, a KDR inhibitor, a VEGF inhibitor, a HIF-1α inhibitor a HIF-2α inhibitor, a fibroblast growth factor (FGF) inhibitor, a RAF inhibitor, a MEK inhibitor, an ERK inhibitor, a PI3K inhibitor, an AKT inhibitor, an MCL-1 inhibitor, a BCL-2 inhibitor, an SHP2 inhibitor, a HER-2 inhibitor, a BRAF-inhibitor, a gene expression modulator, an autophagy inhibitor, an apoptosis inducer, an antiproliferative agent, and a glycolysis inhibitor.

In one embodiment, the additional anti-cancer agent(s) is a chemotherapeutic agent. Non-limiting examples of chemotherapeutic agents include mitotic inhibitors and plant alkaloids, alkylating agents, anti-metabolites, platinum analogs, enzymes, topoisomerase inhibitors, retinoids, aziridines, and antibiotics.

Non-limiting examples of mitotic inhibitors and plant alkaloids include taxanes such as cabazitaxel, docetaxel, larotaxel, ortataxel, paclitaxel, and tesetaxel; demecolcine; epothilone; eribulin; etoposide (VP-16); etoposide phosphate; navelbine; noscapine; teniposide; thaliblastine; vinblastine; vincristine; vindesine; vinflunine; and vinorelbine.

Non-limiting examples of alkylating agents include nitrogen mustards such as chlorambucil, chlornaphazine, cholophosphamide, cytophosphane, estramustine, ifosfamide, mannomustine, mechlorethamine, mechlorethamine oxide hydrochloride, melphalan, novembichin, phenesterine, prednimustine, tris(2-chloroethyl)amine, trofosfamide, and uracil mustard; alkyl sulfonates such as busulfan, improsulfan, and piposulfan; nitrosoureas such as carmustine, chlorozotocin, fotemustine, lomustine, nimustine, ranimustine, streptozotocin, and TA-07; ethylenimines and methylamelamines such as altretamine, thiotepa, triethylenemelamine, triethylenethiophosphaoramide, trietylenephosphoramide, and trimethylolomelamine; ambamustine; bendamustine; dacarbazine; etoglucid; irofulven; mafosfamide; mitobronitol; mitolactol; pipobroman; procarbazine; temozolomide; treosulfan; and triaziquone.

Non-limiting examples of anti-metabolites include folic acid analogues such as aminopterin, denopterin, edatrexate, methotrexate, pteropterin, raltitrexed, and trimetrexate; purine analogs such as 6-mercaptopurine, 6-thioguanine, fludarabine, forodesine, thiamiprine, and thioguanine; pyrimidine analogs such as 5-fluorouracil (5-FU), 6-azauridine, ancitabine, azacytidine, capecitabine, carmofur, cytarabine, decitabine, dideoxyuridine, doxifiuridine, doxifluridine, enocitabine, floxuridine, galocitabine, gemcitabine, and sapacitabine; 3-aminopyridine-2-carboxaldehyde thiosemicarbazone; broxuridine; cladribine; cyclophosphamide; cytarabine; emitefur; hydroxyurea; mercaptopurine; nelarabine; pemetrexed; pentostatin; tegafur; and troxacitabine.

Non-limiting examples of platinum analogs include carboplatin, cisplatin, dicycloplatin, heptaplatin, lobaplatin, nedaplatin, oxaliplatin, satraplatin, and triplatin tetranitrate.

Non-limiting examples of enzymes include asparaginase and pegaspargase.

Non-limiting examples of topoisomerase inhibitors include acridine carboxamide, amonafide, amsacrine, belotecan, elliptinium acetate, exatecan, indolocarbazole, irinotecan, lurtotecan, mitoxantrone, razoxane, rubitecan, SN-38, sobuzoxane, and topotecan.

Non-limiting examples of retinoids include alitretinoin, bexarotene, fenretinide, isotretinoin, liarozole, RII retinamide, and tretinoin.

Non-limiting examples of aziridines include benzodopa, carboquone, meturedopa, and uredopa.

Non-limiting examples of antibiotics include intercalating antibiotics; anthracenediones; anthracycline antibiotics such as aclarubicin, amrubicin, daunomycin, daunorubicin, doxorubicin, epirubicin, idarubicin, menogaril, nogalamycin, pirarubicin, and valrubicin; 6-diazo-5-oxo-L-norleucine; aclacinomysins; actinomycin; authramycin; azaserine; bleomycins; cactinomycin; calicheamicin; carabicin; carminomycin; carzinophilin; chromomycins; dactinomycin; detorubicin; esorubicin; esperamicins; geldanamycin; marcellomycin; mitomycins; mitomycin C; mycophenolic acid; olivomycins; novantrone; peplomycin; porfiromycin; potfiromycin; puromycin; quelamycin; rebeccamycin; rodorubicin; streptonigrin; streptozocin; tanespimycin; tubercidin; ubenimex; zinostatin; zinostatin stimalamer; and zorubicin.

In one embodiment, the additional anti-cancer agent(s) is a hormonal and/or anti-hormonal agent (i.e., hormone therapy). Non-limiting examples of hormonal and anti-hormonal agents include anti-androgens such as abiraterone, apalutamide, bicalutamide, darolutamide, enzalutamide, flutamide, goserelin, leuprolide, and nilutamide; anti-estrogens such as 4-hydroxy tamoxifen, aromatase inhibiting 4(5)-imidazoles, EM-800, fosfestrol, fulvestrant, keoxifene, LY 117018, onapristone, raloxifene, tamoxifen, toremifene, and trioxifene; anti-adrenals such as aminoglutethimide, dexaminoglutethimide, mitotane, and trilostane; androgens such as calusterone, dromostanolone propionate, epitiostanol, mepitiostane, and testolactone; abarelix; anastrozole; cetrorelix; deslorelin; exemestane; fadrozole; finasteride; formestane; histrelin (RL 0903); human chorionic gonadotropin; lanreotide; LDI 200 (Milkhaus); letrozole; leuprorelin; mifepristone; nafarelin; nafoxidine; osaterone; prednisone; thyrotropin alfa; and triptorelin.

In one embodiment, the additional anti-cancer agent(s) is an immunotherapeutic agent (i.e., immunotherapy). Non-limiting examples of immunotherapeutic agents include biological response modifiers, cytokine inhibitors, tumor vaccines, monoclonal antibodies, immune checkpoint inhibitors, colony-stimulating factors, and immunomodulators.

Non-limiting examples of biological response modifiers, including cytokine inhibitors (cytokines) such as interferons and interleukins, include interferon alfa/interferon alpha such as interferon alfa-2, interferon alfa-2a, interferon alfa-2b, interferon alfa-n1, interferon alfa-n3, interferon alfacon-1, peginterferon alfa-2a, peginterferon alfa-2b, and leukocyte alpha interferon; interferon beta such as interferon beta-1a, and interferon beta-1b; interferon gamma such as natural interferon gamma-1a, and interferon ganma-1b; aldesleukin; interleukin-1 beta; interleukin-2; oprelvekin; sonermin; tasonermin; and virulizin.

Non-limiting examples of tumor vaccines include APC 8015, AVICINE, bladder cancer vaccine, cancer vaccine (Biomira), gastrin 17 immunogen, Maruyama vaccine, melanoma lysate vaccine, melanoma oncolysate vaccine (New York Medical College), melanoma vaccine (New York University), melanoma vaccine (Sloan Kettering Institute), TICE® BCG (Bacillus Calmette-Guerin), and viral melanoma cell lysates vaccine (Royal Newcastle Hospital).

Non-limiting examples of monoclonal antibodies include abagovomab, adecatumumab, aflibercept, alemtuzumab, blinatumomab, brentuximab vedotin, CA 125 MAb (Biomira), cancer MAb (Japan Pharmaceutical Development), daclizumab, daratumumab, denosumab, edrecolomab, gemtuzumab zogamicin, HER-2 and Fc MAb (Medarex), ibritumomab tiuxetan, idiotypic 105AD7 MAb (CRC Technology), idiotypic CEA MAb (Trilex), ipilimumab, lintuzumab, LYM-1-iodine 131 MAb (Techni clone), mitumomab, moxetumomab, ofatumumab, polymorphic epithelial mucin-yttrium 90 MAb (Antisoma), ranibizumab, rituximab, and trastuzumab.

Non-limiting examples of immune checkpoint inhibitors include anti-PD-1 agents or antibodies such as cemiplimab, nivolumab, and pembrolizumab; anti-PD-L1 agents or antibodies such as atezolizumab, avelumab, and durvalumab; anti-CTLA-4 agents or antibodies such as ipilumumab; anti-LAG1 agents; and anti-OX40 agents.

Non-limiting examples of colony-stimulating factors include darbepoetin alfa, epoetin alfa, epoetin beta, filgrastim, granulocyte macrophage colony stimulating factor, lenograstim, leridistim, mirimostim, molgramostim, nartograstim, pegfilgrastim, and sargramostim.

Non-limiting examples of additional immunotherapeutic agents include BiTEs, CAR-T cells, GITR agonists, imiquimod, immunomodulatory imides (IMiDs), mismatched double stranded RNA (Ampligen), resiquimod, SRL 172, and thymalfasin.

In one embodiment, the additional anti-cancer agent(s) is a targeted therapy agent (i.e., targeted therapy). Targeted therapy agents include, for example, monoclonal antibodies and small molecule drugs. Non-limiting examples of targeted therapy agents include signal transduction inhibitors, growth factor inhibitors, tyrosine kinase inhibitors, EGFR inhibitors, histone deacetylase (HDAC) inhibitors, proteasome inhibitors, cell-cycle inhibitors, angiogenesis inhibitors, matrix-metalloproteinase (MMP) inhibitors, hepatocyte growth factor inhibitors, TOR inhibitors, KDR inhibitors, VEGF inhibitors, fibroblast growth factors (FGF)

inhibitors, MEK inhibitors, ERK inhibitors, PI3K inhibitors, AKT inhibitors, MCL-1 inhibitors, BCL-2 inhibitors, SHP2 inhibitors, HER-2 inhibitors, BRAF-inhibitors, gene expression modulators, autophagy inhibitors, apoptosis inducers, antiproliferative agents, and glycolysis inhibitors.

Non-limiting examples of signal transduction inhibitors include tyrosine kinase inhibitors, multiple-kinase inhibitors, anlotinib, avapritinib, axitinib, dasatinib, dovitinib, imatinib, lenvatinib, lonidanine, nilotinib, nintedanib, pazopanib, pegvisomant, ponatinib, vandetanib, and EGFR inhibitory agents.

Non-limiting examples of EGFR inhibitory agents include small molecule antagonists of EGFR such as afatinib, brigatinib, erlotinib, gefitinib, lapatinib, and osimertinib; and antibody-based EGFR inhibitors, including any anti-EGFR antibody or antibody fragment that can partially or completely block EGFR activation by its natural ligand. Antibody-based EGFR inhibitory agents may include, for example, those described in Modjtahedi, H., et al., 1993, Br. J. Cancer 67:247-253; Teramoto, T., et al., 1996, Cancer 77:639-645; Goldstein et al, 1995, Clin. Cancer Res. 1: 1311-1318; Huang, S. M., et al., 1999, Cancer Res. 15:59(8): 1935-40; and Yang, X., et al., 1999, Cancer Res. 59: 1236-1243; monoclonal antibody Mab E7.6.3 (Yang, 1999 supra); Mab C225 (ATCC Accession No. HB-8508), or an antibody or antibody fragment having the binding specificity thereof; specific antisense nucleotide or siRNA; afatinib, cetuximab; matuzumab; necitumumab; nimotuzumab; panitumumab; and zalutumumab.

Non-limiting examples of histone deacetylase (HDAC) inhibitors include belinostat, panobinostat, romidepsin, and vorinostat.

Non-limiting examples of proteasome inhibitors include bortezomib, carfilzomib, ixazomib, marizomib (salinosporamide a), and oprozomib.

Non-limiting examples of cell-cycle inhibitors, including CDK inhibitors, include abemaciclib, alvocidib, palbociclib, and ribociclib.

In one embodiment, the additional anti-cancer agent(s) is an anti-angiogenic agent (or angiogenesis inhibitor) including, but not limited to, matrix-metalloproteinase (MMP) inhibitors; VEGF inhibitors; EGFR inhibitors; TOR inhibitors such as everolimus and temsirolimus; PDGFR kinase inhibitory agents such as crenolanib; HIF-1a inhibitors such as PX 478; HIF-2α inhibitors such as belzutifan and the HIF-2α inhibitors described in WO 2015/035223; fibroblast growth factor (FGF) or FGFR inhibitory agents such as B-FGF and RG 13577; hepatocyte growth factor inhibitors; KDR inhibitors; anti-Angl and anti-Ang2 agents; anti-Tie2 kinase inhibitory agents; Tek antagonists (US 2003/0162712; U.S. Pat. No. 6,413,932); anti-TWEAK agents (U.S. Pat. No. 6,727,225); ADAM distintegrin domain to antagonize the binding of integrin to its ligands (US 2002/0042368); anti-eph receptor and/or anti-ephrin antibodies or antigen binding regions (U.S. Pat. Nos. 5,981,245; 5,728,813; 5,969,110; 6,596,852; 6,232,447; and 6,057,124); and anti-PDGF-BB antagonists as well as antibodies or antigen binding regions specifically binding to PDGF-BB ligands.

Non-limiting examples of matrix-metalloproteinase (MMP) inhibitors include MMP-2 (matrix-metalloproteinase 2) inhibitors, MMP-9 (matrix-metalloproteinase 9) inhibitors, prinomastat, RO 32-3555, and RS 13-0830. Examples of useful matrix metalloproteinase inhibitors are described, for example, in WO 96/33172, WO 96/27583, EP 1004578, WO 98/07697, WO 98/03516, WO 98/34918, WO 98/34915, WO 98/33768, WO 98/30566, EP 0606046, EP 0931788, WO 90/05719, WO 99/52910, WO 99/52889, WO 99/29667, WO 1999/007675, EP 1786785, EP 1181017, US 2009/0012085, U.S. Pat. Nos. 5,863,949, 5,861,510, and EP 0780386. Preferred MMP-2 and MMP-9 inhibitors are those that have little or no activity inhibiting MMP-1. More preferred, are those that selectively inhibit MMP-2 and/or MMP-9 relative to the other matrix-metalloproteinases (i.e., MMP-1, MMP-3, MMP-4, MMP-5, MMP-6, MMP-7, MMP-8, MMP-10, MMP-11, MMP-12, and MMP-13).

Non-limiting examples of VEGF and VEGFR inhibitory agents include bevacizumab, cediranib, CEP 7055, CP 547632, KRN 633, orantinib, pazopanib, pegaptanib, pegaptanib octasodium, semaxanib, sorafenib, sunitinib, VEGF antagonist (Borean, Denmark), and VEGF-TRAP™.

The other antitumor agent (s) may also be another anti-angiogenic agent including, but not limited to, 2-methoxyestradiol, AE 941, alemtuzumab, alpha-D148 Mab (Amgen, US), alphastatin, anecortave acetate, angiocidin, angiogenesis inhibitors, (SUGEN, US), angiostatin, anti-Vn Mab (Crucell, Netherlands), atiprimod, axitinib, AZD 9935, BAY RES 2690 (Bayer, Germany, BC 1 (Genoa Institute of Cancer Research, Italy), beloranib, benefin (Lane Labs, US), cabozantinib, CDP 791 (Celltech Group, UK), chondroitinase AC, cilengitide, combretastatin A4 prodrug, CP 564959 (OSI, US), CV247, CYC 381 (Harvard University, US), E 7820, EHT 0101, endostatin, enzastaurin hydrochloride, ER-68203-00 (IVAX, US), fibrinogen-E fragment, Flk-1 (ImClone Systems, US), forms of FLT 1 (VEGFR 1), FR-111142, GCS-100, GW 2286 (GlaxoSmithKline, UK), IL-8, ilomastat, IM-862, irsogladine, KM-2550 (Kyowa Hakko, Japan), lenalidomide, lenvatinib, MAb alpha5beta3 integrin, second generation (Applied Molecular Evolution, USA and MedImmune, US), MAb VEGF (Xenova, UK), marimastat, maspin (Sosei, Japan), metastatin, motuporamine C, M-PGA, ombrabulin, OXI4503, PI 88, platelet factor 4, PPI 2458, ranucirumab, rBPI 21 and BPI-derived antiangiogenic (XOMA, US), regorafenib, SC-236, SD-7784 (Pfizer, US), SDX 103 (University of California at San Diego, US), SG 292 (Telios, US), SU-0879 (Pfizer, US), TAN-1120, TBC-1635, tesevatinib, tetrathiomolybdate, thalidomide, thrombospondin 1 inhibitor, Tie-2 ligands (Regeneron, US), tissue factor pathway inhibitors (EntreMed, US), tumor necrosis factor-alpha inhibitors, tumstatin, TZ 93, urokinase plasminogen activator inhibitors, vadimezan, vandetanib, vasostatin, vatalanib, VE-cadherin-2 antagonists, xanthorrhizol, XL 784 (Exelixis, US), ziv-aflibercept, and ZD 6126.

In embodiments, the other antitumor agent(s) is an additional active agent that disrupts or inhibits RAS-RAF-ERK or PI3K-AKT-TOR signaling pathways or is a PD-1 and/or PD-L1 antagonist. In embodiments, the other antitumor agent(s) is a RAF inhibitor, EGFR inhibitor, MEK inhibitor, ERK inhibitor, PI3K inhibitor, AKT inhibitor, TOR inhibitor, MCL-1 inhibitor, BCL-2 inhibitor, SHP2 inhibitor, proteasome inhibitor, or immune therapy, including monoclonal antibodies, immunomodulatory imides (IMiDs), anti-PD-1, anti-PDL-1, anti-CTLA4, anti-LAG1, and anti-OX40 agents, GITR agonists, CAR-T cells, and BiTEs.

Non-limiting examples of RAF inhibitors include dabrafenib, encorafenib, regorafenib, sorafenib, and vemurafenib.

Non-limiting examples of MEK inhibitors include binimetinib, CI-1040, cobimetinib, PD318088, PD325901, PD334581, PD98059, refametinib, selumetinib, and trametinib.

Non-limiting examples of ERK inhibitors include LY3214996, LTT462, MK-8353, SCH772984, ravoxertinib, ulixertinib, and an ERKi as described in WO 2017/068412.

Non-limiting examples of PI3K inhibitors include 17-hydroxywortmannin analogs (e.g., WO 06/044453); AEZS-136; alpelisib; AS-252424; buparlisib; CAL263; copanlisib; CUDC-907; dactolisib (WO 06/122806); demethoxyviridin; duvelisib; GNE-477; GSK1059615; IC87114; idelalisib; INK1117; LY294002; Palomid 529; paxalisib; perifosine; PI-103; PI-103 hydrochloride; pictilisib (e.g., WO 09/036, 082; WO 09/055,730); PIK 90; PWT33597; SF1126; sonolisib; TGI 00-115; TGX-221; XL147; XL-765; wortmannin; and ZSTK474.

Non-limiting examples of AKT inhibitors include Akt-1-1 (inhibits Aktl) (Barnett et al. (2005) Biochem. J., 385 (Pt. 2), 399-408); Akt-1-1,2 (Barnett et al. (2005) Biochem. J. 385 (Pt. 2), 399-408); API-59CJ-Ome (e.g., Jin et al. (2004) Br. J. Cancer 91, 1808-12); 1-H-imidazo[4,5-c]pyridinyl compounds (e.g., WO05011700); indole-3-carbinol and derivatives thereof (e.g., U.S. Pat. No. 6,656,963; Sarkar and L1 (2004) J Nutr. 134(12 Suppl), 3493S-3498S); perifosine, Dasmahapatra et al. (2004) Clin. Cancer Res. 10(15), 5242-52, 2004); phosphatidylinositol ether lipid analogues (e.g., Gills and Dennis (2004) Expert. Opin. Investig. Drugs 13, 787-97); triciribine (Yang et al. (2004) Cancer Res. 64, 4394-9); imidazooxazone compounds including trans-3-amino-1-methyl-3-[4-(3-phenyl-5H-imidazo[1,2-c]pyrido [3,4-e][1,3]oxazin-2-yl)phenyl]-cyclobutanol hydrochloride (WO 2012/137870); afuresertib; capivasertib; MK2206; and patasertib.

Non-limiting examples of TOR inhibitors include deforolimus; ATP-competitive TORC1/TORC2 inhibitors, including PI-103, PP242, PP30, and Torin 1; TOR inhibitors in FKBP12 enhancer, rapamycins and derivatives thereof, including temsirolimus, everolimus, WO 9409010; rapalogs, e.g. as disclosed in WO 98/02441 and WO 01/14387, e.g. AP23573, AP23464, or AP23841; 40-(2-hydroxyethyl) rapamycin, 40-[3-hydroxy (hydroxymethyl)methylpropanoate]-rapamycin; 40-epi-(tetrazolyl)-rapamycin (also called ABT578); 32-deoxorapamycin; 16-pentynyloxy-32(S)-dihydrorapanycin, and other derivatives disclosed in WO 05/005434; derivatives disclosed in U.S. Pat. No. 5,258,389, WO 94/090101, WO 92/05179, U.S. Pat. Nos. 5,118,677, 5,118,678, 5,100,883, 5,151,413, 5,120,842, WO 93/111130, WO 94/02136, WO 94/02485, WO 95/14023, WO 94/02136, WO 95/16691, WO 96/41807, WO 96/41807 and U.S. Pat. No. 5,256,790; and phosphorus-containing rapamycin derivatives (e.g., WO 05/016252).

Non-limiting examples of MCL-1 inhibitors include AMG-176, MIK665, and S63845.

Non-limiting examples of SHP2 inhibitors include SHP2 inhibitors described in WO 2019/167000 and WO 2020/022323.

Additional non-limiting examples of additional anti-cancer agents that are suitable for combination use include 2-ethylhydrazide, 2,2',2"-trichlorotriethylamine, ABVD, aceglatone, acemannan, aldophosphamide glycoside, alpharadin, amifostine, aminolevulinic acid, anagrelide, ANCER, ancestim, anti-CD22 immunotoxins, antitumorigenic herbs, apaziquone, arglabin, arsenic trioxide, azathioprine, BAM 002 (Novelos), bcl-2 (Genta), bestrabucil, biricodar, bisantrene, bromocriptine, brostallicin, bryostatin, buthionine sulfoximine, calyculin, cell-cycle nonspecific antineoplastic agents, celmoleukin, clodronate, clotrimazole, cytarabine ocfosfate, DA 3030 (Dong-A), defofamine, denileukin diftitox, dexrazoxane, diaziquone, dichloroacetic acid, dilazep, discodermolide, docosanol, doxercalciferol, edelfosine, eflornithine, EL532 (Elan), elfomithine, elsamitrucin, eniluracil, etanidazole, exisulind, ferruginol, folic acid replenisher such as frolinic acid, gacytosine, gallium nitrate, gimeracil/oteracil/tegafur combination (S-1), glycopine, histamine dihydrochloride, HIT diclofenac, HLA-B7 gene therapy (Vical), human fetal alpha fetoprotein, ibandronate, ibandronic acid, ICE chemotherapy regimen, imexon, iobenguane, IT-101 (CRLX101), laniquidar, LC 9018 (Yakult), leflunomide, lentinan, levamisole+fluorouracil, lovastatin, lucanthone, masoprocol, melarsoprol, metoclopramide, miltefosine, miproxifene, mitoguazone, mitozolomide, mopidamol, motexafin gadolinium, MX6 (Galderma), naloxone+pentazocine, nitracrine, nolatrexed, NSC 631570 octreotide (Ukrain), olaparib, P-30 protein, PAC-1, palifermin, pamidronate, pamidronic acid, pentosan polysulfate sodium, phenamet, picibanil, pixantrone, platinum, podophyllinic acid, porfimer sodium, PSK (Polysaccharide-K), rabbit antithymocyte polyclonal antibody, rasburiembodiment, retinoic acid, rhenium Re 186 etidronate, romurtide, samarium (153 Sm) lexidronam, sizofiran, sodium phenylacetate, sparfosic acid, spirogermanium, strontium-89 chloride, suramin, swainsonine, talaporfin, tariquidar, tazarotene, tegafur-uracil, temoporfin, tenuazonic acid, tetrachlorodecaoxide, thrombopoietin, tin ethyl etiopurpurin, tirapazamine, TLC ELL-12, tositumomab-iodine 131, trifluridine and tipiracil combination, troponin I (Harvard University, US), urethan, valspodar, verteporfin, zoledronic acid, and zosuquidar.

The present invention further provides a method for using the compound or pharmaceutically acceptable salt thereof of the present invention or pharmaceutical compositions provided herein, in combination with radiation therapy to treat cancer. Techniques for administering radiation therapy are known in the art, and these techniques can be used in the combination therapy described herein. The administration of the compound or pharmaceutically acceptable salt thereof of the present invention in this combination therapy can be determined as described herein.

Radiation therapy can be administered through one of several methods, or a combination of methods, including, without limitation, external-beam therapy, internal radiation therapy, implant radiation, stereotactic radiosurgery, systemic radiation therapy, radiotherapy and permanent or temporary interstitial brachy therapy. The term "brachytherapy," as used herein, refers to radiation therapy delivered by a spatially confined radioactive material inserted into the body at or near a tumor or other proliferative tissue disease site. The term is intended, without limitation, to include exposure to radioactive isotopes (e.g., At-211, I-131, I-125, Y-90, Re-186, Re-188, Sm-153, Bi-212, P-32, and radioactive isotopes of Lu). Suitable radiation sources for use as a cell conditioner of the present disclosure include both solids and liquids. By way of non-limiting example, the radiation source can be a radionuclide, such as I-125, I-131, Yb-169, Ir-192 as a solid source, I-125 as a solid source, or other radionuclides that emit photons, beta particles, gamma radiation, or other therapeutic rays. The radioactive material can also be a fluid made from any solution of radionuclide(s), e.g., a solution of I-125 or I-131, or a radioactive fluid can be produced using a slurry of a suitable fluid containing small particles of solid radionuclides, such as Au-198, Y-90. Moreover, the radionuclide(s) can be embodied in a gel or radioactive microspheres.

The present invention also provides methods for combination therapies in which the other antitumor agent is known to modulate other pathways, or other components of the same pathway, or even overlapping sets of target enzymes which are used in combination with a compound or pharmaceutically acceptable salt thereof of the present invention. In one embodiment, such therapy includes, but is not limited to, the combination of one or more compound or pharmaceutically acceptable salt thereof of the present invention with chemotherapeutic agents, immunotherapeutic agents, hormonal therapy agents, therapeutic antibodies, targeted therapy agents, and radiation treatment, to provide a synergistic or additive therapeutic effect.

In one embodiment, use of a compound or pharmaceutically acceptable salt thereof that covalently binds to GTP-bound KRAS G12C for manufacturing of an antitumor agent may be provided. In one embodiment, a compound or pharmaceutically acceptable salt thereof that covalently binds to GTP-bound KRAS G12C for use in the treatment of tumor may be provided. In one embodiment, a method for treating tumor, comprising administrating a therapeutically effective amount of the compound or pharmaceutically acceptable salt thereof that covalently binds to GTP-bound KRAS G12C to a subject in need thereof may be provided.

In one embodiment, there is provided a method for modulating an activity of Ras protein including human K-Ras G12C mutant protein, which comprises contacting the Ras protein with an effective amount of the compound of the present invention. Examples of the activity to be modulated includes GTPase activity, nucleotide exchange, effector protein binding, effector protein activation, guanine exchange factor (GEF) binding, GEF-facilitated nucleotide exchange, phosphate release, nucleotide release, nucleotide binding, Ras, e.g., K-Ras, localization in a cell, post-translational processing of Ras, e.g., K-Ras, and posttranslation modification of Ras, e.g., K-Ras, and preferably include K-Ras localization in a cell, post-translational processing of K-Ras, and posttranslation modification of K-Ras. The "modulating" may be increasing or decreasing the activity of the Ras, e.g., K-Ras protein.

In some embodiments, Ras, e.g., K-Ras, protein exists in a living cell, such as a living cell which forms a part of a living object.

The present invention also provides for the compound of the invention or pharmaceutically acceptable salt thereof, for use in therapy, or use of the compound of the invention or pharmaceutically acceptable salt thereof, in therapy. The present invention also provides for a pharmaceutical composition comprising the compound of the invention or pharmaceutically acceptable salt thereof, for use in the treatment of tumor, or use of the pharmaceutical composition comprising the compound of the invention or pharmaceutically acceptable salt thereof, for treating tumor. The present invention also provides for a pharmaceutical composition comprising the compound of the invention or pharmaceutically acceptable salt thereof, and an other antitumor agent, for use in the treatment of cancer, or use of the pharmaceutical composition comprising the compound of the invention or pharmaceutically acceptable salt thereof, and the other antitumor agent, for treating tumor.

EXAMPLES

The following describes the present invention in more detail, showing Examples and Test Examples. However, the present invention is not limited to these Examples.

The reagents used in the Examples are commercially available products unless indicated otherwise. Prepacked columns manufactured by Shoko Scientific Co., Ltd., or Biotage were used in silica gel column chromatography and basic silica gel column chromatography. An AL400 spectrometer (400 MHz; JEOL Ltd. (JEOL)) or Mercury 400 (400 MHz; Varian) spectrometer was used for NMR spectra. For a deuterated solvent containing tetramethylsilane, tetramethylsilane was used as the internal reference. For other cases, measurement was performed using an NMR solvent as the internal reference. All δ values are indicated in ppm. Microwave reaction was performed using an Initiator (trademark) manufactured by Biotage.

The following describes the meanings of the abbreviations.

s: singlet
d: doublet
t: triplet
q: quartet
sep: septet
dd: double doublet
dt: double triplet
td: triple doublet
tt: triple triplet
ddd: double double doublet
ddt: double double triplet
dtd: double triple doublet
tdd: triple double doublet
m: multiplet
br: broad
brs: broad singlet
tert: tertiary
DMSO-d6: deuterated dimethyl sulfoxide
CDCl3: deuterated chloroform
CD3OD: deuterated methanol
THF: tetrahydrofuran
DMF: N,N-dimethylformamide
NMP: 1-methyl-2-pyrrolidinone
DMSO: dimethyl sulfoxide
WSC: 1-(3-dimethylaminopropyl)-3-ethylcarbodiimide
HATU: (dimethylamino)-N,N-dimethyl(3H-[1,2,3]triazolo[4,5-b]pyridin-3-yloxy)methaniminium hexafluorophosphate
Boc: tert-butoxycarbonyl group Preparation of Compounds

Example 1

3-cyano-N-(3-(2-ethyl-1-methyl-6-(trifluoromethyl)-1H-benzo[d]imidazol-5-yl)phenyl)-4-((E)-4-(((1r,4r)-4-methoxycyclohexyl)amino)but-2-enamido)benzamide Step 1: Methylamine (a 2M THF solution, 36 mL) was added to a solution of 2-fluoro-1-nitro-4-(trifluoromethyl)benzene (5.00 g) in THF (60 mL). After stirring at room temperature for 1 hour, the reaction mixture was concentrated under reduced pressure, thereby obtaining crude N-methyl-2-nitro-5-(trifluoromethyl)aniline.

Step 2: Crude N-methyl-2-nitro-5-(trifluoromethyl)aniline obtained in step 1 and N-bromosuccinimide (5.11 g) were added to acetic acid (80 ml). After the mixture was refluxed for 1 hour, the mixture was cooled to room temperature and poured into water. The resulting solid was collected by filtration, thereby obtaining crude 4-bromo-N-methyl-2-nitro-5-(trifluoromethyl)aniline (6.63 g).

Step 3: A suspension of crude 4-bromo-N-methyl-2-nitro-5-(trifluoromethyl)aniline (6.63 g) obtained in step 2 and iron powder (6.19 g) in a 2M ammonium chloride aqueous solution (55 mL), THF (110 mL), and methanol (110 mL) was stirred at 70° C. for 3 hours. The reaction mixture was concentrated under reduced pressure and the resulting mixture was diluted with water and ethyl acetate, followed by filtrating off the insoluble matter. The organic layer was separated and washed with a saturated sodium chloride solution, followed by drying over sodium sulfate. The solvent was evaporated under reduced pressure, and the obtained residue was purified by column chromatography (hexane:ethyl acetate), thereby obtaining 4-bromo-N1-methyl-5-(trifluoromethyl)benzene-1,2-diamine (5.25 g).

Step 4: Concentrated hydrochloric acid (300 μL) was added to a suspension of 4-bromo-N1-methyl-5-(trifluoromethyl)benzene-1,2-diamine (5.25 g) obtained in step 3 in 1,1,1-triethoxypropane (30 mL), followed by stirring at room temperature overnight. The solvent was evaporated under reduced pressure, and the obtained residue was purified by column chromatography (hexane:ethyl acetate), thereby obtaining 5-bromo-2-ethyl-1-methyl-6-(trifluoromethyl)-1H-benzo[d]imidazole (5.22 g).

Step 5: A suspension of 5-bromo-2-ethyl-1-methyl-6-(trifluoromethyl)-1H-benzo[d]imidazole (1.70 g) obtained in step 4, 3-(4,4,5,5-tetramethyl-1,3,2-dioxaborolan-2-yl)aniline (1.80 g), dichlorobis(triphenylphosphine)palladium (190 mg), and a 1M sodium carbonate aqueous solution (14 mL) in 1,2-dimethoxyethane (28 mL) was refluxed for 6 hours. Ethyl acetate and water were added to the reaction mixture to separate the organic layer, and the organic layer was washed with a saturated sodium chloride solution. The washed organic layer was dried over sodium sulfate, and the solvent was evaporated under reduced pressure, followed by purifying the obtained residue by column chromatography (chloroform:methanol), thereby obtaining 3-(2-ethyl-1-methyl-6-(trifluoromethyl)-1H-benzo[d]imidazol-5-yl)aniline (1.77 g).

Step 6: 1-Hydroxybenzotriazole monohydrate (1.12 g), 4-amino-3-cyano-benzoic acid (1.35 g), triethylamine (1.2 mL), and WSC hydrochloride (1.60 g) were added to a solution of 3-(2-ethyl-1-methyl-6-(trifluoromethyl)-1H-benzo[d]imidazol-5-yl)aniline (1.77 g) obtained in step 5 in DMF (55 mL). A reaction was performed at room temperature overnight. Water was added to the reaction mixture, and extraction was performed with ethyl acetate, followed by washing the organic layer with a saturated sodium chloride solution. The washed layer was dried over sodium sulfate, and the solvent was evaporated under reduced pressure. The obtained residue was purified by column chromatography (chloroform:methanol), thereby obtaining 4-amino-3-cyano-N-(3-(2-ethyl-1-methyl-6-(trifluoromethyl)-1H-benzo[d]imidazol-5-yl)phenyl)benzamide (1.91 g).

Step 7: (E)-4-chlorobut-2-enoic acid (745 mg), 1-propanephosphonic acid anhydride cyclic trimer (a 1.7M THF solution, 4.8 mL), and triethylamine (860 μL) were added to a solution of 4-amino-3-cyano-N-(3-(2-ethyl-1-methyl-6-(trifluoromethyl)-1H-benzo[d]imidazol-5-yl)phenyl)benzamide (1.91 g) obtained in step 6 in DMF (21 mL). A reaction was performed at room temperature for 2 hours. Water was added to the reaction mixture, and extraction was performed with ethyl acetate, followed by washing the organic layer with a saturated sodium chloride solution. The washed layer was dried over sodium sulfate, and the solvent was evaporated under reduced pressure. The obtained residue was purified by column chromatography (chloroform: methanol), thereby obtaining (E)-4-(4-chlorobut-2-enamido)-3-cyano-N-(3-(2-ethyl-1-methyl-6-(trifluoromethyl)-1H-benzo[d]imidazol-5-yl)phenyl)benzamide (932 mg).

Step 8: (1r,4r)-4-methoxycyclohexan-1-amine hydrochloride (28.5 mg), potassium carbonate (47.6 mg), and potassium iodide (34.3 mg) were added to a solution of (E)-4-(4-chlorobut-2-enamido)-3-cyano-N-(3-(2-ethyl-1-methyl-6-(trifluoromethyl)-1H-benzo[d]imidazol-5-yl)phenyl) benzamide (39.0 mg) obtained in step 7 in DMF (690 μL). A reaction was performed at room temperature for 2 hours. Water was added to the reaction mixture, and extraction was performed with ethyl acetate, followed by washing the organic layer with a saturated sodium chloride solution. The washed layer was dried over sodium sulfate, and the solvent was evaporated under reduced pressure. The residue was purified by preparative reversed-phase HPLC (water:acetonitrile (0.1% formic acid)). Saturated sodium bicarbonate water was added to the purified fractions containing the title compound, followed by extraction with ethyl acetate. The extract was washed with a saturated sodium chloride solution and dried over sodium sulfate. The solvent was evaporated under reduced pressure, thereby obtaining the title compound (8.50 mg).

Example 2

(E)-4-(4-(tert-butyl(methyl)amino)but-2-enamido)-3-cyano-N-(3-(2-ethyl-1-methyl-6-(trifluoromethyl)-1H-benzo[d]imidazol-5-yl)phenyl)benzamide N,2-dimethylpropan-2-amine (660 μL), potassium carbonate (220 mg), and potassium iodide (132 mg) were added to a solution of (E)-4-(4-chlorobut-2-enamido)-3-cyano-N-(3-(2-ethyl-1-methyl-6-(trifluoromethyl)-1H-benzo[d]imidazol-5-yl)phenyl)benzamide (150 mg) obtained in Example 1 (step 7) in DMF (1.0 mL). A reaction was performed at room temperature for 2 hours. Water was added to the reaction mixture, and extraction was performed with ethyl acetate, followed by washing the organic layer with a saturated sodium chloride solution. The washed layer was dried over sodium sulfate, and the solvent was evaporated under reduced pressure. The obtained residue was purified by basic silica gel column chromatography (chloroform: methanol), and the residue was diluted with diethyl ether. The resulting solid was collected by filtration, thereby obtaining the title compound (70.9 mg).

Example 3

3-cyano-4-((E)-4-(((1r,4r)-4-methoxycyclohexyl)amino)but-2-enamido)-N-(6-(7-methyl-2,3-dihydro-1H-benzo[d]pyrrolo[1,2-a]imidazol-6-yl)pyridin-2-yl)benzamide Step 1: Bis(pinacolato)diboron (1.52 g) was added to a suspension of 6-bromo-7-methyl-2,3-dihydro-1H-benzo[d]pyrrolo[1,2-a]imidazole (1.00 g), potassium acetate (1.17 g), [1,1'-Bis(diphenylphosphino)ferrocene]dichloropalladium (II), complex with dichloromethane (325 mg) in DMSO (10 mL), followed by stirring at 100° C. for 3 hours. Then Xphos Pd G2 (313 mg) and bis(pinacolato)diboron (1.52 g) were added thereto, and the mixture was stirred at 100° C. for 2 hours. Ethyl acetate and water were added thereto, followed by filtrating off the insoluble matter. The organic layer was separated and washed with a saturated sodium chloride solution, followed by drying over sodium sulfate. The solvent was evaporated under reduced pressure, and the obtained residue was purified by column chromatography (ethyl acetate:ethanol), thereby obtaining 7-methyl-6-(4,4,5,5-tetramethyl-1,3,2-dioxaborolan-2-yl)-2,3-dihydro-1H-benzo[d]pyrrolo[1,2-a]imidazole (639 mg).

Step 2: A suspension of 4-amino-3-cyanobenzoic acid (500 mg) and thionyl chloride (2.5 mL) was heated at 100° C. for 15 min. Then the excessive thionyl chloride was evaporated under reduced pressure. Toluene was added to the obtained residue again to dissolve the residue, followed by evaporating the solvent under reduced pressure. The residue was dissolved in dichloromethane (5.0 mL), and 6-bromopyridin-2-amine (800 mg) and triethylamine (1.3 mL) were added thereto, followed by stirring at 50° C. for 1 hour. The mixture was cooled to room temperature, followed by purification by column chromatography (hexane:ethyl acetate), thereby obtaining 4-amino-N-(6-bromopyridin-2-yl)-3-cyanobenzamide (212 mg).

Step 3: A 2M sodium carbonate aqueous solution (340 μL) was added to a suspension of 7-methyl-6-(4,4,5,5-tetramethyl-1,3,2-dioxaborolan-2-yl)-2,3-dihydro-1H-benzo[d]pyrrolo[1,2-a]imidazole (151 mg) obtained in step 1, 4-amino-N-(6-bromopyridin-2-yl)-3-cyanobenzamide (107 mg) obtained in step 2, and Xphos Pd G2 (26.6 mg) in 1,4-dioxane (1.5 mL), followed by stirring at 100° C. for 2 hours. Then Xphos Pd G2 (26.6 mg) was added thereto, and the mixture was stirred at 105° C. for 3 hours. Ethyl acetate and water were added to the reaction mixture. The organic layer was separated, and the solvent was evaporated under reduced pressure. The obtained residue was purified by column chromatography (chloroform: ethanol), thereby obtaining 4-amino-3-cyano-N-(6-(7-methyl-2,3-dihydro-1H-benzo[d]pyrrolo[1,2-a]imidazol-6-yl)pyridin-2-yl)benzamide (127 mg).

Step 4: Triethylamine (170 μL) was added to a solution of 4-amino-3-cyano-N-(6-(7-methyl-2,3-dihydro-1H-benzo[d]pyrrolo[1,2-a]imidazol-6-yl)pyridin-2-yl)benzamide (127 mg) obtained in step 3, (E)-4-chlorobut-2-enoic acid (56.4 mg) and 1-propanephosphonic acid anhydride cyclic trimer (48% in DMF, 390 μL) in DMF (1.5 mL), followed by stirring at room temperature for 1.5 hours. Ethyl acetate and a sodium hydrogen carbonate aqueous solution were added to the reaction mixture. The organic layer was separated and the solvent was evaporated under reduced pressure. The obtained residue was purified by column chromatography (ethyl acetate:ethanol), thereby obtaining (E)-4-(4-chlorobut-2-enamido)-3-cyano-N-(6-(7-methyl-2,3-dihydro-1H-benzo[d]pyrrolo[1,2-a]imidazol-6-yl)pyridin-2-yl)benzamide (106 mg).

Step 5: Potassium carbonate (56.8 mg) was added to a suspension of (E)-4-(4-chlorobut-2-enamido)-3-cyano-N-(6-(7-methyl-2,3-dihydro-1H-benzo[d]pyrrolo[1,2-a]imidazol-6-yl)pyridin-2-yl)benzamide (30.0 mg) obtained in step 4, (1r,4r)-4-methoxycyclohexan-1-amine hydrochloride (24.3 mg), and potassium iodide (29.2 mg) in DMF (400 μL), followed by stirring at room temperature for 2 hours. Insoluble matter of the reaction mixture was filtered off, and the filtrate was purified by preparative reversed-phase HPLC (water:acetonitrile (0.1% formic acid)). Saturated sodium bicarbonate water was added to the purified fractions containing the title compound, followed by extraction with ethyl acetate. The extract was washed with a saturated sodium chloride solution and dried over sodium sulfate. The solvent was evaporated under reduced pressure, thereby obtaining the title compound (9.2 mg).

Example 4

(E)-N-(2-cyano-4-(8-(1,6-dimethyl-1H-benzo[d]imidazol-5-yl)indolizine-3-carbonyl)phenyl)-4-(((1r,4r)-4-methoxycyclohexyl)amino)but-2-enamide Step 1: Dibromocopper (37.6 g) was added to a solution of 5-acetyl-2-fluorobenzonitrile (25.0 g) in ethyl acetate (380 mL), followed by stirring at 70° C. for 6 hours. Another dibromocopper (37.6 g) was added to the reaction mixture, followed by stirring at 70° C. for 2 hours. The reaction mixture was filtered through celite, followed by washing with saturated sodium bicarbonate water and brine. After the organic layer was dried over sodium sulfate and concentrated, diisopropyl ether was added to the obtained residue, followed by stirring at ambient temperature for 30 minutes. The precipitated solid was collected via filtration, thereby obtaining 5-(2-bromoacetyl)-2-fluorobenzonitrile (32.0 g).

Step 2: 3-bromo-2-methylpyridine (30 mL) was added to a solution of 5-(2-bromoacetyl)-2-fluorobenzonitrile (32.0 g) obtained in step 1 in THF (130 mL), and the mixture was stirred at 85° C. for 4 days. Heptane was added to the reaction mixture at ambient temperature, and stirred for 30 minutes. The precipitated solid was collected via filtration, thereby obtaining 3-bromo-1-(2-(3-cyano-4-fluorophenyl)-2-oxoethyl)-2-methylpyridin-1-ium bromide (55.0 g).

Step 3: A mixture of DMF (41 mL) and dimethyl sulfate (50 mL) was stirred at 80° C. for 3 hours. After cooling the mixture to room temperature, the mixture was added to a solution of 3-bromo-1-(2-(3-cyano-4-fluorophenyl)-2-oxoethyl)-2-methylpyridin-1-ium bromide (14.6 g) obtained in step 2 in DMF (44 mL) at room temperature. After stirring at room temperature for 30 minutes, N,N-diisopropylethylamine (61 mL) was added to the reaction mixture, followed by stirring at room temperature for 1 hour. Water (230 mL) was added to the reaction mixture, followed by collecting the precipitated solid. The obtained solid was dried in vacuo overnight, and ethyl acetate was added to the solid, followed by stirring at room temperature for 30 minutes. After heptane was added to the solution, the precipitated solid was collected via filtration, thereby obtaining 5-(8-bromoindolizine-3-carbonyl)-2-fluorobenzonitrile (9.69 g).

Step 4: A 28% ammonia aqueous solution (70 mL) was added to a solution of 5-(8-bromoindolizine-3-carbonyl)-2-fluorobenzonitrile (9.69 g) obtained in step 3 in 1,4-dioxane (60 mL) and 1,2-dimethoxyethane (10 mL), and the mixture was stirred at 115° C. overnight. After cooling to room temperature, water (200 mL) was added to the reaction mixture. The reaction mixture was stirred at room temperature for 3 hours, followed by collecting the precipitated solid. The solid was dried in vacuo at 60° C. overnight, and ethyl acetate was added to the solid. After stirring for 30 minutes, heptane was added to the suspension. The mixture was stirred at room temperature for 30 minutes, followed by collecting the precipitated solid, thereby obtaining 2-amino-5-(8-bromoindolizine-3-carbonyl)benzonitrile (8.06 g).

Step 5: Methylamine (ca. 7% in THF, 53 mL) was added to 1-bromo-4-fluoro-2-methyl-5-nitrobenzene (5.00 g), followed by stirring at room temperature for 1 hour. The solvent was evaporated under reduced pressure, and ethyl acetate and water were added to the residue. The organic layer was separated and washed with a saturated sodium chloride solution, followed by drying over sodium sulfate. The solvent was evaporated under reduced pressure, thereby obtaining crude 4-bromo-N,5-dimethyl-2-nitroaniline (5.45 g).

Step 6: A suspension of crude 4-bromo-N,5-dimethyl-2-nitroaniline (5.45 g) obtained in step 5, iron powder (5.97 g), and ammonium chloride (5.71 g) in methanol (100 mL), THF (100 mL) and water (50 mL) was stirred at 85° C. for 2 hours. The insoluble matter was filtered off, followed by evaporating the solvent under reduced pressure. The residue was diluted with ethyl acetate, and washed with water and a saturated sodium chloride solution, followed by drying over sodium sulfate. The solvent was evaporated under reduced pressure, thereby obtaining crude 4-bromo-$N^1$,5-dimethylbenzene-1,2-diamine (4.80 g).

Step 7: Concentrated hydrochloric acid (250 μL) was added to a suspension of crude 4-bromo-$N^1$,5-dimethylbenzene-1,2-diamine (4.80 g) obtained in step 6 in triethyl orthoformate (50 mL), followed by stirring at room temperature overnight. Ethyl acetate was added to the reaction mixture, followed by collecting the precipitate and washing with a mixture solvent of hexane-ethyl acetate (3:1), thereby obtaining 5-bromo-1,6-dimethyl-1H-benzo[d]imidazole (2.56 g).

Step 8: A suspension of 5-bromo-1,6-dimethyl-1H-benzo[d]imidazole (2.00 g) obtained in step 7, [1,1'-Bis(diphenylphosphino)ferrocene]dichloropalladium(II), complex with dichloromethane (726 mg), bis(pinacolato)diboron (3.38 g), and potassium acetate (2.62 g) in DMSO (30 mL) was heated to 100° C. for 3 hours. After the reaction mixture was cooled to room temperature, ethyl acetate, water and celite were added thereto, followed by stirring for 10 min. Insoluble matter was filtered off through celite pad, and the organic layer was separated and washed with a saturated sodium chloride solution, followed by drying over sodium sulfate. The solvent was evaporated under reduced pressure, and the obtained residue was purified by column chromatography (ethyl acetate:ethanol), thereby obtaining 1,6-dimethyl-5-(4,4,5,5-tetramethyl-1,3,2-dioxaborolan-2-yl)-1H-benzo[d]imidazole (1.16 g).

Step 9: A suspension of 2-amino-5-(8-bromoindolizine-3-carbonyl)benzonitrile (80.0 mg) obtained in step 4, 1,6-dimethyl-5-(4,4,5,5-tetramethyl-1,3,2-dioxaborolan-2-yl)-1H-benzo[d]imidazole (75.0 mg) obtained in step 8, dichlorobis(triphenylphosphine)palladium (18.0 mg), and a 2M sodium carbonate aqueous solution (240 μL) in 1,4-dioxane (2.0 mL) and DMF (2.0 mL) was stirred at 110° C. for 2 hours. Ethyl acetate and water were added to the reaction mixture to separate the organic layer, and the organic layer was washed with a saturated sodium chloride solution. The washed organic layer was dried over sodium sulfate, and the solvent was evaporated under reduced pressure, followed by purifying the obtained residue by column chromatography (ethyl acetate:methanol), thereby obtaining 2-amino-5-(8-(1,6-dimethyl-1H-benzo[d]imidazol-5-yl)indolizine-3-carbonyl)benzonitrile (83.0 mg).

Step 10: The procedure of Example 1 (steps 7 and 8) was performed except that 2-amino-5-(8-(1,6-dimethyl-1H-benzo[d]imidazol-5-yl)indolizine-3-carbonyl)benzonitrile (80.0 mg) obtained in step 9 was used instead of 4-amino-3-cyano-N-(3-(2-ethyl-1-methyl-6-(trifluoromethyl)-1H-benzo[d]imidazol-5-yl)phenyl)benzamide used in Example 1 (step 7), thereby obtaining the title compound (11.0 mg).

Example 5

(E)-4-(tert-butylamino)-N-(2-cyano-4-(8-(1,6-dimethyl-1H-benzo[d]imidazol-5-yl)indolizine-3-carbonyl)phenyl)but-2-enamide Step 1: (E)-4-chlorobut-2-enoic acid (54.2 mg), 1-propanephosphonic acid anhydride cyclic trimer (a 1.7M THF solution, 350 μL), and triethylamine (140 μL) were added to a solution of 2-amino-5-(8-(1,6-dimethyl-1H-benzo[d]imidazol-5-yl)indolizine-3-carbonyl)benzonitrile (104 mg) obtained in Example 4 (step 9) in DMF (2.0 mL). A reaction was performed at room temperature for 2 hours. Water was added to the reaction mixture, and extraction was performed with ethyl acetate, followed by washing the organic layer with a saturated sodium chloride solution. The washed layer was dried over sodium sulfate, and the solvent was evaporated under reduced pressure. The obtained residue was purified by column chromatography (ethyl acetate:methanol), thereby obtaining (E)-4-chloro-N-(2-cyano-4-(8-(1,6-dimethyl-1H-benzo[d]imidazol-5-yl)indolizine-3-carbonyl)phenyl)but-2-enamide (110 mg).

Step 2: 2-methylpropan-2-amine (36 μL) and potassium iodide (35.0 mg) were added to a solution of (E)-4-chloro-N-(2-cyano-4-(8-(1,6-dimethyl-1H-benzo[d]imidazol-5-yl)indolizine-3-carbonyl)phenyl)but-2-enamide (38.0 mg) obtained in step 1 in DMF (1.0 mL). A reaction was performed at room temperature overnight. Water was added to the reaction mixture, and extraction was performed with ethyl acetate, followed by washing the organic layer with a saturated sodium chloride solution. The washed layer was dried over sodium sulfate, and the solvent was evaporated under reduced pressure. The residue was purified by preparative reversed-phase HPLC (water:acetonitrile (0.1% formic acid)). Saturated sodium bicarbonate water was added to the purified fractions containing the title compound, followed by extraction with ethyl acetate. The extract was washed with a saturated sodium chloride solution and dried over sodium sulfate. The solvent was evaporated under reduced pressure, thereby obtaining the title compound (20.1 mg).

Example 6

(E)-N-(2-cyano-4-(8-(1-methyl-6-(trifluoromethyl)-1H-benzo[d]imidazol-5-yl)indolizine-3-carbonyl)phenyl)-4-(((1r,4r)-4-methoxycyclohexyl)amino)but-2-enamide Step 1: Concentrated hydrochloric acid (40 μL) was added to a suspension of 4-bromo-N1-methyl-5-(trifluoromethyl)benzene-1,2-diamine (1.00 g) obtained in Example 1 (step 3) in triethyl orthoformate (5.0 mL), followed by stirring at room temperature for 1 hour. The reaction mixture was neutralized with a 5M sodium hydroxide aqueous solution. Water was added to the mixture, and extraction was performed with ethyl acetate, followed by washing the organic layer with a saturated sodium chloride solution. The washed layer was dried over sodium sulfate, and the solvent was evaporated under reduced pressure. The obtained residue was diluted with ethyl acetate and heptane. The resulting solid was collected by filtration, thereby obtaining 5-bromo-1-methyl-6-(trifluoromethyl)-1H-benzo[d]imidazole (850 mg).

Step 2: A suspension of 5-bromo-1-methyl-6-(trifluoromethyl)-1H-benzo[d]imidazole (597 mg) obtained in step 1, potassium acetate (557 mg), bis(pinacolato)diboron (888 mg), (1,1'-bis(diphenylphosphino)ferrocene)palladium(II) dichloride dichloromethane adduct (189 mg) in DMSO (7.0 mL) was stirred at 105° C. for 17 hours. Ethyl acetate and water were added to the reaction mixture to separate the organic layer, and the organic layer was washed with a saturated sodium chloride solution. The washed organic layer was dried over sodium sulfate, and the solvent was evaporated under reduced pressure, followed by purifying the obtained residue by column chromatography (hexane:ethyl acetate), thereby obtaining 1-methyl-5-(4,4,5,5-tetramethyl-1,3,2-dioxaborolan-2-yl)-6-(trifluoromethyl)-1H-benzo[d]imidazole (565 mg).

Step 3: A suspension of 1-methyl-5-(4,4,5,5-tetramethyl-1,3,2-dioxaborolan-2-yl)-6-(trifluoromethyl)-1H-benzo[d]imidazole (80.0 mg) obtained in step 2, 2-amino-5-(8-bromoindolizine-3-carbonyl)benzonitrile (49.0 mg) obtained in Example 4 (step 4), XPhos Pd G3 (8.0 mg), and a 2M sodium carbonate aqueous solution (200 μL) in 1,4-dioxane (2.0 mL) was refluxed for 18 hours. Ethyl acetate and water were added to the reaction mixture to separate the organic layer, and the organic layer was washed with a saturated sodium chloride solution. The washed organic layer was dried over sodium sulfate, and the solvent was evaporated under reduced pressure. The obtained residue was purified by column chromatography (ethyl acetate: methanol), thereby obtaining 2-amino-5-(8-(1-methyl-6-(trifluoromethyl)-1H-benzo[d]imidazol-5-yl)indolizine-3-carbonyl)benzonitrile (50.7 mg).

Step 4: The procedure of Example 1 (steps 7 and 8) was performed except that 2-amino-5-(8-(1-methyl-6-(trifluoromethyl)-1H-benzo[d]imidazol-5-yl)indolizine-3-carbonyl)benzonitrile (50.7 mg) obtained in step 3 was used instead of 4-amino-3-cyano-N-(3-(2-ethyl-1-methyl-6-(trifluoromethyl)-1H-benzo[d]imidazol-5-yl)phenyl)benzamide used in Example 1 (step 7), thereby obtaining the title compound (13.7 mg).

Example 7

(E)-N-(2-cyano-4-(8-(1,2-dimethyl-6-(trifluoromethyl)-1H-benzo[d]imidazol-5-yl)indolizine-3-carbonyl)phenyl)-4-(((1r,4r)-4-methoxycyclohexyl)amino)but-2-enamide Step 1: Concentrated hydrochloric acid (610 μL) was added to a suspension of 4-bromo-N1-methyl-5-(trifluoromethyl)benzene-1,2-diamine (19.8 g) obtained in Example 1 (step 3) in 1,1,1-trimethoxyethane (130 mL), followed by stirring at room temperature for 1 hour. The reaction mixture was neutralized with a 5M sodium hydroxide aqueous solution. Water was added to the mixture, and extraction was performed with ethyl acetate, followed by washing the organic layer with a saturated sodium chloride solution. The washed layer was dried over sodium sulfate, and the solvent was evaporated under reduced pressure. The obtained residue was purified by column chromatography (hexane:ethyl acetate), thereby obtaining 5-bromo-1,2-dimethyl-6-(trifluoromethyl)-1H-benzo[d]imidazole (19.3 g).

Step 2: A suspension of 5-bromo-1,2-dimethyl-6-(trifluoromethyl)-1H-benzo[d]imidazole (12.6 g) obtained in step 1, potassium acetate (11.0 g), bis(pinacolato)diboron (17.5 g), (1,1'-bis(diphenylphosphino)ferrocene)palladium(II) dichloride dichloromethane adduct (3.51 g) in DMSO (190 mL) was stirred at 105° C. for 12 hours. Ethyl acetate and water were added to the reaction mixture, and the resulting mixture was filtered through celite. The aqueous layer was extracted with ethyl acetate, and the organic layer was washed with water and a saturated sodium chloride solution. The washed organic layer was dried over sodium sulfate, and the solvent was evaporated under reduced pressure, followed by purifying the obtained residue by column chromatography (hexane:ethyl acetate), thereby obtaining 1,2-dimethyl-5-(4,4,5,5-tetramethyl-1,3,2-dioxaborolan-2-yl)-6-(trifluoromethyl)-1H-benzo[d]imidazole (6.61 g)

Step 3: The procedure of Example 6 (steps 3 and 4) was performed except that 1,2-dimethyl-5-(4,4,5,5-tetramethyl-1,3,2-dioxaborolan-2-yl)-6-(trifluoromethyl)-1H-benzo[d]imidazole (167 mg) obtained in step 2 was used instead of 1-methyl-5-(4,4,5,5-tetramethyl-1,3,2-dioxaborolan-2-yl)-6-(trifluoromethyl)-1H-benzo[d]imidazole used in Example 6 (step 3), thereby obtaining the title compound (22.0 mg).

Example 8

(E)-N-(2-cyano-4-(7-(1-methyl-6-(trifluoromethyl)-1H-benzo[d]imidazol-5-yl)-1H-indole-3-carbonyl)phenyl)-4-(((1r,4r)-4-methoxycyclohexyl)amino)but-2-enamide Step 1: Thionyl chloride (20 mL) was added to 4-amino-3-cyanobenzoic acid (2.00 g), followed by stirring at 110° C. for 90 minutes. The solvent was evaporated under reduced pressure, and toluene (20 mL) was added to the obtained residue. The solvent was evaporated under reduced pressure, thereby obtaining crude 4-amino-3-cyanobenzoyl chloride.

Step 2: Aluminum chloride (3.29 g) was added to a solution of 4-amino-3-cyanobenzoyl chloride obtained in step 1 in dichloromethane (40 mL) at 0° C., and the mixture was stirred at 0° C. for 30 minutes. 7-bromoindole (1.93 g) was added to the reaction mixture, followed by stirring at 0° C. for 2 hours. Ice water was added to the reaction mixture, and the mixture was extracted with dichloromethane. The organic layer was washed with brine and dried over sodium sulfate. The solvent was evaporated under reduced pressure, and the obtained residue was purified by column chromatography (chloroform:ethanol), thereby obtaining 2-amino-5-(7-bromo-1H-indole-3-carbonyl)benzonitrile (570 mg).

Step 3: A 2M sodium carbonate aqueous solution (470 μL), XPhos Pd G3 (13.9 mg), and 1-methyl-5-(4,4,5,5-tetramethyl-1,3,2-dioxaborolan-2-yl)-6-(trifluoromethyl)-1H-benzo[d]imidazole (130 mg) obtained in Example 6 (step 2) were added to a solution of 2-amino-5-(7-bromo-1H-indole-3-carbonyl)benzonitrile (80.0 mg) obtained in step 2 in 1,4-dioxane (2.0 mL), followed by stirring at 100° C. overnight. Water was added to the reaction mixture, and the mixture was extracted with ethyl acetate. The organic layer was washed with brine and dried over sodium sulfate. The solvent was evaporated under reduced pressure, and the obtained residue was purified by column chromatography (chloroform:ethanol), thereby obtaining 2-amino-5-(7-(1-methyl-6-(trifluoromethyl)-1H-benzo[d]imidazol-5-yl)-1H-indole-3-carbonyl)benzonitrile (85.0 mg).

Step 4: The procedure of Example 1 (steps 7 and 8) was performed except that 2-amino-5-(7-(1-methyl-6-(trifluoromethyl)-1H-benzo[d]imidazol-5-yl)-1H-indole-3-carbonyl)benzonitrile (85.0 mg) obtained in step 3 was used instead of 4-amino-3-cyano-N-(3-(2-ethyl-1-methyl-6-(trifluoromethyl)-1H-benzo[d]imidazol-5-yl)phenyl)benzamide used in Example 1 (step 7), thereby obtaining the title compound (42.0 mg).

Example 9

(E)-N-(2-cyano-4-(8-(1,6-dimethyl-1H-benzo[d]imidazol-5-yl)imidazo[1,2-a]pyridine-3-carbonyl)phenyl)-4-(((1r,4r)-4-methoxycyclohexyl)amino)but-2-enamide Step 1: 3-bromopyridin-2-amine (220 mg) was dissolved in 1,1-di-tert-butoxy-N,N-dimethylmethanamine (800 μL). After stirring at 50° C. for 30 minutes, the reaction mixture was concentrated under reduced pressure, thereby obtaining (E)-N'-(3-bromopyridin-2-yl)-N,N-dimethylformimidamide (290 mg).

Step 2: 5-acetyl-2-aminobenzonitrile (523 mg) and copper (II) bromide (1.00 g) were added to ethyl acetate (20 ml). After the mixture was refluxed for 2 hours, additional copper (II) bromide (500 mg) was added and further refluxed for 2 hours. The mixture was cooled to room temperature and filtered through a celite pad. The resulting filtrate was washed with a sodium hydrogen carbonate aqueous solution and a saturated sodium chloride solution, and dried over sodium sulfate. The solution was evaporated under reduced pressure, thereby obtaining crude 2-amino-5-(2-bromoacetyl)benzonitrile (360 mg).

Step 3: (E)-N'-(3-bromopyridin-2-yl)-N,N-dimethylformimidamide (176 mg) obtained in step 1 and crude 2-amino-5-(2-bromoacetyl)benzonitrile (176 mg) obtained in step 2 were added to ethanol (5.0 ml), and the resulting mixture was refluxed for 5 hours. After cooling to room temperature, resulting solid was collected by filtration, thereby obtaining 2-amino-5-(8-bromoimidazo[1,2-a]pyridine-3-carbonyl)benzonitrile (107 mg).

Step 4: The mixture of 1,6-dimethyl-5-(4,4,5,5-tetramethyl-1,3,2-dioxaborolan-2-yl)-1H-benzo[d]imidazole (76.0 mg) obtained in Example 4 (step 8), 2-amino-5-(8-bromoimidazo[1,2-a]pyridine-3-carbonyl)benzonitrile (126 mg) obtained in step 3, dichlorobis(triphenylphosphine) palladium (17.0 mg), sodium carbonate (2.0 M in water, 280 μL), and 1,4-dioxane (3.0 ml) was heated at 110° C. for 2 hours. The mixture was diluted with water and the resulting solid was collected by filtration, rinsed with water, and dried under reduced pressure, thereby obtaining 2-amino-5-(8-(1,6-dimethyl-1H-benzo[d]imidazol-5-yl)imidazo[1,2-a]pyridine-3-carbonyl)benzonitrile (136 mg).

Step 5: The procedure of Example 1 (steps 7 and 8) was performed except that 2-amino-5-(8-(1,6-dimethyl-1H-benzo[d]imidazol-5-yl)imidazo[1,2-a]pyridine-3-carbonyl) benzonitrile (80.0 mg) obtained in step 4 was used instead of 4-amino-3-cyano-N-(3-(2-ethyl-1-methyl-6-(trifluoromethyl)-1H-benzo[d]imidazol-5-yl)phenyl)benzamide used in Example 1 (step 7), thereby obtaining the title compound (18.0 mg).

Example 10

(E)-N-(2-cyano-4-(4-(2-ethyl-1-methyl-6-(trifluoromethyl)-1H-benzo[d]imidazol-5-yl)indoline-1-carbonyl)phenyl)-4-(((1r,4r)-4-methoxycyclohexyl)amino)but-2-enamide Step 1: A suspension of 5-bromo-2-ethyl-1-methyl-6-(trifluoromethyl)-1H-benzo[d]imidazole (1.00 g) obtained in Example 1 (step 4), potassium acetate (959 mg), bis(pinacolato) diboron (1.24 g), (1,1'-bis(diphenylphosphino)ferrocene)palladium(II) dichloride dichloromethane adduct (266 mg) in DMSO (15 mL) was stirred at 100° C. for 6 hours. Ethyl acetate and water were added to the reaction mixture to separate the organic layer, and the organic layer was washed with a saturated sodium chloride solution. The washed organic layer was dried over sodium sulfate, and the solvent was evaporated under reduced pressure, followed by purifying the obtained residue by column chromatography (hexane:ethyl acetate), thereby obtaining 2-ethyl-1-methyl-5-(4,4,5,5-tetramethyl-1,3,2-dioxaborolan-2-yl)-6-(trifluoromethyl)-1H-benzo[d]imidazole (942 mg).

Step 2: A solution of 1-Hydroxybenzotriazole monohydrate (804 mg), 4-amino-3-cyano-benzoic acid (851 mg), N,N-diisopropylethylamine (1.4 mL), and WSC hydrochloride (1.00 g) in DMF (4.0 mL) was stirred at room temperature for 30 minutes. A solution of 4-bromoindoline (829 mg) in DMF (4.0 mL) was added to the mixture, and the resulting mixture was stirred at room temperature overnight. Water was added to the reaction mixture, and the resulting solid was collected by filtration, thereby obtaining 2-amino-5-(4-bromoindoline-1-carbonyl)benzonitrile (1.43 g).

Step 3: A suspension of 2-ethyl-1-methyl-5-(4,4,5,5-tetramethyl-1,3,2-dioxaborolan-2-yl)-6-(trifluoromethyl)-1H-benzo[d]imidazole (942 mg) obtained in step 1, 2-amino-5-(4-bromoindoline-1-carbonyl)benzonitrile (445 mg) obtained in step 2, dichlorobis(triphenylphosphine)palladium (91.2 mg), and a 2M sodium carbonate aqueous solution (2.0 mL) in 1,4-dioxane (10 mL) was refluxed for 3 hours. Ethyl acetate and water were added to the reaction mixture to separate the organic layer, and the organic layer was washed with a saturated sodium chloride solution. The washed organic layer was dried over sodium sulfate, and the solvent was evaporated under reduced pressure. The obtained residue was diluted with ethyl acetate and diethyl ether. The resulting solid was collected by filtration, thereby obtaining 2-amino-5-(4-(2-ethyl-1-methyl-6-(trifluoromethyl)-1H-benzo[d]imidazol-5-yl)indoline-1-carbonyl)benzonitrile (587 mg).

Step 4: The procedure of Example 1 (step 7) was performed except that 2-amino-5-(4-(2-ethyl-1-methyl-6-(trifluoromethyl)-1H-benzo[d]imidazol-5-yl)indoline-1-carbonyl)benzonitrile (350 mg) obtained in step 3 was used instead of 4-amino-3-cyano-N-(3-(2-ethyl-1-methyl-6-(trifluoromethyl)-1H-benzo[d]imidazol-5-yl)phenyl)benzamide used in Example 1 (step 7), thereby obtaining (E)-4-chloro-N-(2-cyano-4-(4-(2-ethyl-1-methyl-6-(trifluoromethyl)-1H-benzo[d]imidazol-5-yl)indoline-1-carbonyl)phenyl)but-2-enamide (332 mg).

Step 5: The procedure of Example 1 (step 8) was performed except that (E)-4-chloro-N-(2-cyano-4-(4-(2-ethyl-1-methyl-6-(trifluoromethyl)-1H-benzo[d]imidazol-5-yl)indoline-1-carbonyl)phenyl)but-2-enamide (20.0 mg) obtained in step 4 was used instead of (E)-4-(4-chlorobut-2-enamido)-3-cyano-N-(3-(2-ethyl-1-methyl-6-(trifluoromethyl)-1H-benzo[d]imidazol-5-yl)phenyl)benzamide used in Example 1 (step 8), thereby obtaining the title compound (9.95 mg).

Example 11

(E)-N-(6'-chloro-2',3'-dimethoxy-[1,1'-biphenyl]-3-yl)-3-cyano-4-(4-((1-(methylsulfonyl)piperidin-4-yl)amino)but-2-enamido)benzamide Step 1: 1-Hydroxybenzotriazole monohydrate (1.89 g), 4-amino-3-cyano-benzoic acid (1.00 g), triethylamine (1.7 mL), and WSC hydrochloride (2.36 g) were added to a solution of 3-iodoaniline (2.03 g) in DMF (30 mL). A reaction was performed at room temperature overnight. Water was added to the reaction mixture, and the resulting solid was collected by filtration, thereby obtaining 4-amino-3-cyano-N-(3-iodophenyl)benzamide (2.19 g).

Step 2: A suspension of 4-amino-3-cyano-N-(3-iodophenyl)benzamide (300 mg) obtained in step 1, (6-chloro-2,3-dimethoxyphenyl)boronic acid (268 mg), tetrakis(triphenylphosphine)palladium (47.7 mg), and a 1M sodium carbonate aqueous solution (4.1 mL) in 1,2-dimethoxyethane (4.1 mL) was refluxed for 2 hours. Ethyl acetate and water were added to the reaction mixture to separate the organic layer, and the organic layer was washed with a saturated sodium chloride solution. The washed organic layer was dried over sodium sulfate, and the solvent was evaporated under reduced pressure, thereby obtaining crude 4-amino-N-(6'-chloro-2',3'-dimethoxy-[1,1'-biphenyl]-3-yl)-3-cyanobenzamide (340 mg).

Step 3: (E)-4-chlorobut-2-enoic acid (151 mg), 1-propanephosphonic acid anhydride cyclic trimer (a 1.7M THF solution, 980 μL), and N,N-diisopropylethylamine (580 μL) were added to a solution of crude 4-amino-N-(6'-chloro-2',3'-dimethoxy-[1,1'-biphenyl]-3-yl)-3-cyanobenzamide (340 mg) obtained in step 2 in DMF (4.2 mL). A reaction was performed at room temperature for 2 hours. Water was added to the reaction mixture, and extraction was performed with ethyl acetate, followed by washing the organic layer with a saturated sodium chloride solution. The washed layer was dried over sodium sulfate, and the solvent was evaporated under reduced pressure. The obtained residue was purified by column chromatography (hexane:ethyl acetate), thereby obtaining (E)-N-(6'-chloro-2',3'-dimethoxy-[1,1'-biphenyl]-3-yl)-4-(4-chlorobut-2-enamido)-3-cyanobenzamide (180 mg).

Step 4: 1-(methylsulfonyl)piperidin-4-amine (13.0 mg), potassium carbonate (10.0 mg), and potassium iodide (2.0 mg) were added to a solution of (E)-N-(6'-chloro-2',3'-dimethoxy-[1,1'-biphenyl]-3-yl)-4-(4-chlorobut-2-enamido)-3-cyanobenzamide (15.0 mg) obtained in step 3 in DMF (300 μL). A reaction was performed at room temperature for 2 hours. Water was added to the reaction mixture, and extraction was performed with ethyl acetate, followed by washing the organic layer with a saturated sodium chloride solution. The washed layer was dried over sodium sulfate, and the solvent was evaporated under reduced pressure. The residue was purified by preparative reversed-phase HPLC (water:acetonitrile (0.1% formic acid)). Saturated sodium bicarbonate water was added to the purified fractions containing the title compound, followed by extraction with ethyl acetate. The extract was washed with a saturated sodium chloride solution and dried over sodium sulfate. The solvent was evaporated under reduced pressure, thereby obtaining the title compound (16.2 mg).

Example 12

N-(3-(5-chloro-1-methyl-1H-indazol-4-yl)phenyl)-3-cyano-4-((E)-4-(((1r,4r)-4-(diethylamino)cyclohexyl)amino)but-2-enamido)benzamide Step 1: The procedure of Example 1 (steps 5 to 7) was performed except that 4-bromo-5-chloro-1-methyl-1H-indazole (320 mg) was used instead of 5-bromo-2-ethyl-1-methyl-6-(trifluoromethyl)-1H-benzo[d]imidazole used in Example 1 (step 5), thereby obtaining (E)-N-(3-(5-chloro-1-methyl-1H-indazol-4-yl)phenyl)-4-(4-chlorobut-2-enamido)-3-cyanobenzamide (160 mg).

Step 2: trans-N,N-diethyl-cyclohexane-1,4-diamine dihydrochloride (18.0 mg), potassium carbonate (10.0 mg), and potassium iodide (2.0 mg) were added to a solution of (E)-N-(3-(5-chloro-1-methyl-1H-indazol-4-yl)phenyl)-4-(4-chlorobut-2-enamido)-3-cyanobenzamide (15.0 mg) obtained in step 1 in DMF (300 μL). A reaction was performed at room temperature for 2 hours. Water was added to the reaction mixture, and extraction was performed with chloroform, followed by washing the organic layer with a saturated sodium chloride solution. The washed layer was dried over sodium sulfate, and the solvent was evaporated under reduced pressure. The residue was purified by preparative reversed-phase HPLC (water:acetonitrile (0.1% formic acid)). Saturated sodium bicarbonate water was added to the purified fractions containing the title compound, followed by extraction with chloroform. The extract was washed with a saturated sodium chloride solution and dried over sodium sulfate. The solvent was evaporated under reduced pressure, thereby obtaining the title compound (2.68 mg).

Example 13

N-(3-(6-chloro-1,2-dimethyl-1H-benzo[d]imidazol-5-yl)phenyl)-4-((E)-4-(((1r,4r)-4-(diethylamino)cyclohexyl)amino)but-2-enamido)-3-fluorobenzamide Step 1: The procedure of Example 1 (steps 2 to 4) was performed except that 5-chloro-N-methyl-2-nitroaniline (100 mg) was used instead of N-methyl-2-nitro-5-(trifluoromethyl)aniline used in Example 1 (step 2), and 1,1,1-trimethoxyethane (670 μL) was used instead of 1,1,1-triethoxypropane in Example 1 (step 4), thereby obtaining 5-bromo-6-chloro-1,2-dimethyl-1H-benzo[d]imidazole (67.0 mg).

Step 2: A suspension of 5-bromo-6-chloro-1,2-dimethyl-1H-benzo[d]imidazole (218 mg) obtained in step 1, 3-(4,4,5,5-tetramethyl-1,3,2-dioxaborolan-2-yl)aniline (276 mg), tetrakis(triphenylphosphine)palladium (48.5 mg), and a 2M sodium carbonate aqueous solution (1.4 mL) in 1,4-dioxane (2.8 mL) was refluxed overnight. Ethyl acetate and water were added to the reaction mixture to separate the organic layer, and the organic layer was washed with a saturated sodium chloride solution. The washed organic layer was dried over sodium sulfate, and the solvent was evaporated under reduced pressure. The obtained residue was purified by column chromatography (chloroform:methanol), thereby obtaining 3-(6-chloro-1,2-dimethyl-1H-benzo[d]imidazol-5-yl)aniline (234 mg).

Step 3: 1-Hydroxybenzotriazole monohydrate (99.4 mg), 4-amino-3-fluorobenzoic acid (75.5 mg), triethylamine (140 μL), and WSC hydrochloride (124 mg) were added to a solution of 3-(6-chloro-1,2-dimethyl-1H-benzo[d]imidazol-5-yl)aniline (100 mg) obtained in step 2 in DMF (1.6 mL). A reaction was performed at room temperature overnight. Water was added to the reaction mixture, and extraction was performed with ethyl acetate, followed by washing the organic layer with a saturated sodium chloride solution. The washed layer was dried over sodium sulfate, and the solvent was evaporated under reduced pressure. The obtained residue was purified by column chromatography (chloroform:methanol), thereby obtaining 4-amino-N-(3-(6-chloro-1,2-dimethyl-1H-benzo[d]imidazol-5-yl)phenyl)-3-fluorobenzamide (90.0 mg).

Step 4: The procedure of Example 1 (step 7) was performed except that 4-amino-N-(3-(6-chloro-1,2-dimethyl-1H-benzo[d]imidazol-5-yl)phenyl)-3-fluorobenzamide (90.0 mg) obtained in step 3 was used instead of 4-amino-3-cyano-N-(3-(2-ethyl-1-methyl-6-(trifluoromethyl)-1H-benzo[d]imidazol-5-yl)phenyl)benzamide used in Example 1 (step 7), thereby obtaining (E)-N-(3-(6-chloro-1,2-dimethyl-1H-benzo[d]imidazol-5-yl)phenyl)-4-(4-chlorobut-2-enamido)-3-fluorobenzamide (90.0 mg).

Step 5: The procedure of Example 12 (step 2) was performed except that (E)-N-(3-(6-chloro-1,2-dimethyl-1H-benzo[d]imidazol-5-yl)phenyl)-4-(4-chlorobut-2-enamido)-3-fluorobenzamide (15.0 mg) obtained in step 4 was used instead of (E)-N-(3-(5-chloro-1-methyl-1H-indazol-4-yl)phenyl)-4-(4-chlorobut-2-enamido)-3-cyanobenzamide used in Example 12 (step 2), thereby obtaining the title compound (6.30 mg).

Example 14

N-(3-(6-chloro-1H-benzo[d]imidazol-5-yl)phenyl)-6-((E)-4-(((1r,4r)-4-hydroxycyclohexyl)amino)but-2-enamido)nicotinamide Step 1: The procedure of Example 1 (step 7) was performed except that methyl 6-aminonicotinate (2.00 g) was used instead of 4-amino-3-cyano-N-(3-(2-ethyl-1-methyl-6-(trifluoromethyl)-1H-benzo[d]imidazol-5-yl)phenyl)benzamide used in Example 1 (step 7), thereby obtaining methyl (E)-6-(4-chlorobut-2-enamido)nicotinate (3.35 g).

Step 2: (1r,4r)-4-aminocyclohexan-1-ol (3.03 g), potassium carbonate (5.45 g), and potassium iodide (436 mg) were added to a solution of methyl (E)-6-(4-chlorobut-2- enamido)nicotinate (3.35 g) obtained in step 1 in acetonitrile (66 mL). A reaction was performed at room temperature for 19 hours. Water was added to the reaction mixture, and the resulting solid was collected by filtration. The obtained solid was washed with methanol, thereby obtaining methyl 6-((E)-4-(((1r,4r)-4-hydroxycyclohexyl)amino)but-2-enamido)nicotinate (2.35 g).

Step 3: A 1M sodium hydroxide aqueous solution (10 mL) was added to a solution of methyl 6-((E)-4-(((1r,4r)-4-hydroxycyclohexyl)amino)but-2-enamido)nicotinate (2.30 g) obtained in step 2 in THF (46 mL). A reaction was performed at room temperature for 1 hour, then a 1M hydrogen chloride aqueous solution (10 mL) was added to the reaction mixture. The solvent was evaporated under reduced pressure, and the residue was diluted with water. The resulting solid was collected by filtration, thereby obtaining 6-((E)-4-(((1r,4r)-4-hydroxycyclohexyl)amino)but-2-enamido)nicotinic acid (1, 56 g).

Step 4: A suspension of 5-bromo-6-chloro-1H-benzo[d]imidazole (50.0 mg), 3-(4,4,5,5-tetramethyl-1,3,2-dioxaborolan-2-yl)aniline (71.0 mg), tetrakis(triphenylphosphine)palladium (12.5 mg), and a 2M sodium carbonate aqueous solution (540 μL) in 1,4-dioxane (1.1 mL) was refluxed for 42 hours. Ethyl acetate and water were added to the reaction mixture to separate the organic layer, and the organic layer was washed with a saturated sodium chloride solution. The washed organic layer was dried over sodium sulfate, and the solvent was evaporated under reduced pressure. The obtained residue was purified by column chromatography (chloroform:methanol), thereby obtaining 3-(6-chloro-1H-benzo[d]imidazol-5-yl)aniline (37.0 mg).

Step 5: 1-Hydroxybenzotriazole monohydrate (14.4 mg), 6-((E)-4-(((1r,4r)-4-hydroxycyclohexyl)amino)but-2-enamido)nicotinic acid (15.0 mg) obtained in step 3, triethylamine (13 μL), and WSC hydrochloride (18.0 mg) were added to a solution of 3-(6-chloro-1,2-dimethyl-1H-benzo[d]imidazol-5-yl)aniline (14.9 mg) obtained in step 4 in DMF (470 μL). A reaction was performed at room temperature overnight. Water was added to the reaction mixture, and the resulting solid was collected by filtration. The residue was diluted with DMSO, then purified by preparative reversed-phase HPLC (water:acetonitrile (0.1% formic acid)). Saturated sodium bicarbonate water was added to the purified fractions containing the title compound, followed by extraction with chloroform. The extract was washed with a saturated sodium chloride solution and dried over sodium sulfate. The solvent was evaporated under reduced pressure, thereby obtaining the title compound (11.1 mg).

Example 15

N-(3-(4-chloro-2-ethyl-1-methyl-6-(trifluoromethyl)-1H-benzo[d]imidazol-5-yl)phenyl)-3-cyano-4-((E)-4-(((1r,4r)-4-methoxycyclohexyl)amino)but-2-enamido)benzamide Step 1: Methylamine (a 2M THF solution, 2.0 mL) was added to a solution of 1-chloro-3-fluoro-2-nitro-5-(trifluoromethyl)benzene (350 mg) in THF (3.0 mL). After stirring at room temperature for 1 hour, the reaction mixture was concentrated under reduced pressure. The obtained residue was purified by column chromatography (hexane:ethyl acetate), thereby obtaining 3-chloro-N-methyl-2-nitro-5-(trifluoromethyl)aniline (366 mg).

Step 2: N-bromosuccinimide (281 mg) was added to a solution of 3-chloro-N-methyl-2-nitro-5-(trifluoromethyl)aniline (366 mg) obtained in step 1 in DMF (3.0 ml). After the mixture was stirred at room temperature for 40 minutes, another N-bromosuccinimide (314 mg) was added to the reaction mixture. After the mixture was stirred at room temperature for 2 hours, ethyl acetate and water were added to the reaction mixture to separate the organic layer, and the organic layer was washed with a saturated sodium chloride solution. The washed organic layer was dried over sodium sulfate, and the solvent was evaporated under reduced pressure. The obtained residue was purified by column chromatography (hexane:ethyl acetate), thereby obtaining 4-bromo-3-chloro-N-methyl-2-nitro-5-(trifluoromethyl)aniline (469 mg).

Step 3: The procedure of Example 1 (steps 3 and 4) was performed except that 4-bromo-3-chloro-N-methyl-2-nitro-5-(trifluoromethyl)aniline (670 mg) obtained in step 2 was used instead of 4-bromo-N-methyl-2-nitro-5-(trifluoromethyl)aniline used in Example 1 (step 3), thereby obtaining 5-bromo-4-chloro-2-ethyl-1-methyl-6-(trifluoromethyl)-1H-benzo[d]imidazole (505 mg).

Step 4: The procedure of Example 1 (steps 5 to 7) was performed except that 5-bromo-4-chloro-2-ethyl-1-methyl-6-(trifluoromethyl)-1H-benzo[d]imidazole (500 mg) obtained in step 3 was used instead of 5-bromo-2-ethyl-1-methyl-6-(trifluoromethyl)-1H-benzo[d]imidazole used in Example 1 (step 5), thereby obtaining (E)-N-(3-(4-chloro-2-ethyl-1-methyl-6-(trifluoromethyl)-1H-benzo[d]imidazol-5-yl)phenyl)-4-(4-chlorobut-2-enamido)-3-cyanobenzamide (237 mg).

Step 5: (1r,4r)-4-methoxycyclohexan-1-amine hydrochloride (164 mg), potassium carbonate (409 mg), and potassium iodide (197 mg) were added to a solution of (E)-N-(3-(4-chloro-2-ethyl-1-methyl-6-(trifluoromethyl)-1H-benzo[d]imidazol-5-yl)phenyl)-4-(4-chlorobut-2-enamido)-3-cyanobenzamide (237 mg) obtained in step 4 in DMF (3.0 mL). A reaction was performed at room temperature for 2 hours. Water was added to the reaction mixture, and extraction was performed with ethyl acetate, followed by washing the organic layer with a saturated sodium chloride solution. The washed layer was dried over sodium sulfate, and the solvent was evaporated under reduced pressure. The obtained residue was purified by basic silica gel column chromatography (chloroform:methanol), and the residue was diluted with diethyl ether. The resulting solid was collected by filtration, thereby obtaining the title compound (106 mg).

Example 16

3-cyano-4-((E)-4-(((1r,4r)-4-methoxycyclohexyl)amino)but-2-enamido)-N-(3-(6-methylbenzo[d]thiazol-5-yl)phenyl)benzamide Step 1: The procedure of Example 1 (steps 5 to 7) was performed except that 5-bromo-6-methylbenzo[d]thiazole (297 mg) was used instead of 5-bromo-2-ethyl-1-methyl-6-(trifluoromethyl)-1H-benzo[d]imidazole used in Example 1 (step 5), thereby obtaining (E)-4-(4-chlorobut-2-enamido)-3-cyano-N-(3-(6-methylbenzo[d]thiazol-5-yl)phenyl)benzamide (283 mg).

Step 2: The procedure of Example 1 (step 8) was performed except that (E)-4-(4-chlorobut-2-enamido)-3-cyano-N-(3-(6-methylbenzo[d]thiazol-5-yl)phenyl)benzamide (15.0 mg) obtained in step 1 was used instead of (E)-4-(4-chlorobut-2-enamido)-3-cyano-N-(3-(2-ethyl-1-methyl-6-(trifluoromethyl)-1H-benzo[d]imidazol-5-yl)phenyl)benzamide used in Example 1 (step 8), thereby obtaining the title compound (10.9 mg).

Example 17

(E)-N-(3-(6-chloroimidazo[1,2-a]pyridin-7-yl)phenyl)-3-cyano-4-(4-((1-(methylsulfonyl)piperidin-4-yl)amino)but-2-enamido)benzamide Step 1: The procedure of Example 1 (steps 5 to 7) was performed except that 7-bromo-6-chloroimidazo[1,2-a]pyridine (320 mg) was used instead of 5-bromo-2-ethyl-1-methyl-6-(trifluoromethyl)-1H-benzo[d]imidazole used in Example 1 (step 5), thereby obtaining (E)-4-(4-chlorobut-2-enamido)-N-(3-(6-chloroimidazo[1,2-a]pyridin-7-yl)phenyl)-3-cyanobenzamide (160 mg).

Step 2: 1-(methylsulfonyl)piperidin-4-amine (13.6 mg), potassium carbonate (10.0 mg), and potassium iodide (2.0 mg) were added to a solution of (E)-4-(4-chlorobut-2-enamido)-N-(3-(6-chloroimidazo[1,2-a]pyridin-7-yl)phenyl)-3-cyanobenzamide (15.0 mg) obtained in step 1 in DMF (300 μL). A reaction was performed at room temperature for 2 hours. Water was added to the reaction mixture, and extraction was performed with chloroform, followed by washing the organic layer with a saturated sodium chloride solution. The washed layer was dried over sodium sulfate, and the solvent was evaporated under reduced pressure. The residue was purified by preparative reversed-phase HPLC (water:acetonitrile (0.1% formic acid)). Saturated sodium bicarbonate water was added to the purified fractions containing the title compound, followed by extraction with chloroform. The extract was washed with a saturated sodium chloride solution and dried over sodium sulfate. The solvent was evaporated under reduced pressure, thereby obtaining the title compound (7.61 mg).

Example 18

3-cyano-N-(3-(1,6-dimethyl-1H-benzo[d]imidazol-5-yl)-4,5-difluorophenyl)-4-((E)-4-(((1r,4r)-4-methoxycyclohexyl)amino)but-2-enamido)benzamide Step 1: The procedure of Example 1 (steps 5 to 7) was performed except that 5-bromo-1,6-dimethyl-1H-benzo[d]imidazole (225 mg) obtained in Example 4 (step 7) was used instead of 5-bromo-2-ethyl-1-methyl-6-(trifluoromethyl)-1H-benzo[d]imidazole used in Example 1 (step 5), and (5-amino-2,3-difluorophenyl)boronic acid (259 mg) was used instead of 3-(4,4,5,5-tetramethyl-1,3,2-dioxaborolan-2-yl)aniline used in Example 1 (step 5), thereby obtaining (E)-4-(4-chlorobut-2-enamido)-3-cyano-N-(3-(1,6-dimethyl-1H-benzo[d]imidazol-5-yl)-4,5-difluorophenyl)benzamide (260 mg).

Step 2: The procedure of Example 1 (step 8) was performed except that (E)-4-(4-chlorobut-2-enamido)-3-cyano-N-(3-(1,6-dimethyl-1H-benzo[d]imidazol-5-yl)-4,5-difluorophenyl)benzamide (15.0 mg) obtained in step 1 was used instead of (E)-4-(4-chlorobut-2-enamido)-3-cyano-N-(3-(2-ethyl-1-methyl-6-(trifluoromethyl)-1H-benzo[d]imidazol-5-yl)phenyl)benzamide used in Example 1 (step 8), thereby obtaining the title compound (5.63 mg).

Example 19

N-(3-(6-chloro-1-methyl-1H-benzo[d]imidazol-5-yl)phenyl)-3-cyano-4-((E)-4-(((1r,4r)-4-(diethylamino)cyclohexyl)amino)but-2-enamido)benzamide Step 1: Iodomethane (400 μL) and potassium carbonate (1.49 g) were added to a solution of 5-bromo-6-chloro-1H-benzo[d]imidazole (1.00 g) in DMF (14 mL). After stirring at room temperature for 30 minutes, water was added to the reaction mixture, and extraction was performed with ethyl acetate, followed by washing the organic layer with a saturated sodium chloride solution. The washed layer was dried over sodium sulfate, and the solvent was evaporated under reduced pressure, thereby obtaining crude mixture of 5-bromo-6-chloro-1-methyl-1H-benzo[d]imidazole and 6-bromo-5-chloro-1-methyl-1H-benzo[d]imidazole (1.03 g).

Step 2: A suspension of crude mixture of 5-bromo-6-chloro-1-methyl-1H-benzo[d]imidazole and 6-bromo-5-chloro-1-methyl-1H-benzo[d]imidazole (1.03 g) obtained in step 1, 3-(4,4,5,5-tetramethyl-1,3,2-dioxaborolan-2-yl)aniline (1.38 g), tetrakis(triphenylphosphine)palladium (242 mg), and a 2M sodium carbonate aqueous solution (10 mL) in 1,4-dioxane (21 mL) was stirred at 90° C. for 6 hours. Ethyl acetate and water were added to the reaction mixture to separate the organic layer, and the organic layer was washed with a saturated sodium chloride solution. The washed organic layer was dried over sodium sulfate, and the solvent was evaporated under reduced pressure. The obtained residue was purified by column chromatography (chloroform:methanol), thereby obtaining 3-(6-chloro-1-methyl-1H-benzo[d]imidazol-5-yl)aniline (280 mg) and 3-(5-chloro-1-methyl-1H-benzo[d]imidazol-6-yl)aniline (221 mg).

Step 3: The procedure of Example 1 (steps 6 and 7) was performed except that 3-(6-chloro-1-methyl-1H-benzo[d]imidazol-5-yl)aniline (150 mg) obtained in step 2 was used instead of 3-(2-ethyl-1-methyl-6-(trifluoromethyl)-1H-benzo[d]imidazol-5-yl)aniline used in Example 1 (step 6), thereby obtaining (E)-N-(3-(6-chloro-1-methyl-1H-benzo[d]imidazol-5-yl)phenyl)-4-(4-chlorobut-2-enamido)-3-cyanobenzamide (185 mg).

Step 4: The procedure of Example 12 (step 2) was performed except that (E)-N-(3-(6-chloro-1-methyl-1H-benzo[d]imidazol-5-yl)phenyl)-4-(4-chlorobut-2-enamido)-3-cyanobenzamide (15.0 mg) obtained in step 3 was used instead of (E)-N-(3-(5-chloro-1-methyl-1H-indazol-4-yl)phenyl)-4-(4-chlorobut-2-enamido)-3-cyanobenzamide used in Example 12 (step 2), thereby obtaining the title compound (5.46 mg).

Example 44

(S,E)-N-(2-cyano-4-(8-(1-methyl-6-(trifluoromethyl)-1H-benzo[d]imidazol-5-yl)indolizine-3-carbonyl)phenyl)-3-(pyrrolidin-2-yl) acrylamide Step 1: Triethylamine (0.15 mL) was added to a solution of 2-amino-5-(8-(1-methyl-6-(trifluoromethyl)-1H-benzo[d]imidazol-5-yl)indolizine-3-carbonyl)benzonitrile (100 mg) obtained in Example 6 (step 3), diethylphosphonoacetic acid (0.11 mL) and propylphosphonic acid anhydride cyclic trimer (48% in THF) in DMF (0.41 mL), followed by stirring at room temperature for an hour. Ethyl acetate and a sodium hydrogen carbonate aqueous solution were added to the reaction mixture. The organic layer was separated, followed by washing with brine. The solvent was evaporated under reduced pressure. The obtained residue was purified by column chromatography (ethyl acetate:ethanol), thereby obtaining diethyl (2-((2-cyano-4-(8-(1-methyl-6-(trifluoromethyl)-1H-benzo[d]imidazol-5-yl)indolizine-3-carbonyl)phenyl)amino)-2-oxoethyl)phosphonate (93 mg).

Step 2: Lithium bis(trimethylsilyl)amide (a 1.0 M hexane solution, 78 μL) was added to a solution of diethyl (2-((2- cyano-4-(8-(1-methyl-6-(trifluoromethyl)-1H-benzo[d]imidazol-5-yl)indolizine-3-carbonyl)phenyl)amino)-2-oxoethyl)phosphonate obtained in step 1 in THF (1.0 mL) at −78° C., followed by stirring for 2 hours. Then a solution of boc-L-prolinal (28 mg) in THF (0.2 mL) was added thereto, and the mixture was stirred at room temperature for 2 hours. Ethyl acetate and a saturated ammonium chloride aqueous solution were added to the solution. The organic layer was separated and washed with a saturated sodium chloride solution, followed by drying over sodium sulfate. The solvent was evaporated under reduced pressure, and the obtained residue was purified by column chromatography (hexane:ethyl acetate), thereby obtaining tert-butyl (S,E)-2-(3-((2-cyano-4-(8-(1-methyl-6-(trifluoromethyl)-1H-benzo[d]imidazol-5-yl)indolizine-3-carbonyl)phenyl)amino)-3-oxoprop-1-en-1-yl)pyrrolidine-1-carboxylate (46 mg).

Step 3: Trifluoroacetic acid was added to a solution of tert-butyl (S,E)-2-(3-((2-cyano-4-(8-(1-methyl-6-(trifluoromethyl)-1H-benzo[d]imidazol-5-yl)indolizine-3-carbonyl)phenyl)amino)-3-oxoprop-1-en-1-yl)pyrrolidine-1-carboxylate (15 mg) obtained in step 2 in chloroform (0.5 mL), followed by stirring for 3 hours. Ethyl acetate and saturated sodium hydrogen carbonate aqueous solution were added to the reaction mixture. The organic layer was separated, followed by drying over sodium sulfate. The solvent was evaporated under reduced pressure, and the obtained residue was purified by preparative reversed-phase HPLC (water: acetonitrile (0.1% formic acid)), thereby obtaining (S,E)-N-(2-cyano-4-(8-(1-methyl-6-(trifluoromethyl)-1H-benzo[d]imidazol-5-yl)indolizine-3-carbonyl)phenyl)-3-(pyrrolidin-2-yl)acrylamide (10 mg).

Example 48

(2E)-N-{1-[8-(1,6-dimethyl-1H-1,3-benzodiazol-5-yl)indolizine-3-carbonyl]piperidin-4-yl}-4-{[trans-4-methoxycyclohexyl]amino}but-2-enamide tert-Butyl N-[1-(8-bromoindolizine-3-carbonyl) piperidin-4-yl]carbamate

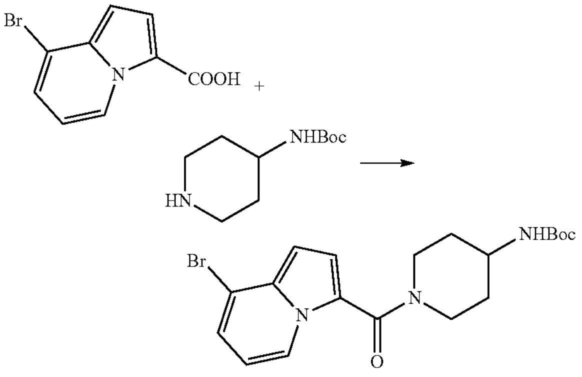

Triethylamine (0.151 mL, 1.08 mmol) was added to a solution of 8-bromoindolizine-3-carboxylic acid (130 mg, 0.542 mmol) and propylphosphonic anhydride solution (50 wt % in EtOAc, 0.387 mL, 0.650 mmol) in DCM (2.00 mL) and stirred at RT for 15 min. 4-(N-Boc-amino)piperidine (109 mg, 0.542 mmol) was added and stirring continued for 4 h. The reaction was diluted with EtOAc and washed successively with sat. aq. $NaHCO_3$ (2×), 1M aq. HCl (2×) and brine then dried ($MgSO_4$) and evaporated. The residue was purified by column chromatography on silica gel (gradient elution, 10-60%, EtOAc/petrol) to give the title compound. MS: $[M+H]^+$=422.

tert-Butyl N-{1-[8-(1,6-dimethyl-1H-1,3-benzodiazol-5-yl) indolizine-3-carbonyl]piperidin-4-yl}carbamate

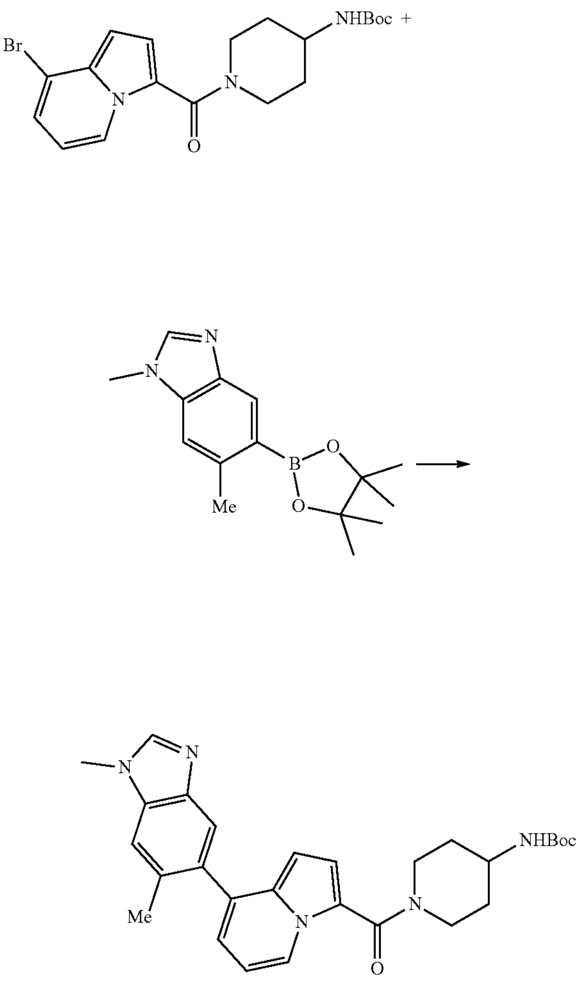

A solution of tert-butyl N-[1-(8-bromoindolizine-3-carbonyl)piperidin-4-yl]carbamate (116 mg, 0.275 mmol), 1,6-dimethyl-5-(4,4,5,5-tetramethyl-1,3,2-dioxaborolan-2-yl)-1H-1,3-benzodiazole (97 mg, 0.357 mmol), [1,1'-bis(diphenylphosphino)ferrocene]dichloropalladium(II) (20 mg, 0.0275 mmol) and $K_2CO_3$ (114 mg, 0.824 mmol) in 1,4-dioxane (4.00 mL) and $H_2O$ (1.00 mL) was evacuated and $N_2$ back-filled (3×) before heating to 80° C. for 2 h. After cooling, the reaction was filtered through a phase separator, rinsing with EtOAc, and the filtrate evaporated. The residue was purified by column chromatography on silica gel (gradient elution, 10-100%, EtOAc/petrol) to give the title compound. MS: $[M+H]^+$=488.

1-[8-(1,6-Dimethyl-1H-1,3-benzodiazol-5-yl)indolizine-3-carbonyl]piperidin-4-amine hydrochloride

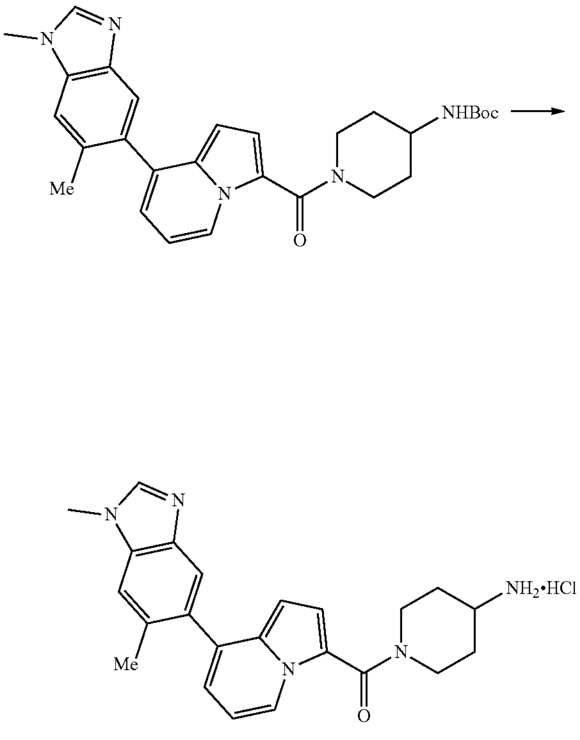

HCl solution (2M in $Et_2O$, 2.00 mL, 4.00 mmol) was added to a solution of tert-butyl N-{1-[8-(1,6-dimethyl-1H-1,3-benzodiazol-5-yl)indolizine-3-carbonyl]piperidin-4-yl}carbamate (84 mg, 0.172 mmol) in $Et_2O$ (2.00 mL) and MeOH (2.00 mL) and stirred at RT overnight. The reaction was evaporated and dried in vacuo to give the title compound. MS: $[M+H]^+=388$.

(2E)-4-Chloro-N-{1-[8-(1,6-dimethyl-1H-1,3-benzodiazol-5-yl) indolizine-3-carbonyl]piperidin-4-yl}but-2-enamide

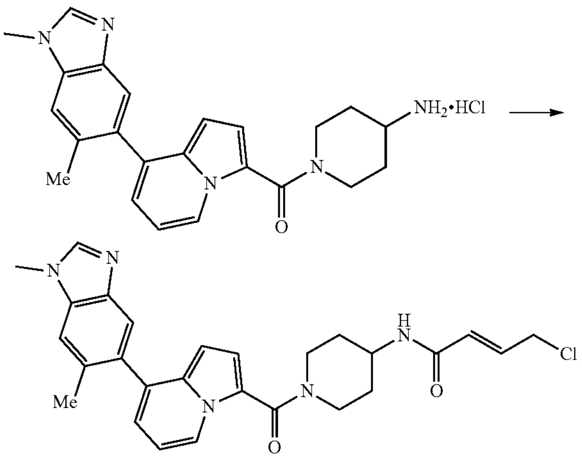

Triethylamine (0.0921 mL, 0.660 mmol) was added to a solution of 1-[8-(1,6-dimethyl-1H-1,3-benzodiazol-5-yl) indolizine-3-carbonyl]piperidin-4-amine hydrochloride (70 mg, 0.165 mmol), 4-chlorocrotonic acid (30 mg, 0.248 mmol) and propylphosphonic anhydride solution (50 wt % in EtOAc, 0.197 mL, 0.330 mmol) in DMF (2.00 mL) and stirred at RT for 2 h. Further triethylamine (0.921 mL, 6.61 mmol), 4-chlorocrotonic acid (199 mg, 1.65 mmol) and propylphosphonic anhydride solution (50 wt % in EtOAc, 0.983 mL, 1.65 mmol) were added and stirring continued for 2 h. The reaction was diluted with EtOAc and washed successively with sat. aq. $NaHCO_3$, $H_2O$ (2×) and brine then dried ($MgSO_4$) and evaporated. The residue was purified by column chromatography on silica gel (gradient elution, 0-10%, MeOH/EtOAc) to give the title compound. MS: $[M+H]^+=490$.

(2E)-N-{1-[8-(1,6-dimethyl-1H-1,3-benzodiazol-5-yl)indolizine-3-carbonyl]piperidin-4-yl}-4-{[trans-4-methoxycyclohexyl]amino}but-2-enamide

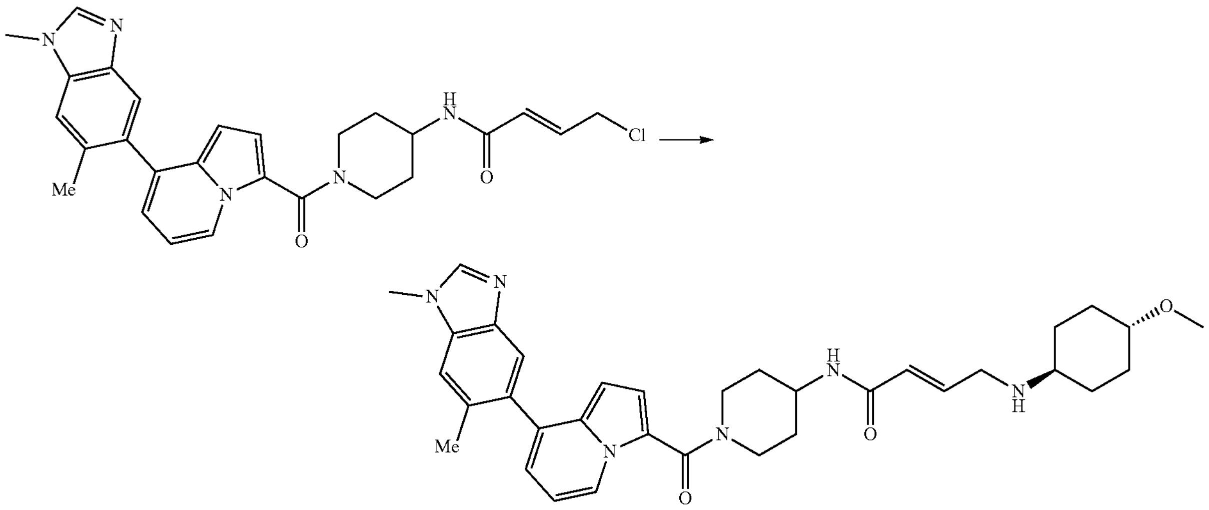

A solution of (2E)-4-chloro-N-{1-[8-(1,6-dimethyl-1H-1,3-benzodiazol-5-yl)indolizine-3-carbonyl]piperidin-4-yl}but-2-enamide (36 mg, 0.0735 mmol), trans-4-methoxy-cyclohexanamine hydrochloride (30 mg, 0.184 mmol), KI (37 mg, 0.220 mmol) and $K_2CO_3$ (71 mg, 0.514 mmol) in DMF (2.00 mL) was stirred at RT for 2 h and then heated to 60° C. overnight. After cooling, the reaction was diluted with EtOAc and washed sequentially with sat. aq. $NaHCO_3$, $H_2O$ and brine (2×) then dried ($MgSO_4$) and evaporated. The residue was purified by column chromatography on NH silica gel (gradient elution, 0-10%, MeOH/EtOAc) to give the title compound.

Example 49

(2E)-4-(tert-Butylamino)-N-(2,6-difluoro-4-{8-[1-methyl-6-(trifluoromethyl)-1H-1,3-benzodiazol-5-yl]indolizine-3-carbonyl}phenyl)but-2-enamide 3-Bromo-2-methyl-1-[2-oxo-2-(3,4,5-trifluorophenyl)ethyl]pyridin-1-ium bromide

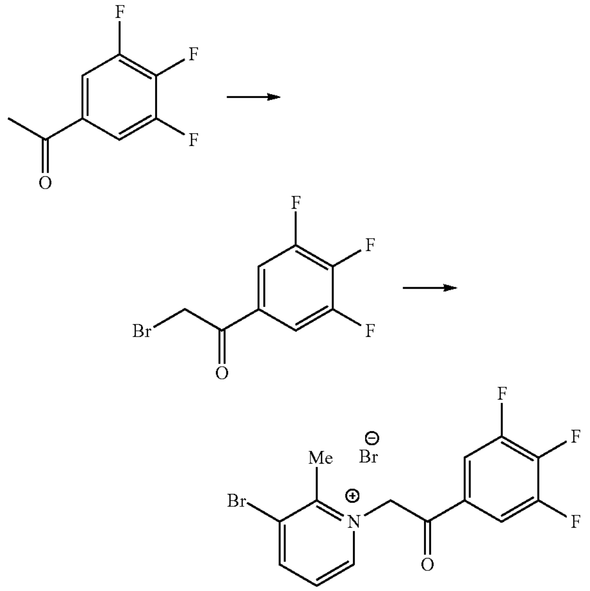

$CuBr_2$ (4.23 g, 19.0 mmol) was added to a solution of 3',4',5'-trifluoroacetophenone (1.50 g, 8.61 mmol) in EtOAc (22.0 mL) and the reaction heated to 70° C. overnight. After cooling, the reaction was filtered through Celite and the filtrate washed sequentially with sat. aq. $NaHCO_3$ (3×) and brine, then dried ($MgSO_4$) and evaporated to give intermediate 2-bromo-1-(3,4,5-trifluorophenyl) ethan-1-one. 3-Bromo-2-methylpyridine (1.64 mL, 14.2 mmol) was added to a solution of 2-bromo-1-(3,4,5-trifluorophenyl) ethan-1-one (1.80 g, 7.11 mmol) in THF (10.0 mL) and the reaction heated to 80° C. for 4 h. Further 3-bromo-2-methylpyridine (0.820 mL, 7.11 mmol) was added and heating continued overnight. After cooling, heptane (15 mL) was added and the resultant precipitate collected via filtration, washing with further heptane, and dried in vacuo to give the title compound. MS: $[M]^+$=344.

8-Bromo-3-(3,4,5-trifluorobenzoyl)indolizine

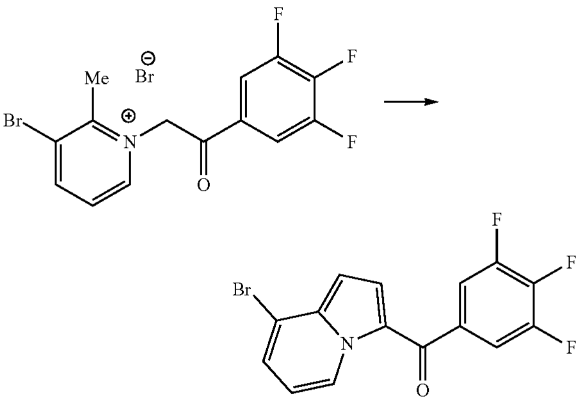

A mixture of DMF (4.08 mL, 52.7 mmol) and dimethyl sulfate (4.99 mL, 52.7 mmol) was heated to 80° C. for 2 h. After cooling, this solution was added to a separate solution of 3-bromo-2-methyl-1-[2-oxo-2-(3,4,5-trifluorophenyl) ethyl]pyridin-1-ium bromide (2.80 g, 6.59 mmol) in DMF (10 mL) and the reaction stirred at RT for 30 min. N,N-Diisopropylethylamine (9.18 mL, 52.7 mmol) was added and the resulting suspension allowed to stand for 30 min. $H_2O$ (~50 mL) was added and, after standing for a further 30 min, the precipitate was collected via filtration, washing with further water, and the solid dried in vacuo. This solid was re-crystallised from boiling EtOAc (~25 mL) to give the title compound. MS: $[M+H]^+$=354.

4-(8-Bromoindolizine-3-carbonyl)-2,6-difluoroaniline

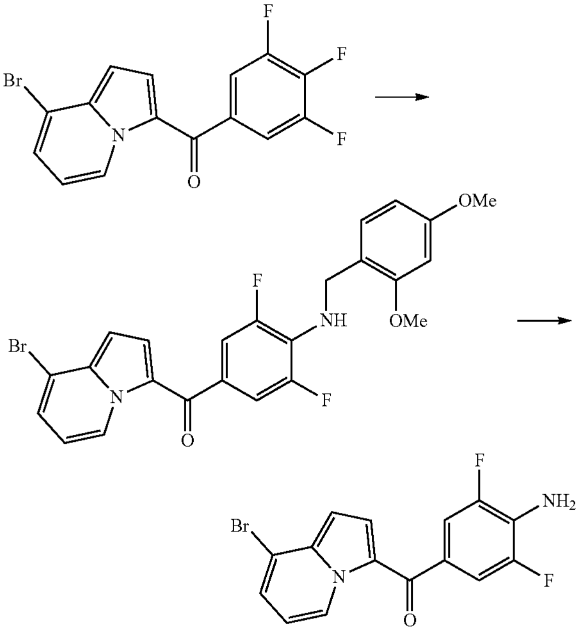

2,4-Dimethoxybenzylamine (0.636 mL, 4.24 mmol) and N,N-diisopropylethylamine (0.984 mL, 5.65 mmol) were added to a solution of 8-bromo-3-(3,4,5-trifluorobenzoyl) indolizine (1.00 g, 2.82 mmol) in NMP (14.0 mL) and the reaction heated to 120° C. overnight. Further 2,4-dimethoxybenzylamine (0.212 mL, 1.41 mmol) was added and heating continued for a further 6 h. After cooling, the reaction was diluted with EtOAc and washed successively with sat. aq. $NH_4Cl$ (2×), $H_2O$ (2×) and brine, then dried ($MgSO_4$) and evaporated. The residue was treated with TFA (5.00 mL) and anisole (0.500 mL) and stirred at RT for 1 h. The reaction was evaporated and the residue suspended in EtOAc (~200 mL) and washed with sat. aq. $NaHCO_3$ (2×) and brine, then passed through a phase separator and evaporated. The residue was triturated with heptane (4×) then stirred in EtOAc (~10 mL) at reflux for 30 min. After cooling, the resultant solid was collected to give the title compound. MS: $[M+H]^+$=351.

2,6-Difluoro-4-{8-[1-methyl-6-(trifluoromethyl)-1H-1,3-benzodiazol-5-yl]indolizine-3-carbonyl}aniline

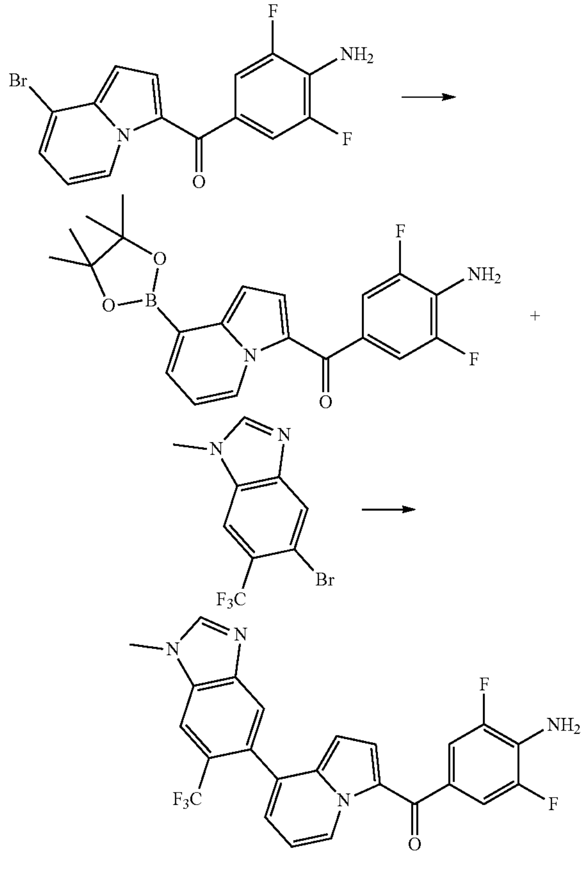

A solution of 4-(8-bromoindolizine-3-carbonyl)-2,6-difluoroaniline (200 mg, 0.570 mmol), bis(pinacolato)diboron (289 mg, 1.14 mmol), [1,1'-bis(diphenylphosphino)ferrocene]dichloropalladium(II) (63 mg, 0.0854 mmol) and potassium acetate (168 mg, 1.71 mmol) in 1,4-dioxane (6.00 mL) was evacuated and $N_2$ back-filled (3×) before heating to 90° C. for 1.5 h. After cooling, 5-bromo-1-methyl-6-(trifluoromethyl)-1H-1,3-benzodiazole (199 mg, 0.712 mmol), further [1,1'-bis(diphenylphosphino)ferrocene]dichloropalladium(II) (42 mg, 0.0570 mmol), $K_2CO_3$ (236 mg, 1.71 mmol) and $H_2O$ (1.50 mL) were added and the reaction evacuated and $N_2$ back-filled (3×) before heating to 90° C. for 1 h. After cooling, the reaction was filtered through Celite, rinsing with EtOAc, and the filtrate evaporated. The residue was purified by column chromatography on NH silica gel (gradient elution, 0-90%, EtOAc/petrol) to give the title compound. MS: $[M+H]^+$=471.

(2E)-4-Chloro-N-(2,6-difluoro-4-{8-[1-methyl-6-(trifluoromethyl)-1H-1,3-benzodiazol-5-yl]indolizine-3-carbonyl}phenyl)but-2-enamide

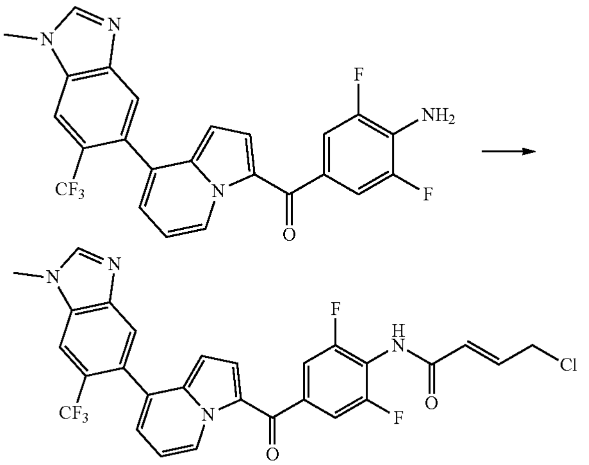

Triethylamine (0.400 mL, 2.87 mmol) was added to a solution of 2,6-difluoro-4-{8-[1-methyl-6-(trifluoromethyl)-1H-1,3-benzodiazol-5-yl]indolizine-3-carbonyl}aniline (135 mg, 0.287 mmol), 4-chlorocrotonic acid (138 mg, 1.15 mmol) and propylphosphonic anhydride solution (50 wt % in EtOAc, 0.854 mL, 1.43 mmol) in DMF (3.00 mL) and stirred at RT overnight. $H_2O$ and sat. aq. $NaHCO_3$ were added and the suspension was extracted with EtOAc (3×) then combined organics washed successively with $H_2O$ then brine (2×), dried ($MgSO_4$) and evaporated. The residue was purified by column chromatography on silica gel (gradient elution, 50-100%, EtOAc/petrol) to give the title compound. MS: $[M+H]^+$=573.

(2E)-4-(tert-Butylamino)-N-(2,6-difluoro-4-{8-[1-methyl-6-(trifluoromethyl)-1H-1,3-benzodiazol-5-yl] indolizine-3-carbonyl}phenyl) but-2-enamide

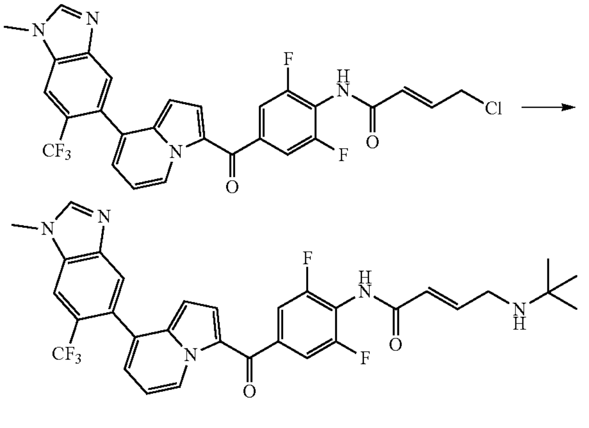

A solution of (2E)-4-chloro-N-(2,6-difluoro-4-{8-[1-methyl-6-(trifluoromethyl)-1H-1,3-benzodiazol-5-yl]indolizine-3-carbonyl}phenyl)but-2-enamide (100 mg, 0.175 mmol), tert-butylamine (0.046 mL, 0.436 mmol), KI (87 mg, 0.524 mmol) and $K_2CO_3$ (169 mg, 1.22 mmol) in DMF (2.00 mL) was heated to 45° C. for 2 h. Further tert-butylamine (0.023 mL, 0.218 mmol) was added and heating continued for a further 2 h. After cooling, $H_2O$ and sat. aq. $NaHCO_3$ were added and the suspension was extracted with EtOAc (3×) then combined organics washed with brine (2×), dried ($MgSO_4$) and evaporated. The residue was purified by column chromatography on NH silica gel (gradient elution, 0-5%, MeOH/EtOAc) to give the title compound.

Example 50

(2E)-4-(tert-Butylamino)-N-(2-cyano-6-methyl-4-{8-[1-methyl-6-(trifluoromethyl)-1H-1,3-benzodiazol-5-yl]indolizine-3-carbonyl}phenyl)but-2-enamide

5-Acetyl-2-fluoro-3-methylbenzonitrile

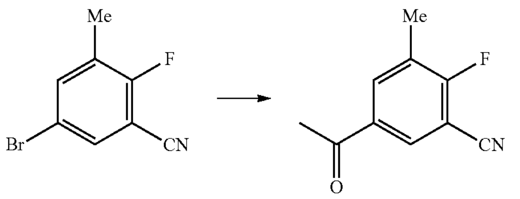

A solution of 5-bromo-2-fluoro-3-methylbenzonitrile (2.10 g, 9.81 mmol), palladium(II) acetate (66.1 mg, 0.294 mmol) and 1,3-bis(diphenylphosphino)propane (243 mg, 0.589 mmol) in 1-butyl-3-methylimidazolium tetrafluoroborate (13.0 mL) was evacuated and $N_2$ back-filled (3×). Butyl vinyl ether (6.35 mL, 49.1 mmol) and triethylamine (1.64 mL, 11.8 mmol) were added and the reaction heated to 115° C. overnight. After cooling, 2M aq. HCl (5 mL) was added and stirring continued at RT for 30 min. The reaction was extracted with DCM (3×) and combined organics dried ($MgSO_4$) and evaporated. The residue was purified by column chromatography on silica gel (gradient elution, 0-30%, EtOAc/petrol) to give the title compound.

3-Bromo-1-[2-(3-cyano-4-fluoro-5-methylphenyl)-2-oxoethyl]-2-methylpyridin-1-ium bromide

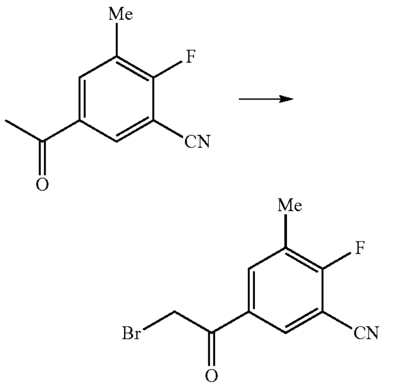

-continued

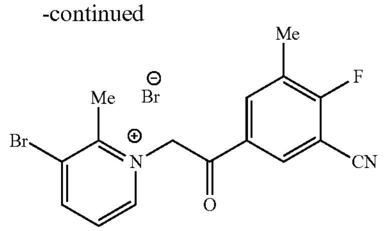

Prepared in a similar manner to 3-bromo-2-methyl-1-[2-oxo-2-(3,4,5-trifluorophenyl)ethyl]pyridin-1-ium bromide, except using 5-acetyl-2-fluoro-3-methylbenzonitrile (1.10 g, 6.21 mmol), to give the title compound. MS: $[M]^+$=347.

5-(8-Bromoindolizine-3-carbonyl)-2-fluoro-3-methylbenzonitrile

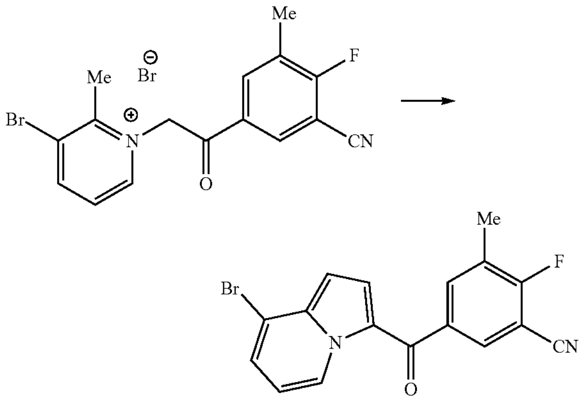

Prepared in a similar manner to 8-bromo-3-(3,4,5-trifluorobenzoyl)indolizine, except using 3-bromo-1-[2-(3-cyano-4-fluoro-5-methylphenyl)-2-oxoethyl]-2-methylpyridin-1-ium bromide (2.00 g, 4.67 mmol) and purifying by re-crystallisation from hot EtOH, to give the title compound. MS: $[M+H]^+$=357.

2-Amino-5-(8-bromoindolizine-3-carbonyl)-3-methylbenzonitrile

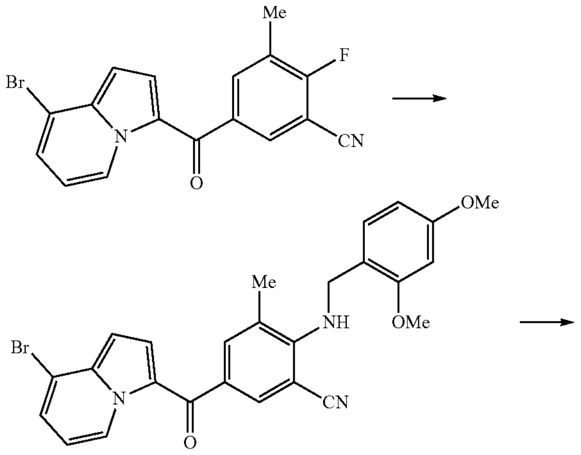

-continued

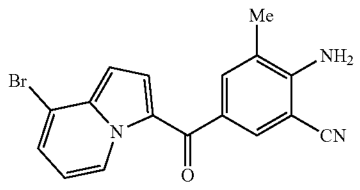

Prepared in a similar manner to 4-(8-bromoindolizine-3-carbonyl)-2,6-difluoroaniline, except using 5-(8-bromoindolizine-3-carbonyl)-2-fluoro-3-methylbenzonitrile (930 mg, 2.60 mmol) and purifying by precipitation from hot EtOAc using heptane, to give the title compound. MS: $[M+H]^+=354$.

2-Amino-3-methyl-5-{8-[1-methyl-6-(trifluoromethyl)-1H-1,3-benzodiazol-5-yl]indolizine-3-carbonyl}benzonitrile

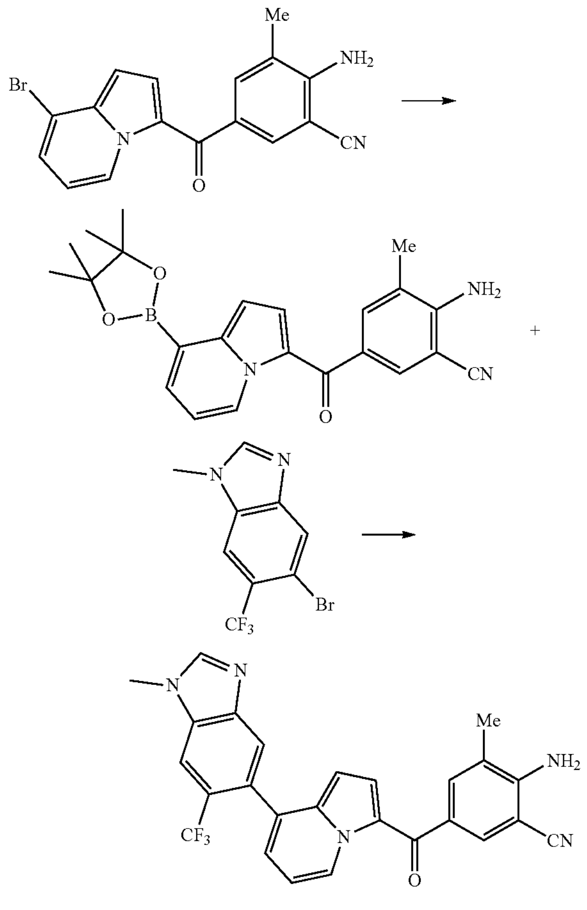

Prepared in a similar manner to 2,6-difluoro-4-{8-[1-methyl-6-(trifluoromethyl)-1H-1,3-benzodiazol-5-yl]indolizine-3-carbonyl}aniline, except using 2-amino-5-(8-bromoindolizine-3-carbonyl)-3-methylbenzonitrile (200 mg, 0.565 mmol), to give the title compound. MS: $[M+H]^+=474$.

(2E)-4-Chloro-N-(2-cyano-6-methyl-4-{8-[1-methyl-6-(trifluoromethyl)-1H-1,3-benzodiazol-5-yl]indolizine-3-carbonyl}phenyl) but-2-enamide

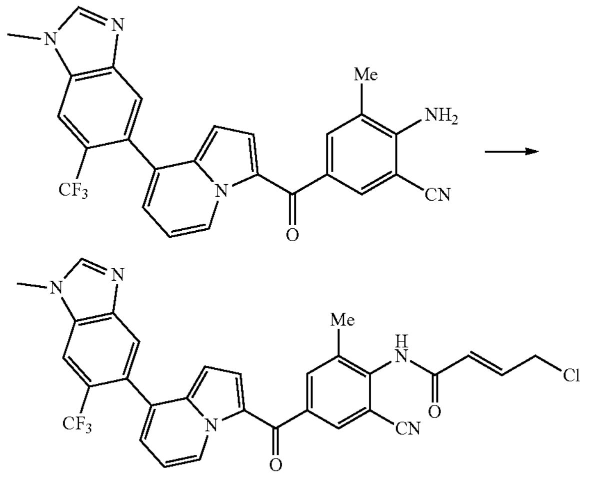

Prepared in a similar manner to (2E)-4-chloro-N-(2,6-difluoro-4-{8-[1-methyl-6-(trifluoromethyl)-1H-1,3-benzodiazol-5-yl]indolizine-3-carbonyl}phenyl)but-2-enamide, except using 2-amino-3-methyl-5-{8-[1-methyl-6-(trifluoromethyl)-1H-1,3-benzodiazol-5-yl]indolizine-3-carbonyl}benzonitrile (75 mg, 0.158 mmol), to give the title compound. MS: $[M+H]^+=576$.

(2E)-4-(tert-Butylamino)-N-(2-cyano-6-methyl-4-{8-[1-methyl-6-(trifluoromethyl)-1H-1,3-benzodiazol-5-yl]indolizine-3-carbonyl}phenyl) but-2-enamide

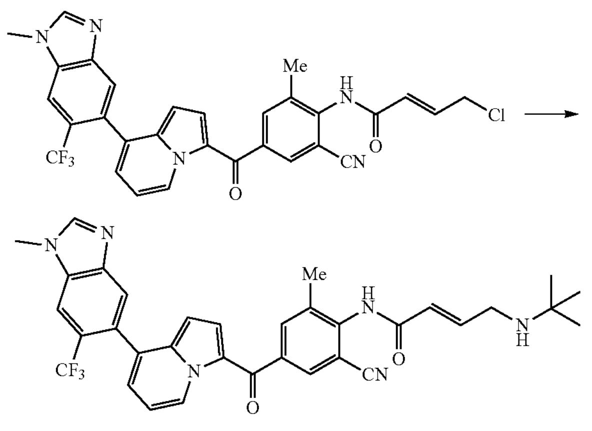

Prepared in a similar manner to (2E)-4-(tert-butylamino)-N-(2,6-difluoro-4-{8-[1-methyl-6-(trifluoromethyl)-1H-1,3-benzodiazol-5-yl]indolizine-3-carbonyl}phenyl)but-2-enamide, except using (2E)-4-chloro-N-(2-cyano-6-methyl-4-{8-[1-methyl-6-(trifluoromethyl)-1H-1,3-benzodiazol-5-yl]indolizine-3-carbonyl}phenyl)but-2-enamide (50 mg, 0.0868 mmol), to give the title compound.

Example 51

(2E)-4-(tert-Butylamino)-N-(2-fluoro-4-{8-[1-methyl-6-(trifluoromethyl)-1H-1,3-benzodiazol-5-yl]indolizine-3-carbonyl}phenyl)but-2-enamide 3-Bromo-1-[2-(3,4-difluorophenyl)-2-oxoethyl]-2-methylpyridin-1-ium bromide

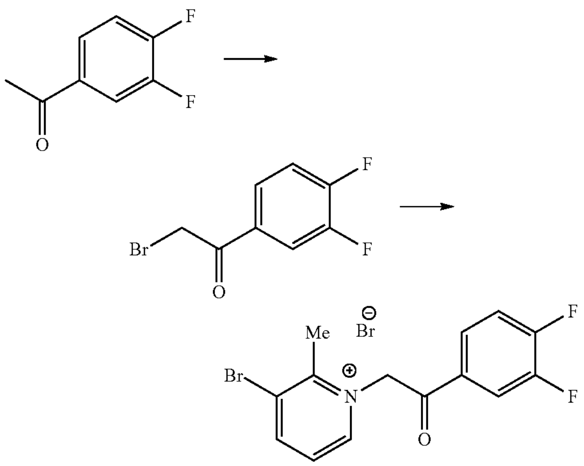

Prepared in a similar manner to 3-bromo-2-methyl-1-[2-oxo-2-(3,4,5-trifluorophenyl)ethyl]pyridin-1-ium bromide, except using 3',4'-difluoroacetophenone (1.10 g, 7.05 mmol), to give the title compound. MS: $[M]^+$=326.

8-Bromo-3-(3,4-difluorobenzoyl)indolizine

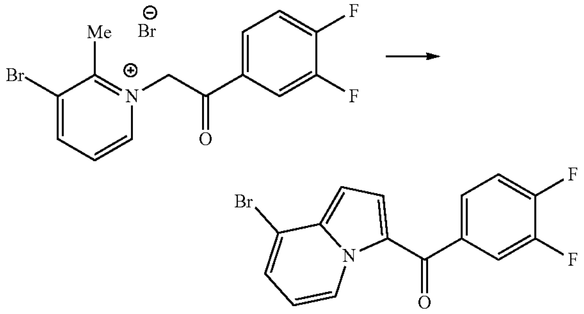

Prepared in a similar manner to 8-bromo-3-(3,4,5-trifluorobenzoyl)indolizine, except using 3-bromo-1-[2-(3,4-difluorophenyl)-2-oxoethyl]-2-methylpyridin-1-ium bromide (2.15 g, 5.28 mmol) and purifying by precipitation from hot EtOAc using heptane, to give the title compound. MS: $[M+H]^+$=336.

4-(8-Bromoindolizine-3-carbonyl)-2-fluoroaniline

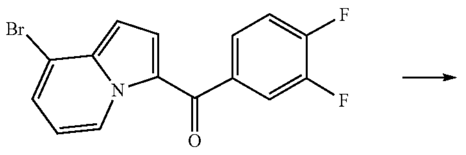

-continued

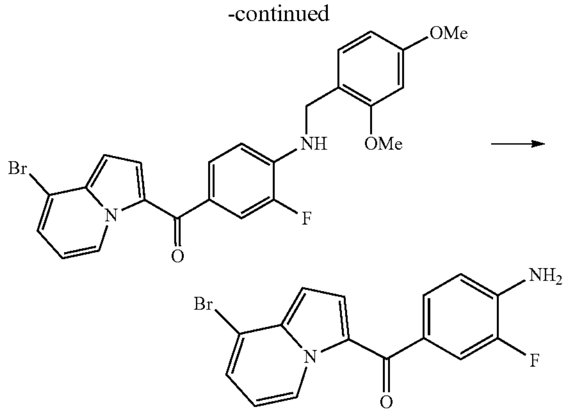

Prepared in a similar manner to 4-(8-bromoindolizine-3-carbonyl)-2,6-difluoroaniline, except using 8-bromo-3-(3,4-difluorobenzoyl)indolizine (870 mg, 2.59 mmol) and purifying by trituration with toluene, to give the title compound. MS: $[M+H]^+$=333.

2-Fluoro-4-{8-[1-methyl-6-(trifluoromethyl)-1H-1,3-benzodiazol-5-yl]indolizine-3-carbonyl}aniline

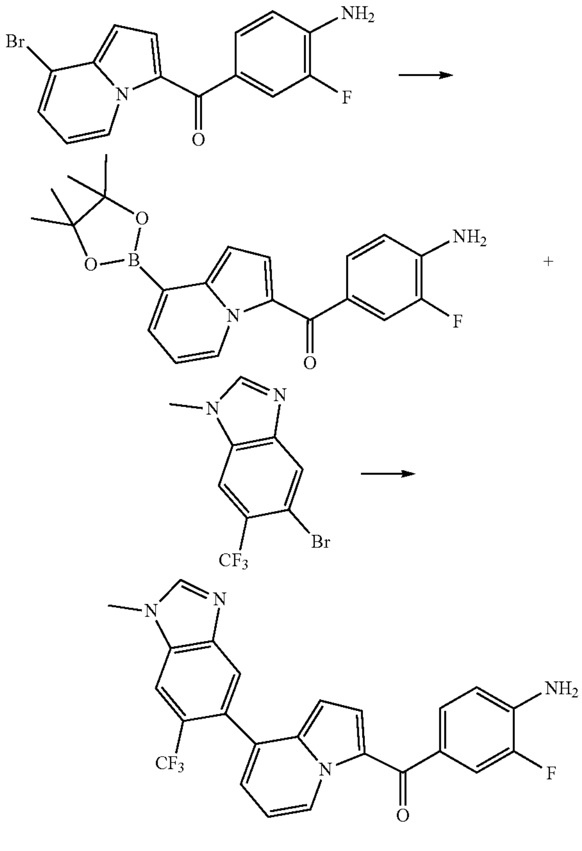

Prepared in a similar manner to 2,6-difluoro-4-{8-[1-methyl-6-(trifluoromethyl)-1H-1,3-benzodiazol-5-yl]indolizine-3-carbonyl}aniline, except using 4-(8-bromoindolizine-3-carbonyl)-2-fluoroaniline (150 mg, 0.450 mmol), to give the title compound. MS: $[M+H]^+$=453.

(2E)-4-Chloro-N-(2-fluoro-4-{8-[1-methyl-6-(trifluoromethyl)-1H-1,3-benzodiazol-5-yl]indolizine-3-carbonyl}phenyl)but-2-enamide

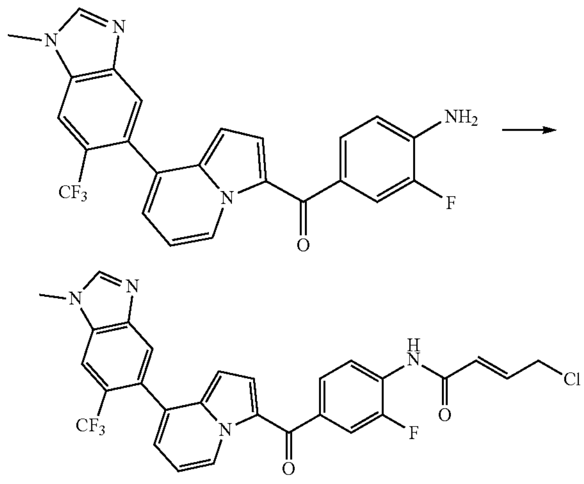

Prepared in a similar manner to (2E)-4-chloro-N-(2,6-difluoro-4-{8-[1-methyl-6-(trifluoromethyl)-1H-1,3-benzodiazol-5-yl]indolizine-3-carbonyl}phenyl)but-2-enamide, except using 2-fluoro-4-{8-[1-methyl-6-(trifluoromethyl)-1H-1,3-benzodiazol-5-yl]indolizine-3-carbonyl}aniline (80 mg, 0.177 mmol), to give the title compound. MS: $[M+H]^+$=555.

(2E)-4-(tert-Butylamino)-N-(2-fluoro-4-{8-[1-methyl-6-(trifluoromethyl)-1H-1,3-benzodiazol-5-yl] indolizine-3-carbonyl}phenyl) but-2-enamide

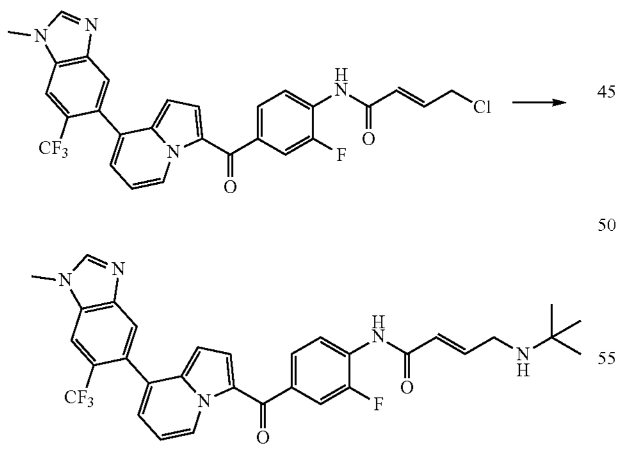

Prepared in a similar manner to (2E)-4-(tert-butylamino)-N-(2,6-difluoro-4-{8-[1-methyl-6-(trifluoromethyl)-1H-1,3-benzodiazol-5-yl]indolizine-3-carbonyl}phenyl)but-2-enamide, except using (2E)-4-chloro-N-(2-fluoro-4-{8-[1-methyl-6-(trifluoromethyl)-1H-1,3-benzodiazol-5-yl] indolizine-3-carbonyl}phenyl)but-2-enamide (88 mg, 0.159 mmol), to give the title compound.

Example 52

(2E)-4-(tert-Butylamino)-N-{4-[8-(4-chloro-2-methyl-2H-indazol-5-yl)indolizine-3-carbonyl]-2-cyanophenyl}but-2-enamide 5-Bromo-4-chloro-2-methyl-2H-indazole

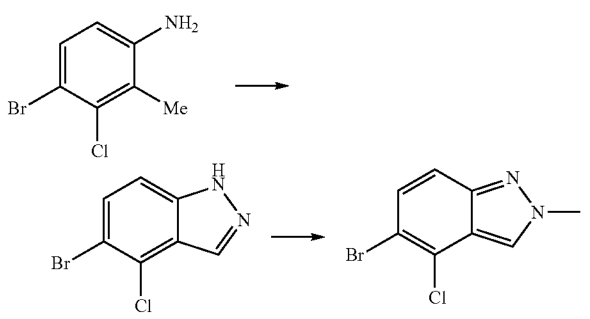

A solution of sodium nitrite (58.6 g, 0.85 mol) in water (98 ml) was added to an ice bath cooled solution of 4-bromo-3-chloro-2-methylaniline (150 g, 0.68 mol) in acetic acid (3 L) with mechanical stirring and the mixture was aged for 1 h at ambient temperature. Most of the solvent was evaporated and the residue suspended in water (500 mL) and filtered, washing with water (250 ml×4), petrol (250 ml×4) and drying in vacuo at 40° C., to give 5-bromo-4-chloro-1H-indazole (130 g), 1H NMR (400 MHz, DMSO-d6): 13.61 (1H, s), 8.16 (1H, s), 7.62 (1H, d), 7.53 (1H, dd).

Solid trimethyloxonium tetrafluoroborate (258, 1.74 mol) was charged to a solution of ice bath cooled 5-bromo-4-chloro-1H-indazole (367 g, 1.59 mol) in EtOAc (1.9 L) and the resulting mixture was stirred at ambient temperature for 4 h. The reaction mixture was diluted with petrol (1.9 L) and aged for 10 min before filtration, washing with petrol (400 mL×2). The filter cake was combined with sat. sodium bicarbonate (1.5 L), EtOAc (2 L) and the phases were separated. The organic phase was washed with sat. sodium bicarbonate, dried (MgSO4) and concentrated in vacuo, to give the title compound (236 g). 1H NMR (400 MHz, DMSO-d6): 8.53 (1H, s), 7.56 (1H, dd), 7.48 (1H, d), 4.20 (3H, s).

4-Chloro-2-methyl-5-(4,4,5,5-tetramethyl-1,3,2-dioxaborolan-2-yl)-2H-indazole

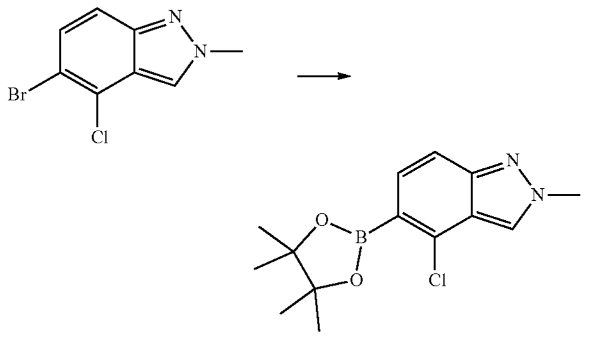

5-Bromo-4-chloro-2-methyl-2H-indazole (5.0 g, 20.50 mmol), bis(pinacolato)diboron (6.25 g, 24.60 mmol), [1,1'-bis(diphenylphosphino)ferrocene]dichloropalladium(II) (0.750 g, 1.02 mmol) and potassium acetate (6.04 g, 61.50 mmol) were slurried in 1,4-dioxane (103 mL) and heated to 95-100° C. for 18 h. The reaction was cooled to RT, filtered and washed with EtOAc. The filtrate was concentrated in vacuo and the residue dissolved in toluene and petrol added until precipitation occurred. The suspension was filtered under vacuum suction and the filtrate concentrated in vacuo, to give the title compound (11.8 g), MS: $[M+H]^+=293$.

2-Amino-5-[8-(4-chloro-2-methyl-2H-indazol-5-yl) indolizine-3-carbonyl]benzonitrile

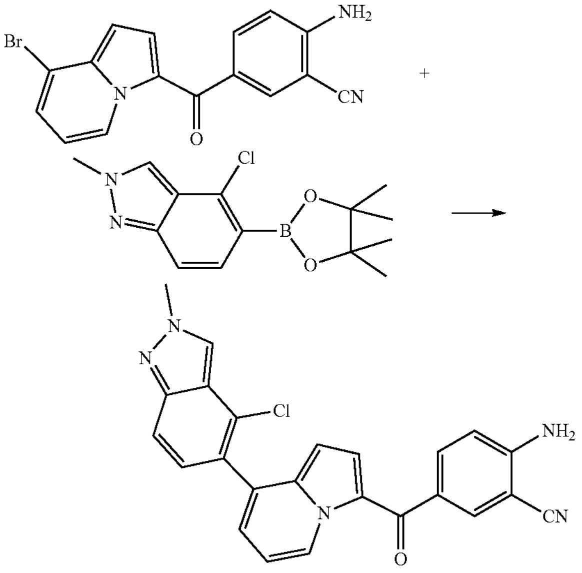

Prepared in a similar manner to tert-butyl N-{1-[8-(1,6-dimethyl-1H-1,3-benzodiazol-5-yl)indolizine-3-carbonyl] piperidin-4-yl}carbamate, except using 2-amino-5-(8-bromoindolizine-3-carbonyl)benzonitrile (125 mg, 0.367 mmol) and 4-chloro-2-methyl-5-(4,4,5,5-tetramethyl-1,3,2-dioxaborolan-2-yl)-2H-indazole (161 mg, 0.551 mmol) and purifying by column chromatography on NH silica gel (gradient elution, 10-100%, EtOAc/petrol), to give the title compound. MS: $[M+H]^+=426$.

(2E)-4-Chloro-N-{4-[8-(4-chloro-2-methyl-2H-indazol-5-yl)indolizine-3-carbonyl]-2-cyanophenyl}but-2-enamide

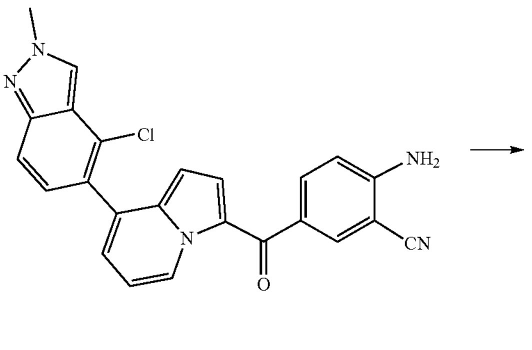

-continued

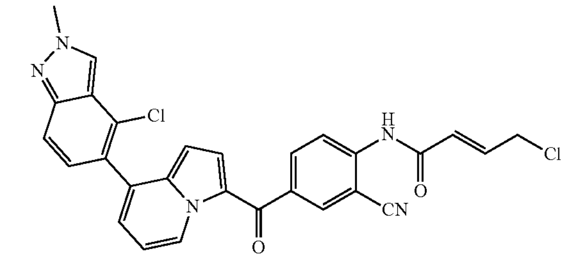

Prepared in a similar manner to (2E)-4-chloro-N-(2,6-difluoro-4-{8-[1-methyl-6-(trifluoromethyl)-1H-1,3-benzodiazol-5-yl]indolizine-3-carbonyl}phenyl)but-2-enamide, except using 2-amino-5-[8-(4-chloro-2-methyl-2H-indazol-5-yl)indolizine-3-carbonyl]benzonitrile (125 mg, 0.294 mmol) and purifying by column chromatography on silica gel (gradient elution, 10-75%, EtOAc/petrol), to give the title compound. MS: $[M+H]^+=528$.

(2E)-4-(tert-Butylamino)-N-{4-[8-(4-chloro-2-methyl-2H-indazol-5-yl) indolizine-3-carbonyl]-2-cyanophenyl}but-2-enamide

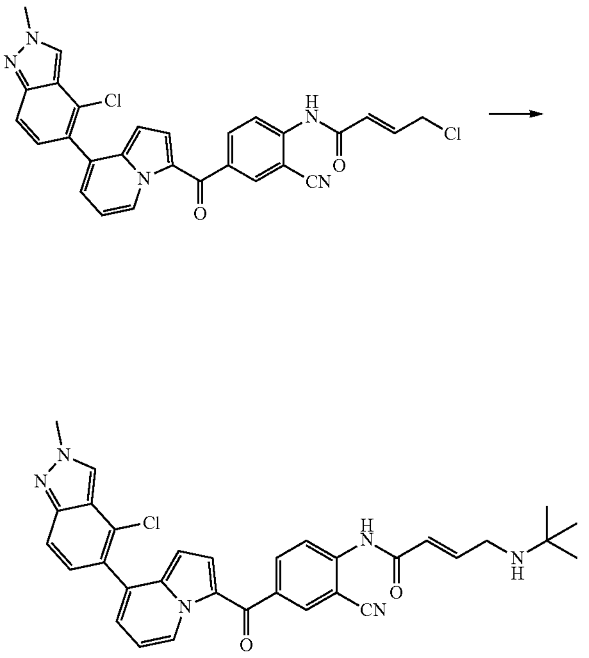

Prepared in a similar manner to (2E)-4-(tert-butylamino)-N-(2,6-difluoro-4-{8-[1-methyl-6-(trifluoromethyl)-1H-1,3-benzodiazol-5-yl]indolizine-3-carbonyl}phenyl)but-2-enamide, except using (2E)-4-chloro-N-{4-[8-(4-chloro-2-methyl-2H-indazol-5-yl)indolizine-3-carbonyl]-2-cyanophenyl}but-2-enamide (115 mg, 0.218 mmol) and purifying by preparative HPLC (Formic acid method), to give the title compound.

Example 53

(2E)-4-(tert-Butylamino)-N-{2-cyano-4-[8-(1,5-dimethyl-1H-indazol-4-yl)indolizine-3-carbonyl]phenyl}but-2-enamide 2-Amino-5-[8-(1,5-dimethyl-1H-indazol-4-yl) indolizine-3-carbonyl]benzonitrile

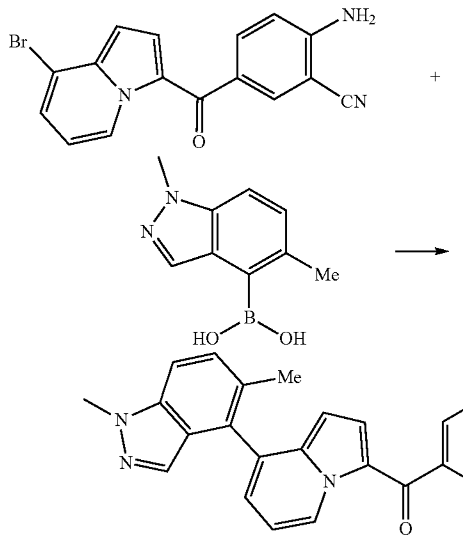

Prepared in a similar manner to tert-butyl N-{1-[8-(1,6-dimethyl-1H-1,3-benzodiazol-5-yl)indolizine-3-carbonyl]piperidin-4-yl}carbamate, except using 2-amino-5-(8-bromoindolizine-3-carbonyl)benzonitrile (125 mg, 0.367 mmol) and (1,5-dimethyl-1H-indazol-4-yl)boronic acid (105 mg, 0.551 mmol) and purifying by column chromatography on NH silica gel (gradient elution, 10-60%, EtOAc/petrol), to give the title compound. MS: $[M+H]^+$=406.

(2E)-4-Chloro-N-{2-cyano-4-[8-(1,5-dimethyl-1H-indazol-4-yl)indolizine-3-carbonyl]phenyl}but-2-enamide

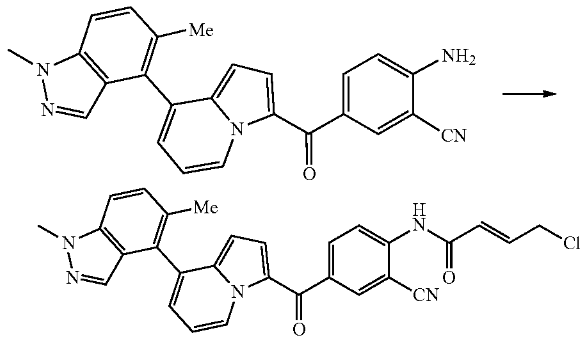

Prepared in a similar manner to (2E)-4-chloro-N-(2,6-difluoro-4-{8-[1-methyl-6-(trifluoromethyl)-1H-1,3-benzodiazol-5-yl]indolizine-3-carbonyl}phenyl)but-2-enamide, except using 2-amino-5-[8-(1,5-dimethyl-1H-indazol-4-yl) indolizine-3-carbonyl]benzonitrile (130 mg, 0.321 mmol) and purifying by column chromatography on silica gel (gradient elution, 10-60%, EtOAc/petrol), to give the title compound. MS: $[M+H]^+$=508.

(2E)-4-(tert-Butylamino)-N-{2-cyano-4-[8-(1,5-dimethyl-1H-indazol-4-yl) indolizine-3-carbonyl]phenyl}but-2-enamide

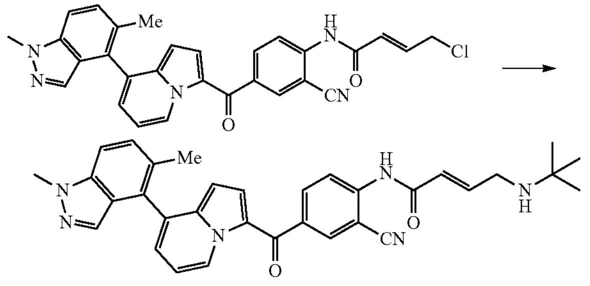

Prepared in a similar manner to (2E)-4-(tert-butylamino)-N-(2,6-difluoro-4-{8-[1-methyl-6-(trifluoromethyl)-1H-1,3-benzodiazol-5-yl]indolizine-3-carbonyl}phenyl)but-2-enamide, except using (2E)-4-chloro-N-{2-cyano-4-[8-(1,5-dimethyl-1H-indazol-4-yl)indolizine-3-carbonyl]phenyl}but-2-enamide (110 mg, 0.217 mmol) and purifying by preparative HPLC (Formic acid method), to give the title compound.

Example 54

(2E)-4-(tert-Butylamino)-N-{2-cyano-4-[8-(1,6-dimethyl-1H-indazol-5-yl)indolizine-3-carbonyl]phenyl}but-2-enamide 2-Amino-5-[8-(1,6-dimethyl-1H-indazol-5-yl) indolizine-3-carbonyl]benzonitrile

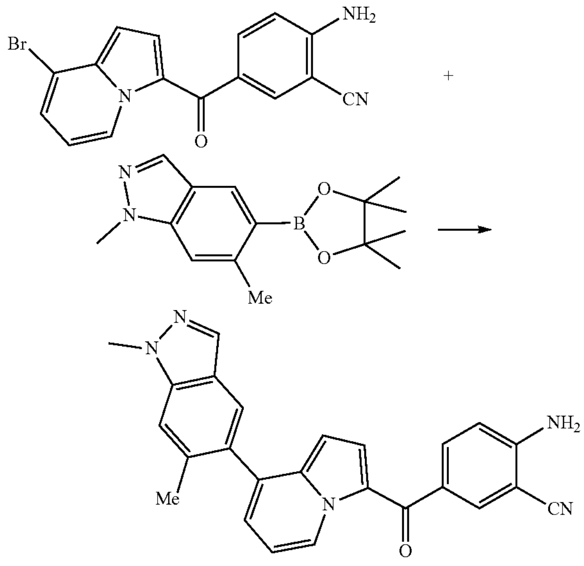

Prepared in a similar manner to tert-butyl N-{1-[8-(1,6-dimethyl-1H-1,3-benzodiazol-5-yl)indolizine-3-carbonyl]piperidin-4-yl}carbamate, except using 2-amino-5-(8-bromoindolizine-3-carbonyl)benzonitrile (100 mg, 0.294 mmol) and 1,6-dimethyl-5-(4,4,5,5-tetramethyl-1,3,2-dioxaborolan-2-yl)-1H-indazole (120 mg, 0.441 mmol) and purifying by column chromatography on NH silica gel (gradient elution, 10-60%, EtOAc/petrol), to give the title compound. MS: $[M+H]^+=406$.

(2E)-4-Chloro-N-{2-cyano-4-[8-(1,6-dimethyl-1H-indazol-5-yl) indolizine-3-carbonyl]phenyl}but-2-enamide

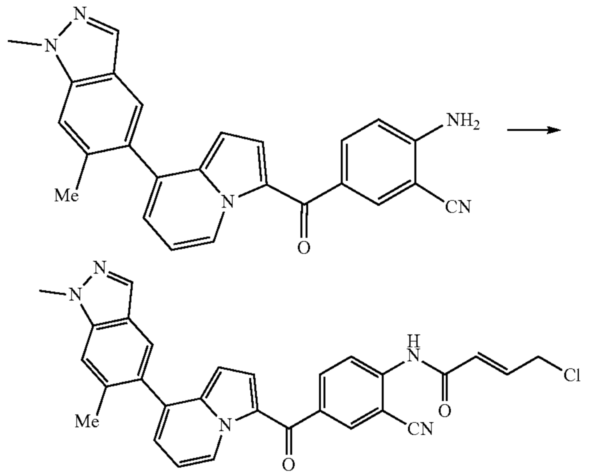

Prepared in a similar manner to (2E)-4-chloro-N-(2,6-difluoro-4-{8-[1-methyl-6-(trifluoromethyl)-1H-1,3-benzodiazol-5-yl]indolizine-3-carbonyl}phenyl)but-2-enamide, except using 2-amino-5-[8-(1,6-dimethyl-1H-indazol-5-yl) indolizine-3-carbonyl]benzonitrile (105 mg, 0.259 mmol) and purifying by column chromatography on silica gel (gradient elution, 10-75%, EtOAc/petrol), to give the title compound. MS: $[M+H]^+=508$.

(2E)-4-(tert-Butylamino)-N-{2-cyano-4-[8-(1,6-dimethyl-1H-indazol-5-yl) indolizine-3-carbonyl] phenyl}but-2-enamide

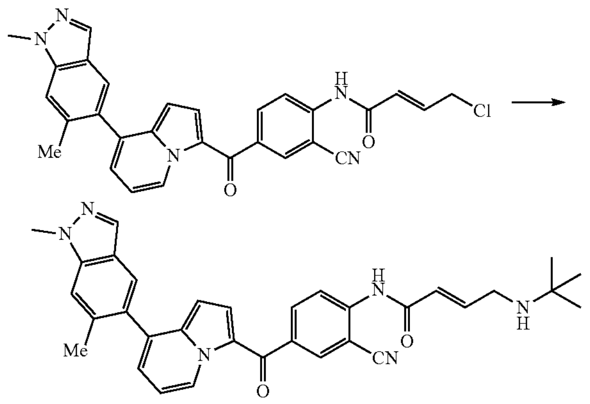

Prepared in a similar manner to (2E)-4-(tert-butylamino)-N-(2,6-difluoro-4-{8-[1-methyl-6-(trifluoromethyl)-1H-1,3-benzodiazol-5-yl]indolizine-3-carbonyl}phenyl)but-2-enamide, except using (2E)-4-chloro-N-{2-cyano-4-[8-(1,6-dimethyl-1H-indazol-5-yl) indolizine-3-carbonyl] phenyl}but-2-enamide (115 mg, 0.226 mmol) and purifying by preparative HPLC (Formic acid method), to give the title compound.

Example 62 and 63

(E)-N-(2-cyano-4-(8-(4,6-dichloro-1-methyl-1H-benzo[d]imidazol-5-yl)indolizine-3-carbonyl)phenyl)-4-(((1r,4r)-4-methoxycyclohexyl)amino)but-2-enamide Step 1: Methylamine (ca. 7% in THF, 33 mL) was added to 1,3,5-trichloro-2-nitro-benzene (3.00 g), and the reaction mixture was stirred at 30° C. for 17 hours, followed by evaporating the solvent under reduced pressure. The residue was diluted with ethyl acetate, and washed with water and a saturated sodium chloride solution, followed by drying over sodium sulfate and the solvent was evaporated under reduced pressure. Diisopropylether (30 mL) was added to the residue and a suspension was stirred at room temperature for 15 minutes. The insoluble matter was filtered off, followed by evaporating the solvent under reduced pressure. The residue was purified by column chromatography (ethyl acetate:hexane), thereby obtaining crude 3,5-dichloro-N-methyl-2-nitro-aniline (1.05 g).

Step 2: A solution of crude 3,5-dichloro-N-methyl-2-nitro-aniline (1.05 g) obtained in step 1 and N-bromosuccinimide (930 mg) in DMF (20 mL) was stirred at room temperature for 15 minutes. The mixture was diluted with ethyl acetate, and extracted with ethyl acetate and washed with water and a saturated sodium chloride solution, followed by drying over sodium sulfate. The solvent was evaporated under reduced pressure, thereby obtaining crude 4-bromo-3,5-dichloro-N-methyl-2-nitro-aniline (1.63 g).

Step 3: A solution of crude 4-bromo-3,5-dichloro-N-methyl-2-nitro-aniline (1.63 g) obtained in step 2, iron powder (1.33 g), and 2 M ammonium chloride solution (5 mL) in methanol (10 mL) and THF (10 mL) was stirred at 70° C. for 3 hours. The insoluble matter was filtered off, followed by evaporating the solvent under reduced pressure. The residue was diluted with ethyl acetate, and washed with water and a saturated sodium chloride solution, followed by drying over sodium sulfate. The solvent was evaporated under reduced pressure, thereby obtaining crude 4-bromo-3,5-dichloro-$N^1$-methyl-benzene-1,2-diamine (1.32 g).

Step 4: Concentrated hydrochloric acid (51.5 μL) was added to a solution of crude 4-bromo-3,5-dichloro-$N^1$-methyl-benzene-1,2-diamine (1.28 g) obtained in step 3 in triethyl orthoformate (13 mL), followed by stirring at room temperature for 15 minutes. 5 M Sodium hydroxide solution (128 μL), water, and ethyl acetate were added to the reaction mixture and the aqueous layer was extracted with ethyl acetate and the organic layer was washed with a saturated sodium chloride solution, followed by drying over sodium sulfate. The solvent was evaporated under reduced pressure.

The residue was suspended with a mixture of ethyl acetate/heptane=6/1, and the suspension was stirred at room temperature for 1 hour. The precipitate was collected, followed by drying thereby obtaining 5-bromo-4,6-dichloro-1-methyl-benzimidazole (0.80 g). The filtrate was evaporated under reduced pressure and the residue was suspended in diisopropylether (5 mL). The suspension was stirred at room temperature for 30 minutes, and the precipitate was collected, followed by drying thereby obtaining 5-bromo-4,6-dichloro-1-methyl-benzimidazole (0.45 g).

Step 5: A suspension of 2-amino-5-(8-bromoindolizine-3-carbonyl)benzonitrile (200 mg), [1,1'-Bis(diphenylphosphino)ferrocene]dichloropalladium(II), complex with dichloromethane (48 mg), bis(pinacolato)diboron (224 mg), and potassium acetate (150 mg) in Dioxane (3.3 mL) was heated to 100° C. for 3 hours using microwave irradiation. After the reaction mixture was cooled to room temperature, ethyl acetate and water were added thereto. Insoluble matter was filtered off through celite pad, and the organic layer was separated and washed with a saturated sodium chloride solution, followed by drying over sodium sulfate. The solvent was evaporated under reduced pressure, thereby obtaining crude 2-amino-5-[8-(4,4,5,5-tetramethyl-1,3,2-dioxaborolan-2-yl)indolizine-3-carbonyl]benzonitrile (332 mg).

Step 6: A suspension of 2-amino-5-[8-(4,4,5,5-tetramethyl-1,3,2-dioxaborolan-2-yl)indolizine-3-carbonyl]benzonitrile (50 mg) obtained in step 5, 5-bromo-4,6-dichloro-1-methyl-benzimidazole (36.0 mg) obtained in step 4, dichlorobis(triphenylphosphine)palladium (9.0 mg), and a 2M sodium carbonate aqueous solution (130 μL) in DMF (0.5 mL) was stirred at 110° C. for 80 minutes using microwave irradiation. 2-amino-5-[8-(4,4,5,5-tetramethyl-1,3,2-dioxaborolan-2-yl)indolizine-3-carbonyl]benzonitrile (110 mg) obtained in step 5 and DMF (1 mL) were added and the reaction mixture was stirred at 110° C. for 4 hours and 40 minutes using microwave irradiation. Ethyl acetate and water were added to the reaction mixture and insoluble matter was filtered off through celite pad and the mixture was extracted with ethyl acetate. The organic layer was washed with water and a saturated sodium chloride solution. The washed organic layer was dried over sodium sulfate, and the solvent was evaporated under reduced pressure, followed by purifying the obtained residue by column chromatography (chloroform:methanol), thereby obtaining 2-amino-5-[8-(4,6-dichloro-1-methyl-benzimidazol-5-yl)indolizine-3-carbonyl]benzonitrile (24.9 mg).

Step 7: The procedure of Example 1 (steps 7 and 8) was performed except that 2-amino-5-[8-(4,6-dichloro-1-methyl-benzimidazol-5-yl)indolizine-3-carbonyl]benzonitrile (24.9 mg) obtained in step 6 was used instead of 4-amino-3-cyano-N-(3-(2-ethyl-1-methyl-6-(trifluoromethyl)-1H-benzo[d]imidazol-5-yl)phenyl)benzamide used in Example 1 (step 7), thereby obtaining (E)-N-(2-cyano-4-(8-(4,6-dichloro-1-methyl-1H-benzo[d]imidazol-5-yl)indolizine-3-carbonyl)phenyl)-4-(((1r,4r)-4-methoxycyclohexyl)amino)but-2-enamide (8.4 mg).

Step 8: (E)-N-(2-cyano-4-(8-(4,6-dichloro-1-methyl-1H-benzo[d]imidazol-5-yl)indolizine-3-carbonyl)phenyl)-4-(((1r,4r)-4-methoxycyclohexyl)amino)but-2-enamide (5.3 mg) obtained in step 7 was dissolved in EtOH and purified by preparative HPLC (CHIRALPAK IC) to afford (E)-N-(2-cyano-4-(8-(4,6-dichloro-1-methyl-1H-benzo[d]imidazol-5-yl)indolizine-3-carbonyl)phenyl)-4-(((1r,4r)-4-methoxycyclohexyl)amino)but-2-enamide (Example 62, 1.92 mg, single isomer, $1^{st}$-eluting isomer) and (E)-N-(2-cyano-4-(8-(4,6-dichloro-1-methyl-1H-benzo[d]imidazol-5-yl)indolizine-3-carbonyl)phenyl)-4-(((1r,4r)-4-methoxycyclohexyl)amino)but-2-enamide (Example 63, 1.95 mg, single isomer, $2^{nd}$-eluting isomer).

Comparative Example 1

N-(3-bromophenyl)-6-((E)-4-(((1r,4r)-4-hydroxycyclohexyl)amino)but-2-enamido)nicotinamide 3-bromoaniline (10.7 mg), N,N-dimethylpyridin-4-amine (5.0 mg), 1-propanephosphonic acid anhydride cyclic trimer (a 1.7M THF solution, 90 μL), and N,N-diisopropylethylamine (40 μL) were added to a solution of 6-((E)-4-(((1r,4r)-4-hydroxycyclohexyl)amino)but-2-enamido)nicotinic acid (10.0 mg) obtained in Example 14 (step 3) in DMF (300 μL). A reaction was performed at room temperature for 10 hours. Water was added to the reaction mixture, and extraction was performed with dichloromethane, followed by washing the organic layer with a saturated sodium chloride solution. The washed layer was dried over sodium sulfate, and the solvent was evaporated under reduced pressure. The residue was purified by preparative reversed-phase HPLC (water:acetonitrile (0.1% formic acid)). Saturated sodium bicarbonate water was added to the purified fractions containing the title compound, followed by extraction with chloroform. The extract was washed with a saturated sodium chloride solution and dried over sodium sulfate. The solvent was evaporated under reduced pressure, thereby obtaining the title compound (2.51 mg).

Comparative Example 2

4-amino-3-cyano-N-(3-(2-(methoxymethyl)-1-methyl-6-(trifluoromethyl)-1H-benzo[d]imidazol-5-yl)phenyl)benzamide Step 1: 2-methoxyacetic acid (1.80 g), HATU (8.63 g), and N,N-diisopropylethylamine (7.9 mL) were added to a solution of 4-bromo-N1-methyl-5-(trifluoromethyl)benzene-1,2-diamine (4.89 g) obtained in Example 1 (step 3) in DMF (61 mL). A reaction was performed at room temperature for 2 hours. Water was added to the reaction mixture, and the resulting solid was collected by filtration, thereby obtaining crude N-(5-bromo-2-(methylamino)-4-(trifluoromethyl)phenyl)-2-methoxyacetamide (4.01 g).

Step 2: A solution of crude N-(5-bromo-2-(methylamino)-4-(trifluoromethyl)phenyl)-2-methoxyacetanide (4.01 g) obtained in step 1 in acetic acid (39 mL) was stirred at room temperature for 2 hours. The reaction mixture was concentrated under reduced pressure, then saturated sodium bicarbonate water was added to the residue, and extraction was performed with ethyl acetate, followed by washing the organic layer with a saturated sodium chloride solution. The washed layer was dried over sodium sulfate, and the solvent was evaporated under reduced pressure, thereby obtaining crude 5-bromo-2-(methoxymethyl)-1-methyl-6-(trifluoromethyl)-1H-benzo[d]imidazole (3.10 g).

Step 3: A suspension of crude 5-bromo-2-(methoxymethyl)-1-methyl-6-(trifluoromethyl)-1H-benzo[d]imidazole (3.10 g) obtained in step 2, 3-(4,4,5,5-tetramethyl-1,3,2-dioxaborolan-2-yl)aniline (3.35 g), dichlorobis(triphenylphosphine)palladium (413 mg), and a 1M sodium carbonate aqueous solution (29 mL) in 1,2-dimethoxyethane (59 mL) was stirred at 80° C. for 3 hours. Ethyl acetate and water were added to the reaction mixture to separate the organic layer, and the organic layer was washed with a saturated sodium chloride solution. The washed organic layer was dried over sodium sulfate, and the solvent was evaporated under reduced pressure, followed by purifying the obtained residue by column chromatography (chloroform:methanol), thereby obtaining 3-(2-(methoxymethyl)-1-methyl-6-(trifluoromethyl)-1H-benzo[d]imidazol-5-yl)aniline (2.99 g).

Step 4: 1-Hydroxybenzotriazole monohydrate (887 mg), 4-amino-3-cyano-benzoic acid (851 mg), triethylamine (910 μL), and WSC hydrochloride (1.26 g) were added to a solution of 3-(2-(methoxymethyl)-1-methyl-6-(trifluoromethyl)-1H-benzo[d]imidazol-5-yl)aniline (1.47 g) obtained in step 3 in DMF (44 mL). A reaction was performed at room temperature overnight. Water was added to the reaction mixture, and the resulting solid was collected by filtration, thereby obtaining 4-amino-3-cyano-N-(3-(2-(methoxymethyl)-1-methyl-6-(trifluoromethyl)-1H-benzo[d]imidazol-5-yl)phenyl)benzamide (2.05 g).

Step 5: Acryloyl chloride (a 1M acetonitrile solution, 94 μL) was added to a solution of 4-amino-3-cyano-N-(3-(2-(methoxymethyl)-1-methyl-6-(trifluoromethyl)-1H-benzo[d]imidazol-5-yl)phenyl)benzamide (30.0 mg) obtained in step 4 and N,N-diisopropylethylamine (21 μL) in THF (1.0 mL) at 0° C. After stirring at room temperature for 1 hour, acryloyl chloride (a 1M acetonitrile solution, 280 μL) was added to the reaction mixture. Saturated sodium bicarbonate water was added to the mixture, and extraction was performed with ethyl acetate, followed by washing the organic layer with a saturated sodium chloride solution. The washed layer was dried over sodium sulfate, and the solvent was evaporated under reduced pressure. The residue was purified by preparative reversed-phase HPLC (water:acetonitrile (0.1% formic acid)), thereby obtaining the title compound (6.32 mg).

The compounds of Examples 20 to 43, 45 to 47, 55 to 61 and 64 to 83 were also prepared and purified. The following is a list of the compounds of Examples 1 to 83 and Comparative examples 1 to 2.

TABLE 1

| Example | Structure | NMR | ESI-MS [M + H]$^+$ |
|---|---|---|---|
| 1 | 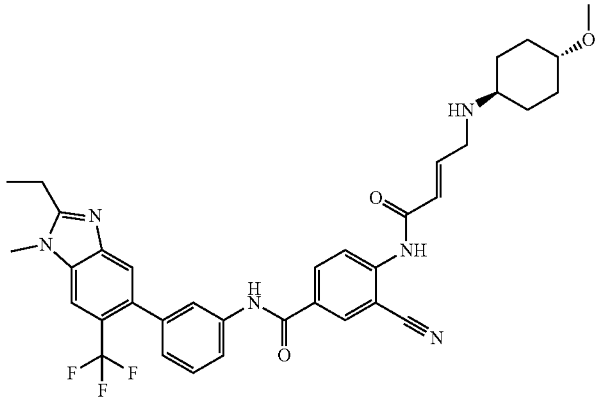 [SMILES: CCc1nc2cc(-c3cccc(NC(=O)c4ccc(NC(=O)/C=C/CN[C@H]5CC[C@H](OC)CC5)c(C#N)c4)c3)c(C(F)(F)F)cc2n1C] | 1H NMR (DMSO-d6) δ: 10.47 (s, 1H), 10.42 (s, 1H), 8.42 (d, J = 2.1 Hz, 1H), 8.22 (dd, J = 8.6, 2.1 Hz, 1H), 8.04 (s, 1H), 7.79-7.88 (m, 3H), 7.50 (s, 1H), 7.42 (t, J = 7.9 Hz, 1H), 7.08 (d, J = 7.6 Hz, 1H), 6.94 (dt, J = 15.4, 5.0 Hz, 1H), 6.41 (d, J = 15.5 Hz, 1H), 3.87 (s, 3H), 3.34-3.44 (m, 3H), 3.22 (s, 3H), 3.03-3.13 (m, 1H), 2.96 (q, J = 7.5 Hz, 2H), 2.40 (br s, 1H), 1.85-2.00 (m, 4H), 1.35 (t, J = 7.5 Hz, 3H), 1.04-1.19 (m, 4H). | 659 |
| 2 | 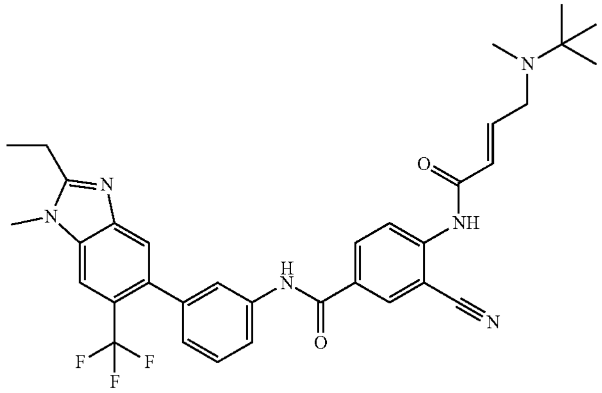 [SMILES: CCc1nc2cc(-c3cccc(NC(=O)c4ccc(NC(=O)/C=C/CN(C)C(C)(C)C)c(C#N)c4)c3)c(C(F)(F)F)cc2n1C] | 1H NMR (DMSO-d6) δ: 10.48 (s, 1H), 10.42 (s, 1H), 8.41 (d, J = 2 1 Hz, 1H), 8.22 (dd, J = 8.5, 2.1 Hz, 1H), 8.04 (s, 1H), 7.80-7.88 (m, 3H), 7.50 (s, 1H), 7.42 (t, J = 7.9 Hz, 1H), 7.08 (d, J = 7.8 Hz, 1H), 6.88 (dt, J = 15.3, 5.3 Hz, 1H), 6.43 (br d, J = 15.4 Hz, 1H), 3.87 (s, 3H), 3.21 (br d, J = 4 6 Hz, 2H), 2.91-3.01 (m2H), 2.15 (s, 3H), 1.36 (t, J = 7.5 Hz, 3H), 1.06 (s, 9H). | 617 |
| 3 | 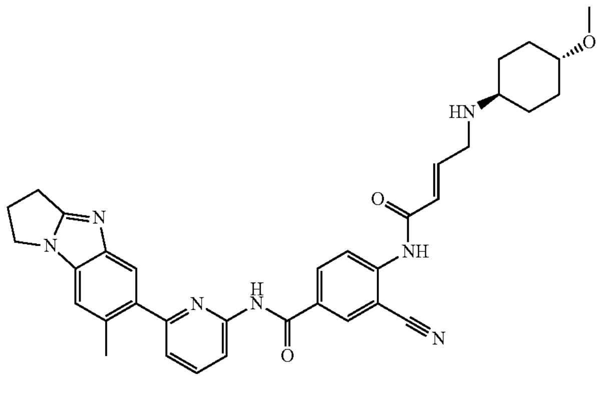 [SMILES: CO[C@H]1CC[C@H](NC/C=C/C(=O)Nc2ccc(C(=O)Nc3cccc(-c4cc5nc6n(c5cc4C)CCC6)n3)cc2C#N)CC1] | 1H NMR (DMS0-d6) δ: 10.96 (s, 1H), 10.46 (s, 1H), 8.50 (d, J = 2.1 Hz, 1H), 8.28 (dd, J = 8.7, 2.2 Hz, 1H), 8.15 (d, J = 8.0 Hz, 1H), 7.83-7.97 (m 2H), 7.56 (s, 1H), 7.36 (s, 1H), 7.29 (dd, J = 7.6, 0.8 Hz, 1H), 6.95 (dt, J = 15.4, 5.0 Hz, 1H), 6.39-6.45 (m, 1H), 4.12 (t, J = 7.1 Hz, 2H), 3.36-3.42 (m, 2H), 3.21-3.25 (m, 3H), 3.04-3.13 (m, 1H), 2.93-2.99 (m, 2H), 2.61-2.70 (m, 2H), 2.45 (s, 3H), 2.35-2.42 (m, 1H), 1.84-2.03 (m, 5H), 1.00-1.17 (m 4H). | 604 |

TABLE 1-continued

| Example | Structure | NMR | ESI-MS [M + H]+ |
|---|---|---|---|
| 4 | 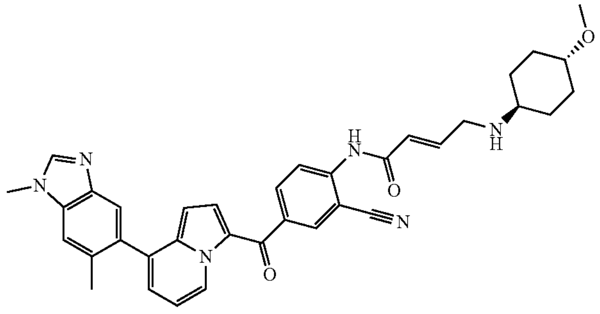 [SMILES: CO[C@H]1CC[C@H](NC/C=C/C(=O)Nc2ccc(C(=O)c3ccc4c(-c5cc6ncn(C)c6cc5C)cccn34)cc2C#N)CC1] | 1H NMR (DMSO-d6) δ: 10.47 (s, 1H), 9.86-9.91 (m, 1H), 8.21 (s, 1H), 8.17 (d, J = 2.0 Hz, 1H), 8.07 (dd, J = 8.6, 2.1 Hz, 1H), 7.85-7.91 (m, 1H), 7.58-7.61 (m, 1H), 7.54-7.57 (m, 1H), 7.41 (d, J = 4.8 Hz, 1H), 7.25-7.31 (m 2H), 6.95 (dt, J = 15.4, 4.9 Hz, 1H), 6.40-6.46 (m, 1H), 6.14 (d, J = 4.8 Hz, 1H), 3.88 (s, 3H), 3.40 (dd, J = 4 7, 1.4 Hz, 2H), 3.22 (s, 3H), 3.05-3.15 (m, 1H), 2.35-2.45 (m, 1H), 2.23 (s, 3H), 1.87-1.99 (m, 5H), 1.01-1.15 (m 4H). | 601 |
| 5 | 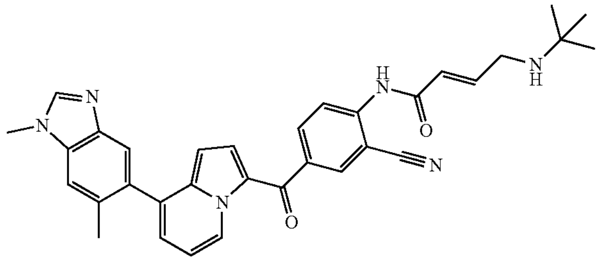 [SMILES: Cc1cc2c(cc1-c1cccn3c(C(=O)c4ccc(NC(=O)/C=C/CNC(C)(C)C)c(C#N)c4)ccc13)ncn2C] | 1H NMR (DMSO-d6) δ: 10.47 (br s, 1H), 9.86-9.91 (m, 1H), 8.21 (s, 1H), 8.17 (d, J = 1.9 Hz, 1H), 8.08 (dd, J = 8.6, 2.1 Hz, 1H), 7.87 (d, J = 8.6 Hz, 1H), 7.59 (s, 1H), 7.55 (s, 1H), 7.41 (d, J = 4.9 Hz, 1H), 7.25-7.32 (m, 2H), 6.95-7.04 (m, 1H), 6.46 (br d, J = 15.6 Hz, 1H), 6.14 (d, J = 4.9 Hz, 1H), 3.88 (s, 3H), 3.34-3.48 (m, 2H), 2.24 (s, 3H), 1.67 (br s, 1H), 1.08 (br s, 9H). | 545 |
| 6 | 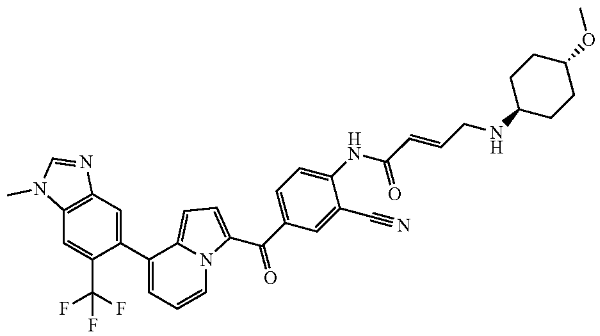 [SMILES: CO[C@H]1CC[C@H](NC/C=C/C(=O)Nc2ccc(C(=O)c3ccc4c(-c5cc6ncn(C)c6cc5C(F)(F)F)cccn34)cc2C#N)CC1] | 1H NMR (DMSO-d6) δ: 10.47 (s, 1H), 9.86-9.93 (m, 1H), 8.52 (s, 1H), 8.26 (s, 1H), 8.17 (s, 1H), 8.07 (d, J = 8.7 Hz, 1H), 7.88 (d, J = 8.6 Hz, 1H), 7.76 (s, 1H), 7.40 (d, J = 4.8 Hz, 1H), 7.25-7.30 (m, 2H), 6.95 (dt, J = 15.4, 5.0 Hz, 1H), 6.43 (br d, J = 15.5 Hz, 1H), 6.08 (d, J = 4.8 Hz, 1H), 4.01 (s, 3H), 3.35-3.44 (m, 2H), 3.23 (s, 3H), 3.05-3.13 (m, 1H), 2.40 (br s, 1H), 1.86-2.02 (m, 5H), 1.01-1.17 (m 4H). | 655 |
| 7 | 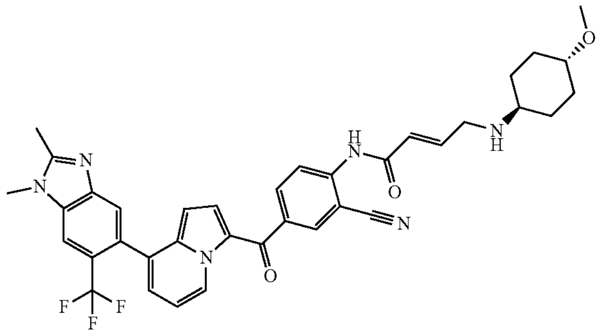 [SMILES: CO[C@H]1CC[C@H](NC/C=C/C(=O)Nc2ccc(C(=O)c3ccc4c(-c5cc6nc(C)n(C)c6cc5C(F)(F)F)cccn34)cc2C#N)CC1] | 1H NMR (DMSO-d6) δ: 10.47 (s, 1H), 9.85-9.93 (m, 1H), 8.17 (s, 1H), 8.15 (s, 1H), 8.08 (br d, J = 8.3 Hz, 1H), 7.87 (d, J = 8.5 Hz, 1H), 7.61 (s, 1H), 7.40 (d, J = 4 6 Hz, 1H), 7.23-7.31 (m, 2H), 6.95 (dt, J = 15.3, 4.8 Hz, 1H), 6.43 (br d, J = 15.5 Hz, 1H), 6.06 (d, J = 4.8 Hz, 1H), 3.90 (s, 3H), 3.37-3.46 (m, 2H), 3.23 (s, 3H), 3.04-3.14 (m, 1H), 2.62 (s, 3H), 2.40 (br s, 1H), 1.83-1.99 (m, 5H), 1.00-1.16 (m 4H). | 669 |
| 8 | 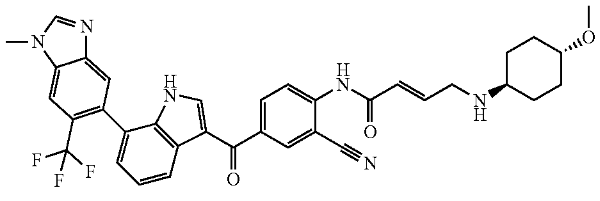 | 1H NMR (DMSO-d6) δ: 11.79 (br s, 1H), 10.45 (s, 1H), 8.50 (s, 1H), 8.31 (d, J = 7.9 Hz, 1H), 8.22 (s, 1H), 8.19 (d, J = 1.6 Hz, 1H), 8.09 (dd, J = 8.7, 1.7 Hz, 1H), 7.90-7.93 (m, 1H), 7.87 (d, J = 8.6 Hz, 1H), 7.66 (s, 1H), 7.32 (t, J = 7.6 Hz, 1H), 7.15 (d, J = 7.3 Hz, 1H), 6.95 (dt, J = 15.4, 4.9 Hz, 1H), 6.43 (br d, J = 15.4 Hz, 1H), 4.02 (s, 3H), 3.37-3.44 (m, 3H), 3.22 (s, 3H), 3.04-3.14 (m, 1H), 2.35-2.45 (m, 1H), 1.86-2.01 (m, 4H), 0.99-1.15 (m 4H). | 655 |

TABLE 1-continued

| Example | Structure | NMR | ESI-MS [M + H]+ |
|---|---|---|---|
| 9 | 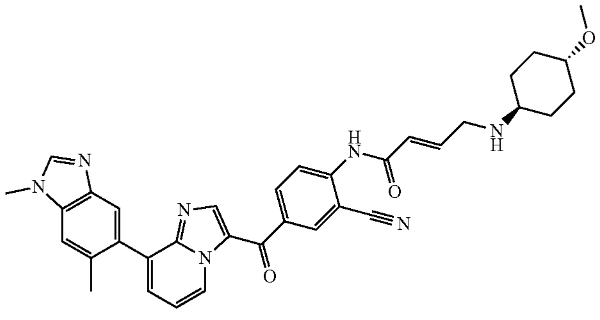 [SMILES: CO[C@H]1CC[C@H](NC/C=C/C(=O)Nc2ccc(C(=O)c3cnc4c(-c5cc6ncn(C)c6cc5C)cccn34)cc2C#N)CC1] | 1HNMR (DMSO-d6) δ: 10.52 (s, 1H), 9.68 (dd, J = 6.9, 1.3 Hz, 1H), 8.35 (s, 1H), 8.29 (d, J = 2.0 Hz, 1H), 8.16-8.21 (m, 2H), 7.94 (d, J = 8.6 Hz, 1H), 7.65 (dd, J = 7.1, 1.3 Hz, 1H), 7.59 (s, 1H), 7.54 (s, 1H), 7.47 (t, J = 6.9 Hz, 1H), 6.96 (dt, J = 15.4, 5.0 Hz, 1H), 6.45 (d, J = 15.4 Hz, 1H), 3.88 (s, 3H), 3.36-3.45 (m, 2H), 3.23 (s, 3H), 3.02-3.16 (m, 1H), 2.37-2.47 (m, 1H), 2.25 (s, 3H), 1.88-2.01 (m, 5H), 1.02-1.16 (m, 4H). | 602 |
| 10 | 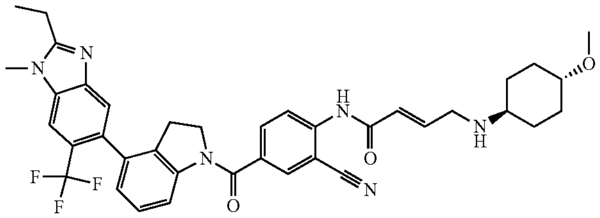 | 1H NMR (DMSO-d6) δ: 10.42 (s, 1H), 8.01-8.20 (m, 3H), 7.93 (dd, J = 8.6, 1.9 Hz, 1H), 7.80 (d, J = 8.6 Hz, 1H), 7.46 (s, 1H), 7.24-7.33 (m, 1H), 6.90-6.98 (m, 2H), 6.40 (br d, J = 15.5 Hz, 1H), 4.01 (br t, J = 8.5 Hz, 2H), 3.86 (s, 3H), 3.36-3.42 (m, 2H), 3.22 (s, 3H), 3.05-3.14 (m, 1H), 2.84-2.98 (m, 3H), 2.56-2.63 (m, 1H), 2.35-2.43 (m, 1H), 1.78-2.02 (m, 5H), 1.35 (t, J = 7.5 Hz, 3H), 1.02-1.17 (m, 4H). | 685 |
| 11 | 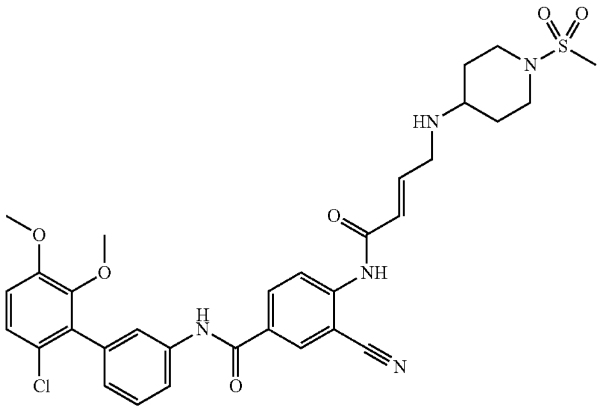 [SMILES: COc1ccc(Cl)c(-c2cccc(NC(=O)c3ccc(NC(=O)/C=C/CNC4CCN(S(C)(=O)=O)CC4)c(C#N)c3)c2)c1OC] | 1H NMR (DMSO-d6) δ: 10.46 (br s, 1H), 10.38 (s, 1H), 8.34-8.39 (m 1H), 8.17 (dd, J = 8.6, 1.9 Hz, 1H), 7.80 (d, J = 8.7 Hz, 1H), 7.75 (br d, J = 7.9 Hz, 1H), 7.65 (s, 1H), 7.39 (t, J = 7.9 Hz, 1H), 7.24 (d, J = 8.9 Hz, 1H), 7.08 (d, J = 8.9 Hz, 1H), 6.87-6.97 (m, 2H), 6.38 (br d, J = 15.4 Hz, 1H), 3.81 (s, 3H), 3.48 (s, 3H), 3.39-3.46 (m, 4H), 2.71-2.83 (m, 5H), 2.47-2.56 (m, 2H), 1.82-1.92 (m, 2H), 1.24-1.37 (m 2H). | 652 |
| 12 | 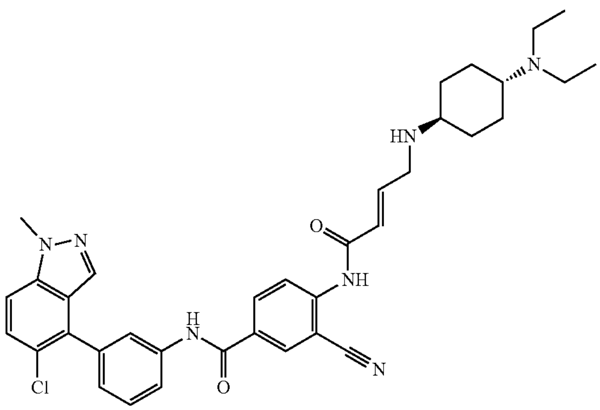 [SMILES: CCN(CC)[C@H]1CC[C@H](NC/C=C/C(=O)Nc2ccc(C(=O)Nc3cccc(-c4c(Cl)ccc5c4cnn5C)c3)cc2C#N)CC1] | 1H NMR (DMSO-d6) δ: 10.42-10.51 (m, 2H), 8.36-8.42 (m, 1H), 8.16-8.23 (m, 1H), 7.91 (s, 1H), 7.79-7.87 (m, 2H), 7.63-7.73 (m, 2H), 7.47-7.53 (m, 2H), 7.23 (br d, J = 7.8 Hz, 1H), 6.81-6.96 (m, 1H), 6.29-6.46 (m, 1H), 4.04 (s, 3H), 3.38-3.57 (m, 4H), 2.48-2.65 (m3H), 1.86-1.97 (m, 2H), 1.65-1.81 (m2H), 1.10-1.37 (m, 6H), 0.91-1.09 (m, 6H). | 638 |

TABLE 1-continued

| Example | Structure | NMR | ESI-MS $[M + H]^+$ |
| --- | --- | --- | --- |
| 13 | 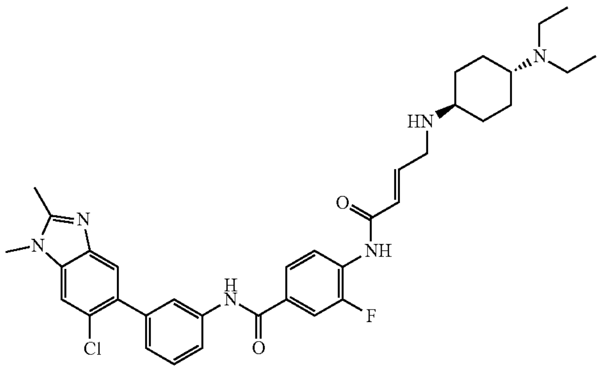 [SMILES: CCN(CC)[C@H]1CC[C@H](NC/C=C/C(=O)Nc2ccc(C(=O)Nc3cccc(-c4cc5nc(C)n(C)c5cc4Cl)c3)cc2F)CC1] | 1H NMR (DMSO-d6) δ: 10.30 (s, 1H), 10.09 (s, 1H), 8.26 (t, J = 8.2 Hz, 1H), 7.82-7.90 (m, 4H), 7.78 (s, 1H), 7.49 (s, 1H), 7.44 (t, J = 7.9 Hz, 1H), 7.14-7.21 (m, 1H), 6.84-6.93 (m, 1H), 6.52 (br d, J = 15.3 Hz, 1H), 3.78 (s, 3H), 3.40-3.43 (m, 4H), 2.58-2.64 (m 3H), 2.55-2.56 (m, 3H), 2.39-2.47 (m 2H), 1.97 (br d, J = 12.4 Hz, 2H), 1.77 (br d, J = 11.0 Hz, 2H), 1.23-1.36 (m, 2H), 1.05-1.12 (m, 2H), 1.01 (br t, J = 7.0 Hz, 6H). | 645 |
| 14 | 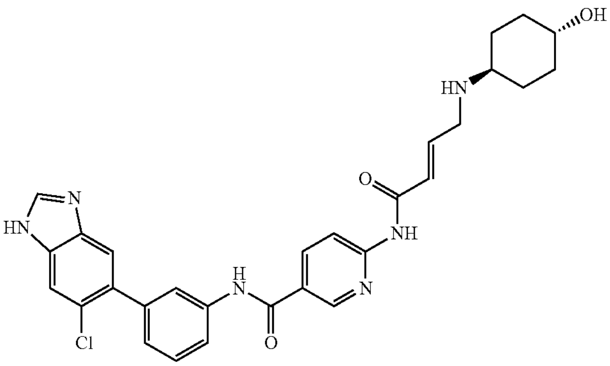 [SMILES: O=C(/C=C/CN[C@H]1CC[C@H](O)CC1)Nc1ccc(C(=O)Nc2cccc(-c3cc4nc[nH]c4cc3Cl)c2)cn1] | 1H NMR (DMS0-d6) δ: 12.55-12.82 (m, 1H), 10.93 (s, 1H), 10.40 (s, 1H), 8.91-8.94 (m, 1H), 8.29-8.36 (m, 4H), 8.24 (s, 1H), 7.89 (s, 1H), 7.81-7.85 (m, 1H), 7.46 (t, J = 8.0 Hz, 1H), 7.20 (d, J = 7.9 Hz, 1H), 6.87-6.95 (m 1H), 6.46 (d, J = 15.3 Hz, 1H), 4.48 (br s, 1H), 2.52-2.56 (m, 2H), 2.45-2.48 (m, 2H), 2.31-2.36 (m, 1H), 1.77-1.88 (m, 4H), 1.09-1.19 (m, 2H), 0.99-1.08 (m, 2H). | 545 |
| 15 | 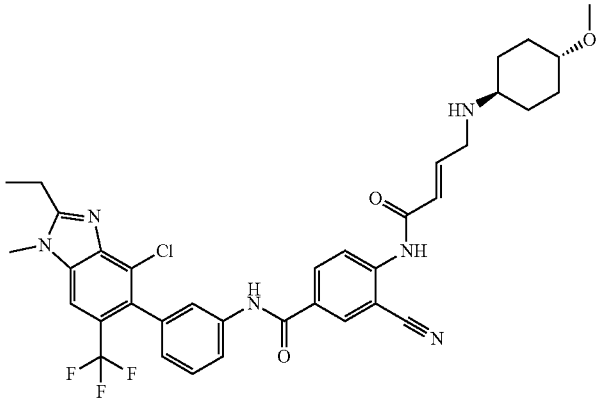 [SMILES: CCc1nc2c(Cl)c(-c3cccc(NC(=O)c4ccc(NC(=O)/C=C/CN[C@H]5CC[C@H](OC)CC5)c(C#N)c4)c3)c(C(F)(F)F)cc2n1C] | 1H NMR (DMSO-d6) δ: 10.39-10.52 (m, 2H), 8.42 (d, J = 2.1 Hz, 1H), 8.22 (dd, J = 8.7, 2.2 Hz, 1H), 8.10 (s, 1H), 7.83-7.91 (m, 2H), 7.71 (s, 1H), 7.46 (t, J = 7.9 Hz, 1H), 6.91-7.01 (m, 2H), 6.37-6.45 (m, 1H), 3.90 (s, 3H), 3.38-3.43 (m, 2H), 3.20-3.24 (m, 3H), 3.04-3.13 (m, 1H), 2.99 (q, J = 7.5 Hz, 2H), 2.34-2.43 (m, 1H), 1.81-2.01 (m, 5H), 1.37 (t, J = 7.5 Hz, 3H), 1.04-1.14 (m, 4H). | 693 |
| 16 | 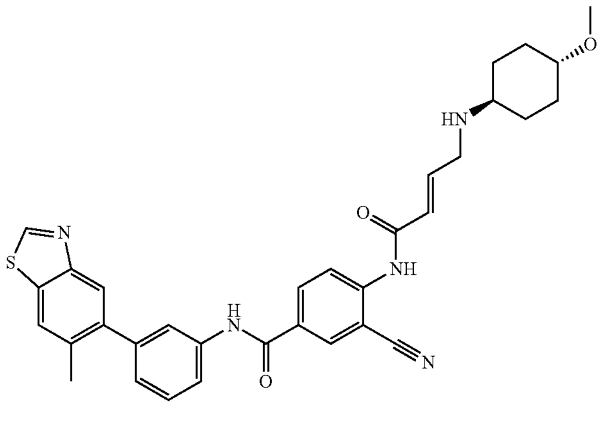 [SMILES: CO[C@H]1CC[C@H](NC/C=C/C(=O)Nc2ccc(C(=O)Nc3cccc(-c4cc5ncsc5cc4C)c3)cc2C#N)CC1] | 1H NMR (DMSO-d6) δ: 10.48 (s, 1H), 10.44 (s, 1H), 9.37 (s, 1H), 8.43 (d, J = 2.1 Hz, 1H), 8.24 (dd, J = 8.7, 2.2 Hz, 1H), 8.12 (s, 1H), 7.82-7.91 (m, 4H), 7.46-7.53 (m, 1H), 7.17-7.22 (m 1H), 6.95 (dt, J = 15.4, 5.0 Hz, 1H), 6.38-6.45 (m, 1H), 3.35-3.42 (m, 2H), 3.23 (s, 3H), 3.05-3.14 (m, 1H), 2.38-2.42 (m, 4H), 1.85-2.02 (m, 5H), 1.06-1.16 (m, 4H). | 580 |

TABLE 1-continued

| Example | Structure | NMR | ESI-MS [M + H]+ |
|---|---|---|---|
| 17 | 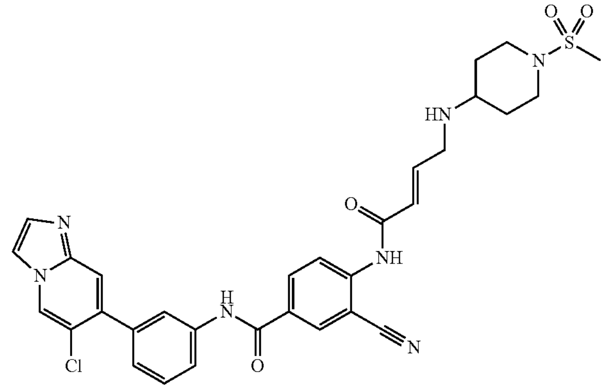 [SMILES: CS(=O)(=O)N1CCC(NC/C=C/C(=O)Nc2ccc(C(=O)Nc3cccc(-c4cc5nccn5cc4Cl)c3)cc2C#N)CC1] | 1H NMR (DMSO-d6) δ: 10.41-10.52 (m, 2H), 8.94 (s, 1H), 8.36-8.42 (m, 1H), 8.18-8.21 (m, 1H), 7.93 (s, 1H), 7.90 (s, 1H), 7.79-7.85 (m, 2H), 7.63 (s, 1H), 7.56 (s, 1H), 7.45 (t, J = 7.9 Hz, 1H), 7.22 (br d, J = 7.8 Hz, 1H), 6.91 (dt, J = 15.3, 5.0 Hz, 1H), 6.38 (br d, J = 15.4 Hz, 1H), 3.45-3.50 (m, 4H), 2.71-2.81 (m 5H), 2.48-2.58 (m, 2H), 1.81-1.92 (m 2H), 1.24-1.35 (m 2H). | 632 |
| 18 | 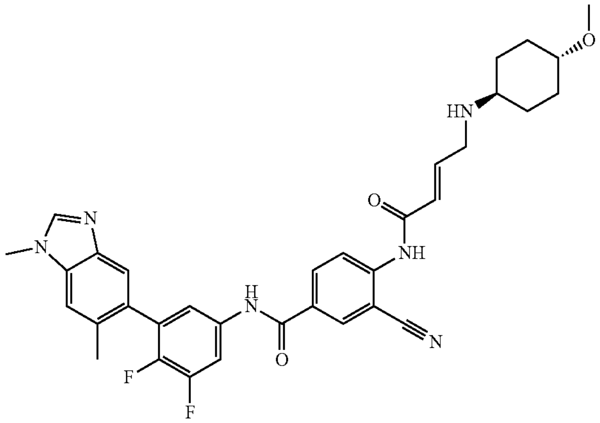 | 1H NMR (DMSO-d6) δ: 10.57 (s, 1H), 10.49 (s, 1H), 8.41 (d, J = 2.1 Hz, 1H), 8.22 (dd, J = 8.7, 2.2 Hz, 1H), 8.20 (s, 1H), 7.98 (ddd, J = 12.7, 6.9, 2.5 Hz, 1H), 7.88 (d, J = 8.8 Hz, 1H), 7.48-7.57 (m, 3H), 6.95 (dt, J = 15.4, 5.0 Hz, 1H), 6.38-6.45 (m, 1H), 3.87 (s, 3H), 3.36-3.42 (m, 2H), 3.22 (s, 3H), 3.05-3.15 (m, 1H), 2.35-2.43 (m, 1H), 2.28-2.33 (m, 3H), 1.86-2.02 (m, 5H), 1.06-1.18 (m, 4H). | 613 |
| 19 | 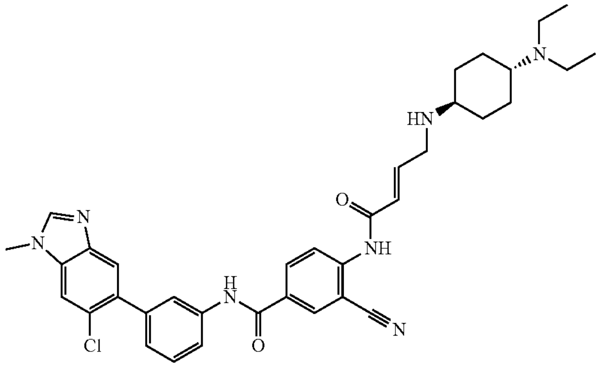 [SMILES: CCN(CC)[C@H]1CC[C@H](NC/C=C/C(=O)Nc2ccc(C(=O)Nc3cccc(-c4cc5ncn(C)c5cc4Cl)c3)cc2C#N)CC1] | 1H NMR (DMSO-d6) δ: 10.49 (s, 1H), 10.44 (s, 1H), 8.43 (d, J = 2.1 Hz, 1H), 8.29 (s, 1H), 8.23-8.25 (m, 1H), 7.83-7.90 (m 4H), 7.64 (s, 1H), 7.46 (t, J = 7.9 Hz, 1H), 7.19-7.22 (m, 1H), 6.91-6.98 (m, 1H), 6.39-6.45 (m, 1H), 3.89 (s, 3H), 3.41-3.43 (m, 4H), 2.45-2.49 (m, 3H), 2.31-2.36 (m, 1H), 1.92-1.99 (m, 2H), 1.70-1.77 (m, 2H), 1.20-1.31 (m, 3H), 1.00-1.10 (m, 2H), 0.95-1.00 (m, 6H). | 638 |
| 20 | 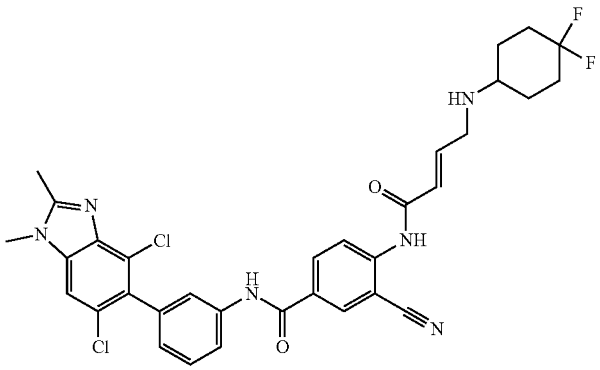 [SMILES: Cc1nc2c(Cl)c(-c3cccc(NC(=O)c4ccc(NC(=O)/C=C/CNC5CCC(F)(F)CC5)c(C#N)c4)c3)c(Cl)cc2n1C] | 1H NMR (DMSO-d6) δ: 10.49 (s, 1H), 10.45 (s, 1H), 8.43 (d, J = 2.1 Hz, 1H), 8.31 (s, 1H), 8.23 (dd, J = 8.7, 2.1 Hz, 1H), 7.84-7.88 (m, 3H), 7.69-7.71 (m, 1H), 7.49 (t, J = 7.9 Hz, 1H), 7.01 (dt, J = 7.9, 1.2 Hz, 1H), 6.96 (dt, J = 15.4, 5.0 Hz, 1H), 6.41-6.46 (m, 1H), 3.80 (s, 3H), 3.39-3.43 (m, 4H), 2.59 (s, 3H), 1.98-2.09 (m, 2H), 1.84 (br d, J = 11.1 Hz, 3H), 1.42 (br d, J = 9.5 Hz, 2H). | 651 |

TABLE 1-continued

| Example | Structure | NMR | ESI-MS [M + H]+ |
| --- | --- | --- | --- |
| 21 | 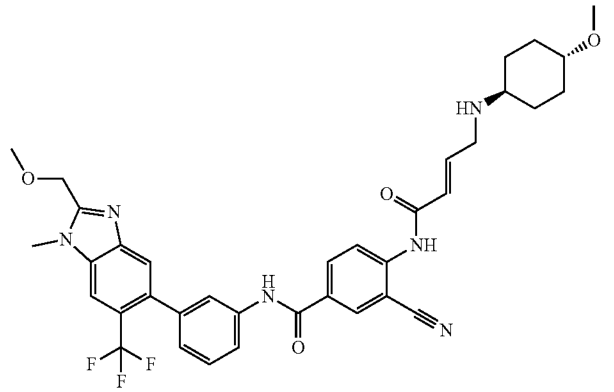 | 1H NR (DMSO-d6) δ: 10.48 (s, 1H), 10.43 (s, 1H), 8.42 (d, J = 2.3 Hz, 1H), 8.22 (dd, J = 8.8, 2.1 Hz, 1H), 8.14 (s, 1H), 7.81-7.91 (m, 3H), 7.59 (s, 1H), 7.43 (t, J = 7.9 Hz, 1H), 7.10 (d, J = 7.8 Hz, 1H), 6.95 (dt, J = 15.4, 4.9 Hz, 1H), 6.38-6.46 (m, 1H), 4.78 (s, 2H), 3.95 (s, 3H), 3.36-3.41 (m, 7H), 3.23 (s, 3H), 3.05-3.13 (m, 1H), 1.86-2.01 (m, 4H), 1.01-1.19 (m 4H). | 675 |
| 22 | 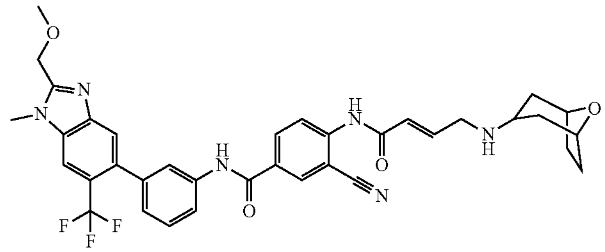 [SMILES: COCc1nc2cc(-c3cccc(NC(=O)c4ccc(NC(=O)/C=C/CNC5CC6CCC(C5)O6)c(C#N)c4)c3)c(C(F)(F)F)cc2n1C] | 1H NMR (DMSO-d6) δ: 10.49 (s, 1H), 10.44 (s, 1H), 8.42 (d, J = 2.1 Hz, 1H), 8.23 (dd, J = 8.6, 2.1 Hz, 1H), 8.14 (s, 1H), 7.81-7.87 (m, 3H), 7.59 (s, 1H), 7.43 (t, J = 7.9 Hz, 1H), 7.10 (d, J = 7.6 Hz, 1H), 6.97 (dt, J = 15.5, 5.3 Hz, 1H), 6.34-6.41 (m, 1H), 4.78 (s, 2H), 4.19-4.24 (m, 2H), 3.95 (s, 3H), 3.36-3.37 (m, 5H), 2.88 (br t, J = 5.6 Hz, 1H), 2.19-2.24 (m, 2H), 1.93-1.98 (m, 1H), 1.82-1.89 (m, 2H), 1.72-1.79 (m, 2H), 1.53-1.59 (m, 2H). | 673 |
| 23 | 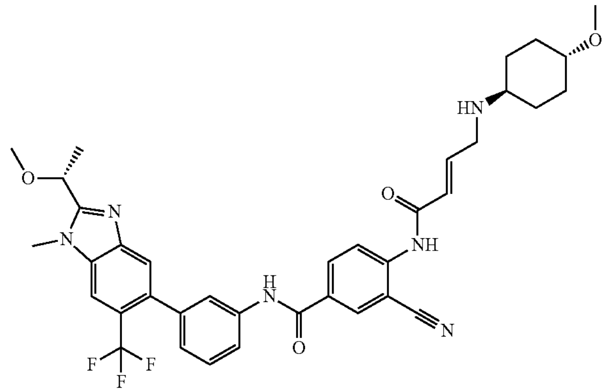 | 1H NMR (DMSO-d6) δ: 10.47 (s, 1H), 10.43 (s, 1H), 8.42 (d, J = 2.3 Hz, 1H), 8.22 (dd, J = 8.6, 2.1 Hz, 1H), 8.13 (s, 1H), 7.81-7.88 (m, 3H), 7.58 (s, 1H), 7.43 (t, J = 7.9 Hz, 1H), 7.09 (d, J = 7.5 Hz, 1H), 6.95 (dt, J = 15.4, 5.0 Hz, 1H), 6.38-6.45 (m, 1H), 4.89-4.96 (m 1H), 3.98 (s, 3H), 3.38-3.40 (m, 2H), 3.28 (s, 3H), 3.22 (s, 3H), 3.05-3.12 (m, 1H), 2.34-2.42 (m, 1H), 1.82-2.01 (m, 5H), 1.60 (d, J = 6.5 Hz, 3H), 1.00-1.18 (m, 4H). | 689 |
| 24 | 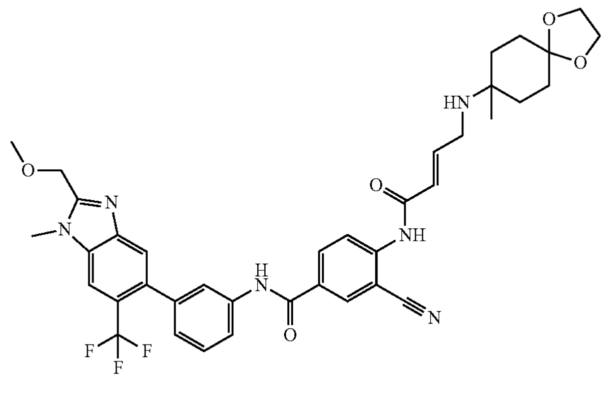 [SMILES: COCc1nc2cc(-c3cccc(NC(=O)c4ccc(NC(=O)/C=C/CNC5(C)CCC6(CC5)OCCO6)c(C#N)c4)c3)c(C(F)(F)F)cc2n1C] | 1H NMR (DMSO-d6) δ: 10.48 (s, 1H), 10.43 (s, 1H), 8.42 (d, J = 2.1 Hz, 1H), 8.22 (dd, J = 8.6, 2.1 Hz, 1H), 8.14 (s, 1H), 7.81-7.88 (m, 3H), 7.59 (s, 1H), 7.43 (t, J = 7.9 Hz, 1H), 7.10 (d, J = 7.6 Hz, 1H), 7.00 (dt, J = 15.4, 4.9 Hz, 1H), 6.41-6.49 (m, 1H), 4.78 (s, 2H), 3.95 (s, 3H), 3.85 (s, 3H), 3.36 (s, 3H), 3.30-3.32 (m, 2H), 1.73-1.82 (m, 2H), 1.55-1.68 (m, 3H), 1.37-1.50 (m, 4H), 1.04 (s, 3H). | 717 |

TABLE 1-continued

| Example | Structure | NMR | ESI-MS [M + H]+ |
|---|---|---|---|
| 25 | 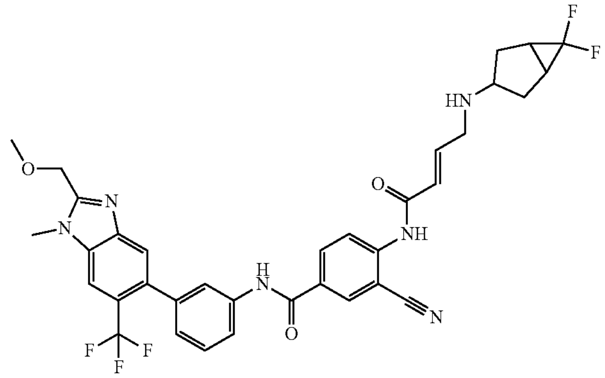 [SMILES: COCc1nc2cc(-c3cccc(NC(=O)c4ccc(NC(=O)/C=C/CNC5CC6C(C5)C6(F)F)c(C#N)c4)c3)c(C(F)(F)F)cc2n1C] | 1H NNR (DMSO-d6) δ: 10.49 (s, 1H), 10.43 (s, 1H), 8.42 (d, J = 2.1 Hz, 1H), 8.22 (dd, J = 8.8, 2.1 Hz, 1H), 8.14 (s, 1H), 7.81-7.88 (m, 3H), 7.59 (s, 1H), 7.43 (t, J = 7.9 Hz, 1H), 7.10 (d, J = 7.4 Hz, 1H), 6.92 (dt, J = 15.4, 5.0 Hz, 1H), 6.38-6.44 (m, 1H), 4.78 (s, 2H), 3.95 (s, 3H), 3.36 (s, 3H), 3.28-3.32 (m, 2H), 3.02 (br s, 1H), 2.14-2.21 (m 2H), 2.04-2.13 (m, 3H), 1.70-1.80 (m, 2H). | 679 |
| 26 | 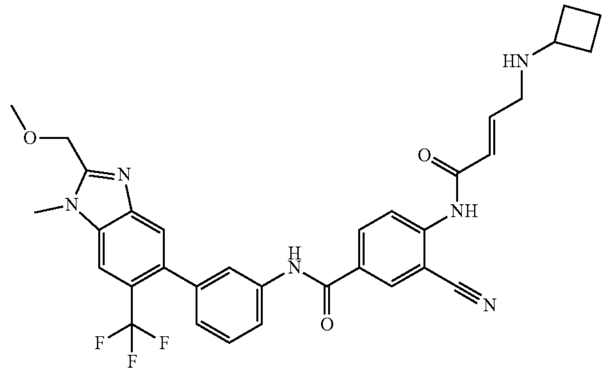 [SMILES: COCc1nc2cc(-c3cccc(NC(=O)c4ccc(NC(=O)/C=C/CNC5CCC5)c(C#N)c4)c3)c(C(F)(F)F)cc2n1C] | 1H NMR (DMSO-d6) δ: 10.48 (s, 1H), 10.43 (s, 1H), 8.40-8.44 (m 1H), 8.22 (dd, J = 8.6, 2.1 Hz, 1H), 8.14 (s, 1H), 7.81-7.89 (m, 3H), 7.59 (s, 1H), 7.40-7.46 (m, 1H), 7.10 (br d, J = 7.6 Hz, 1H), 6.92 (dt, J = 15.4, 5.1 Hz, 1H), 6.38-6.45 (m, 1H), 4.78 (s, 2H), 3.95 (s, 3H), 3.36-3.38 (m, 5H), 3.29-3.31 (m 2H), 2.09-2.17 (m, 2H), 1.51-1.75 (m, 4H). | 617 |
| 27 | 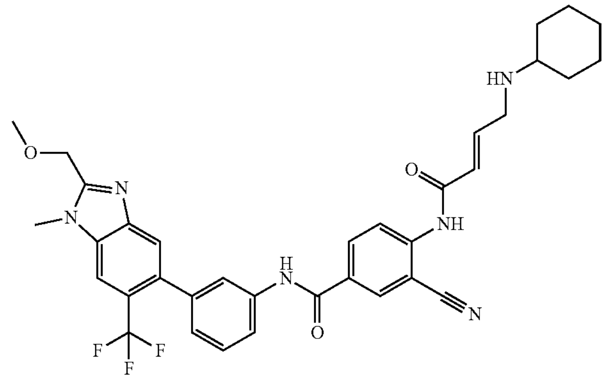 [SMILES: COCc1nc2cc(-c3cccc(NC(=O)c4ccc(NC(=O)/C=C/CNC5CCCCC5)c(C#N)c4)c3)c(C(F)(F)F)cc2n1C] | 1H NMR (DMSO-d6) δ: 10.48 (s, 1H), 10.43 (s, 1H), 8.42 (d, J = 2.1 Hz, 1H), 8.22 (dd, J = 8.8, 2.1 Hz, 1H), 8.14 (s, 1H), 7.80-7.89 (m, 3H), 7.59 (s, 1H), 7.43 (t, J = 7.9 Hz, 1H), 7.10 (d, J = 7.6 Hz, 1H), 6.96 (dt, J = 15.4, 5.0 Hz, 1H), 6.39-6.46 (m, 1H), 4.78 (s, 2H), 3.95 (s, 3H), 3.36-3.36 (m, 5H), 3.27-3.31 (m, 1H), 1.81-1.91 (m, 2H), 1.65-1.73 (m, 2H), 1.50-1.61 (m, 1H), 1.10-1.29 (m, 4H), 0.99-1.10 (m, 2H). | 645 |
| 28 | 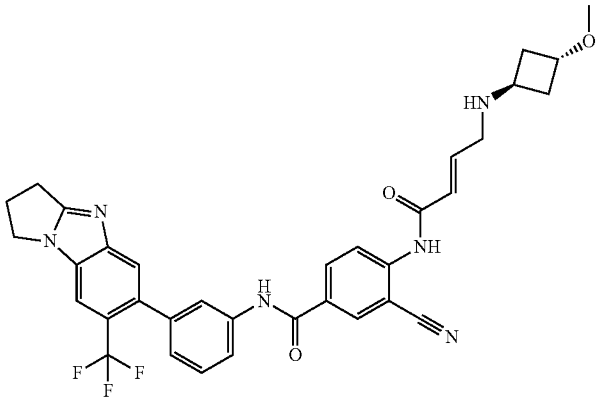 [SMILES: CO[C@H]1C[C@H](NC/C=C/C(=O)Nc2ccc(C(=O)Nc3cccc(-c4cc5nc6n(c5cc4C(F)(F)F)CCC6)c3)cc2C#N)C1] | 1H NMR (DMSO-d6) δ: 10.49 (s, 1H), 10.42 (s, 1H), 8.42 (d, J = 2 1 Hz, 1H), 8.22 (dd, J = 8.6, 2.1 Hz, 1H), 8.02 (s, 1H), 7.79-7.89 (m, 3H), 7.48 (s, 1H), 7.42 (t, J = 7.9 Hz, 1H), 7.09 (d, J = 7.6 Hz, 1H), 6.93 (dt, J = 15.4, 5.1 Hz, 1H), 6.38-6.44 (m, 1H), 4.22-4.28 (m, 2H), 3.93-3.99 (m, 1H), 3.25-3.32 (m, 4H), 3.11-3.15 (m, 3H), 3.01-3.08 (m, 2H), 2.68-2.73 (m, 2H), 1.92-2.10 (m, 4H). | 629 |

TABLE 1-continued

| Example | Structure | NMR | ESI-MS [M + H]+ |
|---|---|---|---|
| 29 | 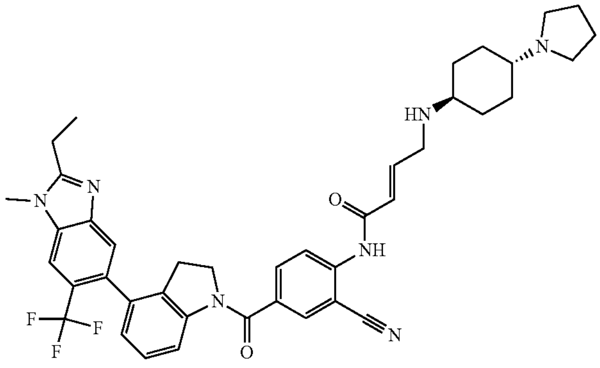 [SMILES: CCc1nc2cc(-c3cccc4c3CCN4C(=O)c3ccc(NC(=O)/C=C/CN[C@H]4CC[C@H](N5CCCC5)CC4)c(C#N)c3)c(C(F)(F)F)cc2n1C] | 1H NMR (DMSO-d6) δ: 10.42 (br s, 1H), 8.01-8.20 (m, 3H), 7.87-7.98 (m 1H), 7.72-7.86 (m, 1H), 7.46 (s, 1H), 7.17-7.37 (m 1H), 6.89-7.00 (m, 2H), 6.32-6.44 (m, 1H), 4.01 (br t, J = 8.5 Hz, 2H), 3.86 (s, 3H), 3.35-3.47 (m, 2H), 2.84-3.00 (m3H), 2.55-2.65 (m, 2H), 2.40-2.49 (m4H), 1.97-2.12 (m, 2H), 1.86-1.96 (m, 2H), 1.60-1.70 (m, 4H), 1.41-1.56 (m, 3H), 1.35 (t, J = 7.5 Hz, 3H), 0.95-1.21 (m, 3H). | 724 |
| 30 | 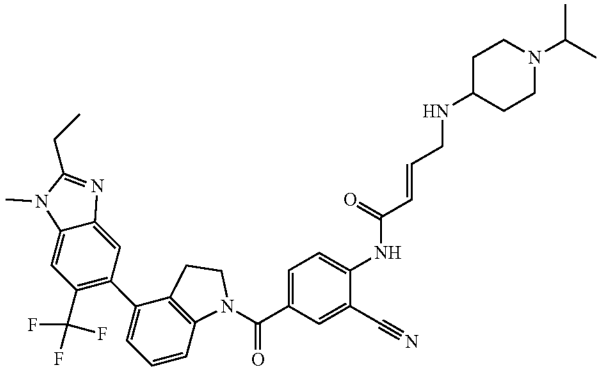 [SMILES: CCc1nc2cc(-c3cccc4c3CCN4C(=O)c3ccc(NC(=O)/C=C/CNC4CCN(C(C)C)CC4)c(C#N)c3)c(C(F)(F)F)cc2n1C] | 1H NWR (DMSO-d6) δ: 10.42 (s, 1H), 8.02-8.20 (m, 3H), 7.93 (dd, J = 8.6, 1.9 Hz, 1H), 7.80 (d, J = 8.6 Hz, 1H), 7.46 (s, 1H), 7.23-7.33 (m, 1H), 6.90-6.98 (m, 2H), 6.37-6.44 (m, 1H), 4.01 (br t, J = 8.4 Hz, 2H), 3.86 (s, 3H), 3.35-3.43 (m, 2H), 2.84-2.99 (m, 3H), 2.70-2.76 (m, 2H), 2.57-2.67 (m, 2H), 2.34-2.40 (m, 1H), 1.99-2.14 (m, 2H), 1.77-1.87 (m, 2H), 1.35 (t, J = 7.5 Hz, 3H), 1.15-1.27 (m 3H), 0.91-0.99 (m 6H). | 698 |
| 31 | 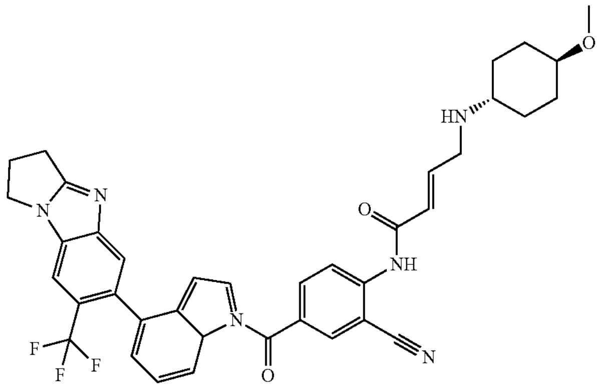 | 1H-NMR (DMSO-D6) δ: 10.47 (1H, s), 9.89 (1H, t, J = 4.0 Hz), 8.17 (1H, d, J = 1.6 Hz), 8.13 (1H, s), 8.08 (1H, dd, J = 8.5, 1.6 Hz), 7.87 (1H, d, J = 8.5 Hz), 7.63 (1H, s), 7.40 (1H, d, J = 4.8 Hz), 7.27-7.26 (2H, m), 6.95 (1H, dt, J = 15.4, 4.3 Hz), 6.43 (1H, d, J = 15.4 Hz), 6.07 (1H, d, J = 4.3 Hz), 4.28 (2H, t, J = 7.1 Hz), 3.40 (2H, s), 3.22 (3H, s), 3.11-3.04 (3H, m), 2.74-2.68 (2H, m), 2.40 (1H, br s), 1.99-1.89 (5H, m), 1.18-1.04 (4H, m). | 681 |
| 32 | 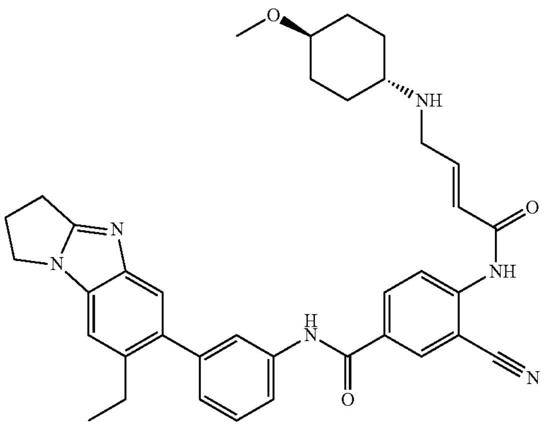 [SMILES: CCc1cc2c(cc1-c1cccc(NC(=O)c3ccc(NC(=O)/C=C/CN[C@H]4CC[C@H](OC)CC4)c(C#N)c3)c1)nc1n2CCC1] | 1H-NMR (DMSO-D6) δ: 10.47 (1H, s), 10.39 (1H, s), 8.42 (1H, d, J = 2.1 Hz), 8.23 (1H, dd, J = 8.6, 2.1 Hz), 7.87 (1H, d, J = 8.6 Hz), 7.81-7.78 (1H, m), 7.77 (1H, t, J = 1.7 Hz), 7.43 (1H, t, J = 7.8 Hz), 7.38 (1H, s), 7.29 (1H, s), 7.08 (1H, dt, J = 7.8, 1.3 Hz), 6.95 (1H, dt, J = 15.4, 4.9 Hz), 6.41 (1H, d, J = 15.4 Hz), 4.13 (2H, t, J = 7.0 Hz), 3.39 (2H, d, J = 4.8 Hz), 3.23 (3H, s), 3.13-3.04 (1H, m), 2.96 (2H, t, J = 7.6 Hz), 2.72-2.63 (4H, m), 2.43-2.35 (1H, m), 1.99-1.88 (4H, m), 1.18-1.01 (8H, m). | 617 |

TABLE 1-continued
| Example | Structure | NMR | ESI-MS [M + H]+ |
|---|---|---|---|
| 33 | 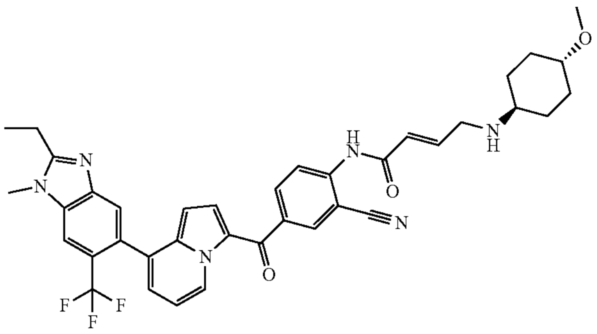 [SMILES: CCc1nc2cc(-c3cccn4c(C(=O)c5ccc(NC(=O)/C=C/CN[C@H]6CC[C@H](OC)CC6)c(C#N)c5)ccc34)c(C(F)(F)F)cc2n1C] | 1H NMR (DMSO-d6) δ: 10.47 (s, 1H), 9.86-9.92 (m, 1H), 8.13-8.19 (m 2H), 8.04-8.11 (m, 1H), 7.87 (d, J = 8.6 Hz, 1H), 7.65 (s, 1H), 7.40 (d, J = 4.9 Hz, 1H), 7.23-7.30 (m, 2H), 6.95 (dt, J = 15.4, 4.8 Hz, 1H), 6.39-6.48 (m, 1H), 6.08 (d, J = 4.8 Hz, 1H), 3.90 (s, 3H), 3.35-3.52 (m, 2H), 3.23 (s, 3H), 3.04-3.17 (m, 1H), 2.98 (q, J = 7.5 Hz, 2H), 2.36-2.45 (m, 1H), 1.86-2.00 (m 5H), 1.36 (t, J = 7.5 Hz, 3H), 1.00-1.17 (m, 4H). | 683 |
| 34 | 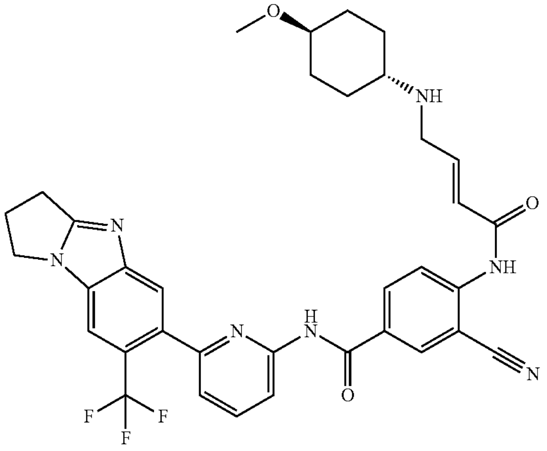 [SMILES: CO[C@H]1CC[C@H](NC/C=C/C(=O)Nc2ccc(C(=O)Nc3cccc(-c4cc5nc6n(c5cc4C(F)(F)F)CCC6)n3)cc2C#N)CC1] | 1H-NMR (DMSO-D6) δ: 11.03 (1H, s), 10.45 (1H, s), 8.50 (1H, s), 8.28 (1H, d, J = 8.6 Hz), 8.24 (1H, d, J = 8.6 Hz), 8.04 (1H, s), 7.94 (1H, t, J = 7.9 Hz), 7.85 (1H, d, J = 8.6 Hz), 7.65 (1H, s), 7.24 (1H, d, J = 7.5 Hz), 6.94 (1H, dt, J = 15.4, 4.8 Hz), 6.41 (1H, d, J = 15.4 Hz), 4.25 (2H, t, J = 6.9 Hz), 3.39 (2H, s), 3.22 (3H,s), 3.12-3.02 (3H, m), 2.73-2.66 (2H,m), 2.42-2.35 (1H, m), 2.00-1.86 (4H,m), 1.17-1.01 (4H, m). | 658 |
| 35 | 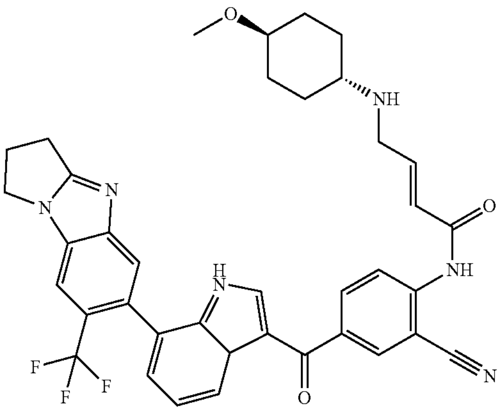 | 1H-NMR (DMSO-D6) δ: 11.77 (1H, s), 10.45 (1H, s), 8.30 (1H, d, J = 7.9 Hz), 8.19 (1H, d, J = 1.9 Hz), 8.11-8.07 (2H, m), 7.90-7.86 (2H, m), 7.53 (1H, s), 7.32 (1H, t, J = 7.6 Hz), 7.14 (1H, d, J = 7.4 Hz), 6.95 (1H, dt, J = 15.3, 4.9 Hz), 6.43 (1H, d, J = 15.3 Hz), 4.28 (2H, t, J = 7.1 Hz), 3.40 (2H, s), 3.23 (3H, s), 3.12-3.03 (3H, m), 2.75-2.67 (2H, m), 2.40 (1H, s), 2.00-1.86 (5H, m), 1.24-1.01 (4H, m). | 681 |

TABLE 1-continued

| Example | Structure | NMR | ESI-MS [M + H]+ |
|---|---|---|---|
| 36 | 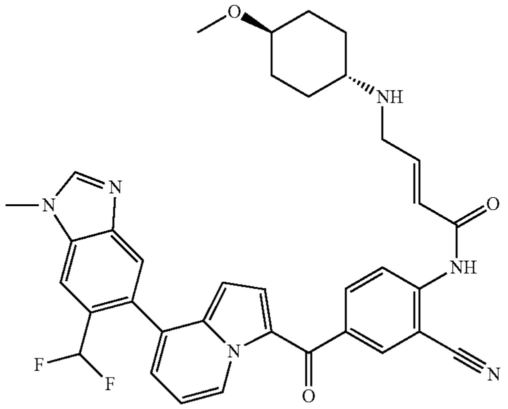 [SMILES: CO[C@H]1CC[C@H](NC/C=C/C(=O)Nc2ccc(C(=O)c3ccc4c(-c5cc6ncn(C)c6cc5C(F)F)cccn34)cc2C#N)CC1] | 1H-NMR (DMSO-D6) δ: 10.48 (s, 1H), 9.90 (d, J = 6.3 Hz, 1H), 8.45 (s, 1H), 8.17 (d, J = 2.0 Hz, 1H), 8.06-8.08 (m, 2H), 7.88 (d, J = 8.5 Hz, 1H), 7.73 (s, 1H), 7.43 (d, J = 4.8 Hz, 1H), 7.27-7.31 (m, 2H), 6.95 (dt, J = 15.5, 5.0, Hz, 1H), 6.80 (t, J = 55.7 Hz, 1H), 6.43 (d, J = 15.5 Hz, 1H), 6.16 (d, J = 4.8 Hz, 1H), 3.99 (s, 3H), 3.40 (d, J = 4.3 Hz, 2H), 3.22 (s, 3H), 3.09 (br s, 1H), 2.40 (br s, 1H), 1.89-1.99 (m, 4H), 1.04-1.18 (m, 4H). | 637 |
| 37 | 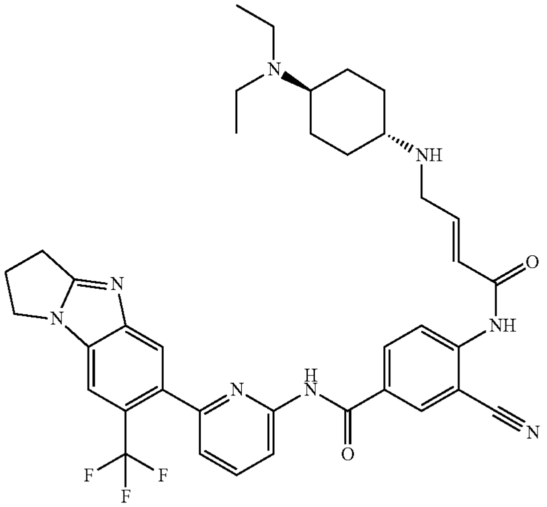 [SMILES: CCN(CC)[C@H]1CC[C@H](NC/C=C/C(=O)Nc2ccc(C(=O)Nc3cccc(-c4cc5nc6n(c5cc4C(F)(F)F)CCC6)n3)cc2C#N)CC1] | 1H-NMR (DMSO-D6) δ: 11.03 (1H, s), 10.45 (1H, s), 8.50 (1H, d, J = 2.1 Hz), 8.27 (1H, dd, J = 8.7, 2.1 Hz), 8.24 (1H, d, J = 8.7 Hz), 8.04 (1H, s), 7.94 (1H, t, J = 7.9 Hz), 7.85 (1H, d, J = 8.8 Hz), 7.65 (1H, s), 7.24 (1H, d, J = 7.5 Hz), 6.94 (1H, dt, J = 15.4, 4.9 Hz), 6.41 (1H, d, J = 15.4 Hz), 4.25 (2H, t, J = 7.1 Hz), 3.39 (2H, d, J = 3.8 Hz), 3.05 (2H, t, J = 7.6 Hz), 2.74-2.65 (3H, m), 2.49-2.40 (5H, m), 1.94 (2H, d, J = 10.8 Hz), 1.81 (1H, br s), 1.70 (2H, d, J = 12.0 Hz), 1.22 (2H, dd, J = 24.1, 10.8 Hz), 1.03 (2H, t, J = 11.7 Hz), 0.95 (6H, d, J = 7.1 Hz). | 699 |
| 38 | 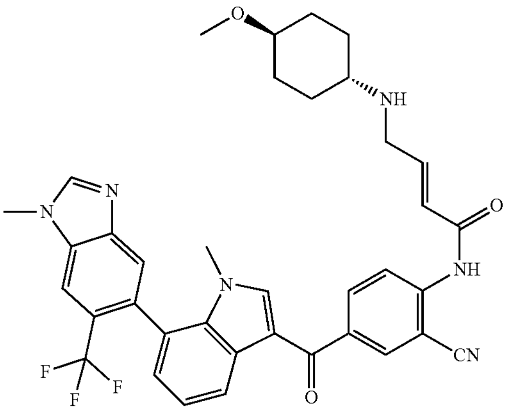 [SMILES: CO[C@H]1CC[C@H](NC/C=C/C(=O)Nc2ccc(C(=O)c3cn(C)c4c(-c5cc6ncn(C)c6cc5C(F)(F)F)cccc34)cc2C#N)CC1] | 1H-NMVR (DMSO-D6) δ: 10.47 (s, 1H), 8.52 (s, 1H), 8.40 (d, J = 8.0 Hz, 1H), 8.19-8.22 (m, 2H), 8.06-8.10 (m, 2H), 7.87 (d, J = 8.5 Hz, 1H), 7.76 (s, 1H), 7.33 (t, J = 7.8 Hz, 1H), 7.13 (d, J = 7.5 Hz, 1H), 6.95 (dt, J = 15.5, 5.0 Hz, 1H), 6.44 (d, J = 15.5 Hz, 1H), 4.01 (s, 3H), 3.41 (d, J = 4 0 Hz, 2H), 3.22 (s, 3H), 3.14 (s, 3H), 3.09 (br s, 1H), 2.42 (br s, 1H), 1.90-1.99 (m, 4H), 1.04-1.18 (m, 4H). | 669 |

TABLE 1-continued

| Example | Structure | NMR | ESI-MS [M + H]+ |
| --- | --- | --- | --- |
| 39 | 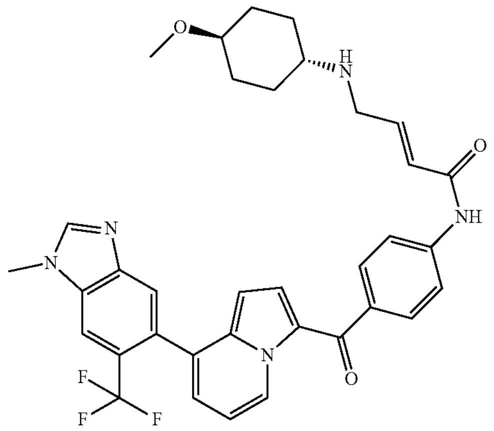 [SMILES: CO[C@H]1CC[C@H](NC/C=C/C(=O)Nc2ccc(C(=O)c3ccc4c(-c5cc6ncn(C)c6cc5C(F)(F)F)cccn34)cc2)CC1] | 1H NMR (CHLOROFORM-d) δ: 10.00-10.03 (m, 1H), 8.11 (s, 1H), 7.92 (s, 1H), 7.81-7.91 (m, 3H), 7.68-7.74 (m2H), 7.59 (s, 1H), 7.32 (d, J = 4.6 Hz, 1H), 7.13-7.18 (m, 1H), 7.02-7.13 (m2H), 6.15-6.22 (m, 1H), 6.07-6.11 (m1H), 4.01 (s, 3H), 3.49-3.53 (m, 2H), 3.37 (s, 3H), 3.12-3.20 (m, 1H), 2.51-2.59 (m, 1H), 2.07-2.14 (m, 2H), 1.96-2.04 (m, 2H), 1.10-1.33 (m, 5H). | 630 |
| 40 | 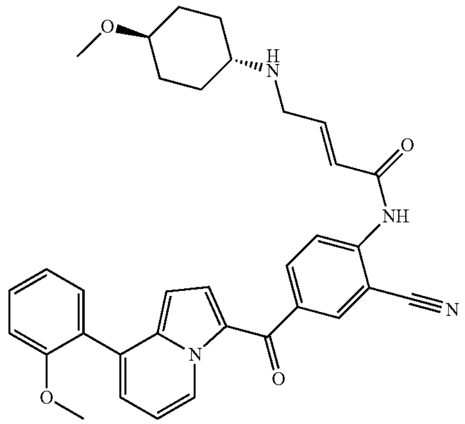 [SMILES: COc1ccccc1-c1cccn2c(C(=O)c3ccc(NC(=O)/C=C/CN[C@H]4CC[C@H](OC)CC4)c(C#N)c3)ccc12] | 1H-NMR (DMSO-D6) δ: 10.47 (s, 1H), 9.86 (dd, J = 4 3, 3.5 Hz, 1H), 8.15 (d, J = 2.0 Hz, 1H), 8.06 (dd, J = 8.6, 2.1 Hz, 1H), 7.88 (d, J = 8.8 Hz, 1H), 7.49 (ddd, J = 8.8, 7.0, 1.3 Hz, 1H), 7.40 (d, J = 4.8 Hz, 1H), 7.37 (dd, J = 7.5, 1.8 Hz, 1H), 7.30 (dd, J = 7.0, 1.0 Hz, 1H), 7.21-7.25 (m, 2H), 7.11 (td, J = 7.4, 0.9 Hz, 1H), 6.96 (dt, J = 15.3, 5.0 Hz, 1H), 6.43 (dt, J = 15.5, 1.8 Hz, 1H), 6.28 (dd, J = 4 8, 0.8 Hz, 1H), 3.74 (s, 3H), 3.41-3.39 (m, 2H), 3.23 (s, 3H), 1.88-1.99 (m, 4H), 1.04-1.15 (m, 4H). | 563 |
| 41 | 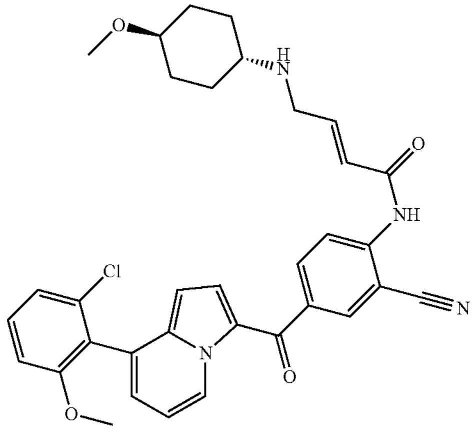 [SMILES: COc1cccc(Cl)c1-c1cccn2c(C(=O)c3ccc(NC(=O)/C=C/CN[C@H]4CC[C@H](OC)CC4)c(C#N)c3)ccc12] | 1H-NMR (DMSO-D6) δ: 10.47 (s, 1H), 9.87 (td, J = 4 1, 0.7 Hz, 1H), 8.17 (d, J = 2.0 Hz, 1H), 8.07 (dd, J = 8.6, 2.1 Hz, 1H), 7.87 (d, J = 8.5 Hz, 1H), 7.52 (t, J = 8.3 Hz, 1H), 7.39 (d, J = 5.0 Hz, 1H), 7.20-7.26 (m, 4H), 6.95 (dt, J = 15.3, 5.3 Hz, 1H), 6.43 (dt, J = 15.5, 1.8 Hz, 1H), 6.10 (dd, J = 4.8, 0.8 Hz, 1H), 3.69 (s, 3H), 3.40 (dd, J = 4.9, 1.4 Hz, 2H), 3.23 (s, 3H), 3.09 (br s, 1H), 2.40 (br s, 1H), 1.89-1.99 (m, 4H), 1.03-1.15 (m, 4H). | 597 |

TABLE 1-continued

| Example | Structure | NMR | ESI-MS [M + H]$^+$ |
|---|---|---|---|
| 42 | 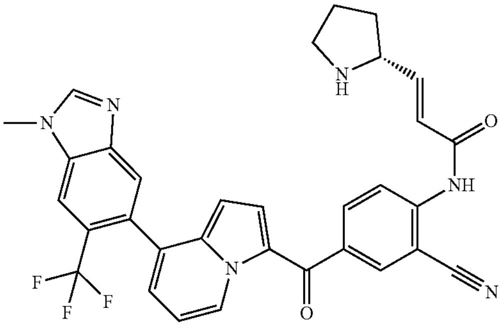 [SMILES: Cn1cnc2cc(-c3cccn4c(C(=O)c5ccc(NC(=O)/C=C/[C@H]6CCCN6)c(C#N)c5)ccc34)c(C(F)(F)F)cc21] | 1H-NMR (DMSO-D6) δ: 10.46 (1H, s), 9.89 (1H, dd, J = 5.3, 2.8 Hz), 8.51 (1H, s), 8.25 (1H, s), 8.16 (1H, d, J = 2.1 Hz), 8.07 (1H, dd, J = 8.6, 2.1 Hz), 7.87 (1H, d, J = 8.6 Hz), 7.76 (1H, s), 7.39 (1H, d, J = 4.8 Hz), 7.28-7.24 (2H, m), 6.87 (1H, dd, J = 15.2, 6.3 Hz), 6.41 (1H, dd, J = 15.2, 1.4 Hz), 6.07 (1H,d, J = 4.8 Hz), 4.00 (3H, s), 3.73 (1H,dd, J = 13.4, 6.3 Hz), 2.91-2.80 (2H,m), 1.99-1.90 (1H,m), 1.74-1.63 (2H,m), 1.49-1.40 (1H,m), 1.23 (1H, s). | 583 |
| 43 | 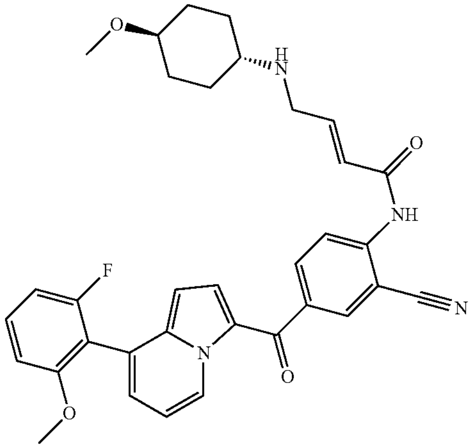 [SMILES: COc1cccc(F)c1-c1cccn2c(C(=O)c3ccc(NC(=O)/C=C/CN[C@H]4CC[C@H](OC)CC4)c(C#N)c3)ccc12] | 1H-NMR (DMSO-D6) δ: 10.47 (s, 1H), 9.88 (d, J = 7.0 Hz, 1H), 8.17 (s, 1H), 8.07 (d, J = 8.5 Hz, 1H), 7.88 (d, J = 8.5 Hz, 1H), 7.53 (q, J = 7.8 Hz, 1H), 7.41 (d, J = 5.0 Hz, 1H), 7.32 (d, J = 7.0 Hz, 1H), 7.25 (t, J = 7.0 Hz, 1H), 7.08 (d, J = 8.5 Hz, 1H), 7.01 (t, J = 8.8 Hz, 1H), 6.95 (dt, J = 15.0, 5.0 Hz, 1H), 6.43 (d, J = 15.5 Hz, 1H), 6.20 (d, J = 5.0 Hz, 1H), 3.74 (s, 3H), 3.41 (d, J = 4.5 Hz, 2H), 3.23 (s, 3H), 3.09 (br s, 1H), 2.40 (br s, 1H), 1.88-1.99 (m, 4H), 1.02-1.18 (m, 4H). | 581 |
| 44 | 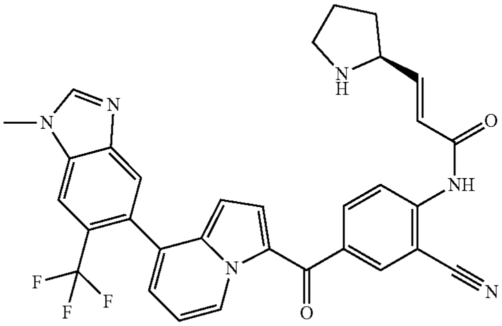 [SMILES: Cn1cnc2cc(-c3cccn4c(C(=O)c5ccc(NC(=O)/C=C/[C@@H]6CCCN6)c(C#N)c5)ccc34)c(C(F)(F)F)cc21] | 1H-NMR (DMSO-D6) δ: 10.46 (1H, s), 9.89 (1H, dd, J = 5.3, 2.8 Hz), 8.51 (1H, s), 8.25 (1H, s), 8.16 (1H, d, J = 2.1 Hz), 8.07 (1H, dd, J = 8.6, 2.1 Hz), 7.87 (1H, d, J = 8.6 Hz), 7.76 (1H, s), 7.39 (1H, d, J = 4.8 Hz), 7.28-7.24 (2H, m), 6.87 (1H, dd, J = 15.2, 6.3 Hz), 6.41 (1H, dd, J = 15.2, 1.4 Hz), 6.07 (1H,d, J = 4.8 Hz), 4.00 (3H, s), 3.73 (1H,dd, J = 13.4, 6.3 Hz), 2.91-2.80 (2H,m), 1.99-1.90 (1H,m), 1.74-1.63 (2H,m), 1.49-1.40 (1H,m), 1.23 (1H, s). | 583 |
| 45 | 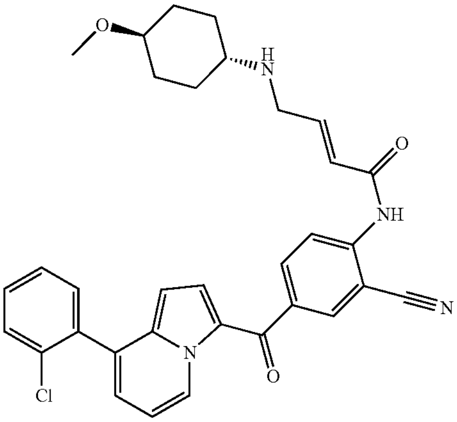 [SMILES: CO[C@H]1CC[C@H](NC/C=C/C(=O)Nc2ccc(C(=O)c3ccc4c(-c5ccccc5Cl)cccn34)cc2C#N)CC1] | 1H-NMR (DMSO-D6) δ: 10.48 (s, 1H), 9.89 (dd, J = 4.5, 3.5 Hz, 1H), 8.17 (d, J = 1.8 Hz, 1H), 8.08 (dd, J = 8.6, 2.1 Hz, 1H), 7.89 (d, J = 8.8 Hz, 1H), 7.68 (dt, J = 6.7, 1.4 Hz, 1H), 7.52-7.58 (m, 3H), 7.45 (d, J = 4.8 Hz, 1H), 7.35 (dd, J = 7.0, 1.0 Hz, 1H), 7.28 (t, J = 7.0 Hz, 1H), 6.95 (dt, J = 15.3, 5.2 Hz, 1H), 6.44 (dt, J = 15.3, 1.8, 1H), 6.23 (dd, J = 4.9, 0.6 Hz, 1H), 3.41 (dd, J = 4.8, 1.5 Hz, 2H), 3.23 (s, 3H), 3.09 (br s, 1H), 2.40 (br s, 1H), 1.90-1.99 (m, 4H), 1.02-1.18 (m, 4H). | 567 |

TABLE 1-continued
| Example | Structure | NMR | ESI-MS [M + H]+ |
| --- | --- | --- | --- |
| 46 | 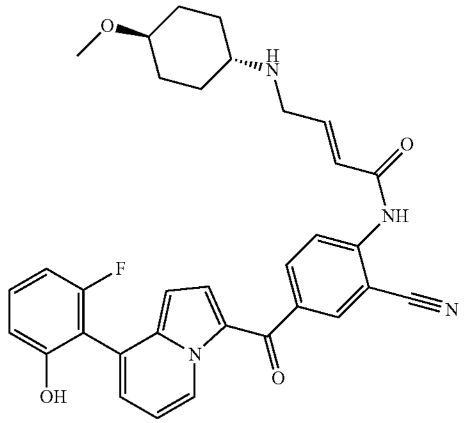 [SMILES: CO[C@H]1CC[C@H](NC/C=C/C(=O)Nc2ccc(C(=O)c3ccc4c(-c5c(O)cccc5F)cccn34)cc2C#N)CC1] | 1H-NMR (DMSO-D6) δ: 10.47 (s, 1H), 9.87-9.89 (in 1H), 8.16 (t, J = 1.3 Hz, 1H), 8.07 (dd, J = 8.6, 2.1 Hz, 1H), 7.88 (d, J = 8.5 Hz, 1H), 7.41 (d, J = 4 8 Hz, 1H), 7.29-7.35 (m, 2H), 7.25 (t, J = 7.0 Hz, 1H), 6.96 (dt, J = 15.5, 5.1 Hz, 1H), 6.85-6.89 (m, 2H), 6.79-6.84 (m 1H), 6.42-6.46 (m, 1H), 6.24 (d, J = 4.8 Hz, 1H), 3.40 (dd, J = 4.9, 1.6 Hz, 2H), 3.22 (s, 3H), 3.09 (br s, 1H), 2.40 (br s, 1H), 1.90-1.99 (m, 4H), 1.04-1.20 (m, 4H). | 567 |
| 47 | 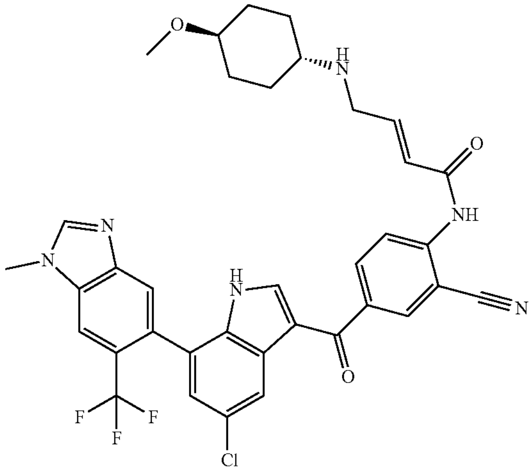 [SMILES: CO[C@H]1CC[C@H](NC/C=C/C(=O)Nc2ccc(C(=O)c3c[nH]c4c(-c5cc6ncn(C)c6cc5C(F)(F)F)cc(Cl)cc34)cc2C#N)CC1] | 1H-NMR (DMSO-D6) δ: 12.03 (s, 1H), 10.46 (s, 1H), 8.52 (s, 1H), 8.31 (d, J = 2.0 Hz, 1H), 8.25 (s, 1H), 8.21 (d, J = 2.3 Hz, 1H), 8.10 (dd, J = 8.5, 2.0 Hz, 1H), 8.03 (s, 1H), 7.88 (d, J = 8.8 Hz, 1H), 7.72 (s, 1H), 7.18 (d, J = 1.5 Hz, 1H), 6.95 (dt, J = 15.2, 5.2 Hz, 1H), 6.43 (dt, J = 15.5, 1.8 Hz, 1H), 4.02 (s, 3H), 3.40 (dd, J = 4.9, 1.6 Hz, 2H), 3.22 (s, 3H), 3.09 (br s, 1H), 2.39 (br s, 1H), 1.89-1.98 (m, 4H), 1.09-1.15 (m, 4H). | 689 |
| 48 | 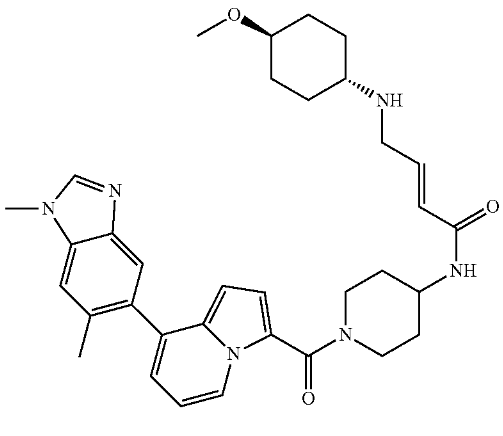 [SMILES: CO[C@H]1CC[C@H](NC/C=C/C(=O)NC2CCN(C(=O)c3ccc4c(-c5cc6ncn(C)c6cc5C)cccn34)CC2)CC1] | 1H NMR (DMSO-d6, 400 MHz) δ 8.82 (1H,dt), 8.18 (1H,s), 7.98 (1H,d), 7.55 (1H,s), 7.51 (1H,s), 7.06 (1H,d), 6.88 (1H,t), 6.82 (1H,dd), 6.65 (1H, dt), 6.04 (1H,dt), 5.96 (1H,dd), 4.33-4.25 (2H, m), 3.99-3.90 (1H, m), 3.87 (3H, s), 3.32-3.27 (2H, m), 3.27-3.16 (2H, m), 3.22 (3H, s), 3.13-3.01 (1H, m), 2.41-2.35 (1H, m), 2.24 (3H, s), 1.98-1.92 (2H, m), 1.90-1.82 (4H, m), 1.48-1.36 (2H, m), 1.18-0.95 (4H, m). | 583 |

TABLE 1-continued
| Example | Structure | NMR | ESI-MS [M + H]+ |
|---|---|---|---|
| 49 | 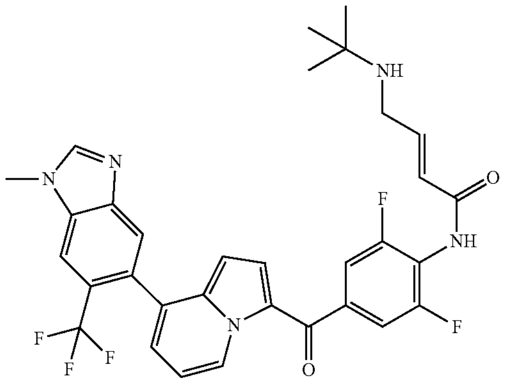 [SMILES: Cn1cnc2cc(-c3cccn4c(C(=O)c5cc(F)c(NC(=O)/C=C/CNC(C)(C)C)c(F)c5)ccc34)c(C(F)(F)F)cc21] | 1H NMR (DMSO-d6, 400 MHz) δ 9.99 (1H,s), 9.94-9.85 (1H, m), 8.52 (1H, s), 8.25 (1H, s), 7.76 (1H, s), 7.60-7.51 (2H, m), 7.42 (1H, d), 7.34-7.24 (2H,m), 6.92 (1H, dt), 6.38 (1H, dt), 6.08 (1H, dd), 4.01 (3H, s), 3.35 (2H, dd), 1.07 (9H, s). 19F NMR (DMSO-d6, 376 MHz) δ −55.0 (3 × F), −115.9 (2 × F). | 610 |
| 50 | 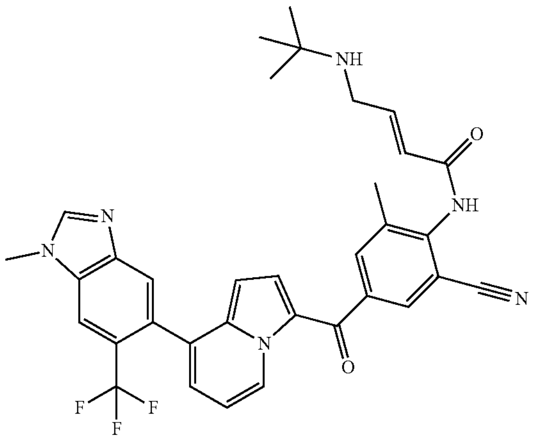 [SMILES: Cc1cc(C(=O)c2ccc3c(-c4cc5ncn(C)c5cc4C(F)(F)F)cccn23)cc(C#N)c1NC(=O)/C=C/CNC(C)(C)C] | 1H NMR (DMSO-d6, 400 MHz) δ 10.20 (1H, s), 9.95-9.88 (1H, m), 8.52 (1H, s), 8.25 (1H, s), 8.05-7.97 (2H, m), 7.76 (1H, s), 7.39 (1H, d), 7.32-7.24 (2H, m), 6.95 (1H, dt), 6.42 (1H, d), 6.08 (1H, dd), 4.01 (3H, s), 3.40 (2H, dd), 2.31 (3H, s), 1.10 (9H, s). 19F NMR (DMSO-d6, 376 MHz) δ −54.9 (3 × F). | 613 |
| 51 | 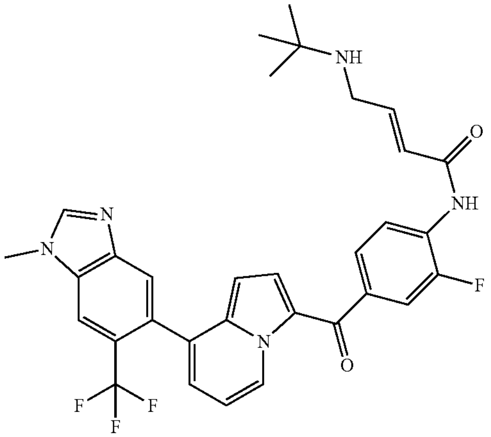 [SMILES: Cn1cnc2cc(-c3cccn4c(C(=O)c5ccc(NC(=O)/C=C/CNC(C)(C)C)c(F)c5)ccc34)c(C(F)(F)F)cc21] | 1H NMR (DMSO-d6, 400 MHz) δ 10.05 (1H,d), 9.91-9.84 (1H, m), 8.52 (1H, s), 8.31-8.22 (2H, m), 7.77 (1H, s), 7.71-7.60 (2H, m), 7.40 (1H, d), 7.30-7.19 (2H, m), 6.94 (1H, dt), 6.55 (1H,dt), 6.07 (1H, dd), 4.01 (3H, s), 3.35 (2H, dd), 1.07 (9H, s). 19F NMR (DMSO-d6, 376 MHz) δ −54.9 (3 × F), −124.5 (1 × F). | 592 |

TABLE 1-continued
| Example | Structure | NMR | ESI-MS [M + H]+ |
|---|---|---|---|
| 52 | 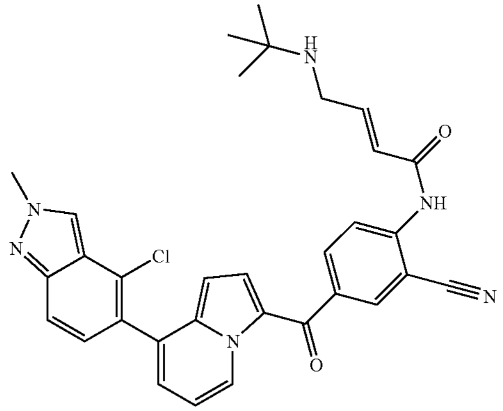 [SMILES: Cn1cc2c(Cl)c(-c3cccn4c(C(=O)c5ccc(NC(=O)/C=C/CNC(C)(C)C)c(C#N)c5)ccc34)ccc2n1] | 1H NMR (DMSO-d6, 400 MHz) δ 10.50 (1H,s), 9.90 (1H,dt), 8.61 (1H,s), 8.17 (1H,d), 8.08 (1H,dd), 7.88 (1H,d), 7.73 (1H, dd), 7.45 (1H, d), 7.41 (1H, dd), 7.34 (1H,d), 7.30 (1H,t), 6.99 (1H,dt), 6.48 (1H,dt), 6.27 (1H,dd), 4.25 (3H, s), 3.43 (2H, s), 1.11 (9H, s). | 565 |
| 53 | 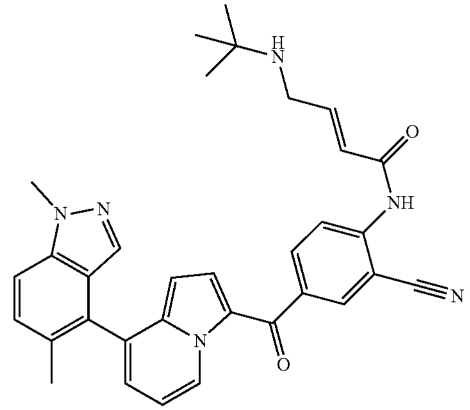 [SMILES: Cc1ccc2c(cnn2C)c1-c1cccn2c(C(=O)c3ccc(NC(=O)/C=C/CNC(C)(C)C)c(C#N)c3)ccc12] | 1H NMR (DMS0-d6, 400 MHz) δ 10.49 (1H,s), 9.94 (1H, dt), 8.17 (1H, d), 8.08 (1H, dd), 7.87 (1H, d), 7.69 (1H, dd), 7.47 (1H,d), 7.45 (1H,d), 7.40 (1H,d), 7.37 (1H,dd), 7.33 (1H,t), 6.99 (1H, dt), 6.47 (1H, dt), 6.04 (1H,dd), 4.08 (3H,s), 3.44-3.38 (2H,m), 2.20 (3H, s), 1.10 (9H, s). | 545 |
| 54 | 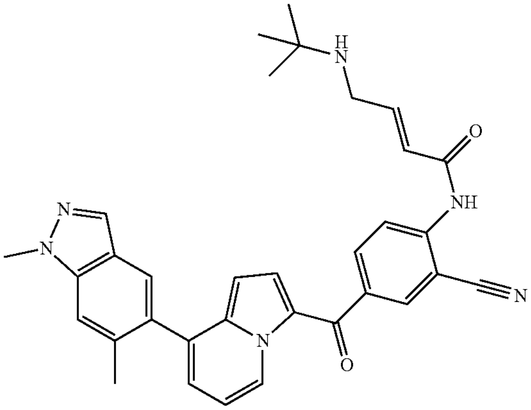 [SMILES: Cc1cc2c(cnn2C)cc1-c1cccn2c(C(=O)c3ccc(NC(=O)/C=C/CNC(C)(C)C)c(C#N)c3)ccc12] | 1H NMR (DMSO-d6, 400 MHz) δ 10.46 (1H,s), 9.89 (1H, ddd), 8.16 (1H, d), 8.07 (1H, dd), 8.04 (1H, d), 7.87 (1H, d), 7.69 (1H,s), 7.67-7.65 (1H, m), 7.41 (1H,d), 7.33-7.23 (2H,m), 7.00 (1H,dt), 6.46 (1H,dt), 6.16 (1H,dd), 4.08 (3H,s), 3.42-3.34 (2H,m), 2.25 (3H, s), 1.08 (9H, s). | 545 |
| 55 | 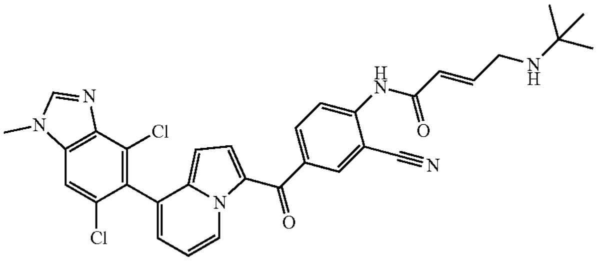 [SMILES: Cn1cnc2c(Cl)c(-c3cccn4c(C(=O)c5ccc(NC(=O)/C=C/CNC(C)(C)C)c(C#N)c5)ccc34)c(Cl)cc21] | 1H NMR (DMSO-d6) δ: 10.46 (s, 1H), 9.89-9.91 (in 1H), 8.42 (s, 1H), 8.17 (d, J = 2.0 Hz, 1H), 8.07 (dd, J = 8.6, 2.0 Hz, 1H), 8.02 (s, 1H), 7.85 (d, J = 8.6 Hz, 1H), 7.41 (d, J = 4.8 Hz, 1H), 7.26-7.34 (m, 2H), 6.98 (dt, J = 15.2, 4.8 Hz, 1H), 6.44 (d, J = 15.2 Hz, 1H), 6.08 (d, J = 4 8 Hz, 1H), 3.92 (s, 3H), 3.33-3.36 (m 2H), 1.06 (s, 9H). | 599 |

TABLE 1-continued

| Example | Structure | NMR | ESI-MS [M + H]+ |
|---|---|---|---|
| 56 | 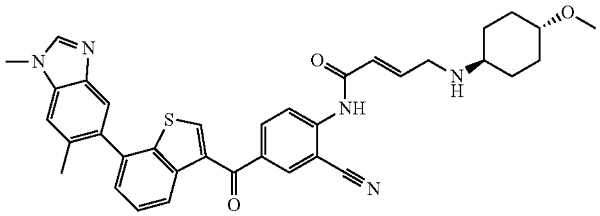 | 1H-NMR (CDCl3) δ: 8.72 (d, J = 8.8 Hz, 1H), 8.51 (d, J = 8.3 Hz, 1H), 8.17 (s, 1H), 8.15 (d, J = 8.8 Hz, 1H), 7.97 (s, 1H), 7.90 (s, 1H), 7.77 (s, 1H), 7.62 (t, J = 7.6 Hz, 1H), 7.38 (s, 1H), 7.37 (d, J = 7.0 Hz, 1H), 7.18 (td, J = 10.1, 5.0 Hz, 1H), 6.30 (d, J = 15.3 Hz, 1H), 3.90 (s, 3H), 3.57 (d, J = 5.0 Hz, 2H), 3.35 (s, 3H), 3.20-3.12 (m, 1H), 2.62-2.54 (m, 1H), 2.28 (s, 3H), 2.14-1.98 (m, 4H), 2.86-2.86 (m, 4H). | 618 |
| 57 | 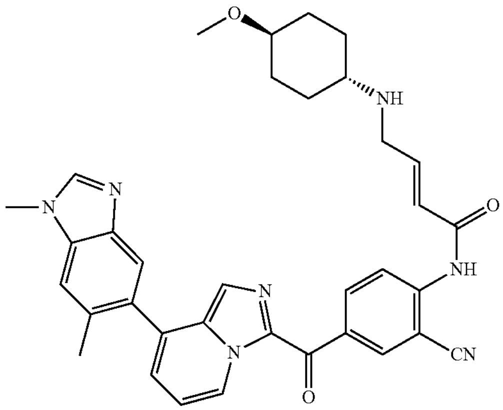 [SMILES: CO[C@H]1CC[C@H](NC/C=C/C(=O)Nc2ccc(C(=O)c3ncc4c(-c5cc6ncn(C)c6cc5C)cccn34)cc2C#N)CC1] | 1H-NMR (DMSO-D6) δ: 10.53 (s, 1H), 9.79 (d, J = 7.0 Hz, 1H), 8.82 d, J = 1.8 Hz, 1H), 8.58 (dd, J = 8.8, 1.8 Hz, 1H), 8.23 (s, 1H), 7.92 (d, J = 8.8 Hz, 1H), 7.63 (d, J = 3.8 Hz, 2H), 7.43 (t, J = 6.9 Hz, 2H), 7.36 (d, J = 6.8 Hz, 1H), 6.96 (td, J = 10.1, 5.3 Hz, 1H), 6.44 (d, J = 15.5 Hz, 1H), 3.89 (s, 3H), 3.41 (d, J = 4.3 Hz, 2H), 3.23 (s, 3H), 3.04-3.11 (m, 1H), 2.37-2.44 (m 1H), 2.28 (s, 3H), 1.88-1.99 (m, 4H), 1.01-1.20 (m, 4H). | 602 |
| 58 | 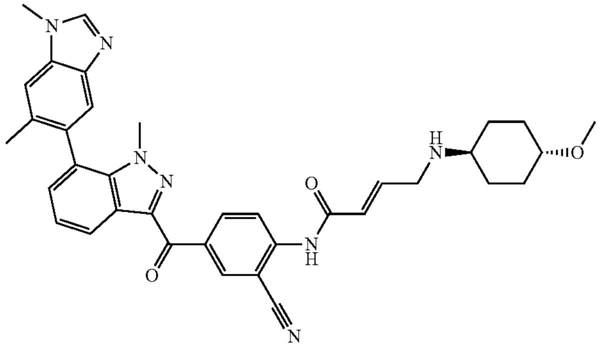 | 1H-NMR (CDCl3) δ: 8.78 (d, J = 1.8 Hz, 1H), 8.74 (d, J = 9.0 Hz, 1H), 8.64 (dd, J = 9.1, 1.9 Hz, 1H), 8.51 (d, J = 8.3 Hz, 1H), 7.92 (s, 1H), 7.83 (br s, 1H), 7.75 (s, 1H), 7.44 (t, J = 7.5 Hz, 1H), 7.36 (s, 1H), 7.30 (d, J = 7.0 Hz, 1H), 7.17 (td, J = 10.1, 5.1 Hz, 1H), 6.25 (d, J = 15.3 Hz, 1H), 3.92 (s, 3H), 3.57 (s, 3H), 3.54 (dd, J = 5.0, 1.3 Hz, 2H), 3.36 (s, 3H), 3.20-3.12 (m, 1H), 2.57-2.50 (m, 1H), 2.17 (s, 3H), 2.13-2.06 (m, 2H), 2.02-1.97 (m, 2H), 1.32-1.11 (m, 4H). | 616 |
| 59 | 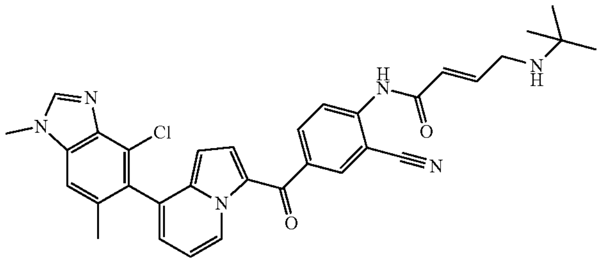 [SMILES: Cc1cc2c(ncn2C)c(Cl)c1-c1cccn2c(C(=O)c3ccc(NC(=O)/C=C/CNC(C)(C)C)c(C#N)c3)ccc12] | 1H NMR (CDCl3) δ: 10.01 (d, J = 6.5 Hz, 1H), 8.67 (d, J = 8.5 Hz, 1H), 8.18-8.02 (m, 2H), 7.96 (s, 1H), 7.31 (d, J = 0.8 Hz, 1H), 7.30-7.13 (m 5H), 6.33 (br d, J = 15.3 Hz, 1H), 6.09 (dd, J = 4.8, 0.6 Hz, 1H), 3.92 (s, 3H), 3.52 (dd, J = 5.0, 1.8 Hz, 2H), 2.23 (s, 3H), 1.20 (s, 9H). | 580 |

TABLE 1-continued
| Example | Structure | NMR | ESI-MS [M + H]+ |
| --- | --- | --- | --- |
| 60 | 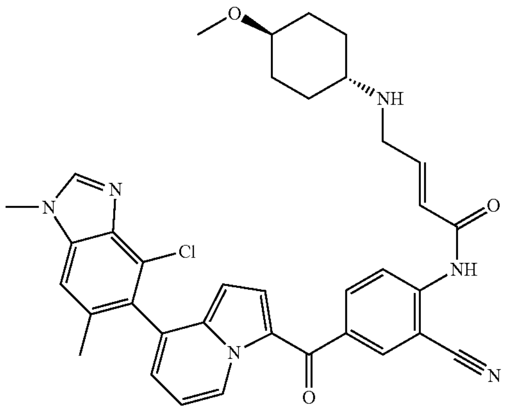 | 1H-NMR (CDCl3) δ: 9.99 (m, 1H), 8.68 (d, J = 8.44 Hz, 1H), 8.08 (m 2H), 7.94 (s, 1H), 7.85-7.80 (br s, 1H), 7.29-7.24 (m 2H), 7.19-7.11 (m, 3H), 6.26 (d, J = 15.4 Hz, 1H), 6.07 (dd, J = 4.8, 0.8 Hz, 1H), 3.90 (s, 3H), 3.55 (dd, J = 4.9, 1.6 Hz, 2H), 3.35 (s, 3H), 3.19-3.12 (m, 1H), 2.60-2.51 (m, 1H), 2.12 (s, 3H), 2.13-1.97 (m, 4H), 1.33-1.14 (m, 4H). | 636 |
| 61 | 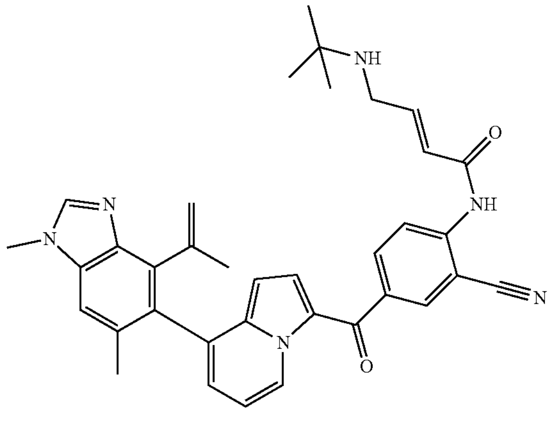 [SMILES: C=C(C)c1c(-c2cccn3c(C(=O)c4ccc(NC(=O)/C=C/CNC(C)(C)C)c(C#N)c4)ccc23)c(C)cc2c1ncn2C] | 1H NMR (CDCl3) δ: 9.94 (dd, J = 5.6, 3.0 Hz, 1H), 8.50-8.40 (br s, 1H), 8.11-8.06 (m, 2H), 7.89 (s, 1H), 7.74-7.73 (m 1H), 7.55-7.54 (m, 2H), 7.28-7.24 (m, 3H), 6.13 (d, J = 5.1 Hz, 1H), 6.08 (d, J = 4.8 Hz, 1H), 5.11-5.08 (br s, 1H), 4.82-4.78 (br s, 1H), 3.88 (s, 3H), 3.70-3.68 (m, 2H), 2.15 (s, 3H), 1.94 (s, 3H), 1.30 (s, 9H). | 586 |
| 62 | 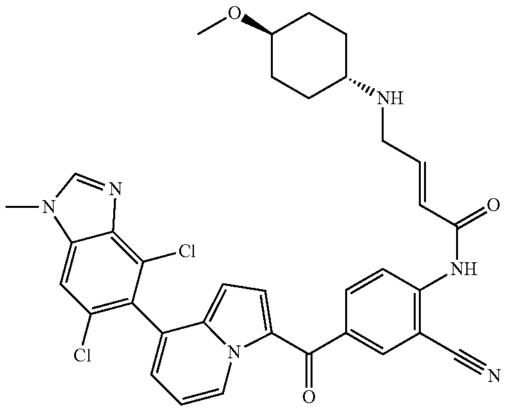 [SMILES: CO[C@H]1CC[C@H](NC/C=C/C(=O)Nc2ccc(C(=O)c3ccc4c(-c5c(Cl)cc6c(ncn6C)c5Cl)cccn34)cc2C#N)CC1] | 1H NMR (CDCl3) δ: 10.02 (d, J = 6.9 Hz, 1H), 8.69 (dd, J = 8.8, 0.8 Hz, 1H), 8.12-8.09 (m 2H), 8.01 (s, 1H), 7.85-7.80 (br s, 1H), 7.59 (s, 1H), 7.30-7.26 (m 1H), 7.22-7.16 (m, 3H), 6.25 (m, 1H), 6.11 (dd, J = 4.8, 0.8 Hz, 1H), 3.92 (s, 3H), 3.54 (dd, J = 5.2, 2.0 Hz, 2H), 3.36 (s, 3H), 3.22-3.12 (m, 1H), 2.60-2.50 (m, 1H), 2.20-1.98 (m, 4H), 1.40-1.15 (m 4H). | 655 |

TABLE 1-continued

| Example | Structure | NMR | ESI-MS [M + H]+ |
|---|---|---|---|
| 63 | 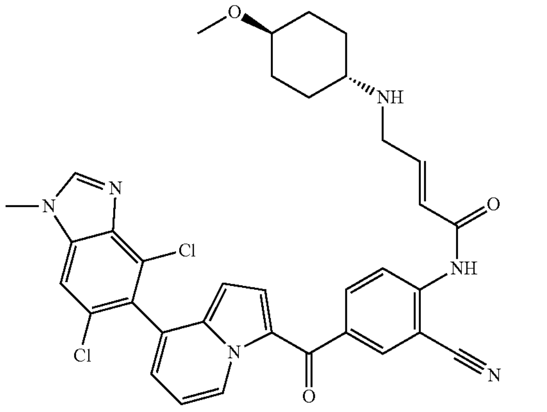 [SMILES: CO[C@H]1CC[C@H](NC/C=C/C(=O)Nc2ccc(C(=O)c3ccc4c(-c5c(Cl)cc6c(ncn6C)c5Cl)cccn34)cc2C#N)CC1] | 1H NMR (CDCl3) δ: 10.02 (d, J = 6.9 Hz, 1H), 8.69 (dd, J = 8.8, 0.8 Hz, 1H), 8.12-8.09 (m 2H), 8.01 (s, 1H), 7.85-7.80 (br s, 1H), 7.59 (s, 1H), 7.30-7.26 (m 1H), 7.22-7.16 (m, 3H), 6.25 (m, 1H), 6.11 (dd, J = 4.8, 0.8 Hz, 1H), 3.92 (s, 3H), 3.54 (dd, J = 5.2, 2.0 Hz, 2H), 3.36 (s, 3H), 3.22-3.12 (m, 1H), 2.60-2.50 (m, 1H), 2.20-1.98 (m, 4H), 1.40-1.15 (m 4H). | 655 |
| 64 | 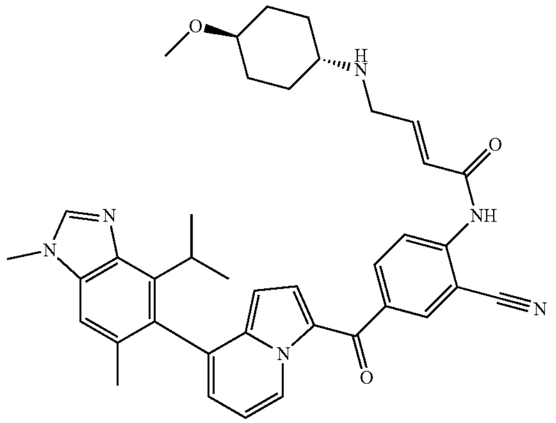 [SMILES: CO[C@H]1CC[C@H](NC/C=C/C(=O)Nc2ccc(C(=O)c3ccc4c(-c5c(C)cc6c(ncn6C)c5C(C)C)cccn34)cc2C#N)CC1] | 1H NMR (CDCl3) δ: 9.96 (d, J = 5.6 Hz, 1H), 8.68 (dd, J = 8.0, 1.2 Hz, 1H), 8.11-8.09 (m 2H), 7.88 (s, 1H), 7.90-7.80 (br s, 1H), 7.26-7.05 (m, 5H), 6.30-6.26 (m, 1H), 6.08 (dd, J = 4.8, 0.4 Hz, 1H), 3.85 (s, 3H), 3.54 (dd, J = 4.8, 1.6 Hz, 2H), 3.35 (s, 3H), 3.21 -3.15 (m, 1H), 2.90-2.78 (m 1H), 2.60-2.50 (m 1H), 2.14-1.97 (m, 4H), 2.04 (s, 3H), 1.46-1.43 (m, 6H), 1.31-1.15 (m 4H). | 643 |
| 65 | 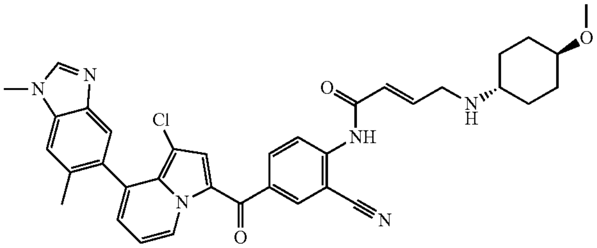 | 1H-NMR (CDCl3) δ: 10.00 (dd, J = 6.8, 1.3 Hz, 1H), 8.68 (d, J = 8.5 Hz, 1H), 8.09-8.02 (m, 2H), 7.96 (br s, 1H), 7.88 (s, 1H), 7.64 (s, 1H), 7.28 (s, 1H), 7.20-7.07 (m 4H), 6.29 (d, J = 15.3 Hz, 1H), 3.89 (s, 3H), 3.55 (dd, J = 5.3, 1.8 Hz, 2H), 3.35 (s, 3H), 3.20-3.12 (m, 1H), 2.60-2.52 (m, 1H), 2.13-2.07 (m, 2H), 2.04-1.97 (m, 2H), 1.32-1.14 (m, 4H). | 635 |
| 66 | 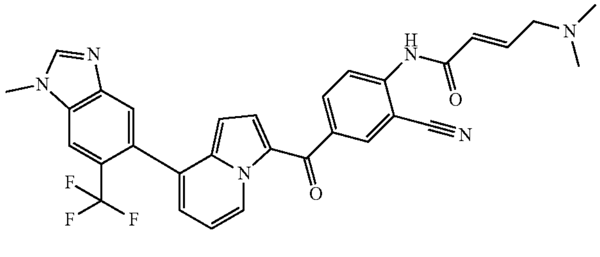 | 1H NMR (CDCl3) δ: 10.00 (d, J = 5.6 Hz, 1H), 8.71 (d, J = 8.4 Hz, 1H), 8.12-8.09 (m 3H), 7.94 (s, 1H), 7.86-7.84 (m, 2H), 7.26 (d, J = 4.8 Hz, 1H), 7.26 (d, J = 6.9 Hz, 1H), 7.15-7.10 (m, 2H), 6.25 (d, J = 15.0 Hz, 1H), 6.13 (d, J = 4.8 Hz, 1H), 4.02 (s, 3H), 3.19 (dd, J = 5.6, 1.2 Hz, 2H), 2.33 (s, 6H). | 571 |
| 67 | 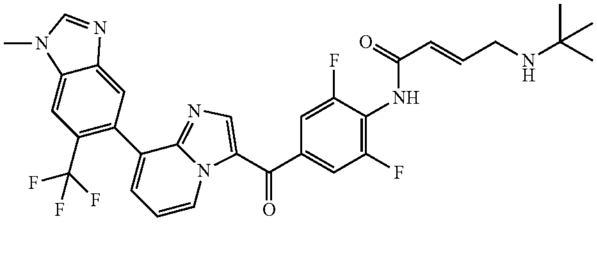 [SMILES: Cn1cnc2cc(-c3cccn4c(C(=O)c5cc(F)c(NC(=O)/C=C/CNC(C)(C)C)c(F)c5)cnc34)c(C(F)(F)F)cc21] | 1H-NMR (CDCl3) δ: 9.75 (dd, J = 6.9, 2.1 Hz, 1H), 8.18 (s, 1H), 8.08 (s, 1H), 7.88 (d, J = 3.3 Hz, 1H), 7.84 (d, J = 3.8 Hz, 1H), 7.56 (d, J = 7.0 Hz, 1H), 7.52-7.46 (m, 2H), 7.30-7.23 (m 1H), 7.15-7.06 (m 1H), 6.26 (d, J = 15.5 Hz, 1H), 3.96 (s, 3H), 3.45-3.40 (m, 2H), 1.14 (s, 9H). | 611 |

TABLE 1-continued

| Example | Structure | NMR | ESI-MS [M + H]⁺ |
|---|---|---|---|
| 68 | 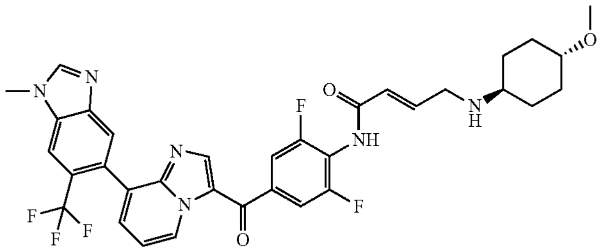 | 1H-NMR (CDCl3) δ: 9.76 (dd, J = 6.9, 1.1 Hz, 1H), 8.18 (s, 1H), 8.07 (s, 1H), 7.90 (s, 1H), 7.85 (s, 1H), 7.57 (d, J = 7.0 Hz, 1H), 7.51 (d, J = 7.8 Hz, 2H), 7.45 (br s, 1H), 7.28 (t, J = 7.0 Hz, 1H), 7.10 (dt, J = 15.3, 5.5 Hz, 1H), 6.22 (d, J = 15.3 Hz, 1H), 3.97 (s, 3H), 3.49 (dd, J = 5.3, 1.5 Hz, 2H), 3.35 (s, 3H), 3.18-3.10 (m, 1H), 2.57-2.48 (m, 1H), 2.11-2.05 (m, 2H), 2.01-1.93 (m, 2H), 1.30-1.08 (m 4H). | 667 |
| 69 | 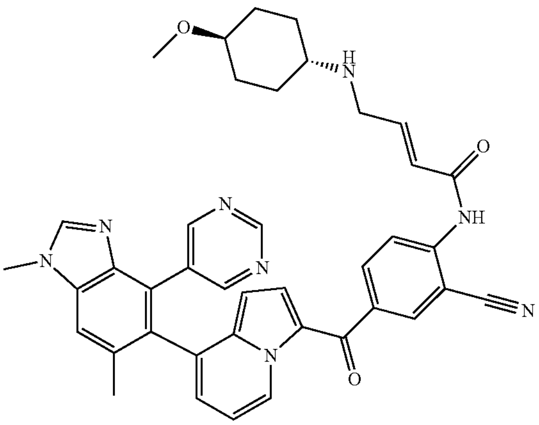 [SMILES: CO[C@H]1CC[C@H](NC/C=C/C(=O)Nc2ccc(C(=O)c3ccc4c(-c5c(C)cc6c(ncn6C)c5-c5cncnc5)cccn34)cc2C#N)CC1] | 1H NMR (CDCl3) δ: 9.85 (dd, J = 6.4, 0.8 Hz, 1H), 8.99 (s, 1H), 8.70-8.65 (br s, 1H), 8.66 (s, 2H), 8.09-8.05 (m, 2H), 7.92 (s, 1H), 7.48 (s, 1H), 7.25 (d, J = 4.8 Hz, 1H), 7.18 (dt, J = 15.2, 5.2 Hz, 1H), 6.32 (d, J = 15.2 Hz, 1H), 6.13 (d, J = 4.8 Hz, 1H), 3.97 (s, 3H), 3.59 (d, J = 4.0 Hz, 2H), 3.38 (s, 3H), 3.21-3.15 (m 1H), 2.65-2.55 (m, 1H), 2.27 (s, 3H), 2.18-1.97 (m, 4H), 1.31-1.20 (m 4H). | 679 |
| 70 | 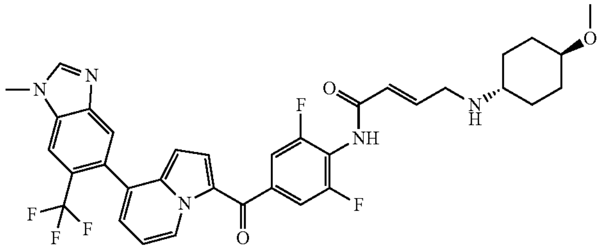 | 1H-NMR (CDCl3) δ: 9.98 (d, J = 7.0 Hz, 1H), 8.10 (s, 1H), 7.91 (s, 1H), 7.83 (s, 1H), 7.50 (br s, 1H), 7.45-7.39 (m, 2H), 7.31 (dd, J = 4.8, 1.0 Hz, 1H), 7.20 (d, J = 7.0 Hz, 1H), 7.15-7.05 (m, 2H), 6.28 (d, J = 15.3 Hz, 1H), 6.10 (d, J = 4.8 Hz, 1H), 4.00 (s, 3H), 3.50 (d, J = 5.3 Hz, 2H), 3.35 (s, 3H), 3.18-3.10 (m, 1H), 2.59-2.50 (m, 1H), 2.11-2.04 (m, 2H), 2.02-1.94 (m, 2H), 1.39-1.08 (m, 4H). | 666 |
| 71 | 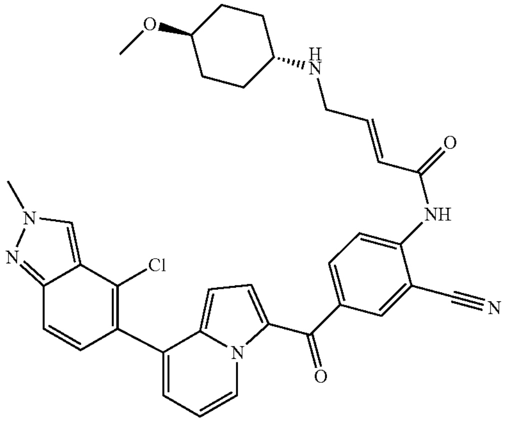 [SMILES: CO[C@H]1CC[C@H](NC/C=C/C(=O)Nc2ccc(C(=O)c3ccc4c(-c5ccc6nn(C)cc6c5Cl)cccn34)cc2C#N)CC1] | 1H NMR (CDCl3) δ: 10.00 (d, J = 7.2 Hz, 1H), 8.70 (d, J = 8.4 Hz, 1H), 8.10-8.08 (m 3H), 7.95-7.80 (br s, 1H), 7.72 (d, J = 8.8 Hz 1H), 7.34-7.28 (m, 3H), 7.21-7.1 (m, 2H), 6.34 (d, J = 4.8 Hz, 1H), 6.28 (d, J = 15.2 Hz, 1H), 4.31 (s, 3H), 3.57-3.56 (m, 2H), 3.36 (s, 3H), 3.25-3.20 (m, 1H), 2.65-2.50 (m 1H), 2.20-1.98 (m, 4H), 1.40-1.15 (m, 4H). | 621 |

TABLE 1-continued

| Example | Structure | NMR | ESI-MS [M + H]+ |
| --- | --- | --- | --- |
| 72 | 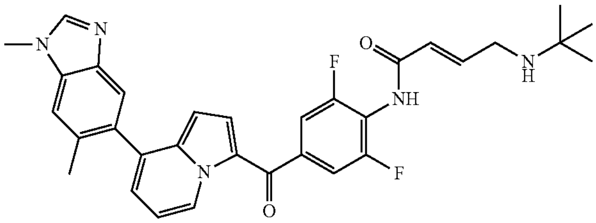 [SMILES: Cc1cc2c(cc1-c1cccn3c(C(=O)c4cc(F)c(NC(=O)/C=C/CNC(C)(C)C)c(F)c4)ccc13)ncn2C] | 1H-NMR (CDCl3) δ: 9.96 (d, J = 7.0 Hz, 1H), 7.90 (s, 1H), 7.69 (s, 1H), 7.40 (s, 1H), 7.38 (s, 1H), 7.35 (s, 1H), 7.31 (d, J = 4.8 Hz, 1H), 7.18-7.05 (m, 3H), 6.35 (d, J = 15.3 Hz, 1H), 6.17 (d, J = 4.8 Hz, 1H), 3.89 (s, 3H), 3.45 (d, J = 5.0 Hz, 2H), 2.28 (s, 3H), 1.15 (s, 9H). | 556 |
| 73 | 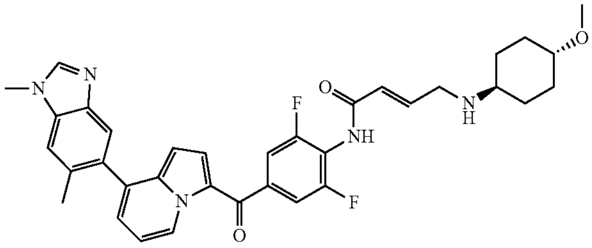 | 1H-NMR (CDCl3) δ: 9.96 (d, J = 7.0 Hz, 1H), 7.90 (s, 1H), 7.82 (br s, 1H), 7.70 (s, 1H), 7.41 (s, 1H), 7.39 (s, 1H), 7.35 (s, 1H), 7.32 (d, J = 5.0 Hz, 1H), 7.18-7.06 (m 3H), 6.30 (d, J = 15.3 Hz, 1H), 6.17 (d, J = 4.8 Hz, 1H), 3.89 (s, 3H), 3.50 (d, J = 4.0 Hz, 2H), 3.34 (s, 3H), 3.17-3.10 (m, 1H), 2.58-2.49 (m, 1H), 2.28 (s, 3H), 2.10-2.04 (m, 2H), 2.01-1.93 (m, 2H), 1.27-1.09 (m, 4H). | 612 |
| 74 | 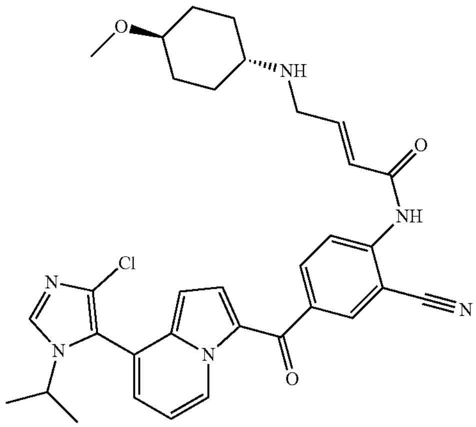 [SMILES: CO[C@H]1CC[C@H](NC/C=C/C(=O)Nc2ccc(C(=O)c3ccc4c(-c5c(Cl)ncn5C(C)C)cccn34)cc2C#N)CC1] | 1H-NMR (DMSO-D6) δ: 10.48 (s, 1H), 9.91 (dd, J = 4.5, 3.5 Hz, 1H), 8.32 (s, 1H), 8.18 (t, J = 1.3 Hz, 1H), 8.09 (dd, J = 8.1, 2.4 Hz, 2H), 7.89 (d, J = 8.8 Hz, 1H), 7.51 (d, J = 4.8 Hz, 1H), 7.47 (dd, J = 7.0, 1.0 Hz, 1H), 7.29 (t, J = 7.0 Hz, 1H), 6.96 (td, J = 10.2, 5.1 Hz, 1H), 6.42-6.46 (m, 1H), 6.36 (dd, J = 4.8, 0.8 Hz, 1H), 4.05 (td, J = 13.6, 6.8 Hz, 1H), 3.40-3.41 (m, 2H), 3.23 (s, 3H), 3.09 (dt, J = 11.2, 3.9 Hz, 1H), 2.40 (dt, J = 11.3, 4.1 Hz, 1H), 1.89-1.99 (m 4H), 1.36 (d, J = 6.8 Hz, 3H), 1.32 (d, J = 6.8 Hz, 3H), 1.20-1.02 (m, 4H). | 599 |
| 75 | 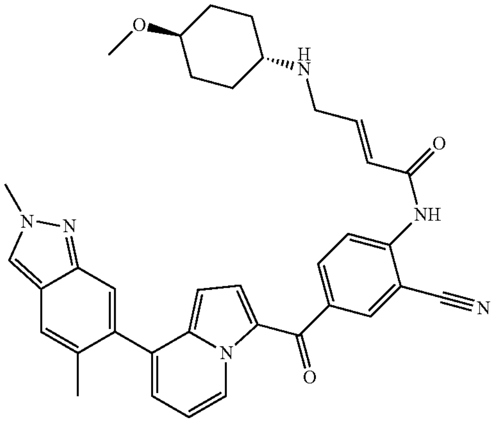 [SMILES: CO[C@H]1CC[C@H](NC/C=C/C(=O)Nc2ccc(C(=O)c3ccc4c(-c5cc6nn(C)cc6cc5C)cccn34)cc2C#N)CC1] | 1H NMR (CDCl3) δ: 9.97 (d, J = 6.8 Hz, 1H), 8.62 (d, J = 8.4 Hz, 1H), 8.09-8.05 (m 3H), 7.90 (s, 1H), 7.62 (s, 1H), 7.58 (s, 1H), 7.26 (d, J = 4.8 Hz, 1H), 7.20-7.07 (m, 2H), 7.09 (t, J = 6.8 Hz, 1H), 6.34 (d, J = 13.6 Hz, 1H), 6.24 (d, J = 4.8 Hz, 1H), 4.26 (s, 3H), 3.58-3.57 (m 2H), 3.36 (s, 3H), 3.25-3.10 (m, 1H), 2.65-2.50 (m 1H), 2.20 (s, 3H), 2.20-1.98 (m, 4H), 1.40-1.15 (m, 4H). | 601 |

TABLE 1-continued

| Example | Structure | NMR | ESI-MS [M + H]$^{+}$ |
| --- | --- | --- | --- |
| 76 | 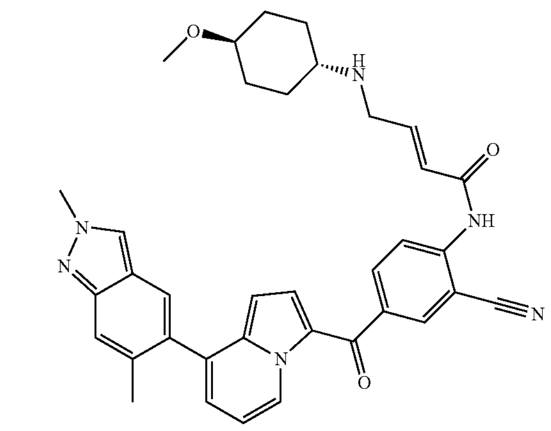 [SMILES: CO[C@H]1CC[C@H](NC/C=C/C(=O)Nc2ccc(C(=O)c3ccc4c(-c5cc6cn(C)nc6cc5C)cccn34)cc2C#N)CC1] | 1H NMR (CDCl3) δ: 9.97 (d, J = 7.2 Hz, 1H), 8.63 (d, J = 8.4 Hz, 1H), 8.10-8.06 (m 3H), 7.90 (s, 1H), 7.62 (s, 1H), 7.58 (s, 1H), 7.27 (d, J = 4.8 Hz, 1H), 7.20-7.07 (m, 2H), 7.09 (t, J = 6.8 Hz, 1H), 6.34 (d, J = 15.2 Hz, 1H), 6.24 (dd, J = 4.8, 0.8 Hz, 1H), 4.27 (s, 3H), 3.61-3.60 (m, 2H), 3.36 (s, 3H), 3.25-3.10 (m 1H), 2.70-2.55 (m, 1H), 2.24 (s, 3H), 2.20-1.98 (m, 4H), 1.40-1.15 (m 4H). | 601 |
| 77 | 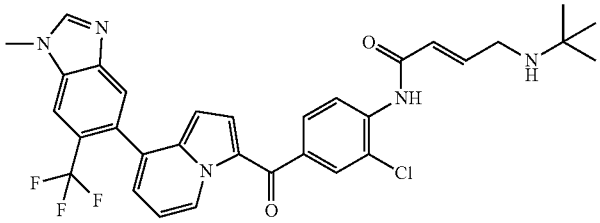 [SMILES: Cn1cnc2cc(-c3cccn4c(C(=O)c5ccc(NC(=O)/C=C/CNC(C)(C)C)c(Cl)c5)ccc34)c(C(F)(F)F)cc21] | 1H-NMR (CDCl3) δ: 9.98 (d, J = 7.0 Hz, 1H), 8.62 (d, J = 8.5 Hz, 1H), 8.09 (s, 1H), 7.91-7.84 (m, 4H), 7.77 (dd, J = 8.6, 1.9 Hz, 1H), 7.29 (d, J = 4.8 Hz, 1H), 7.19-7.10 (m, 2H), 7.04 (t, J = 7.0 Hz, 1H), 6.26 (d, J = 15.3 Hz, 1H), 6.09 (d, J = 4.8 Hz, 1H), 3.99 (s, 4H), 3.49 (d, J = 3.5 Hz, 2H), 1.18 (s, 9H). | 608 |
| 78 | 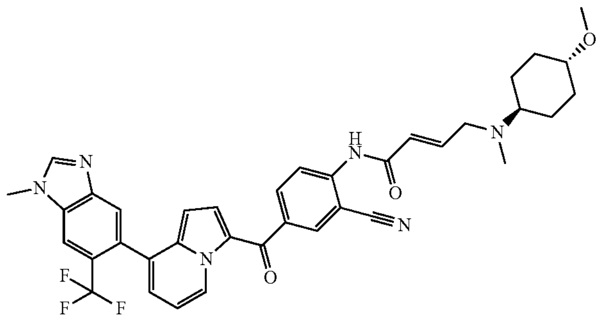 [SMILES: CO[C@H]1CC[C@H](N(C)C/C=C/C(=O)Nc2ccc(C(=O)c3ccc4c(-c5cc6ncn(C)c6cc5C(F)(F)F)cccn34)cc2C#N)CC1] | 1H NMR (CDCl3) δ: 10.00 (d, J = 7.2 Hz, 1H), 8.71 (d, J = 8.8 Hz, 1H), 8.12-8.08 (m 3H), 7.93 (s, 1H), 7.86 (s, 1H), 7.82 (s, 1H), 7.26 (d, J = 4.8 Hz, 1H), 7.21 (d, J = 7.2 Hz, 1H), 7.08-7.03 (m, 2H), 6.27 (d, J = 15.2 Hz, 1H), 6.13 (d, J = 4.8 Hz, 1H), 4.02 (s, 3H), 3.37 (s, 3H), 3.33-3.11 (m, 2H), 3.20-3.05 (in 1H), 2.50-2.40 (m 1H), 2.30 (s, 3H), 2.16-2.13 (m, 2H), 1.98-1.90 (m, 2H), 1.50-1.20 (m 4H). | 669 |
| 79 | 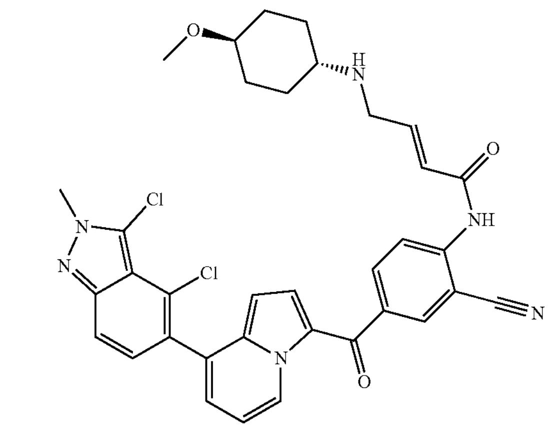 [SMILES: CO[C@H]1CC[C@H](NC/C=C/C(=O)Nc2ccc(C(=O)c3ccc4c(-c5ccc6nn(C)c(Cl)c6c5Cl)cccn34)cc2C#N)CC1] | 1H NMR (CDCl3) δ: 10.00 (d, J = 7.2 Hz, 1H), 8.71 (d, J = 9.2 Hz, 1H), 8.11-8.07 (m 2H), 7.90-7.80 (br s, 1H), 7.66 (d, J = 8.4 Hz, 1H), 7.31-7.29 (m, 3H), 7.20-7.10 (m, 2H), 6.32-6.21 (m 2H), 4.27 (s, 3H), 3.59-3.52 (m, 2H), 3.36 (s, 3H), 3.25-3.10 (m, 1H), 2.60-2.55 (m, 1H), 2.20-1.98 (m, 4H), 1.40-1.15 (m 4H). | 655 |

TABLE 1-continued

| Example | Structure | NMR | ESI-MS $[M + H]^+$ |
|---|---|---|---|
| 80 | 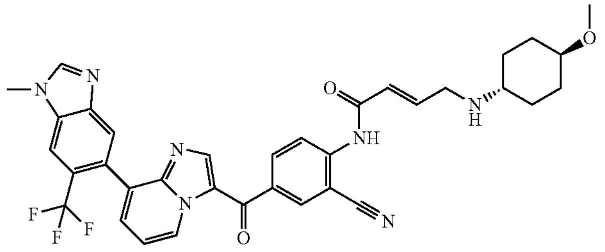 | 1H-NMR (CDCl3) δ: 9.76 (dd, J = 7.0, 1.3 Hz, 1H), 8.75 (d, J = 8.8 Hz, 1H), 8.17-8.12 (m, 3H), 8.07 (s, 1H), 7.91 (s, 1H), 7.89 (br s, 1H), 7.87 (s, 1H), 7.57 (d, J = 7.0 Hz, 1H), 7.30-7.27 (m, 1H), 7.17 (dt, J = 15.2, 5.1 Hz, 1H), 6.26 (dt, J = 15.2, 1.8 Hz, 1H), 3.97 (s, 3H), 3.54 (dd, J = 5.0, 1.8 Hz, 2H), 3.35 (s, 3H), 3.20-3.12 (m, 1H), 2.57-2.50 (m 1H), 2.13-2.06 (m, 2H), 2.03-1.96 (m 2H), 1.32-1.11 (m 4H). | 656 |
| 81 | 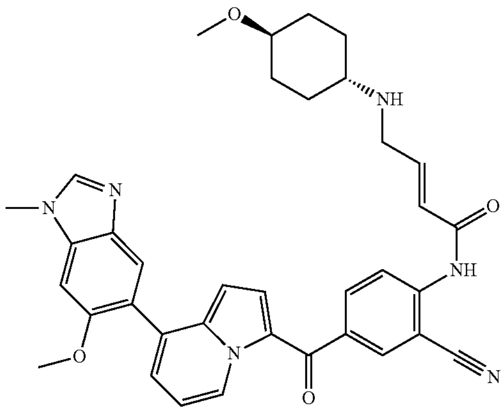 [SMILES: COc1cc2c(cc1-c1cccn3c(C(=O)c4ccc(NC(=O)/C=C/CN[C@H]5CC[C@H](OC)CC5)c(C#N)c4)ccc13)ncn2C] | 1H-NMR (CDCl3) δ: 9.99 (dt, J = 7.0, 0.9 Hz, 1H), 8.69 (d, J = 9.0 Hz, 1H), 8.10-8.07 (m, 2H), 7.87 (d, J = 8.8 Hz, 2H), 7.79 (s, 1H), 7.27 (dd, J = 4.5, 3.0 Hz, 2H), 7.18 (td, J = 10.2, 5.1 Hz, 1H), 7.11 (t, J = 7.0 Hz, 1H), 6.98 (s, 1H), 6.34 (dd, J = 4.8, 0.8 Hz, 1H), 6.28 (dt, J = 15.3, 1.8 Hz, 1H), 3.92 (s, 3H), 3.86 (s, 3H), 3.55-3.57 (m, 2H), 3.38 (d, J = 2.3 Hz, 3H), 3.18 (tt, J = 8.8, 3.4 Hz, 1H), 2.54-2.59 (m, 1H), 1.99-2.12 (m, 4H), 1.15-1.33 (m, 4H). | 617 |
| 82 | 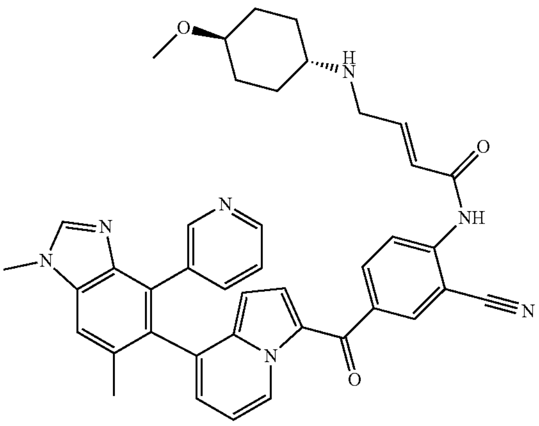 [SMILES: CO[C@H]1CC[C@H](NC/C=C/C(=O)Nc2ccc(C(=O)c3ccc4c(-c5c(C)cc6c(ncn6C)c5-c5cccnc5)cccn34)cc2C#N)CC1] | 1H NVR (CDCl3) δ: 9.83 (d, J = 6.8 Hz, 1H), 8.62 (d, J = 8.0 Hz, 1H), 8.44 (dd, J = 2.4, 0.8 Hz, 1H), 8.38 (dd, J = 4.8, 1.6 Hz, 1H), 8.08-8.05 (m, 2H), 7.93 (s, 1H), 7.65 (dt, J = 8.0, 2.0 Hz, 1H), 7.42 (s, 1H), 7.24 (d, J = 4.8 Hz, 1H), 7.23-7.15 (m, 2H), 6.95-6.85 (m, 2H), 6.35 (d, J = 15.2 Hz, 1H), 6.15 (dd, J = 4.8, 0.4 Hz, 1H), 3.97 (s, 3H), 3.61 (d, J = 4.4 Hz, 2H), 3.39 (s, 3H), 3.25-3.25 (m, 1H), 2.70-2.60 (m 1H), 3.08 (s, 3H), 2.18-2.02 (m, 4H), 1.35-1.20 (m, 4H). | 678 |
| 83 | 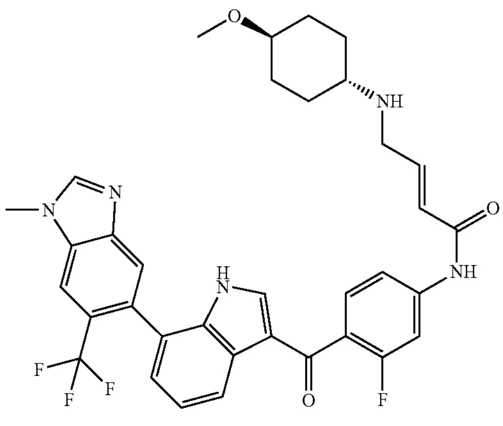 [SMILES: CO[C@H]1CC[C@H](NC/C=C/C(=O)Nc2ccc(C(=O)c3c[nH]c4c(-c5cc6ncn(C)c6cc5C(F)(F)F)cccc34)c(F)c2)CC1] | 1H-NMR (DMSO-d6) δ: 11.72 (d, J = 3.0 Hz, 1H), 10.49 (s, 1H), 8.50 (s, 1H), 8.27 (d, J = 7.5 Hz, 1H), 8.22 (s, 1H), 7.82 (dd, J = 12.5, 2.0 Hz, 1H), 7.67-7.66 (m 2H), 7.57 (t, J = 8.5 Hz, 1H), 7.46 (dd, J = 8.0, 1.5 Hz, 1H), 7.31 (t, J = 7.5 Hz, 1H), 7.14 (d, J = 7.0 Hz, 1H), 6.90 (dt, J = 15.0, 5.5 Hz, 1H), 6.31 (d, J = 15.5 Hz, 1H), 4.01 (s, 3H), 3.43 (br s, 2H), 3.11 (s, 3H), 3.12-3.05 (m, 1H), 2.50-2.40 (m, 1H), 2.00-1.88 (m, 4H), 1.20-1.05 (m, 4H). | 648 |

TABLE 1-continued

| Example | Structure | NMR | ESI-MS [M + H]+ |
|---|---|---|---|
| Comparative example 1 | 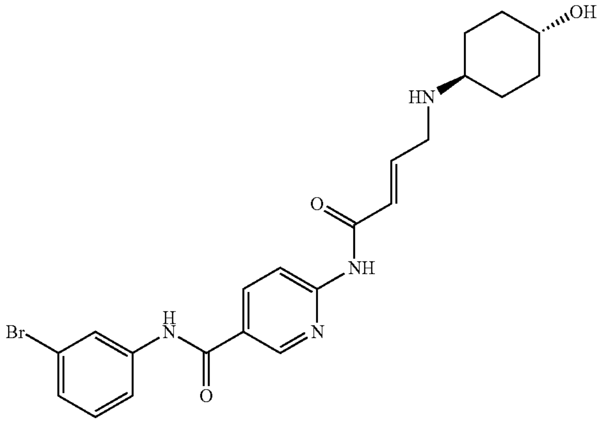 [SMILES: O=C(/C=C/CN[C@H]1CC[C@H](O)CC1)Nc1ccc(C(=O)Nc2cccc(Br)c2)cn1] | 1H NMR (DMSO-d6) δ: 10.88 (s, 1H), 10.40 (s, 1H), 8.81 (s, 1H), 8.19-8.24 (m, 2H), 7.98-8.02 (m, 1H), 7.62-7.67 (m, 1H), 7.20-7.28 (m, 2H), 6.77-6.87 (m, 1H), 6.32-6.43 (m, 1H), 3.05-3.12 (m, 2H), 2.44-2.46 (m, 3H), 2.23-2.34 (m, 1H), 1.65-1.83 (m, 4H), 0.91-1.17 (m, 4H). | 473 |
| Comparative example 2 | 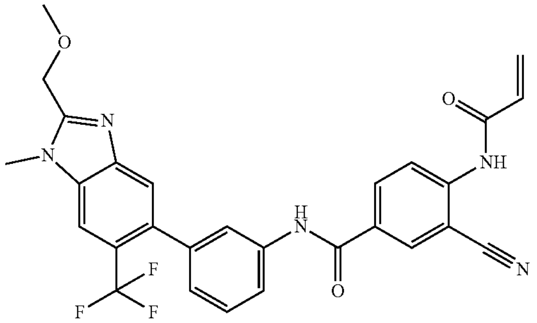 [SMILES: C=CC(=O)Nc1ccc(C(=O)Nc2cccc(-c3cc4nc(COC)n(C)c4cc3C(F)(F)F)c2)cc1C#N] | 1H NMR (DMSO-d6) δ: 10.61 (s, 1H), 10.45 (s, 1H), 8.44 (d, J = 2 1 Hz, 1H), 8.24 (dd, J = 8.6, 2.1 Hz, 1H), 8.14 (s, 1H), 7.80-7.90 (m, 3H), 7.58 (s, 1H), 7.43 (t, J = 7.9 Hz, 1H), 7.10 (d, J = 7.8 Hz, 1H), 6.54-6.62 (m, 1H), 6.37 (dd, J = 17.1, 1.8 Hz, 1H), 5.88-5.92 (m, 1H), 4.78 (s, 2H), 3.95 (s, 3H), 3.35-3.37 (m, 3H). | 534 |

Test Example 1: KRASG12C Binding Assay

As test compounds for the KRASG12C binding assay, the compounds obtained in the "Preparation of Compounds" section were used. Sample solutions each containing a test compound were prepared in the form of a 10 mM DMSO solution.

Gppcp-bound recombinant K-Ras4B G12C mutant protein (amino acids 1-169, C51S/C80L/C118S, SEQ ID NO:1) was diluted with a buffer (1×TBS, 0.1 mM TCEP, 0.25 mM $MgCl_2$, 50 μM Gppcp) to prepare a 50 nM protein solution. K-Ras4B is the major splicing variant of K-Ras. Amino acid sequence of residues 1 to 150 including the compounds' binding region of K-Ras4B is exactly same as that of K-Ras4A, the other splicing variant (Oncotarget. 2016 Jul. 19; 7(29): 46717-46733). A sample solution containing 10 mM test compound was diluted ten-fold with DMSO to make a 1 mM sample solution, and then diluted twenty-fold with DMSO to make a 50 μM sample solution. 1 μL of a 50 μM sample solution was added to 100 μL of a 50 nM protein solution to adjust the final concentration of a test compound to be 0.5 μM in the mixture. The mixtures were stored in an incubator at 25° C. for 1 hour, and 10 μL of a 1×TBS solution containing 2% formic acid was added to stop the reaction, followed by LC-MS measurement. LC-MS measurement was performed using Xevo G2-S Q-Tof manufactured by Waters, and reverse-phase chromatography was performed with a desalting column. A mass spectrum of positive ions was obtained by electrospray. For a mass spectrum, a spectrum of polyvalent ions was collectively converted to a molecular weight by using OpenLynx software by the MaxEnt technique, and a compound binding rate was calculated from the ratio of the signal intensity of a peak that corresponds to the molecular weight of the protein to the signal intensity of a peak that corresponds to the molecular weight of the protein conjugated with the compound.

The binding assay of the test compounds was conducted at a final concentration of 0.5 μM. A binding rate of 80% or more is rated "A", a binding rate of 60% or more and less than 80% is rated "B", a binding rate of 40% or more and less than 60% is rated "C", a binding rate of 20% or more and less than 40% is rated "D", and a binding rate of less than 20% is rated "E". N.D.=not determined. Binding rate % is the ratio of KRAS signal intensity at the molecular weight of one molecule adduct to the sum of all the KRAS signal intensity (unbound form and adducts) in mass spectrum.

Thus, binding rate 100% means that only the one molecule adduct was observed without any unbound KRAS. The following table shows the results.

The test results reveal that the compound of the present invention has excellent binding ability to Gppcp-bound K-Ras4B G12C mutant protein, and A and J parts in the formula of "A-L1-L2-G-J" are important to show the effect.

TABLE 2

| Example | |
|---|---|
| 1 | A |
| 2 | D |
| 3 | B |
| 4 | A |

TABLE 2-continued

| Example | |
|---|---|
| 5 | A |
| 6 | A |
| 7 | A |
| 8 | A |
| 9 | B |
| 10 | A |
| 11 | B |
| 12 | B |
| 13 | B |
| 14 | D |
| 15 | A |
| 16 | C |
| 17 | B |
| 18 | A |
| 19 | A |
| 20 | A |
| 21 | A |
| 22 | A |
| 23 | A |
| 24 | A |
| 25 | A |
| 26 | C |
| 27 | B |
| 28 | A |
| 29 | A |
| 30 | A |
| 31 | A |
| 32 | B |
| 33 | A |
| 34 | A |
| 35 | A |
| 36 | A |
| 37 | A |
| 38 | A |
| 39 | A |
| 40 | B |
| 41 | A |
| 42 | D |
| 43 | A |
| 44 | A |
| 45 | B |
| 46 | A |
| 47 | A |
| 48 | E |
| 49 | A |
| 50 | E |
| 51 | B |
| 52 | B |
| 53 | A |
| 54 | A |
| 55 | A |
| 56 | A |
| 57 | C |
| 58 | B |
| 59 | A |
| 60 | A |
| 61 | A |
| 62 | A |
| 63 | A |
| 64 | A |
| 65 | B |
| 66 | C |
| 67 | B |
| 68 | B |
| 69 | B |
| 70 | A |
| 71 | A |
| 72 | A |
| 73 | A |
| 74 | B |
| 75 | A |
| 76 | A |
| 77 | C |
| 78 | C |
| 79 | A |
| 80 | A |
| 81 | A |
| 82 | A |
| 83 | A |
| Comparative example 1 | E |
| Comparative example 2 | E |
| ARS-1620 | E |

Test Example 2: Evaluation of Inhibitory Activity of Compounds on Interaction Between KRAS G12C and cRAF (In Vitro)

Interaction between recombinant K-Ras4B G12C mutant protein (amino acids 1-169, SEQ ID NO:2) and cRAF RAS-binding domain (cRAF-RBD, amino acids 50-132, Jena Biosciences GmbH) was measured using Alpha technology (PerkinElmer Inc.).

Recombinant KRAS G12C protein with an N-terminal His-tag was expressed in *E. coli* and purified by affinity chromatography. To prepare GTP-bound form and GDP-bound form of KRAS G12C protein, 50 μM KRAS G12C protein was incubated with 1 mM GMPPNP (Guanosine-5'-[(β,γ)-imido]triphosphate, Tetralithium salt) (Jena Bioscience GmbH) and 1 mM GDP, respectively, in a loading buffer (20 mM Tris-HCl (pH 7.5), 50 mM NaCl, 1 mM DTT and 2.5 mM EDTA) for 1 hour on ice. After the incubation, $MgCl_2$ was added to a final concentration of 10 mM, followed by incubation at room temperature for 30 minutes. The mixture was allowed to pass through a NAP-5 column to remove free nucleotides and purified, and the resultant nucleotide-bound KRAS G12C protein was used for compound evaluation.

For the measurement of the inhibitory activity of compounds on interaction between KRAS G12C and cRAF-RBD, GMPPNP-bound KRAS G12C protein was incubated with various concentrations of compound in a reaction buffer (20 mM Tris-HCl (pH 7.5), 100 mM NaCl, 1 mM $MgCl_2$, 1 mM TCEP, 0.1% Tween 20) at 25° C. for 1 hour. After the incubation, recombinant cRAF-RBD and Alpha detection reagents were added and incubated at room temperature for 1.5 hours for binding. Interaction 5 of KRAS G12C and cRAF-RBD was monitored by measuring Alpha signal. Inhibition % was calculated using the signal from the reaction without test compound (DMSO control) as 0% inhibition and the signal from the reaction using GDP-bound KRAS G12C in place of GMPPNP-bound KRAS G12C as 100% inhibition. $IC_{50}$ values were calculated from dose titration curve using curve fitting by XLfit software (IDBS).

The test results reveal that the compound of the present invention has excellent inhibitory activity, and A and J parts in the formula of "A-L1-L2-G-J" are important to show the effect.

TABLE 3

| Example | $IC_{50}$ (μM) |
|---|---|
| 1 | 0.18 |
| 2 | 0.88 |
| 3 | 0.050 |
| 4 | 0.023 |

TABLE 3-continued

| Example | $IC_{50}$ (μM) |
|---|---|
| 5 | 0.029 |
| 6 | 0.015 |
| 7 | 0.035 |
| 8 | 0.019 |
| 9 | 0.066 |
| 10 | 0.19 |
| 11 | 0.63 |
| 12 | 0.27 |
| 13 | 0.41 |
| 14 | 0.83 |
| 15 | 0.20 |
| 16 | 0.70 |
| 17 | 0.075 |
| 18 | 0.14 |
| 19 | 0.034 |
| 20 | 0.15 |
| 21 | 0.22 |
| 22 | 0.14 |
| 23 | 0.22 |
| 24 | 0.15 |
| 25 | 0.25 |
| 26 | 0.42 |
| 27 | 0.35 |
| 28 | 0.10 |
| 29 | 0.095 |
| 30 | 0.075 |
| 31 | 0.026 |
| 32 | 0.027 |
| 33 | 0.045 |
| 34 | 0.031 |
| 35 | 0.019 |
| 36 | 0.023 |
| 37 | 0.012 |
| 38 | 0.067 |
| 39 | 0.30 |
| 40 | 0.20 |
| 41 | 0.085 |
| 42 | 0.36 |
| 43 | 0.17 |
| 44 | 0.061 |
| 45 | 0.32 |
| 46 | 0.17 |
| 47 | 0.56 |
| 48 | >6.7 |
| 49 | 0.031 |
| 50 | 1.2 |
| 51 | 0.095 |
| 52 | 0.26 |
| 53 | 0.15 |
| 54 | 0.18 |
| 55 | 0.021 |
| 56 | 0.086 |
| 57 | 0.16 |
| 58 | 0.24 |
| 59 | 0.019 |
| 60 | 0.020 |
| 61 | 0.23 |
| 62 | 0.057 |
| 63 | 0.21 |
| 64 | 0.082 |
| 65 | 0.14 |
| 66 | 0.084 |
| 67 | 0.063 |
| 68 | 0.057 |
| 69 | 0.26 |
| 70 | 0.027 |
| 71 | 0.14 |
| 72 | 0.034 |
| 73 | 0.032 |
| 74 | 0.17 |
| 75 | 0.15 |
| 76 | 0.13 |
| 77 | 0.33 |
| 78 | 0.096 |
| 79 | 0.44 |
| 80 | 0.027 |

TABLE 3-continued

| Example | $IC_{50}$ (μM) |
|---|---|
| 81 | 0.021 |
| 82 | 0.15 |
| 83 | 0.44 |
| Comparative example 1 | 20 |
| Comparative example 2 | 15 |
| ARS-1620 | >67 |

Test Example 3: Assay of Growth Inhibition Activity on KRAS-G12C Mutant Cell Line (MIA PaCa-2) (In Vitro)

MIA PaCa-2 cells (given by Sumitomo Dainippon Pharma Co., Ltd.), which are a KRAS-G12C mutant human pancreas cancer cell line, were suspended in a 10% fetal bovine serum-containing RPMI1640 medium (manufactured by Fujifilm Wako Pure Chemical Corporation.). The cell suspension was seeded into each well of a 384-well U bottom microplate and cultured in an incubator containing 5% $CO_2$ gas at 37° C. for 1 day. The compounds obtained in the "Preparation of Compounds" section were used as test compounds and were dissolved in DMSO, respectively, and each test compound was diluted with DMSO to give a concentration 500 times the final concentration. The resultant solution of the test compound in DMSO was diluted with the medium used for suspending cells and added to each well of the cell-culture plate to give a DMSO final concentration of 0.2%, followed by culture in an incubator containing 5% $CO_2$ gas at 37° C. for another 3 days. The cell count after 3-day culture in the presence of the test compound was measured using CellTiter-Glo 3D Reagent (manufactured by Promega Corporation). All wells were added with CellTiter-Glo 3D Reagent and mixed for 10 minutes. 30 minutes after mixing, luminescence was measured by a plate reader. The growth inhibition rate was calculated from the following equation, and the concentration of the test compound at which 50% inhibition was achieved ($IC_{50}$ (nM)) was determined. The following table shows the results.

$$\text{Growth Inhibition Rate (\%)}=(C-T)/(C)\times 100$$

T: the emission intensity in a well into which a test compound was added.

C: the emission intensity in a well into which a test compound was not added.

The test results reveal that the compound of the present invention has excellent cell growth inhibition activity on KRAS-G12C mutant cell line MIA PaCa-2.

TABLE 4

| Example | $IC_{50}$ (μM) |
|---|---|
| 3 | 0.083 |
| 4 | 0.14 |
| 5 | 0.080 |
| 6 | 0.043 |
| 7 | 0.049 |
| 8 | 0.052 |
| 9 | 0.10 |
| 29 | 0.41 |
| 30 | 0.37 |
| 31 | 0.086 |

TABLE 4-continued

| Example | $IC_{50}$ (μM) |
|---|---|
| 32 | 0.31 |
| 33 | 0.048 |
| 34 | 0.092 |
| 35 | 0.039 |
| 36 | 0.070 |
| 37 | 0.55 |
| 38 | 0.088 |
| 41 | 0.37 |
| 44 | 0.35 |
| 49 | 0.075 |
| 51 | 0.17 |
| 55 | 0.14 |
| 56 | 0.35 |
| 59 | 0.064 |
| 60 | 0.059 |
| 62 | 0.043 |
| 64 | 0.069 |
| 66 | 0.24 |
| 67 | 0.56 |
| 68 | 0.24 |
| 70 | 0.072 |
| 72 | 0.20 |
| 73 | 0.28 |
| 78 | 0.40 |
| 80 | 0.19 |
| 81 | 0.070 |

The above Table 4 shows the growth inhibition data of the compounds showing Raf binding IC50<0.1 microM, assuming that it well correlates to the KRAS inhibition-dependent growth inhibition.

Test Example 4: Assay of the Amount of Activated KRAS on KRAS-G12C Mutant Cell Lines (NCI-H358, MIA PaCa-2) (In Vitro)

NCI-H358 [H358, H358] (ATCC® CRL5807™), which is a KRAS-G12C mutant human lung cancer cell line, and MIA PaCa-2 (ATCC® CRL-1420™), which is a KRAS-G12C mutant human pancreas cancer cell line, were suspended in a 10% fetal bovine serum-containing RPMI1640 medium (manufactured by Thermo Fischer SCIENTIFIC), respectively. The cell suspension was seeded into a cell culture plate and cultured in an incubator containing 5% $CO_2$ gas at 37° C. for 1 day. The lyophilized recombinant human EGF protein (R&D systems, Cat #: 236-EG-200) was dissolved in PBS to make 0.5 mg/ml solution. The EGF solution in PBS was diluted by 0.4% with the medium used for suspending cells and added to each cell-culture plate to give an EGF final concentration of 100 ng/ml, followed by leaving to stand at ambient temperature for 5 minutes. Then, the compounds obtained in the "Preparation of Compounds" section were used as test compounds and were dissolved in DMSO, and each test compound was diluted with DMSO to give a concentration 200 times the final concentration. The solution of the test compound in DMSO was diluted with the medium used for suspending cells and added to each well of the cell-culture plate to give a DMSO final concentration of 0.5%, followed by culture in an incubator containing 5% $CO_2$ gas at 37° C. for another 1 hour. The amount of activated KRAS after 1 hour culture in the presence of the compound was measured using Ras GTPase Chemi ELISA Kit (manufactured by Active Motif). The ratio of KRAS activity was calculated from the following equation, and the concentration of the test compound at which activity was suppressed to 50% ($IC_{50}$ (μM)) was determined. The following table shows the results.

$$\text{The Ratio of KRAS activity to control (\%)}=(T-BG)/(C-BG)\times 100$$

T: the emission intensity in a well into which a test compound was added.

C: the emission intensity in a well into which a test compound was not added.

BG: the emission intensity in a well into which neither a test compound nor a cell suspension was added.

The test results reveal that the KRAS inhibition activity of the compound of the present invention is not affected by EGF treatment on KRAS-G12C mutant cell line NCI-H358 and MIA PaCa-2, while the KRAS inhibition activity of ARS-1620 (synthesized in reference to Cell. 172 (3), 578-89, 2018), an inhibitor which binds to inactive form of KRAS G12C mutation, is attenuated by EGF treatment.

TABLE 5

| | $IC_{50}$ (μM) | | | |
|---|---|---|---|---|
| | NCI-H358 | | MIA PaCa-2 | |
| Cell line | without EGF | with EGF | without EGF | with EGF |
| Example 1 | 0.75 | 0.85 | 0.78 | 1.0 |
| Example 4 | 0.39 | 0.47 | 0.30 | 0.44 |
| ARS-1620 | 1.4 | 5.4 | 0.65 | 4.2 |

Test Example 5: Cocrystal Structural Analysis of KRAS G12C with Compound of Example 19

Sample solution containing the compound of Example 19 was prepared in the form of a 10 mM DMSO solution.

Gppcp-bound recombinant K-Ras4B G12C mutant protein (amino acids 1-169, C51S/C80L/C118S, SEQ ID NO:1) in a buffer (50 mM Tris-HCl, pH7.5, 200 mM NaCl, 0.1 mM TCEP) was concentrated to 100 μM protein solution. 200 μL of a 10 mM solution of the compound of Example 19 was added to 10 mL of a 100 μM protein solution. The mixture was stored in an incubator at 4° C. for 16 hour, and further purification of drug conjugated protein was conducted by MonoQ 10/100 GL column (GE Healthcare). An eluted protein was concentrated to 2 mM solution.

Crystals were obtained using the hanging drop method at 24° C. Drops were prepared by adding 1 μl of protein to 1 μl drop of the reservoir solution (100 mM Bis-Tris, pH 5.5, 25% PEG 3350, 200 mM $MgCl_2$). Crystals appeared in a week and grew to full size (100×100×100 micron) after another week.

The diffraction data were collected at BL-1A in Photon Factory. The data were processed using the program iMOSFLM (Battye T. G., Kontogiannis L., Johnson O., Powell H. R., Leslie A. G. iMOSFLM: a new graphical interface for diffraction-image processing with MOSFLM. Acta. Crystallogr. D Biol. Crystallogr. 2011, 67, 271-281) from the CCP4 suite (Collaborative Computational Project No. 4. The CCP4 suite: programs for protein crystallography. *Acta Crystallogr.* 1994, D50, 760-763). The space group was P43. The structure of Gppcp-bound K-Ras4B G12C complexed with the compound of Example 19 was determined by molecular replacement using the program MOLREP (Vagin A, Teplyakov A. MOLREP: an automated program for molecular replacement. *J Appl Crystallogr* 1997, 30, 1022-1025.) The search model was based on GDP-bound K-Ras4B G12C mutant structure (PDB ID: 4LRW). The structure of Gppcp-bound K-Ras4B G12C in complex with the compound of Example 19 was refined using REFMAC5 (Murshudov, G. N., Vagin A. A., Dodson E. J. Refinement of macromolecular structures by the maximum-likelihood method. *Acta Crystallogr.* 1997, D53, 240-255). Manual rebuilding of the models and electron density map interpretation were carried out using COOT (Emsley, P., Lohkamp, B., Scott, W. G., Cowtan, K. Features and development of Coot. *Acta. Crystallogr. D Biol. Crystallogr.* 2010, 66, 486-501).

Figure 2:
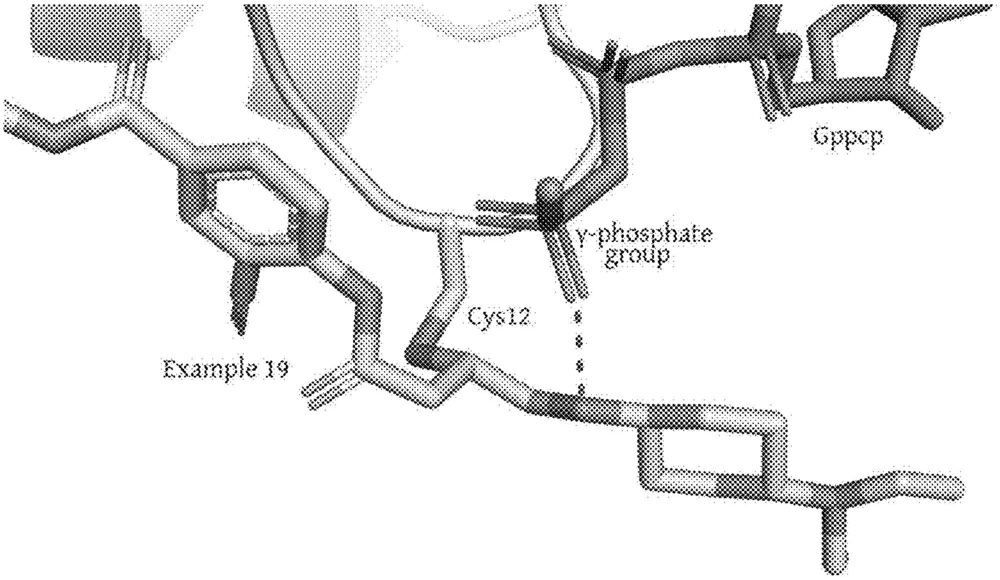
FIG. 2 illustrates cocrystal structure of Example 19 and Gppcp-bound K-Ras4B G12C, focused on covalent binding between the chemical moiety G of Example 19 and cysteine 12 of K-Ras4B G12C, and hydrogen bond (shown as black dashed lines) between the chemical moiety J of Example 19 and the γ-phosphate group of Gppcp.

Based on the X-ray analysis of the compound of Example 19, direct interaction between amine group in a position corresponding to "J" in the formula of "A-L1-L2-G-J" of the compound of Example 19 and γ-phosphate group of Gppcp was observed in addition to covalent interaction of crotonamide moiety in a position corresponding to "G" in the formula of "A-L1-L2-G-J" with Cys12 (FIG. 2). Benzimidazole moiety of the compound of Example 19 is in a position corresponding to "A" in the formula of "A-L1-L2-G-J", and FIG. 1 shows that the benzimidazole moiety interacts with Arg68 and Asp69 in a Switch 2 region, and with Gln99 in an α3-Helix region.

```
Sequences
Gppcp-bound recombinant K-Ras4B G12C mutant
protein (amino acids 1-169, C51S/C80L/C118S)
                                  (SEQ ID NO: 1)
GMTEYKLVVVGACGVGKSALTIQLIQNHFVDEYDPTIEDSYRKQVV

IDGETSLLDILDTAGQEEYSAMRDQYMRTGEGFLLVFAINNTKSFE

DIHHYREQIKRVKDSEDVPMVLVGNKSDLPSRTVDTKQAQDLARSY

GIPFIETSAKTRQGVDDAFYTLVREIRKHKEK

Recombinant K-Ras4B G12C mutant protein
                                  (SEQ ID NO: 2)
MASSHHHHHHSSENLYFQGMTEYKLVVVGACGVGKSALTIQLIQNH

FVDEYDPTIEDSYRKQVVIDGETCLLDILDTAGQEEYSAMRDQYMR

TGEGFLCVFAINNTKSFEDIHHYREQIKRVKDSEDVPMVLVGNKCD

LPSRTVDTKQAQDLARSYGIPFIETSAKTRQGVDDAFYTLVREIRK

HKEK
```

Sequence Listing Free Text

SEQ ID NOs: 1 to 2: synthetic proteins

The invention claimed is:

1. An antitumor agent comprising a compound or a pharmaceutically acceptable salt thereof that covalently binds to GTP-bound KRAS G12C as an active ingredient, wherein the compound has the formula:

A-L1-L2-G-J wherein,

A is a chemical moiety capable of interacting with a region between Switch 2 and α3-Helix;

L1 is a linker;

L2 is a linker;

G is an electrophilic chemical moiety capable of forming a covalent bond with cysteine 12 of GTP-bound KRAS G12C; and J is a chemical moiety capable of interacting with GTP;

wherein, G is represented by the following formula:

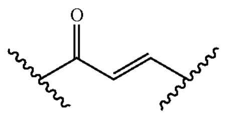

wherein L1 is represented by D with —C(=O)—, L2 is represented by E with $—NR_1—$ and J is represented by $—CHR_2'—NR_2R_3$ in the formula A-L1-L2-G-J; and wherein the compound is represented by Formula (x):

(x)

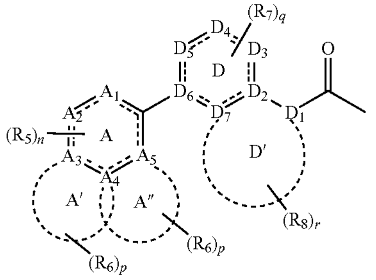

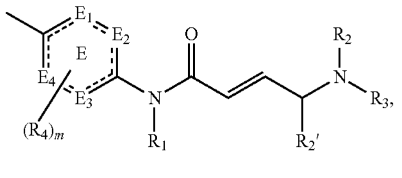

wherein:

$R_1$ is hydrogen or C1-C6 alkyl;

$R_2$ and $R_2$' join together to form a 4- to 10-membered saturated heterocyclic ring which is unsubstituted or substituted with 1-2 substituents independently represented by Ra; or $R_2$, $R_2$' and $R_3$ are independently represented, and $R_2$ is hydrogen, or C1-C10 alkyl, C2-C10 alkenyl, C2-C10 alkynyl, C3-C10 cycloalkyl, C1-C10 alkoxy, C6-C10 aromatic hydrocarbon, a 4- to 10-membered saturated heterocyclic group, a 4- to 10-membered partially saturated heterocyclic group or a 4- to 10-membered unsaturated heterocyclic group, each of which is unsubstituted or substituted with 1-2 substituents independently represented by Ra;

$R_2$' is hydrogen or C1-C6 alkyl which is unsubstituted or substituted with 1-2 substituents independently represented by Ra; and $R_3$ is hydrogen;

Ra represents independently halogen, hydroxy, C1-C10 alkyl, C2-C6 alkenyl, C2-C6 alkynyl, C3-C10 cycloalkyl, C1-C10 haloalkyl, C1-C10 monoalkylamino, C1-C10 dialkylamino, C1-C10 alkoxy, C1-C10 haloalkoxy, C1-C10 alkylsulfonyl, C1-C10 acyl, C1-C10 alkoxycarbonyl or a 4- to 10-membered saturated heterocyclic group;

wherein E is an unsaturated 6-membered ring which is unsubstituted or substituted with $R_4$, wherein $E_1$, $E_2$, $E_3$ and $E_4$ represent independently C, CH, $CH_2$, N or NH;

$R_4$ is halogen or cyano;

wherein A is a ring system selected from a substituted or unsubstituted single ring or a substituted or unsubstituted fused ring;

wherein when A is a single ring, A' and A" are absent, and the single ring is represented by ring A, which is an unsaturated 6-membered ring which is unsubstituted or substituted with $R_5$, wherein $A_1$, $A_2$, $A_3$, $A_4$ and As represent independently C, CH, or $CH_2$;

wherein when A is a fused ring, the fused ring is represented by ring A and ring A' or ring A and ring A", wherein ring A is an unsaturated 6-membered ring which is unsubstituted or substituted with $R_5$, wherein $A_1$, $A_2$, $A_3$, $A_4$ and As represent independently C, CH, $CH_2$, N or NH, and ring A' or A" is a saturated or unsaturated ring which is unsubstituted or substituted with $R_6$ and forms a fused ring with ring A containing $A_3$ and $A_4$ or $A_4$ and $A_5$;

$R_5$ is halogen, cyano, amino, hydroxy, substituted or unsubstituted C1-C10 alkyl, C2-C6 alkenyl, C2-C6 alkynyl, C1-C6 haloalkyl, C1-C10 alkoxy, C1-C10 acyl, C1-C10 alkoxycarbonyl, or C1-C10 alkylsulfonyl;

two $R_6$ may join together to form a C3-C10 hydrocarbon ring or a 4- to 10-membered saturated heterocyclic ring sharing two adjacent atoms with ring A' or ring A" when the number of $R_6$ is two or more; or each $R_6$ may independently represent halogen, cyano, amino, hydroxy, substituted or unsubstituted C1-C10 alkyl, C2-C6 alkenyl, C2-C6 alkynyl, substituted or unsubstituted C1-C6 haloalkyl, substituted or unsubstituted C1-C10 alkoxy, C1-C10 acyl, C1-C10 alkoxycarbonyl or C1-C10 alkylsulfonyl;

D is a single ring having at least one amino group which binds to carbonyl between D and E to form amide, wherein the single ring may be additionally substituted with a substituent other than said amino, or D is a substituted or unsubstituted fused ring;

wherein when D is a single ring, D' is absent, and the single ring is represented by ring D, which is an unsaturated 6-membered ring which is unsubstituted or substituted with $R_7$, wherein $D_1$ represents N or NH, and $D_2$, $D_3$, $D_4$, $D_5$, $D_6$ and $D_7$ represent independently C, CH, $CH_2$, N or NH;

wherein when D is a fused ring, the fused ring is represented by ring D and ring D', wherein ring D is an unsaturated 6-membered ring which is unsubstituted or substituted with $R_7$, wherein Di, $D_2$, $D_3$, $D_4$, $D_5$, $D_6$ and $D_7$ represent independently C, CH, $CH_2$, N or NH, and ring D' is a saturated or unsaturated ring which is unsubstituted or substituted with $R_8$ and forms a fused ring with ring D containing $D_1$, $D_2$ and $D_7$;

$R_7$ is halogen, cyano, hydroxy, amino, carboxamide, substituted or unsubstituted C1-C10 alkyl, substituted or unsubstituted C2-C6 alkenyl, substituted or unsubstituted C2-C6 alkynyl, substituted or unsubstituted C1-C6 haloalkyl, substituted or unsubstituted C1-C10 alkoxy, substituted or unsubstituted C1-C10 acyl, substituted or unsubstituted C1-C10 alkoxycarbonyl or substituted or unsubstituted C1-C10 alkylsulfonyl;

$R_8$ is halogen or C1-C10 alkyl;

q and r represent independently 0, 1, or 2;

n is an integer of 0 to 5;

p is 0, 1, or 2; and m is an integer of 0 to 4; or a pharmaceutically acceptable salt thereof.

2. The antitumor agent according to claim 1, wherein ring A' forms a fused ring with ring A containing $A_3$ and $A_4$, and $A_1$ and As are C, CH, or $CH_2$.

3. The antitumor agent according to claim 1, wherein the compound is represented by Formula (xi):

(xi)

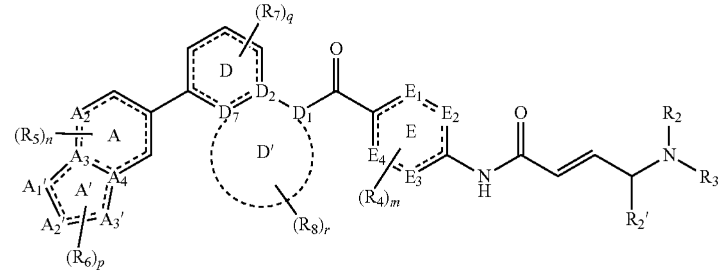

wherein ring A' is a saturated or unsaturated 5-membered ring forming a fused ring containing $A_3$ and $A_4$ with ring A, wherein $A_1$', $A_2$', $A_3$' represent independently C, CH, $CH_2$, N, NH, O or S, two $R_6$ may join together to form a C3-C10 hydrocarbon ring or a 4- to 10-membered saturated heterocyclic ring when the number of $R_6$ is two or more; or each $R_6$ may be independently halogen, cyano, hydroxy, substituted or unsubstituted C1-C10 alkyl, substituted or unsubstituted C1-C6 haloalkyl or substituted or unsubstituted C1-C10 alkoxy.

4. The antitumor agent according to claim 3, wherein the compound is represented by Formula (xii):

(xii)

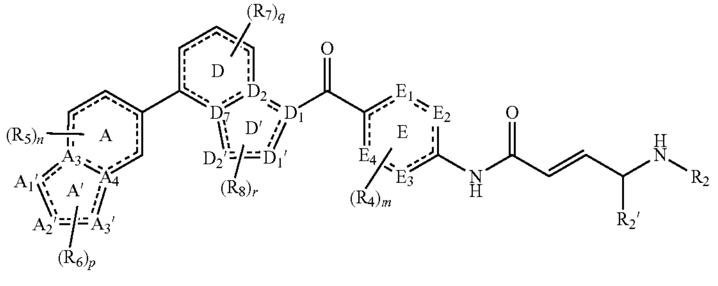

wherein $R_2$ and $R_2$' join together to form a 4- to 6-membered saturated heterocyclic ring which is unsubstituted or substituted with 1-2 substituents independently represented by Ra; or $R_2$, and $R_2$' are independently represented, and $R_2$ is C1-C10 alkyl which is unsubstituted or substituted with Ra, C3-C10 cycloalkyl which is unsubstituted or substituted with Ra, or a 4- to 10-membered saturated heterocyclic group which is unsubstituted or substituted with Ra;

wherein $R_5$ is hydroxy, halogen, C1-C10 alkyl, C1-C6 haloalkyl or C1-C10 alkoxy;

wherein two $R_6$ may join together to form a C3-C10 hydrocarbon ring or a 4- to 10-membered saturated heterocyclic ring when the number of $R_6$ is two or more; or each $R_6$ may be independently substituted or unsubstituted C1-C10 alkyl or substituted or unsubstituted C1-C10 alkoxy;

D is a fused ring represented by ring D and ring D', and ring D' is a saturated or unsaturated 5-membered ring forming a fused ring containing $D_1$, $D_2$ and $D_7$ with ring D, and $D_1$' and $D_2$' represent independently C, CH, $CH_2$, N, NH or S, and $R_7$ is halogen, cyano, hydroxy, amino, carboxamide, substituted or unsubstituted C1-C10 alkyl, substituted or unsubstituted C1-C6 haloalkyl or substituted or unsubstituted C1-C10 alkoxy.

5. A compound represented by Formula (x):

(x)

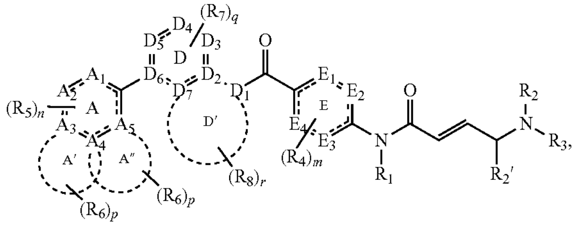

wherein:

$R_1$ is hydrogen or C1-C6 alkyl;

$R_2$ and $R_2$' join together to form a 4- to 10-membered saturated heterocyclic ring which is unsubstituted or substituted with 1-2 substituents independently represented by Ra; or $R_2$, $R_2$' and $R_3$ are independently represented, and $R_2$ is hydrogen, or C1-C10 alkyl, C2-C10 alkenyl, C2-C10 alkynyl, C3-C10 cycloalkyl, C1-C10 alkoxy, C6-C10 aromatic hydrocarbon, a 4- to 10-membered saturated heterocyclic group, a 4- to 10-membered partially saturated heterocyclic group or a 4- to 10-membered unsaturated heterocyclic group, each of which is unsubstituted or substituted with 1-2 substituents independently represented by Ra;

$R_2$' is hydrogen or C1-C6 alkyl which is unsubstituted or substituted with 1-2 substituents independently represented by Ra; and $R_3$ is hydrogen;

Ra represents independently halogen, hydroxy, C1-C10 alkyl, C2-C6 alkenyl, C2-C6 alkynyl, C3-C10 cycloalkyl, C1-C10 haloalkyl, C1-C10 monoalkylamino, C1-C10 dialkylamino, C1-C10 alkoxy, C1-C10 haloalkoxy, C1-C10 alkylsulfonyl, C1-C10 acyl, C1-C10 alkoxycarbonyl or a 4- to 10-membered saturated heterocyclic group;

wherein E is an unsaturated 6-membered ring which is unsubstituted or substituted with $R_4$, wherein $E_1$, $E_2$, $E_3$ and $E_4$ represent independently C, CH, $CH_2$, N or NH;

$R_4$ is halogen or cyano;

wherein A is a ring system selected from a substituted or unsubstituted single ring or a substituted or unsubstituted fused ring;

wherein when A is a single ring, A' and A" are absent, and the single ring is represented by ring A, which is an unsaturated 6-membered ring which is unsubstituted or substituted with $R_5$, wherein $A_1$, $A_2$, $A_3$, $A_4$ and As represent independently C, CH, or $CH_2$;

wherein when A is a fused ring, the fused ring is represented by ring A and ring A' or ring A and ring A", wherein ring A is an unsaturated 6-membered ring which is unsubstituted or substituted with $R_5$, wherein $A_1$, $A_2$, $A_3$, $A_4$ and As represent independently C, CH, $CH_2$, N or NH, and ring A' or A" is a saturated or unsaturated ring which is unsubstituted or substituted with $R_6$ and forms a fused ring with ring A containing $A_3$ and $A_4$ or $A_4$ and $A_5$;

$R_5$ is halogen, cyano, amino, hydroxy, substituted or unsubstituted C1-C10 alkyl, C2-C6 alkenyl, C2-C6 alkynyl, C1-C6 haloalkyl, C1-C10 alkoxy, C1-C10 acyl, C1-C10 alkoxycarbonyl, or C1-C10 alkylsulfonyl;

two $R_6$ may join together to form a C3-C10 hydrocarbon ring or a 4- to 10-membered saturated heterocyclic ring sharing two adjacent atoms with ring A' or ring A" when the number of $R_6$ is two or more; or each $R_6$ may independently represent halogen, cyano, amino, hydroxy, substituted or unsubstituted C1-C10 alkyl, C2-C6 alkenyl, C2-C6 alkynyl, substituted or unsubstituted C1-C6 haloalkyl, substituted or unsubstituted C1-C10 alkoxy, C1-C10 acyl, C1-C10 alkoxycarbonyl or C1-C10 alkylsulfonyl;

D is a single ring having at least one amino group which binds to carbonyl between D and E to form amide, wherein the single ring may be additionally substituted with a substituent other than said amino, or D is a substituted or unsubstituted fused ring;

wherein when D is a single ring, D' is absent, and the single ring is represented by ring D, which is an unsaturated 6-membered ring which is unsubstituted or substituted with $R_7$, wherein $D_1$ represents N or NH, and $D_2$, $D_3$, $D_4$, $D_5$, $D_6$ and $D_7$ represent independently C, CH, $CH_2$, N or NH;

wherein when D is a fused ring, the fused ring is represented by ring D and ring D', wherein ring D is an unsaturated 6-membered ring which is unsubstituted or substituted with $R_7$, wherein Di, $D_2$, $D_3$, $D_4$, $D_5$, $D_6$ and $D_7$ represent independently C, CH, $CH_2$, N or NH, and ring D' is a saturated or unsaturated ring which is unsubstituted or substituted with $R_8$ and forms a fused ring with ring D containing $D_1$, $D_2$ and $D_7$;

$R_7$ is halogen, cyano, hydroxy, amino, carboxamide, substituted or unsubstituted C1-C10 alkyl, substituted or unsubstituted C2-C6 alkenyl, substituted or unsubstituted C2-C6 alkynyl, substituted or unsubstituted C1-C6 haloalkyl, substituted or unsubstituted C1-C10 alkoxy, substituted or unsubstituted C1-C10 acyl, substituted or unsubstituted C1-C10 alkoxycarbonyl or substituted or unsubstituted C1-C10 alkylsulfonyl;

$R_8$ is halogen or C1-C10 alkyl;

q and r represent independently 0, 1, or 2;

n is an integer of 0 to 5;

p is 0, 1, or 2; and m is an integer of 0 to 4; or a pharmaceutically acceptable salt thereof.

6. The compound according to claim 5, wherein the compound is represented by Formula (xi):

(xi)

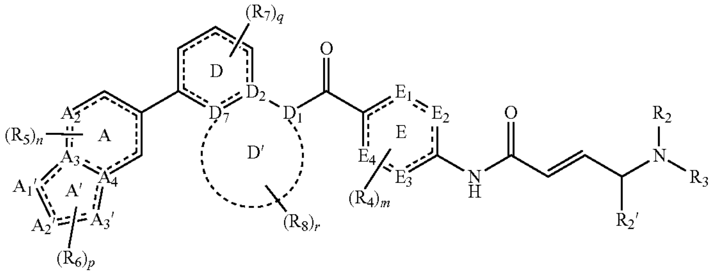

wherein ring A' is a saturated or unsaturated 5-membered ring forming a fused ring containing $A_3$ and $A_4$ with ring A, wherein $A_1'$, $A_2'$, $A_3'$ represent independently C, CH, $CH_2$, N, NH, O or S, two $R_6$ may join together to form a C3-C10 hydrocarbon ring or a 4- to 10-membered saturated heterocyclic ring when the number of $R_6$ is two or more; or each $R_6$ may be independently halogen, cyano, hydroxy, substituted or unsubstituted C1-C10 alkyl, substituted or unsubstituted C1-C6 haloalkyl or substituted or unsubstituted C1-C10 alkoxy;

or a pharmaceutically acceptable salt thereof.

7. The compound according to claim 6, wherein the compound is represented by Formula (xii) or a salt thereof:

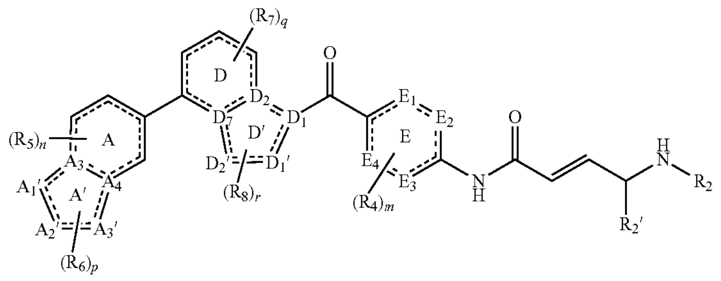

(xii)

wherein $R_2$ and $R_2$' join together to form a 4- to 6-membered saturated heterocyclic ring which is unsubstituted or substituted with 1-2 substituents independently represented by Ra; or $R_2$, and $R_2$' are independently represented, and $R_2$ is C1-C10 alkyl which is unsubstituted or substituted with Ra, C3-C10 cycloalkyl which is unsubstituted or substituted with Ra, or a 4- to 10-membered saturated heterocyclic group which is unsubstituted or substituted with Ra;

wherein $R_5$ is hydroxy, halogen, C1-C10 alkyl, C1-C6 haloalkyl or C1-C10 alkoxy;

wherein two $R_6$ may join together to form a C3-C10 hydrocarbon ring or a 4- to 10-membered saturated heterocyclic ring when the number of $R_6$ is two or more; or each $R_6$ may be independently substituted or unsubstituted C1-C10 alkyl or substituted or unsubstituted C1-C10 alkoxy;

D is a fused ring represented by ring D and ring D', and ring D' is a saturated or an unsaturated 5-membered ring forming a fused ring containing $D_1$, $D_2$ and $D_7$ with ring D, and Di' and $D_2$' represents independently C, CH, $CH_2$, N, NH or S, and $R_7$ is halogen, cyano, hydroxy, amino, carboxamide, substituted or unsubstituted C1-C10 alkyl, substituted or unsubstituted C1-C6 haloalkyl or substituted or unsubstituted C1-C10 alkoxy;

or a pharmaceutically acceptable salt thereof.

8. A pharmaceutical composition comprising the compound or pharmaceutically acceptable salt thereof of claim 5 and a pharmaceutically acceptable carrier.

9. The antitumor agent of claim 1, wherein the antitumor agent is suitable for oral administration.

10. A method for treating a tumor, comprising administering a therapeutically effective amount of the compound of claim 5 or pharmaceutically acceptable salt thereof to a subject in need thereof, wherein the tumor is KRAS G12C mutation-positive.

11. An antitumor agent comprising a compound of claim 5 or a pharmaceutically acceptable salt thereof, and one or more other antitumor agents as an active ingredient.

12. A method for treating a tumor, the method comprising administering a therapeutically effective amount of the compound of claim 5 or pharmaceutically acceptable salt thereof, and one or more other antitumor agents to a subject in need thereof, wherein the tumor is KRAS G12C mutation-positive.

13. A method for treating a tumor, the method comprising administering a therapeutically effective amount of the compound of claim 5 or pharmaceutically acceptable salt thereof in combination with one or more other antitumor agents to a subject in need thereof, wherein the tumor is KRAS G12C mutation-positive.

14. The antitumor agent of claim 1, wherein the tumor is a cancer and wherein the tumor is KRAS G12C mutation-positive.

15. The antitumor agent of claim 14, wherein the cancer is one or more selected from the group consisting of a carcinoma, squamous carcinoma, adenocarcinoma, sarcoma, leukemia, neuroma, melanoma, and lymphoma.

16. The antitumor agent of claim 15, wherein the squamous carcinoma is a cancer of uterine cervix, tarsus, conjunctiva, vagina, lung, oral cavity, skin, bladder, tongue, larynx or esophagus.

17. The antitumor agent of claim 15, wherein the adenocarcinoma is a cancer of prostate, small intestine, endometrium, uterine cervix, large intestine, lung, pancreas, esophagus, rectum, uterus, stomach, breast or ovary.

18. The antitumor agent of claim 14, wherein the tumor is rectal cancer, colon cancer, colorectal cancer, pancreatic cancer, lung cancer, breast cancer or leukemia.

19. A compound selected from the group consisting of:
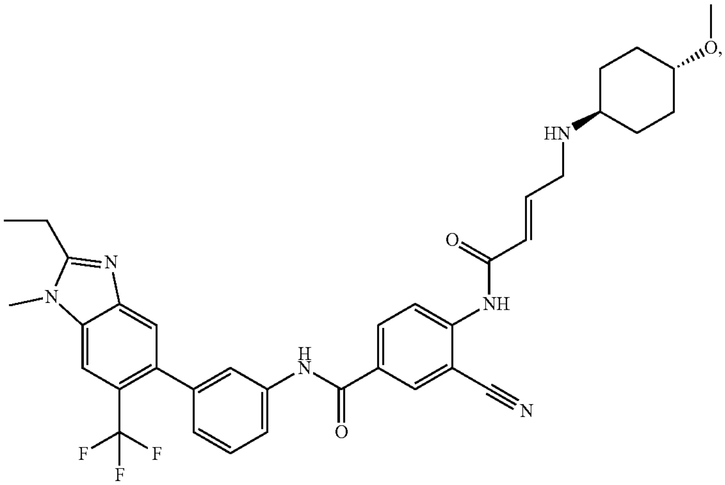
,
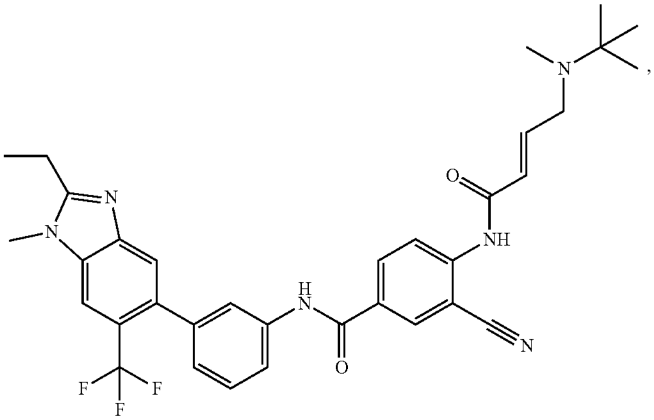
,
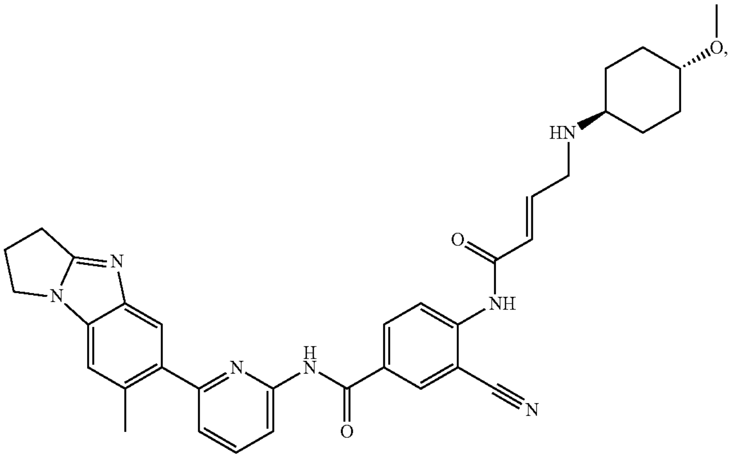
, -continued
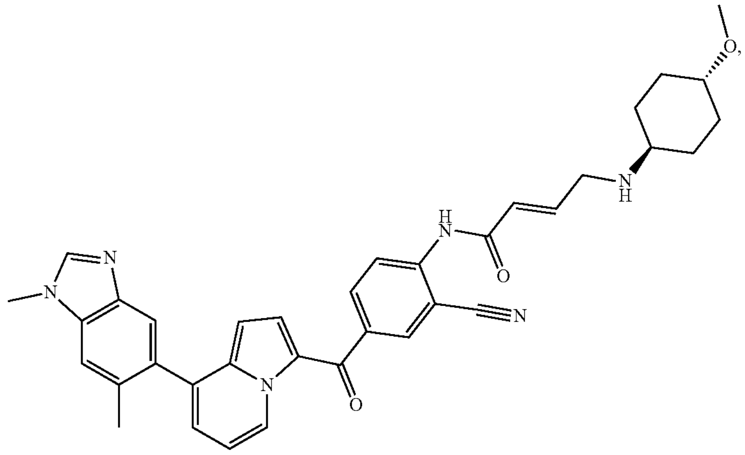
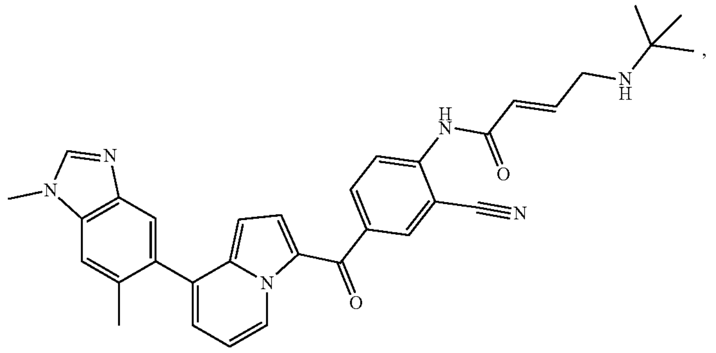
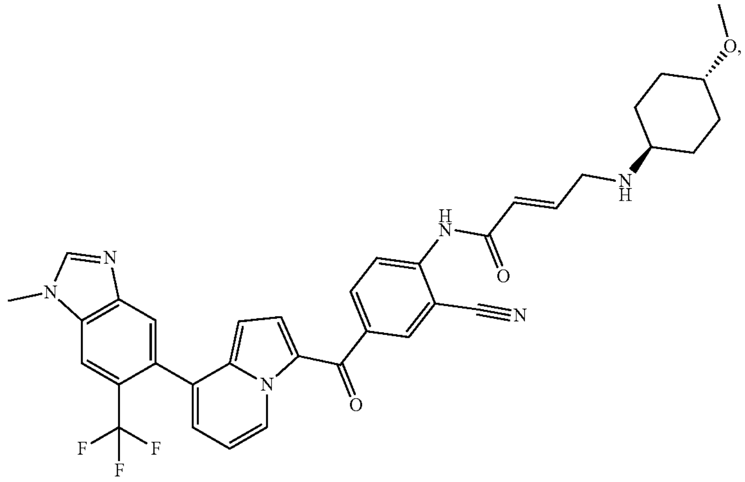

-continued
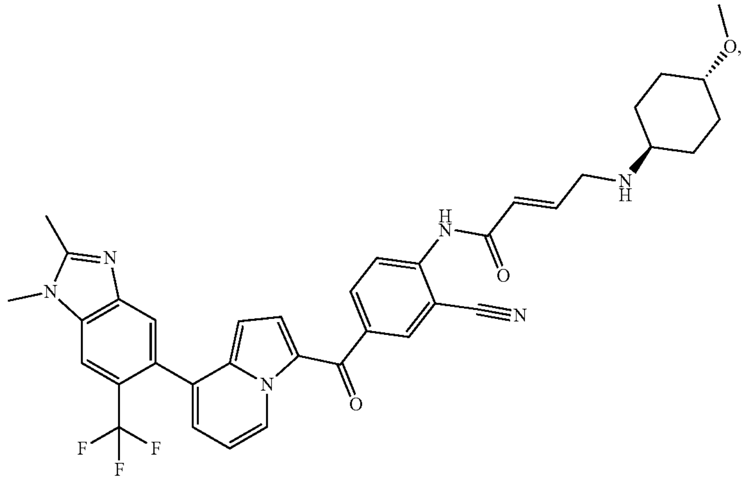
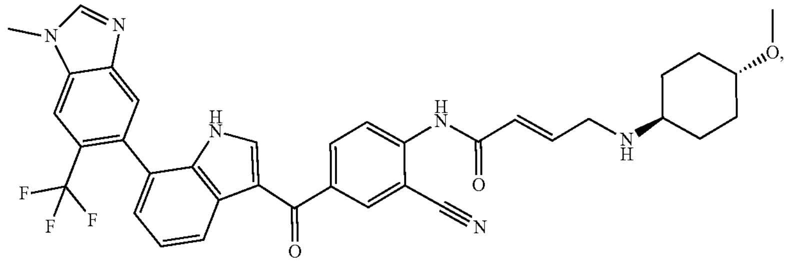
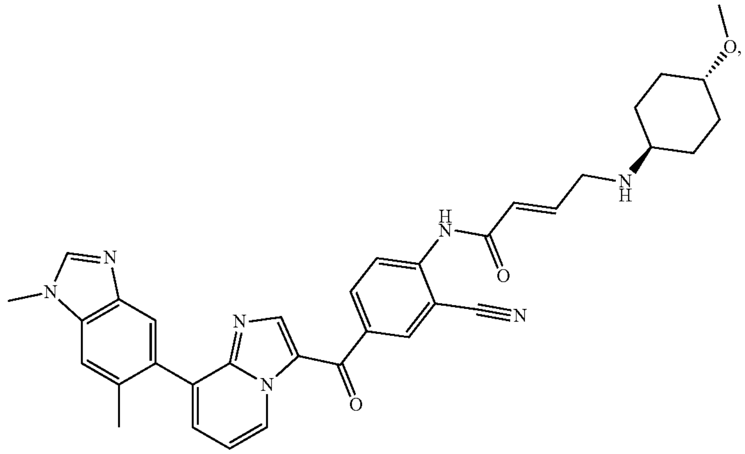
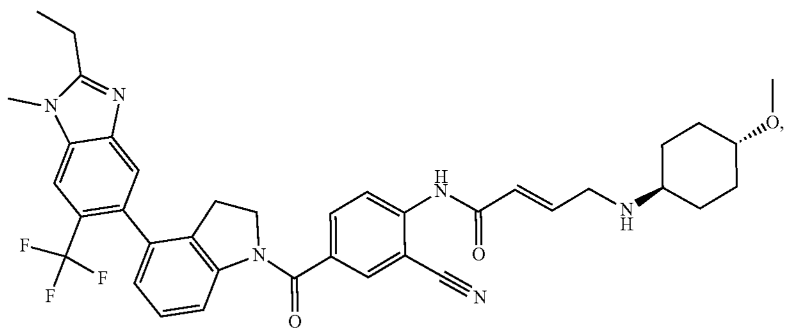

-continued
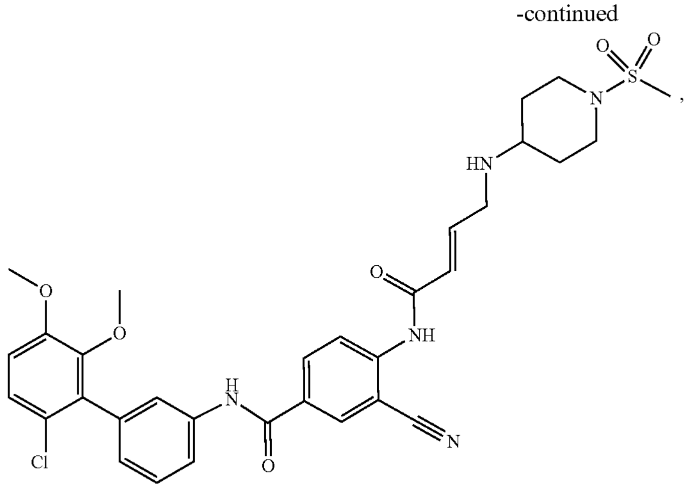
,
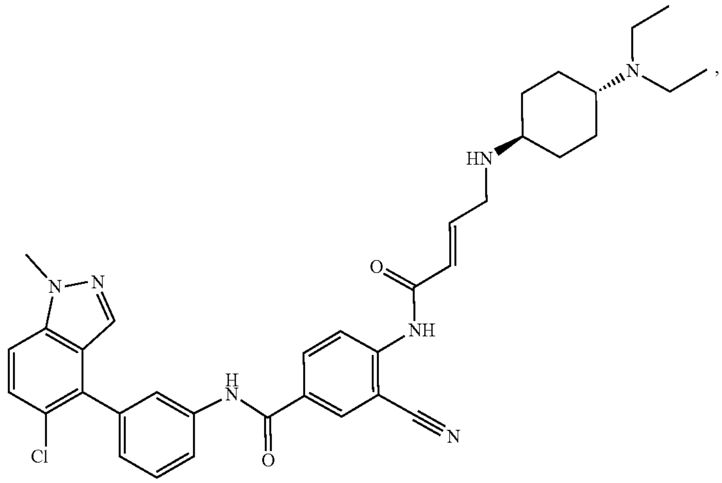
,
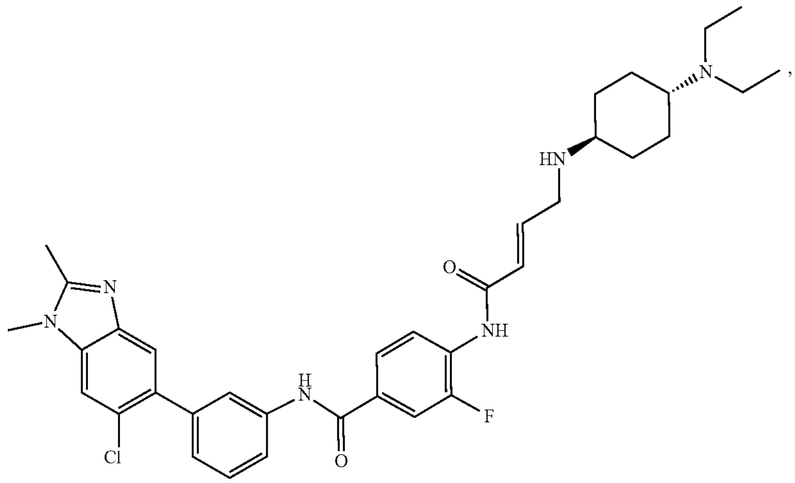
,

-continued
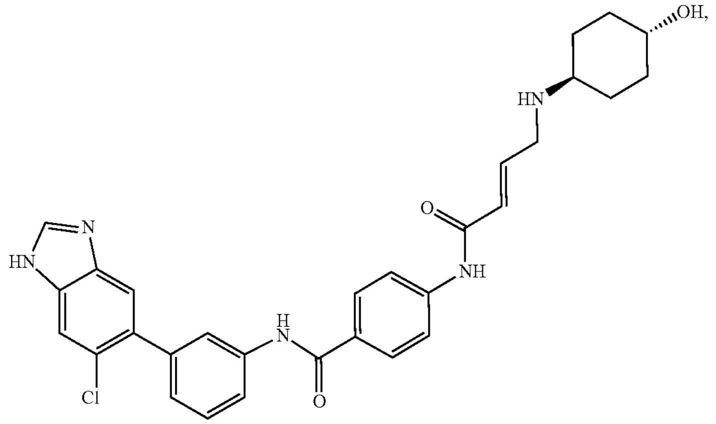
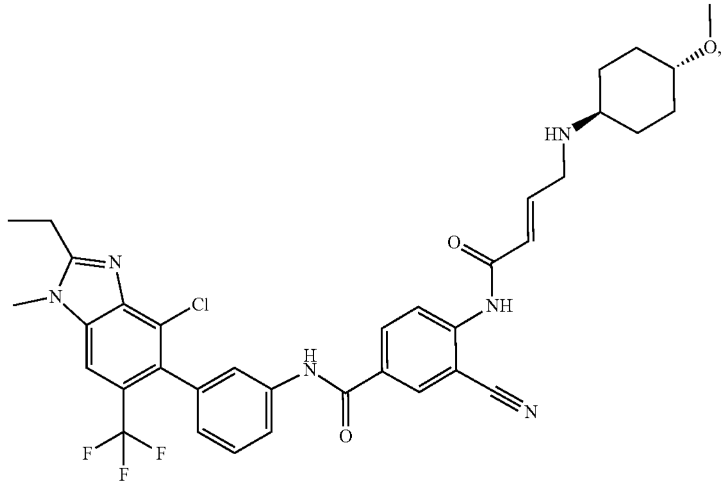
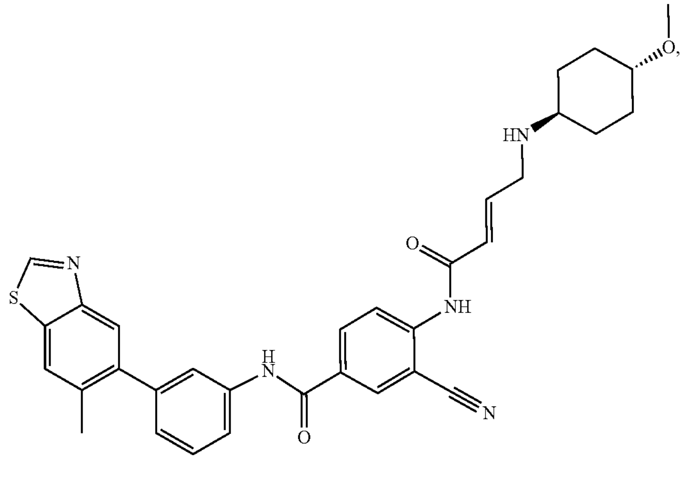

-continued
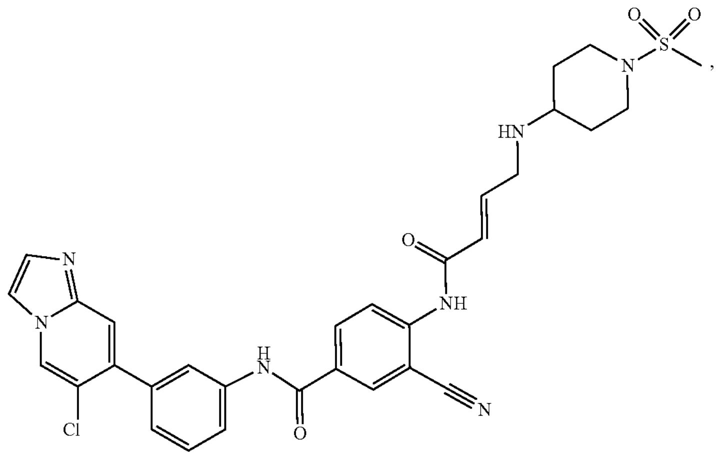
,
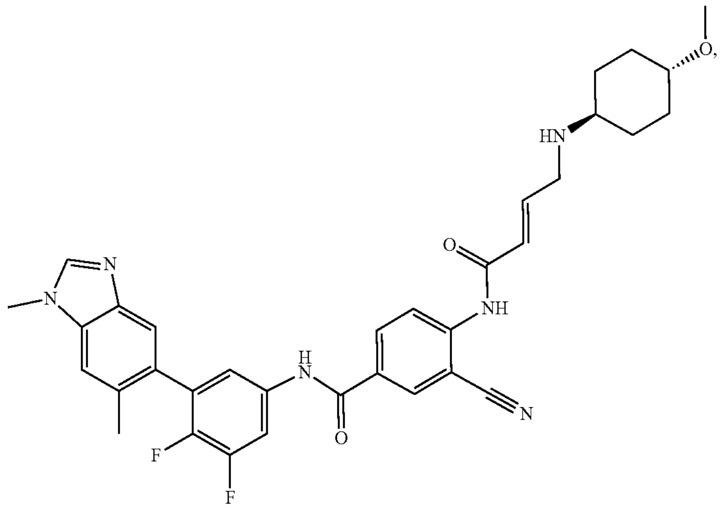
,
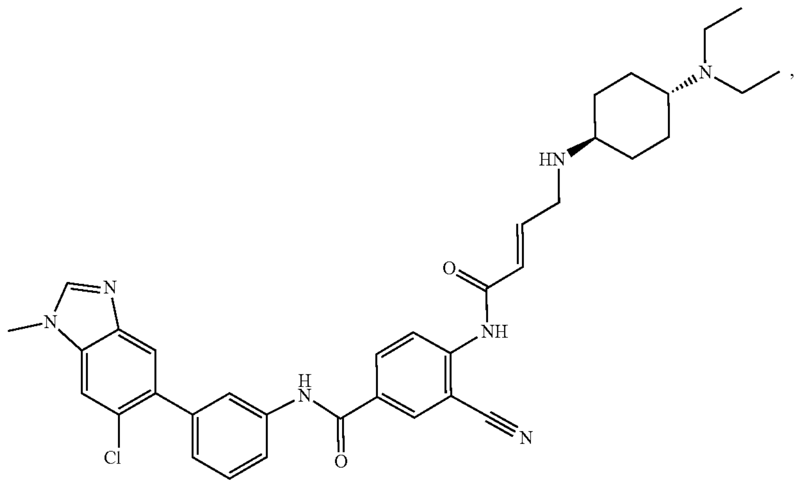
,

-continued
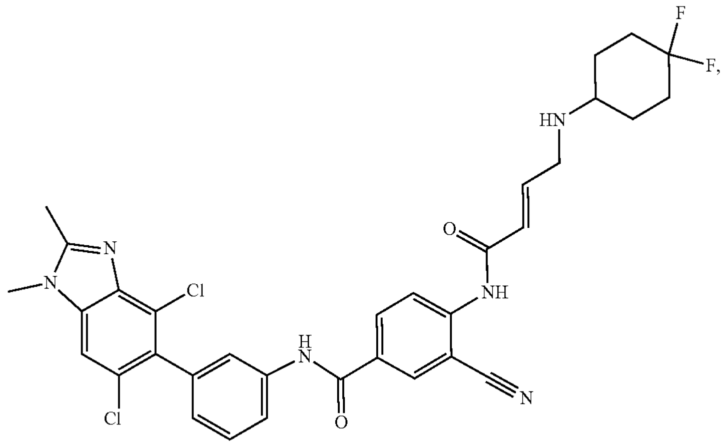
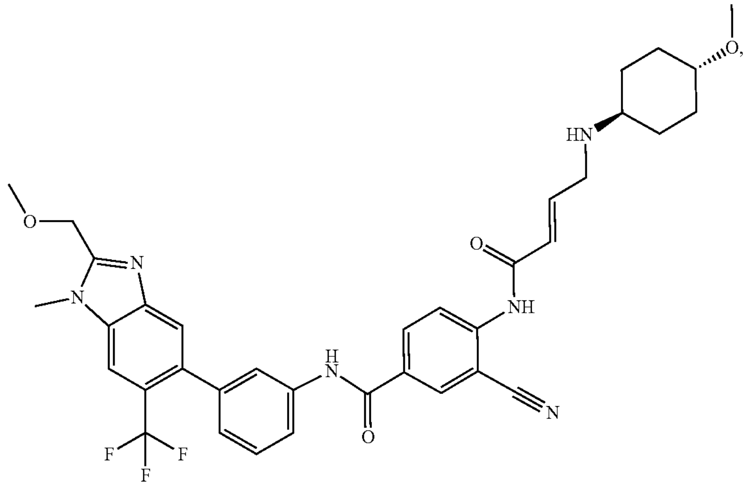
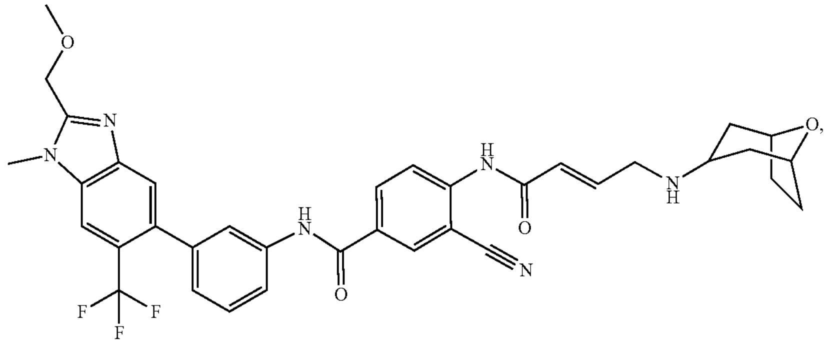

-continued
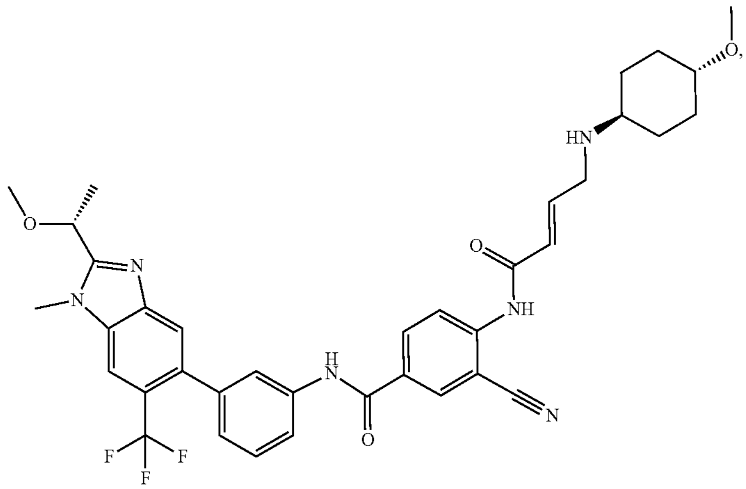
,
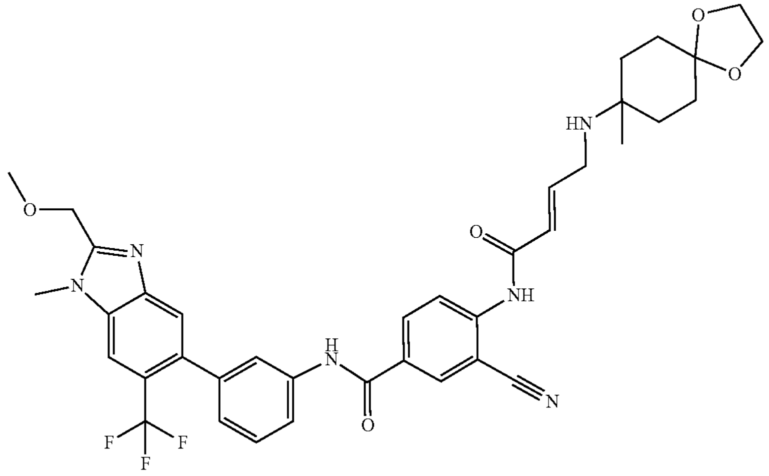
,
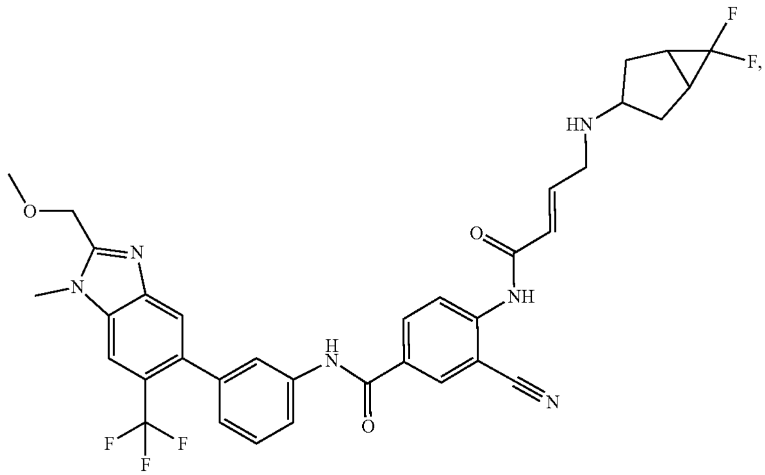
,

-continued
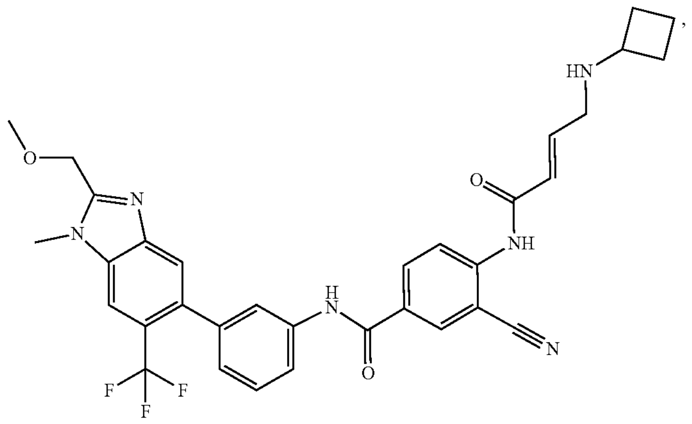
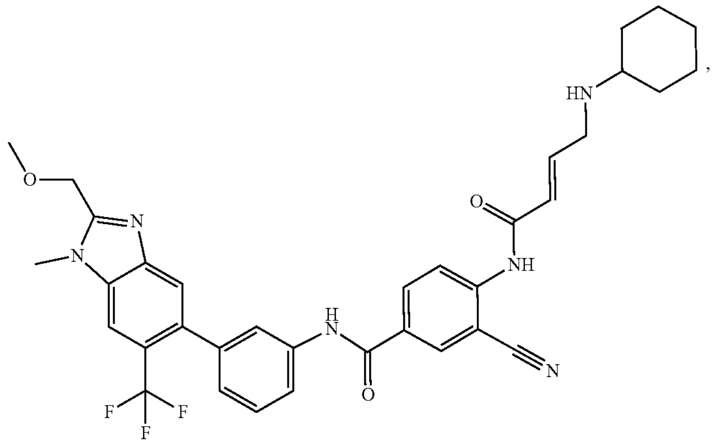
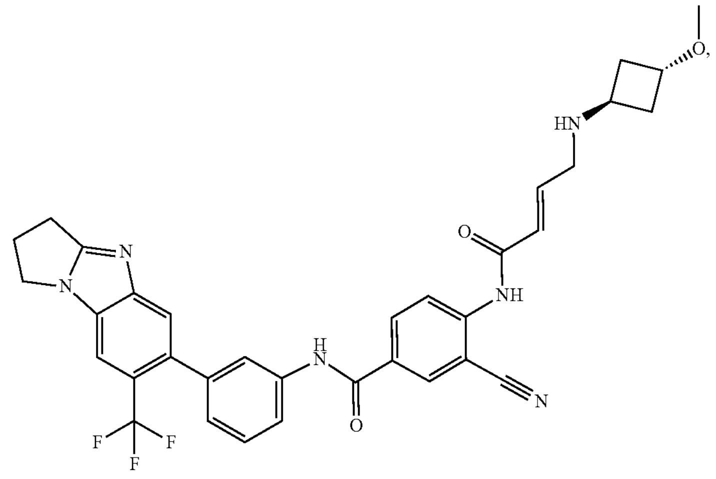

-continued
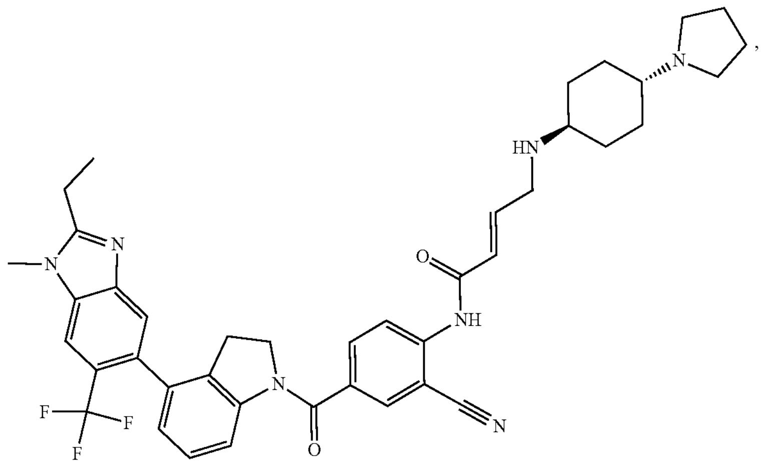
,
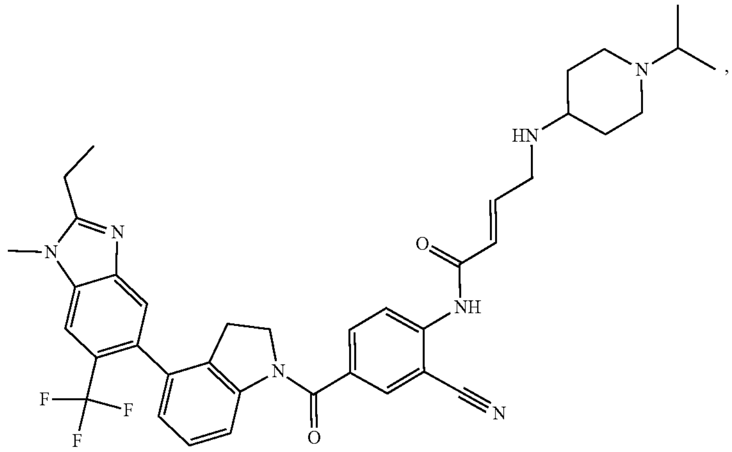
,
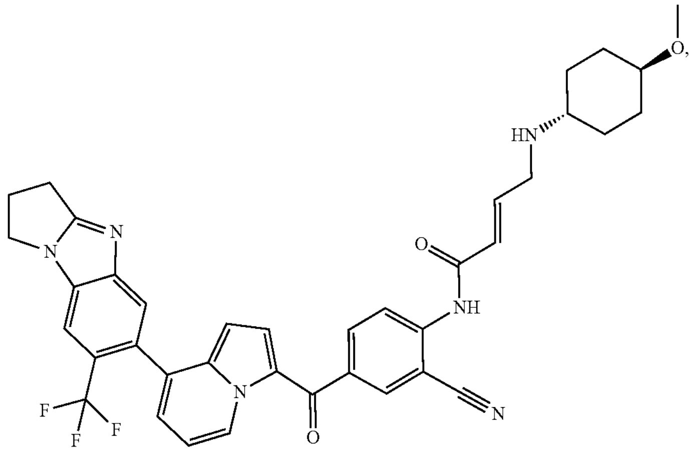
,

-continued
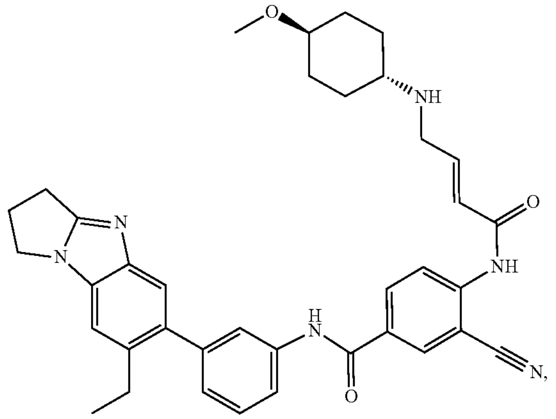
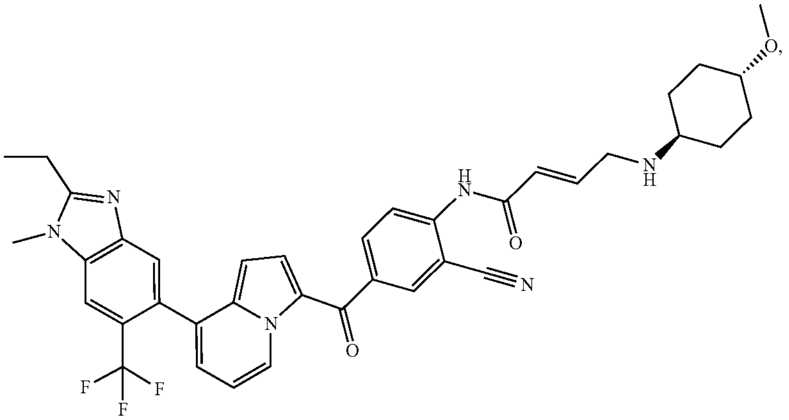
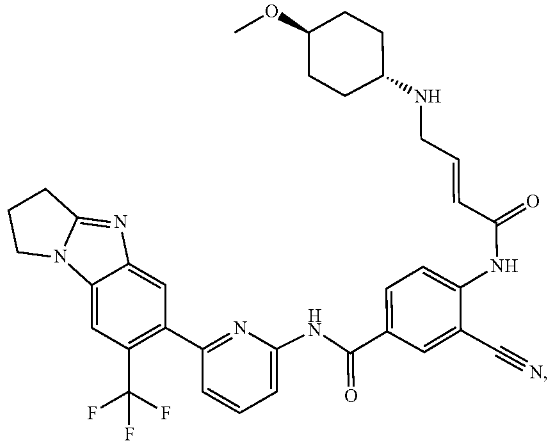
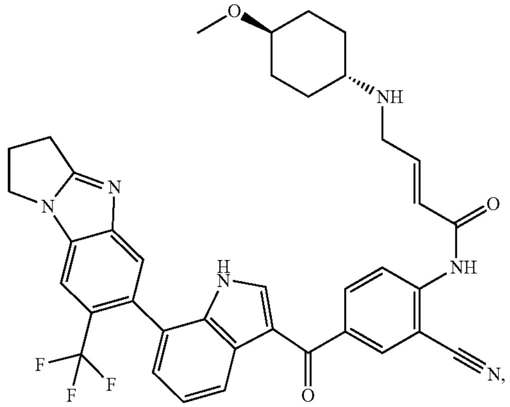
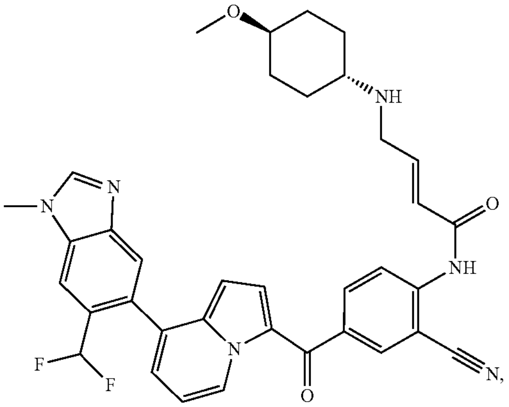

-continued
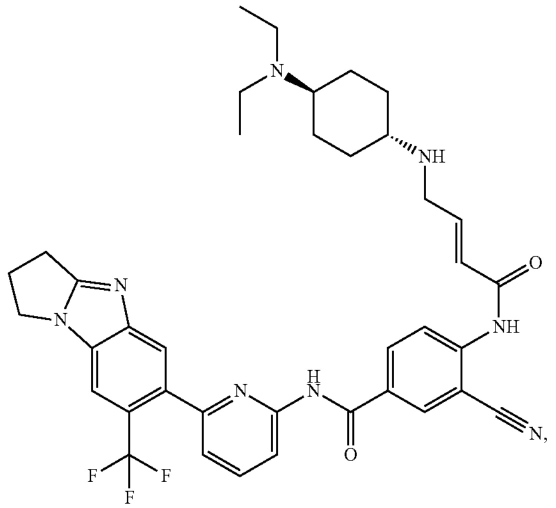
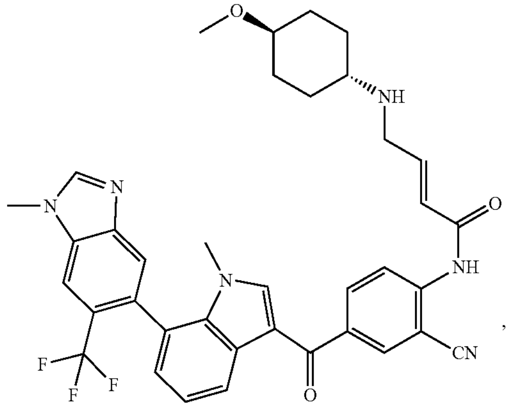
,
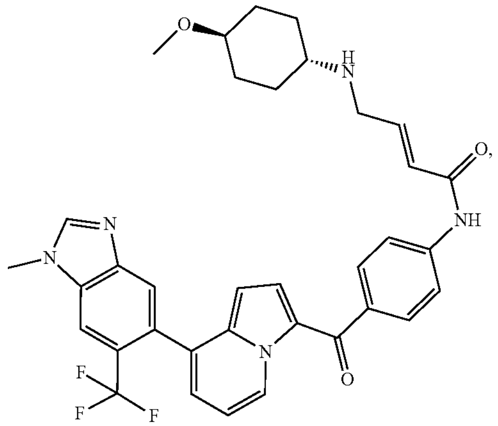
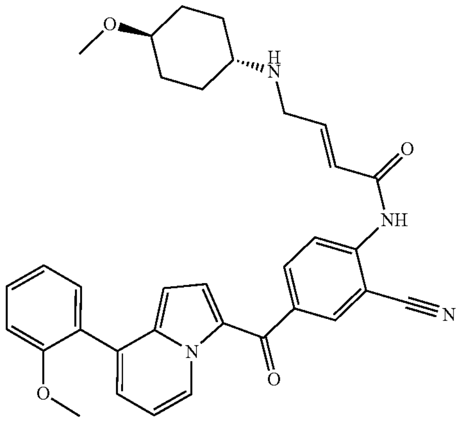
,
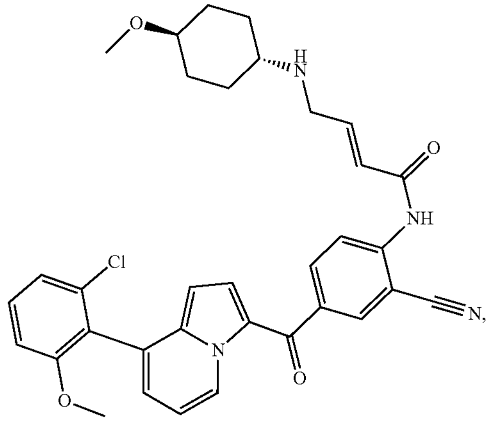
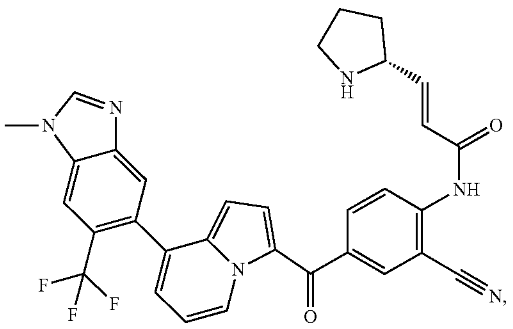

-continued
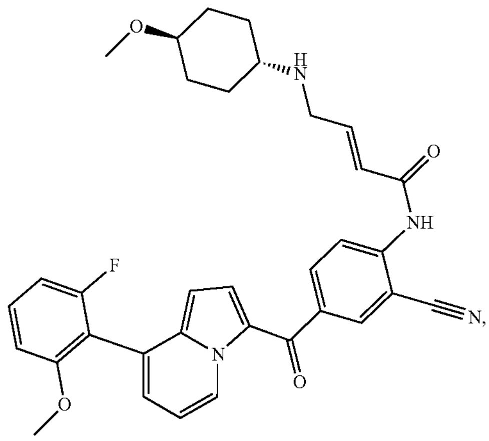
,
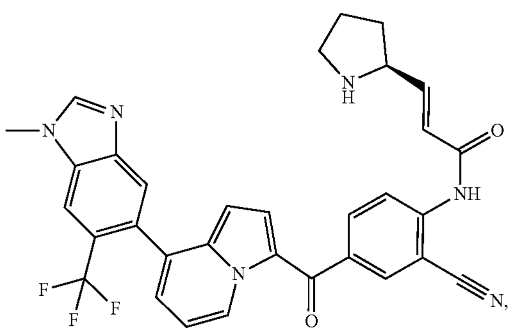
,
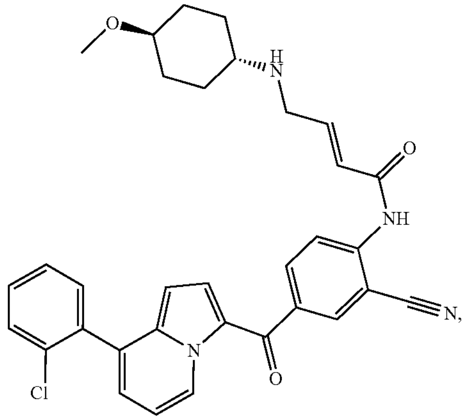
,
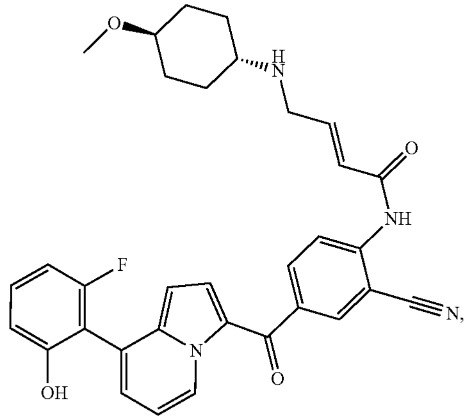
,
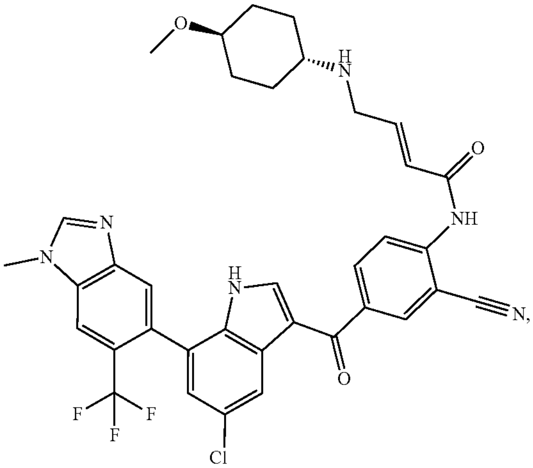
,
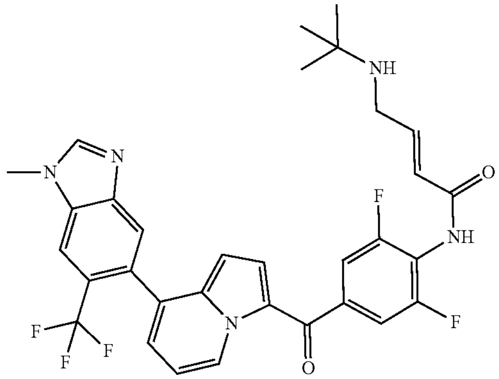
, -continued
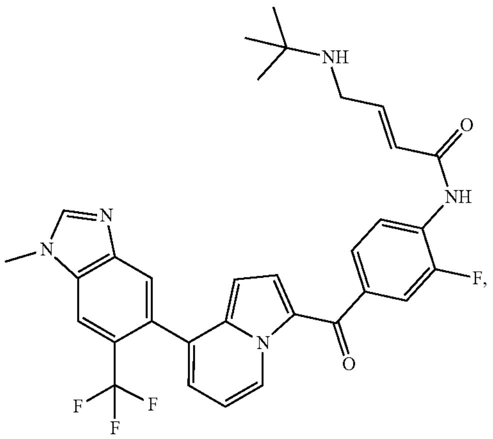
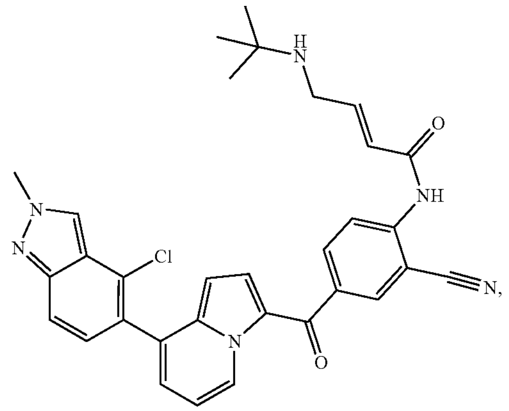
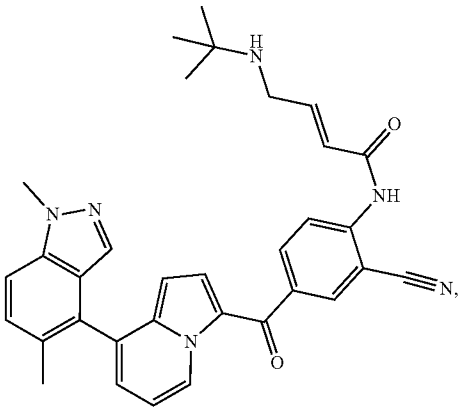
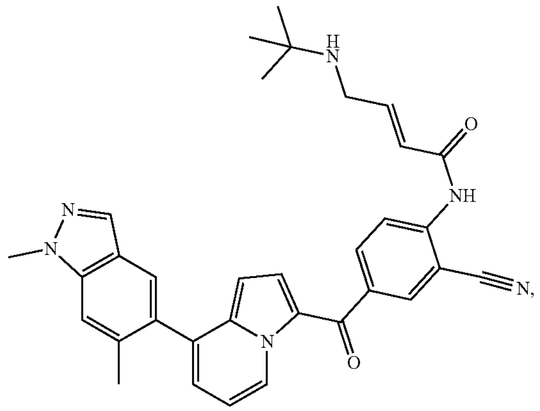
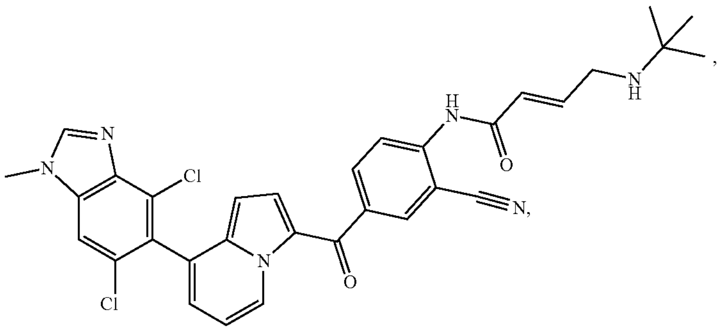
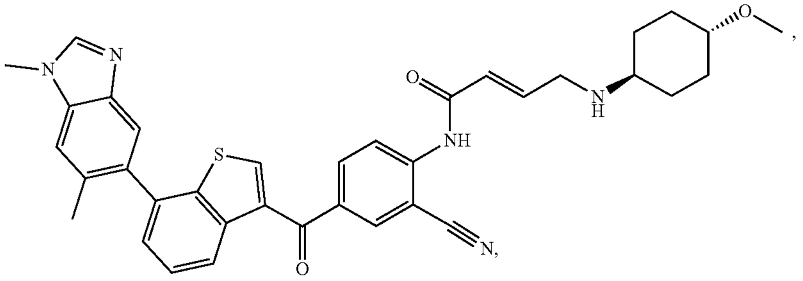

-continued
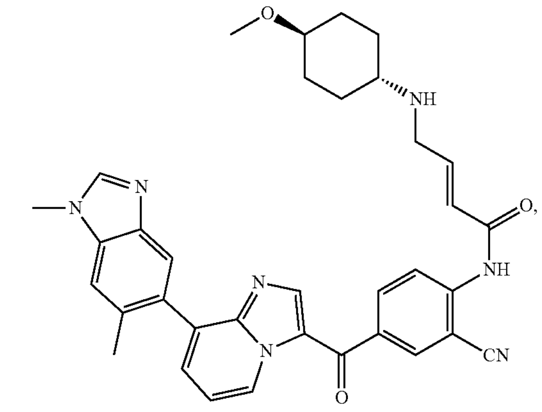
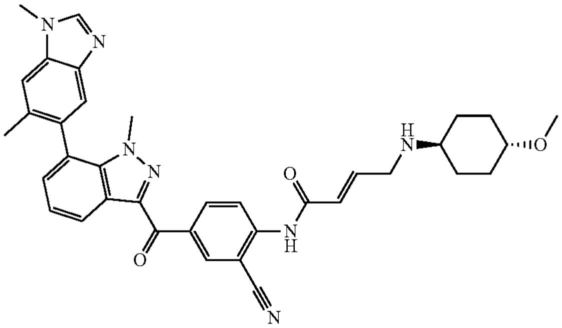
,
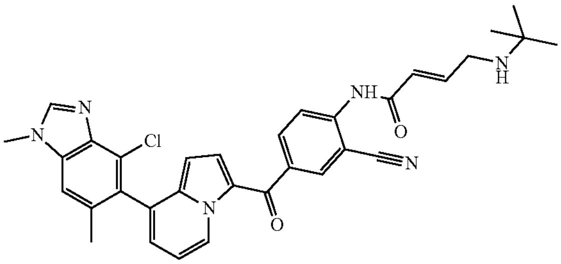
,
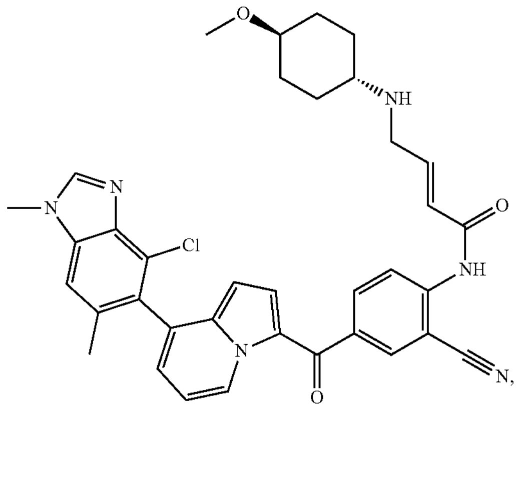
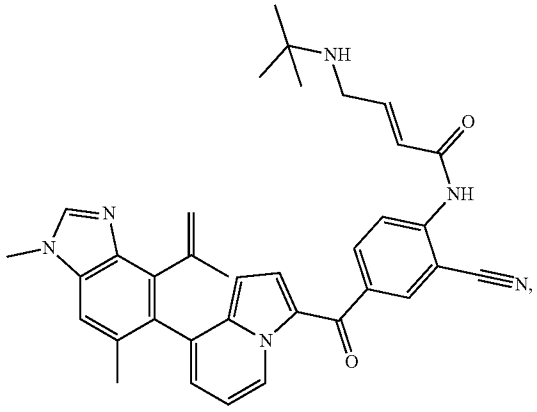
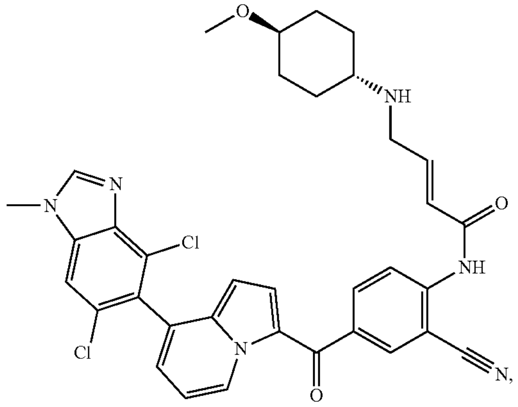
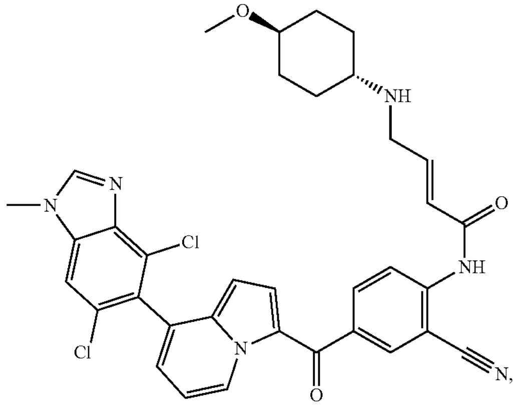
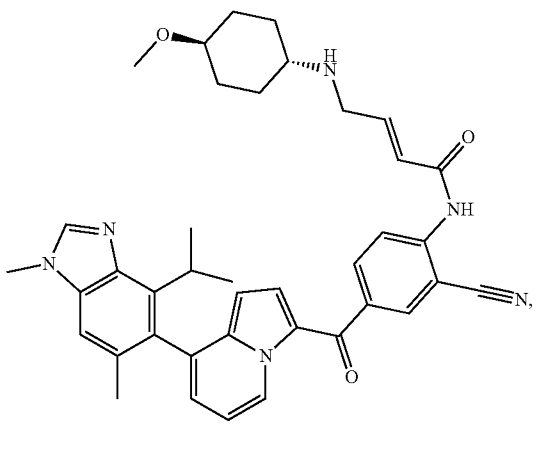

-continued
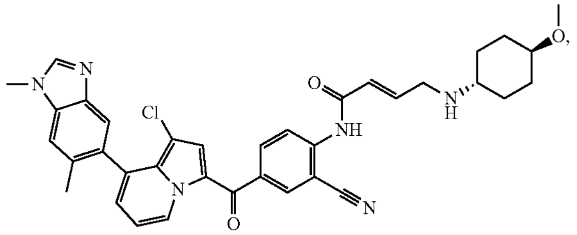
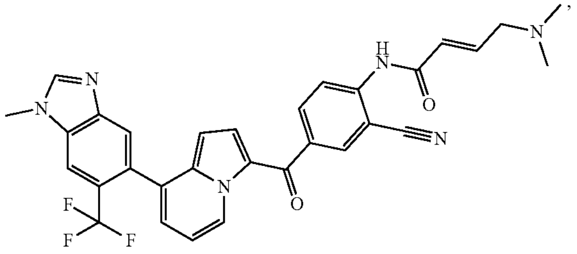
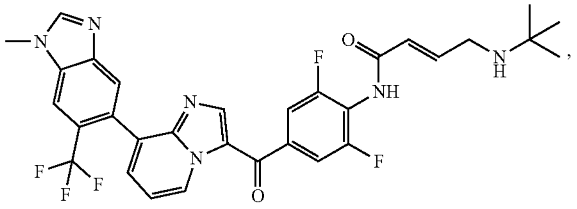
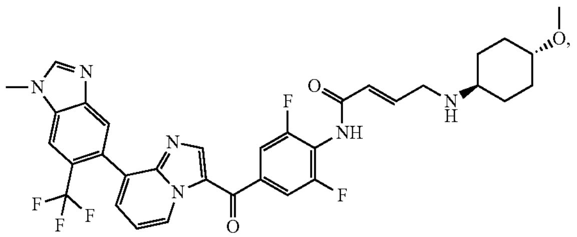
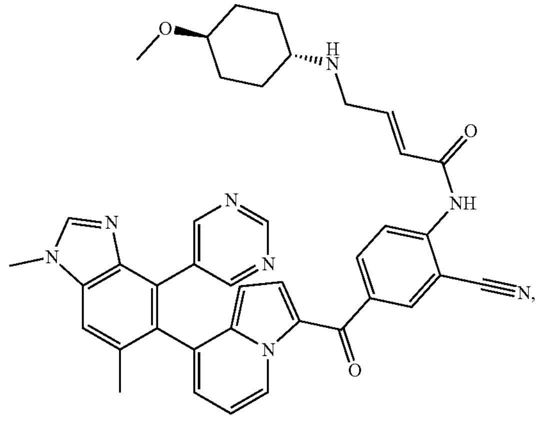
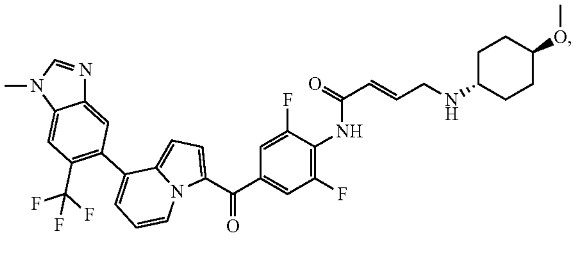
-continued
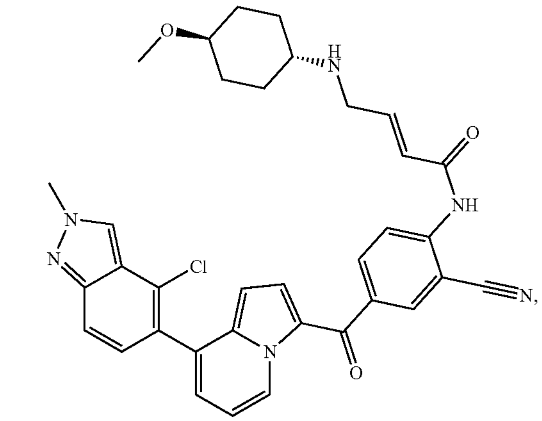
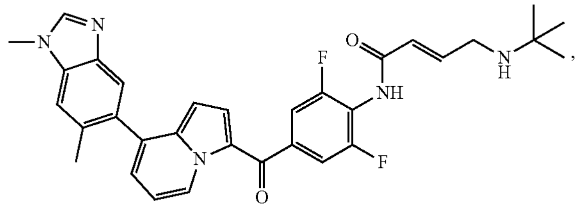
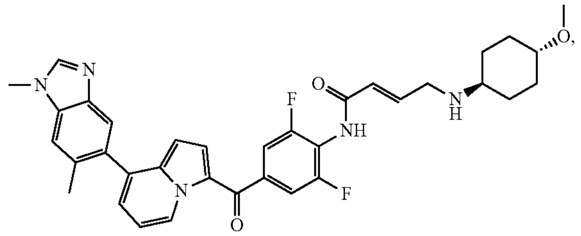
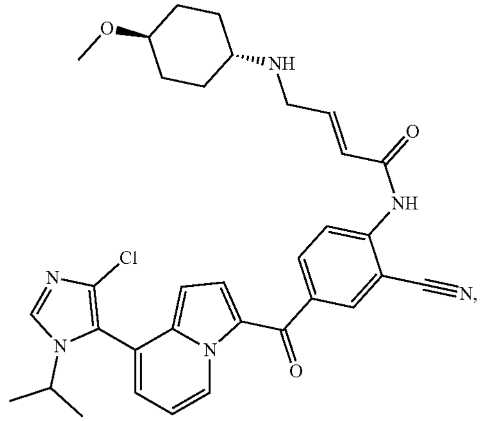
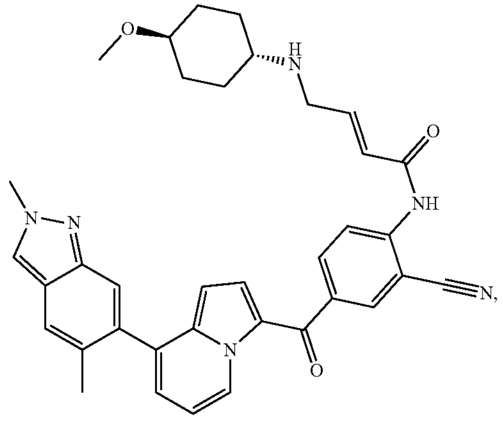

-continued
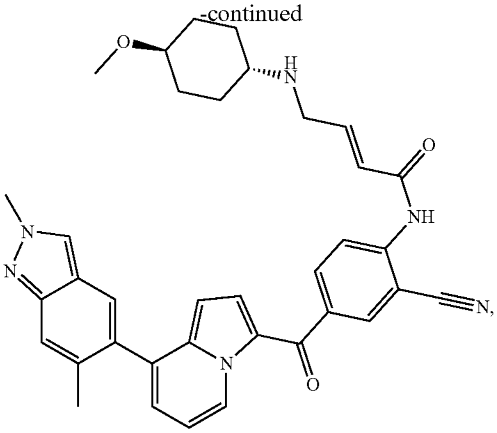
,
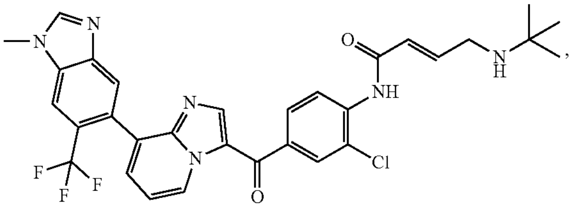
,
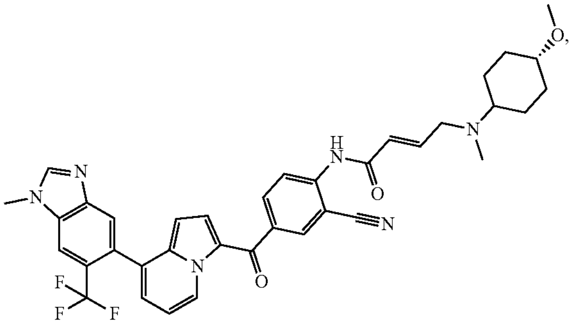
,
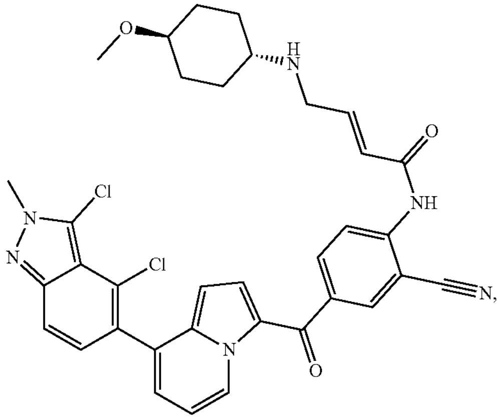
,
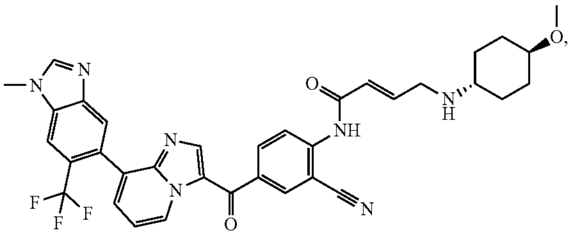
,
-continued
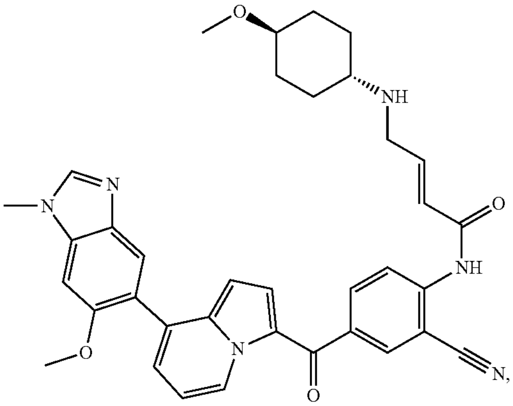
,
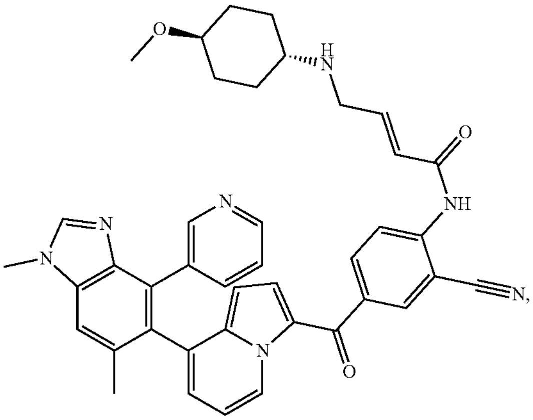
and
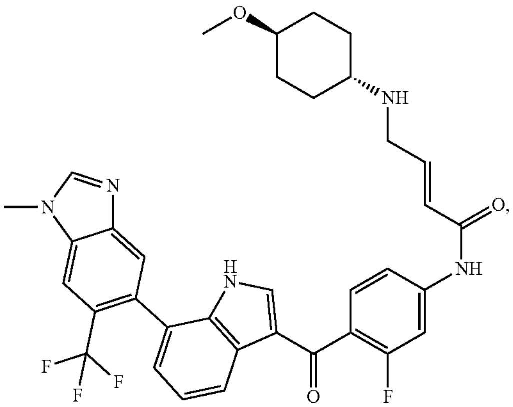
,
or a pharmaceutically acceptable salt thereof.
* * * * *